(12) United States Patent
Lam et al.

(10) Patent No.: US 6,906,070 B2
(45) Date of Patent: Jun. 14, 2005

(54) GUANIDINE MIMICS AS FACTOR XA INHIBITORS

(75) Inventors: Patrick Y. Lam, Chadds Ford, PA (US); Charles G. Clark, Cherry Hill, NJ (US); Celia Dominguez, Westlake, CA (US); John M. Fevig, Lincoln University, PA (US); Qi Han, Wilmington, DE (US); Renhua Li, Wilmington, DE (US); Donald J. P. Pinto, Kennett Square, PA (US); James R. Pruitt, Landenberg, PA (US); Mimi L. Quan, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 677 days.

(21) Appl. No.: 09/924,381

(22) Filed: Aug. 8, 2001

(65) Prior Publication Data

US 2002/0025963 A1 Feb. 28, 2002

Related U.S. Application Data

(62) Division of application No. 09/099,358, filed on Jun. 18, 1998, now Pat. No. 6,339,099.
(60) Provisional application No. 60/050,265, filed on Jun. 20, 1997.

(51) Int. Cl.[7] .................. A61K 31/4725; C07D 401/04
(52) U.S. Cl. ................... 514/248; 514/249; 514/266.2; 514/266.23; 514/300; 514/310; 514/313; 514/314; 514/373; 514/379; 514/395; 514/405; 514/406; 544/237; 544/258; 544/259; 544/260; 544/284; 544/293; 546/122; 546/143; 546/159; 548/207; 548/241; 548/304.7; 548/306.1; 548/362.1; 548/364.1; 548/364.4
(58) Field of Search ........................ 514/266.2, 266.23, 514/266.4, 310, 313, 314, 379, 394, 395, 405, 406; 544/284, 293; 546/143, 159; 548/241, 304.7, 306.1, 356.1, 362.1, 364.1, 364.4

(56) References Cited

U.S. PATENT DOCUMENTS

| 5,202,330 | A |   | 4/1993  | Atwal et al. ................. 514/274 |
| 5,317,103 | A |   | 5/1994  | Baker et al. ................. 544/367 |
| 5,342,851 | A |   | 8/1994  | Sanfilippo et al. .......... 514/370 |
| 5,463,071 | A |   | 10/1995 | Himmelsbach et al. ..... 548/251 |
| 5,616,601 | A |   | 4/1997  | Khanna et al. .............. 514/399 |
| 5,681,838 | A |   | 10/1997 | Zoller et al. ................. 514/307 |
| 5,707,998 | A |   | 1/1998  | Takase et al. ................ 514/259 |
| 5,932,576 | A | * | 8/1999  | Anantanarayan et al. 514/235.5 |
| 5,998,424 | A | * | 12/1999 | Galemmo et al. ........... 514/269 |
| 6,020,357 | A |   | 2/2000  | Pinto et al. .................. 514/406 |
| 6,403,620 | B1| * | 6/2002  | Galemmo et al. ........... 514/359 |

FOREIGN PATENT DOCUMENTS

| EP | 234830 A    | 9/1987  |
| EP | 236902 A    | 9/1987  |
| EP | 513387 B    | 11/1992 |
| EP | 554829 A    | 8/1993  |
| JP | 4247081 A   | 9/1992  |
| WO | WO 9402477 A | 2/1994 |
| WO | WO 9514683 A | 6/1995 |
| WO | WO 9518111 A | 7/1995 |
| WO | WO 9628427 A | 9/1996 |
| WO | WO 9640143 A | 12/1996 |
| WO | WO 9723212 A | 7/1997 |
| WO | WO 9732583 A | 9/1997 |

OTHER PUBLICATIONS

Tidwell et al. "Diarylamidine derivatives with one or both of the aryl moieties consisting of an indole or indole–like ring. Inhibitors of arginine–specific esteroproteases", J. Med. Chem. (1978), 21(7), 613–623.

* cited by examiner

*Primary Examiner*—Richard L. Raymond
(74) *Attorney, Agent, or Firm*—David H. Vance; Jing S. Belfield

(57) ABSTRACT

The present application describes nitrogen containing heteroaromatics and derivatives thereof of formula I:

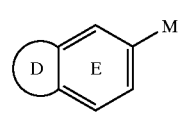

or pharmaceutically acceptable salt forms thereof, wherein rings D-E represent guanidine mimics, which are useful as inhibitors of factor Xa.

18 Claims, No Drawings

GUANIDINE MIMICS AS FACTOR XA INHIBITORS

This application is a divisional application of U.S. application Ser. No. 09/099,358 filed on Jun. 18, 1998 and issued as U.S. Pat. No. 6,339,099 on Jan. 15, 2002, which claims the benefit of U.S. Provisional Application No. 60/050,265 filed on Jun. 20, 1997.

FIELD OF THE INVENTION

This invention relates generally to novel guanidine mimics which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO 96/28427 describes benzamidine anticoagulants of the formula:

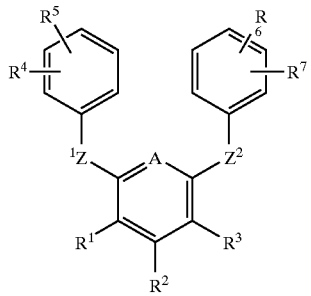

wherein $Z^1$ and $Z^2$ are O, N(R), S or $OCH_2$ and the central ring may be phenyl or a variety of heterocycles. The presently claimed compounds do not contain the $Z^1$ linker or the substitution pattern of the above compounds.

WO 95/13155 and PCT International Application US 96/07692 describe isoxazoline and isoxazole fibrinogen receptor antagonists of the formula:

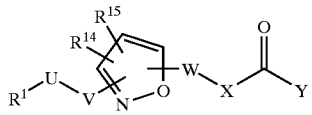

wherein $R^1$ may be a basic group, U—V may be a six-membered aromatic ring, W—X may be a variety of linear or cyclic groups, and Y is an oxy group. Thus, these compounds all contain an acid functionality (i.e., W—X—C(=O)—Y). In contrast, the presently claimed compounds do not contain such an acid functionality.

EP 0,513,387 depicts active oxygen inhibitors which are oxazoles or thiazoles of the formula:

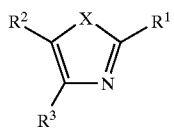

wherein X is O or S, $R^2$ is preferably hydrogen, and both $R^1$ and $R^3$ are substituted cyclic groups, with at least one being phenyl. The presently claimed invention does not relate to these types of oxazoles or thiazoles.

WO 95/18111 addresses fibrinogen receptor antagonists, containing basic and acidic termini, of the formula:

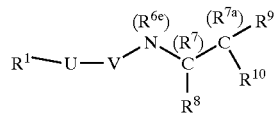

wherein $R^1$ represents the basic termini, U is an alkylene or heteroatom linker, V may be a heterocycle, and the right hand portion of the molecule represents the acidic termini. The presently claimed compounds do not contain the acidic termini of WO 95/18111.

In U.S. Pat. No. 5,463,071, Himmelsbach et al depict cell aggregation inhibitors which are 5-membered heterocycles of the formula:

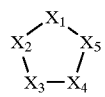

wherein the heterocycle may be aromatic and groups A-B-C— and F-E-D- are attached to the ring system. A-B-C— can be a wide variety of substituents including a basic group attached to an aromatic ring. The F-E-D- group, however, would appear to be an acidic functionality which differs from the present invention. Furthermore, use of these compounds as inhibitors of factor Xa is not discussed.

Baker et al, in U.S. Pat. No. 5,317,103, discuss $5-HT_1$ agonists which are indole substituted five-membered heteroaromatic compounds of the formula:

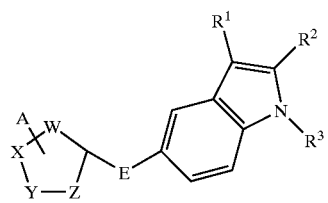

wherein $R^1$ may be pyrrolidine or piperidine and A may be a basic group including amino and amidino. Baker et al, however, do not indicate that A can be a substituted ring system like that contained in the presently claimed heteroaromatics.

Baker et al, in WO 94/02477, discuss $5-HT_1$ agonists which are imidazoles, triazoles, or tetrazoles of the formula:

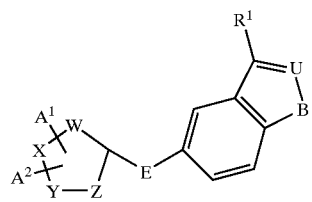

wherein $R^1$ represents a nitrogen containing ring system or a nitrogen substituted cyclobutane, and A may be a basic group including amino and amidino. But, Baker et al do not indicate that A can be a substituted ring system like that contained in the presently claimed heteroaromatics.

Tidwell et al, in *J. Med. Chem.* 1978, 21(7), 613–623, describe a series of diarylamidine derivatives including 3,5-bis(4-amidinophenyl)isoxazole. This series of compounds was tested against thrombin, trypsin, and pancreatic kallikrein. The presently claimed invention does not include these types of compounds.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel guanidine mimics which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

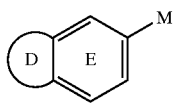

or pharmaceutically acceptable salt or prodrug forms thereof, wherein D, E, and M are defined below, are effective factor Xa inhibitors.

DETAILED DESCRIPTION OF PREFERRED EMBODIMENTS

[1] Thus, in a first embodiment, the present invention provides novel compounds of formula I:

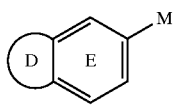

I or a stereoisomer or pharmaceutically acceptable salt thereof, wherein;

ring D is selected from —$CH_2N=CH$—, —$CH_2CH_2N=CH$—, a 5–6 membered aromatic system containing from 0–2 heteroatoms selected from the group N, O, and S;

ring D is substituted with 0–2 R, provided that when ring D is unsubstituted, it contains at least one heteroatom;

ring E contains 0–2 N atom and is substituted by 0–1 R

R is selected from Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

M is selected from the group:

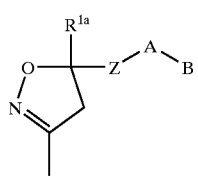

a

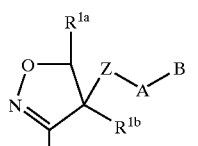

b

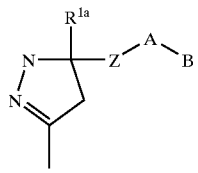

c

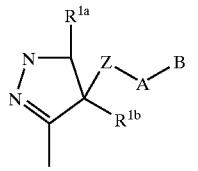

d

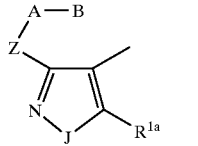

e

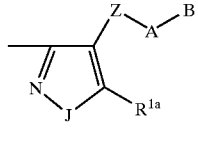

f

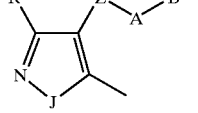

g

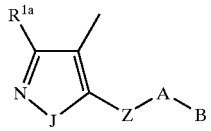

h

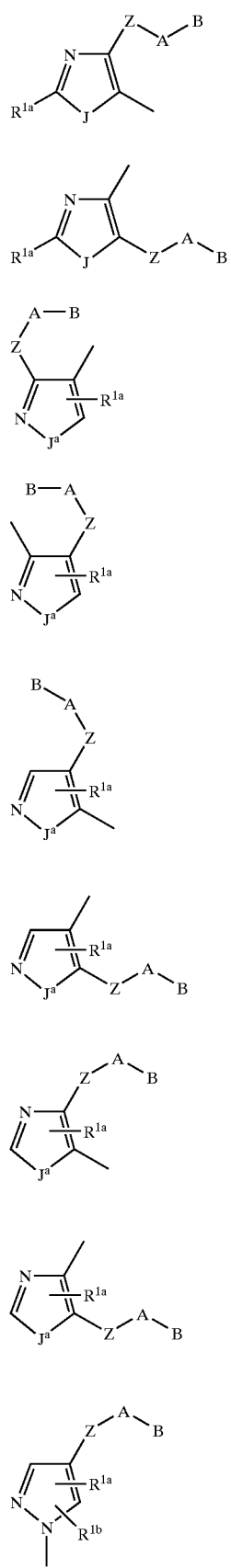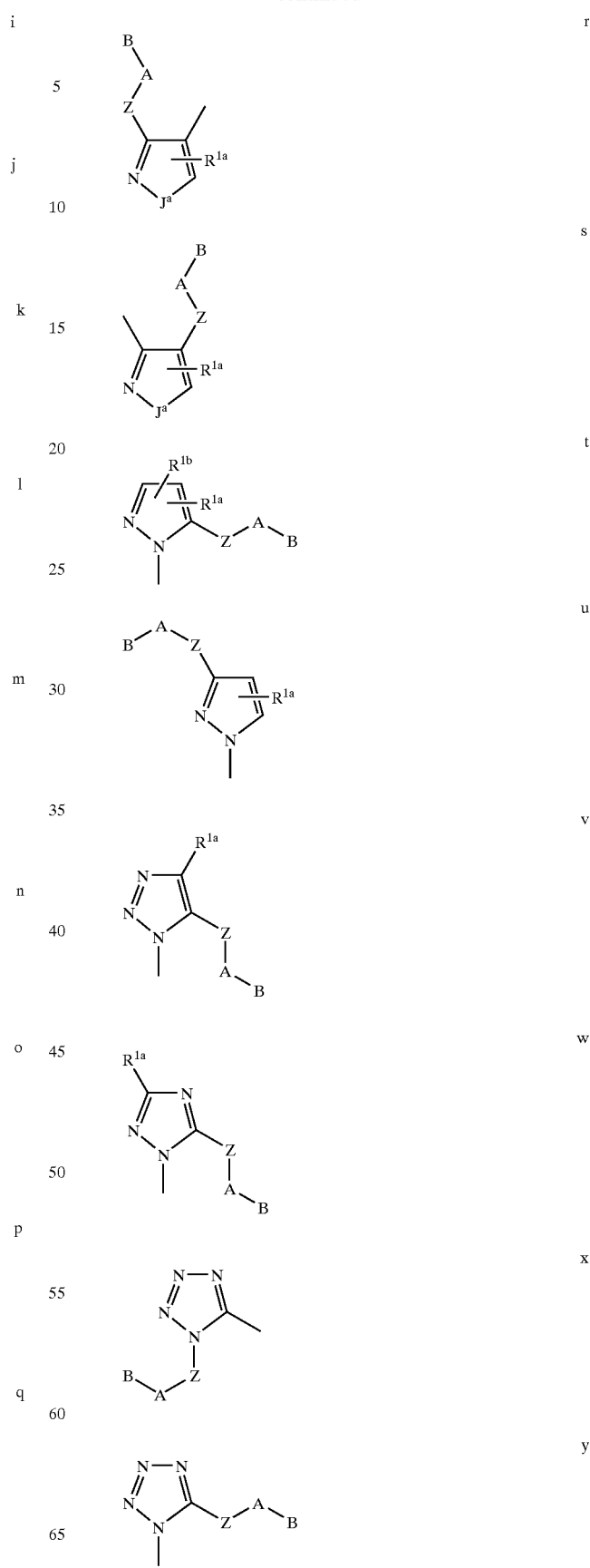

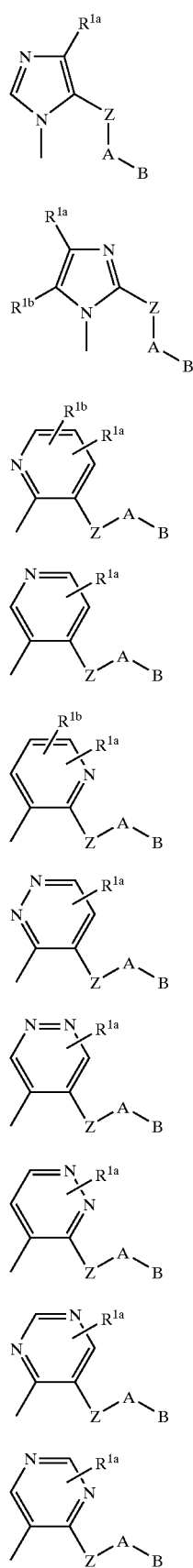
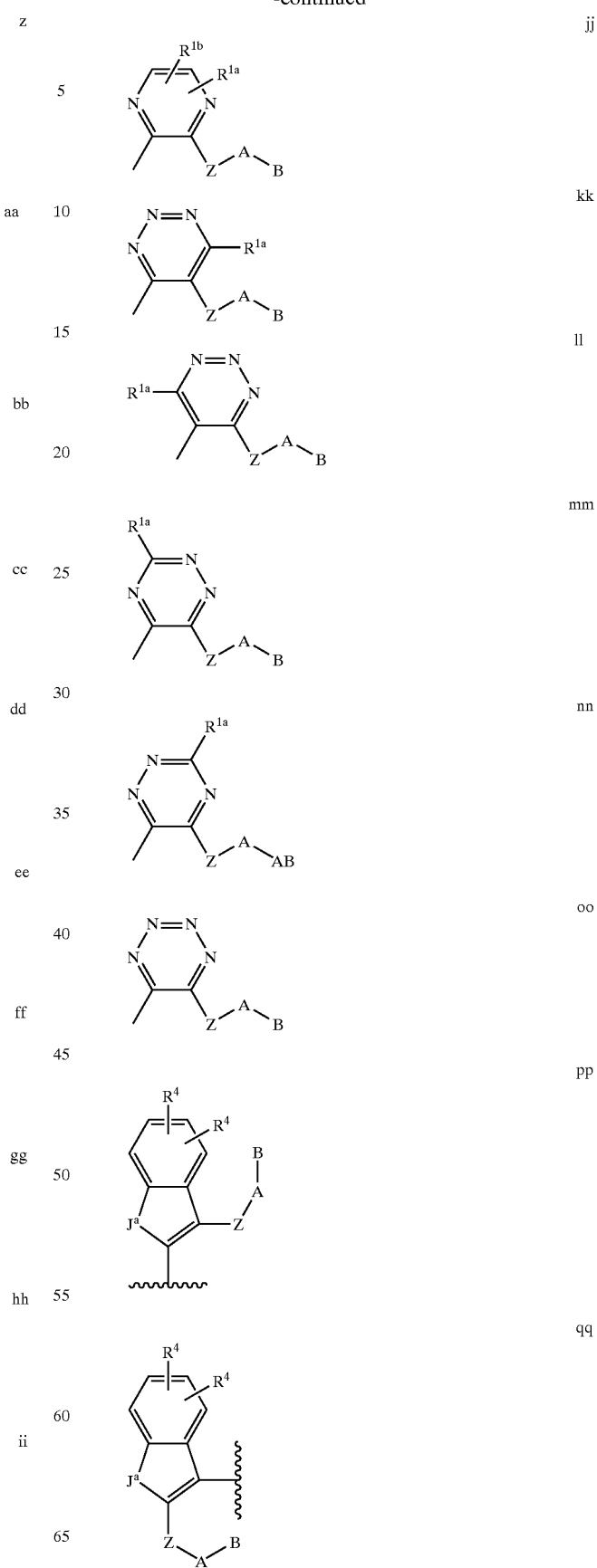

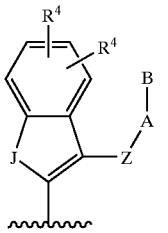
rr

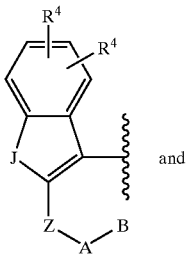
and
ss

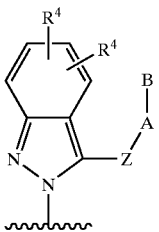
tt

J is O or S;

J$^a$ is NH or NR$^{1a}$;

Z is selected from a bond, C$_{1-4}$ alkylene, (CH$_2$)$_r$O(CH$_2$)$_r$, (CH$_2$)$_r$NR$^3$(CH$_2$)$_r$, (CH$_2$)$_r$C(O)(CH$_2$)$_r$, (CH$_2$)$_r$C(O)O(CH$_2$)$_r$, (CH$_2$)$_r$OC(O)(CH$_2$)$_r$, (CH$_2$)$_r$C(O)NR$^3$(CH$_2$)$_r$, (CH$_2$)$_r$NR$^3$C(O)(CH$_2$)$_r$, (CH$_2$)$_r$OC(O)O(CH$_2$)$_r$, (CH$_2$)$_r$OC(O)NR$^3$(CH$_2$)$_r$, (CH$_2$)$_r$NR$^3$C(O)O(CH$_2$)$_r$, (CH$_2$)$_r$NR$^3$C(O)NR$^3$(CH$_2$)$_r$, (CH$_2$)$_r$S(O)$_p$(CH$_2$)$_r$, (CH$_2$)$_r$SO$_2$NR$^3$(CH$_2$)$_r$, (CH$_2$)$_r$NR$^3$SO$_2$(CH$_2$)$_r$, and (CH$_2$)$_r$NR$^3$SO$_2$NR$^3$(CH$_2$)$_r$, provided that Z does not form a N—N, N—O, N—S, NCH$_2$N, NCH$_2$O, or NCH$_2$S bond with ring M or group A;

R$^{1a}$ and R$^{1b}$ are independently absent or selected from —(CH$_2$)$_r$—R$^{1'}$, —CH=CH—R$^{1'}$, NCH$_2$R$^{1'}$, OCH$_2$R$^{1'}$, SCH$_2$R$^{1'}$, NH(CH$_2$)$_2$(CH$_2$)$_r$R$^{1'}$, O(CH$_2$)$_2$(CH$_2$)$_r$R$^{1'}$, and S(CH$_2$)$_2$(CH$_2$)$_r$R$^{1'}$;

alternatively, R$^{1a}$ and R$^{1b}$, when attached to adjacent carbon atoms, together with the atoms to which they are attached form a 5–8 membered saturated, partially saturated or unsaturated ring substituted with 0–2 R$^4$ and which contains from 0–2 heteroatoms selected from the group consisting of N, O, and S;

alternatively, when Z is C(O)NH and R$^{1a}$ is attached to a ring carbon adjacent to Z, then R$^{1a}$ is a C(O) which replaces the amide hydrogen of Z to form a cyclic imide;

R$^{1'}$ is selected from H, C$_{1-3}$ alkyl, F, Cl, Br, I, —CN, —CHO, (CF$_2$)$_r$CF$_3$, (CH$_2$)$_r$OR$^2$, NR$^2$R$^{2a}$, C(O)R$^{2c}$, OC(O)R$^2$, (CF$_2$)$_r$CO$_2$R$^{2c}$, S(O)$_p$R$^{2b}$, NR$^2$(CH$_2$)$_r$OR$^2$, CH(=NR$^{2c}$)NR$^2$R$^{2a}$, NR$^2$C(O)R$^{2b}$, NR$^2$C(O)NHR$^{2b}$, NR$^2$C(O)$_2$R$^{2a}$, OC(O)NR$^{2a}$R$^{2b}$, C(O)NR$^2$R$^{2a}$, C(O)NR$^2$(CH$_2$)$_r$OR$^2$, SO$_2$NR$^2$R$^{2a}$, NR$^2$SO$_2$R$^{2b}$, C$_{3-6}$ carbocyclic residue substituted with 0–2 R$^4$, and 5–10 membered heterocyclic system containing from 1–4 heteroatoms selected from the group consisting of N, O, and S substituted with 0–2 R$^4$;

R$^{1''}$ is selected from H, CH(CH$_2$OR$^2$)$_2$, C(O)R$^{2c}$, C(O)NR$^2$R$^{2a}$, S(O)R$^{2b}$, S(O)$_2$R$^{2b}$, and SO$_2$NR$^2$R$^{2a}$;

R$^2$, at each occurrence, is selected from H, CF$_3$, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2a}$, at each occurrence, is selected from H, CF$_3$, C$_{1-6}$ alkyl, benzyl, phenethyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, R$^2$ and R$^{2a}$, together with the atom to which they are attached, combine to form a 5 or 6 membered saturated, partially saturated or unsaturated ring substituted with 0–2 R$^{4b}$ and containing from 0–1 additional heteroatoms selected from the group consisting of N, O, and S;

R$^3$, at each occurrence, is selected from H, C$_{1-4}$ alkyl, and phenyl;

R$^{3a}$, at each occurrence, is selected from H, C$_{1-4}$ alkyl, and phenyl;

R$^{3b}$, at each occurrence, is selected from H, C$_{1-4}$ alkyl, and phenyl;

R$^{3c}$, at each occurrence, is selected from C$_{1-4}$ alkyl, and phenyl;

A is selected from:

C$_{3-10}$ carbocyclic residue substituted with 0–2 R$^4$, and
  5–10 membered heterocyclic system containing from 1–4 heteroatoms selected from the group consisting of N, O, and S substituted with 0–2 R$^4$;

B is selected from: H, Y, and X—Y;

X is selected from C$_{1-4}$ alkylene, —CR$^2$(CR$^2$R$^{2b}$)(CH$_2$)$_r$—, —C(O)—, —C(=NR$^{1''}$)—, —CR$^2$(NR$^{1''}$R$^2$)—, —CR$^2$(OR$^2$)—, —CR$^2$(SR$^2$)—, —C(O)CR$^2$R$^{2a}$—, —CR$^2$R$^{2a}$C(O), —S(O)$_p$—, —S(O)$_p$CR$^2$R$^{2a}$—, —CR$^2$R$^{2a}$S(O)$_p$—, —S(O)$_2$NR$^2$—, —NR$^2$S(O)$_2$—, NR$^2$S(O)$_2$CR$^2$R$^{2a}$—, —CR$^2$R$^{2a}$S(O)$_2$NR$^2$—, —NR$^2$S(O)$_2$NR$^2$—, —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)O—, —OC(O)NR$^2$—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is selected from:

(CH$_2$)$_r$NR$^2$R$^{2a}$, provided that X—Y do not form a N—N, O—N, or S—N bond,
  C$_{3-10}$ carbocyclic residue substituted with 0–2 R$^{4a}$, and
  5–10 membered heterocyclic system containing from 1–4 heteroatoms selected from the group consisting of N, O, and S substituted with 0–2 R$^{4a}$;

R$^4$, at each occurrence, is selected from H, =O, (CH$_2$)$_r$OR$^2$, F, Cl, Br, I, C$_{1-4}$ alkyl, —CN, NO$_2$, (CH$_2$)$_r$NR$^2$R$^{2a}$, (CH$_2$)$_r$C(O)R$^{2c}$, NR$^2$C(O)R$^{2b}$, C(O)NR$^2$R$^{2a}$, NR$^2$C(O)NR$^2$R$^{2a}$, CH(=NR$^2$)NR$^2$R$^{2a}$, CH(=NS(O)$_2$R$^5$)NR$^2$R$^{2a}$, NHC(=NR$^2$)NR$^2$R$^{2a}$, C(O)NHC(=NR$^2$)NR$^2$R$^{2a}$, SO$_2$NR$^2$R$^{2a}$, NR$^2$SO$_2$NR$^2$R$^{2a}$, NR$^2$SO$_2$—C$_{1-4}$ alkyl, NR$^2$SO$_2$R$^5$, S(O)$_p$R$^5$, (CF$_2$)$_r$CF$_3$, NCH$_2$R$^{1''}$, OCH$_2$R$^{1''}$, SCH₂R¹'', N(CH₂)₂(CH₂)ₜR¹', O(CH₂)₂(CH₂)ₜR¹', and S(CH₂)₂(CH₂)ₜR¹';
alternatively, one R⁴ is a 5–6 membered aromatic heterocycle containing from 1–4 heteroatoms selected from the group consisting of N, O, and S;
provided that if B is H, then R⁴ is other than tetrazole, C(O)-alkoxy, and C(O)NR²R²ᵃ;
R⁴ᵃ, at each occurrence, is selected from H, =O, (CH₂)ᵣOR², (CH₂)ᵣ—F, (CH₂)ᵣ—Br, (CH₂)ᵣ—Cl, I, C₁₋₄ alkyl, —CN, NO₂, (CH₂)ᵣNR²R²ᵃ, (CH₂)ᵣNR²R²ᵇ, (CH₂)ᵣC(O)R²ᶜ, NR²C(O)R²ᵇ, C(O)NR²R²ᵃ, C(O)NH(CH₂)₂NR²R²ᵃ, NR²C(O)NR²R²ᵃ, CH(=NR²)NR²R²ᵃ, NHC(=NR²)NR²R²ᵃ, SO₂NR²R²ᵃ, NR²SO₂NR²R²ᵃ, NR²SO₂—C₁₋₄ alkyl, C(O)NHSO₂—C₁₋₄ alkyl, NR²SO₂R⁵, S(O)ₚR⁵, and (CF₂)ᵣCF₃;
alternatively, one R⁴ᵃ is a 5–6 membered aromatic heterocycle containing from 1–4 heteroatoms selected from the group consisting of N, O, and S and substituted with 0–1 R⁵;
R⁴ᵇ, at each occurrence, is selected from H, =O, (CH₂)ᵣOR³, F, Cl, Br, I, C₁₋₄ alkyl, —CN, NO₂, (CH₂)ᵣNR³R³ᵃ, (CH₂)ᵣC(O)R³, (CH₂)ᵣC(O)OR³ᶜ, NR³C(O)R³ᵃ, C(O)NR³R³ᵃ, NR³C(O)NR³R³ᵃ, CH(=NR³)NR³R³ᵃ, NH³C(=NR³)NR³R³ᵃ, S₂NR³R³ᵃ, NR³SO₂NR³R³ᵃ, NR³SO₂—C₁₋₄ alkyl, NR³SO₂CF₃, NR³SO₂-phenyl, S(O)ₚCF₃, S(O)ₚ—C₁₋₄ alkyl, S(O)ₚ-phenyl, and (CF₂)ᵣCF₃;
R⁵, at each occurrence, is selected from CF₃, C₁₋₆ alkyl, phenyl substituted with 0–2 R⁶, and benzyl substituted with 0–2 R⁶;
R⁶, at each occurrence, is selected from H, OH, (CH₂)ᵣOR², F, Cl, Br, I, C₁₋₄ alkyl, CN, NO₂, (CH₂)ᵣNR²R²ᵃ, (CH₂)ᵣC(O)R²ᵇ, NR²C(O)R²ᵇ, NR²C(O)NR²R²ᵃ, CH(=NH)NH₂, NHC(=NH)NH₂, SO₂NR²R²ᵃ, NR²SO₂NR²R²ᵃ, and NR²SO₂C₁₋₄ alkyl;
n is selected from 0, 1, 2, and 3;
m is selected from 0, 1, and 2;
p is selected from 0, 1, and 2;
r is selected from 0, 1, 2, and 3;
s is selected from 0, 1, and 2; and,
t is selected from 0 and 1.

[2] In a preferred embodiment, the present invention provides novel compounds, wherein:
D-E is selected from the group:
1-aminoisoquinolin-7-yl; 1,3-diaminoisoquinolin-7-yl; 1,4-diaminoisoquinolin-7-yl; 1,5-diaminoisoquinolin-7-yl; 1,6-diaminoisoquinolin-7-yl; 1-amino-3-hydroxy-isoquinolin-7-yl; 1-amino-4-hydroxy-isoquinolin-7-yl; 1-amino-5-hydroxy-isoquinolin-7-yl; 1-amino-6-hydroxy-isoquinolin-7-yl; 1-amino-3-methoxy-isoquinolin-7-yl; 1-amino-4-methoxy-isoquinolin-7-yl; 1-amino-5-methoxy-isoquinolin-7-yl; 1-amino-6-methoxy-isoquinolin-7-yl; 1-hydroxy-isoquinolin-7-yl; 4-aminoquinazol-6-yl; 2,4-diaminoquinazol-6-yl; 4,7-diaminoquinazol-6-yl 4,8-diaminoquinazol-6-yl; 1-aminophthalaz-7-yl; 1,4-diaminophthalaz-7-yl; 1,5-diaminophthalaz-7-yl; 1,6-diaminophthalaz-7-yl; 4-aminopterid-6-yl; 2,4-aminopterid-6-yl; 4,6-diaminopterid-6-yl; 8-amino-1,7-naphthyrid-2-yl; 6,8-diamino-1,7-naphthyrid-2-yl; 5,8-diamino-1,7-naphthyrid-2-yl; 4,8-diamino-1,7-naphthyrid-2-yl; 3,8-diamino-1,7-naphthyrid-2-yl; 5-amino-2,6-naphthyrid-3-yl; 5,7-diamino-2,6-naphthyrid-3-yl; 5,8-diamino-2,6-naphthyrid-3-yl; 1,5-diamino-2,6-naphthyrid-3-yl; 5-amino-1,6-naphthyrid-3-yl; 5,7-diamino-1,6-naphthyrid-3-y; 5,8-diamino-1,6-naphthyrid-3-yl; 2,5-diamino-1,6-naphthyrid-3-yl; 3-aminoindazol-5-yl; 3-hydroxyindazol-5-yl; 3-aminobenzisoxazol-5-yl; 3-hydroxybenzisoxazol-5-yl; 3-aminobenzisothiazol-5-yl; 3-hydroxybenzisothiazol-5-yl; 1-amino-3,4-dihydroisoquinolin-7-yl; and, 1-aminoisoindol-6-yl;

M is selected from the group:

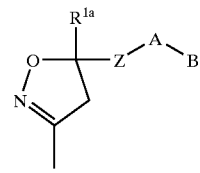

a

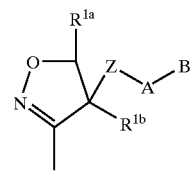

b

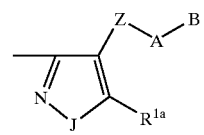

f

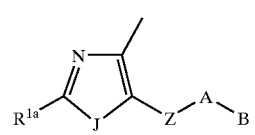

j

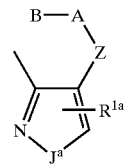

l

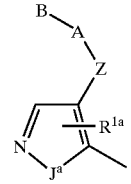

m

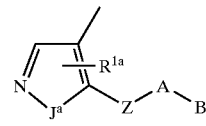

n

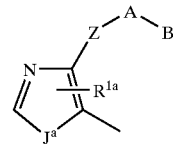

o q 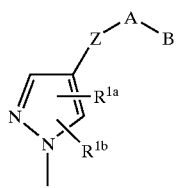

s 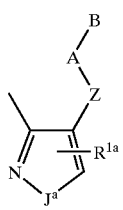

t 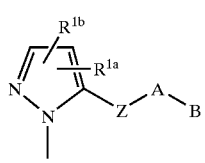

v 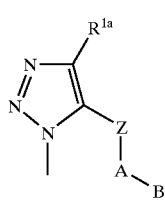

w 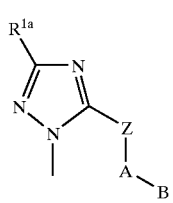

y 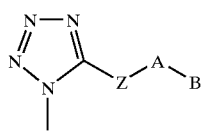

bb 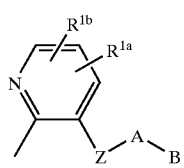

ee 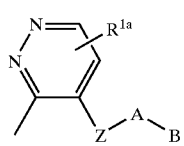

hh 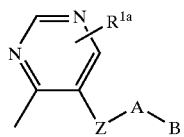

jj 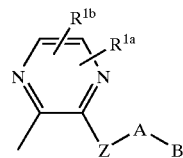

kk 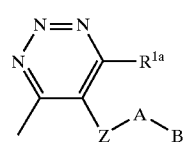

mm 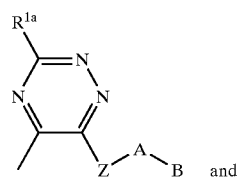

and nn 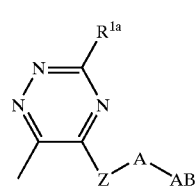

Z is selected from $(CH_2)_rC(O)(CH_2)_r$, $(CH_2)_rC(O)O(CH_2)_r$, $(CH_2)_rC(O)NR^3(CH_2)_r$, $(CH_2)_rS(O)_p(CH_2)_r$, and $(CH_2)_rSO_2NR^3(CH_2)_r$; and, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole;

Y may also be selected from the following bicyclic heteroaryl ring systems:

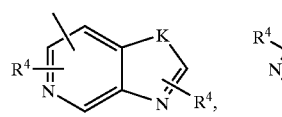 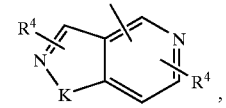

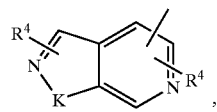 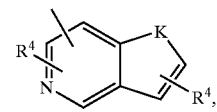

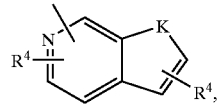 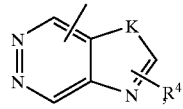

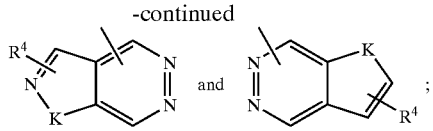 and ;

K is selected from O, S, NH, and N.

[3] In a more preferred embodiment, the present invention provides novel compounds, wherein;

D-E is selected from the group:

1-aminoisoquinolin-7-yl; 1,3-diaminoisoquinolin-7-yl; 1,4-diaminoisoquinolin-7-yl; 1,5-diaminoisoquinolin-7-yl; 1,6-diaminoisoquinolin-7-yl; 1-hydroxy-isoquinolin-7-yl; 4-aminoquinazol-6-yl; 2,4-diaminoquinazol-6-yl; 4,7-diaminoquinazol-6-yl; 4,8-diaminoquinazol-6-yl; 1-aminophthalaz-7-yl; 1,4-diaminophthalaz-7-yl; 1,5-diaminophthalaz-7-yl; 1,6-diaminophthalaz-7-yl; 4-aminopterid-6-yl; 8-amino-1,7-naphthyrid-2-yl; 5-amino-1,6-naphthyrid-3-y; 5-amino-2,6-naphthyrid-3-yl; 3-aminobenzisoxazol-5-yl; 3-aminobenzisothiazol-5-yl; 1-amino-3,4-dihydroisoquinolin-7-yl; and, 1-aminoisoindol-6-yl;

M is selected from the group:

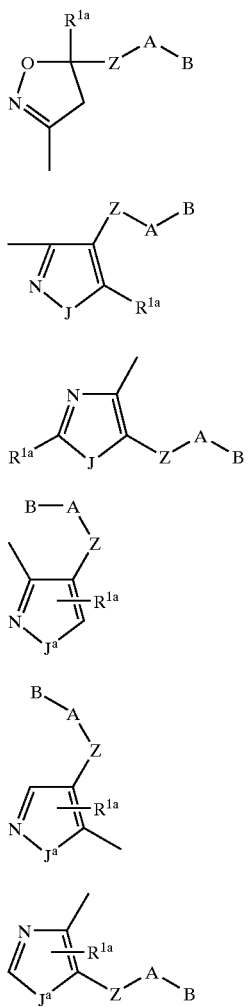

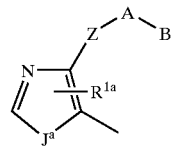

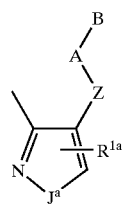

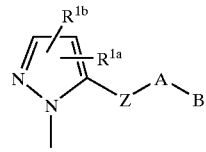

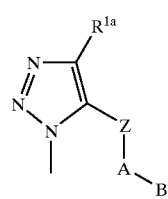

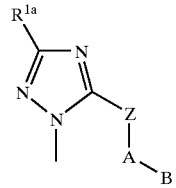

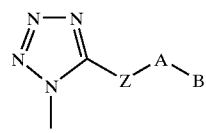

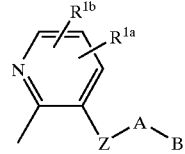

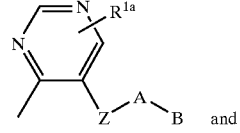 and

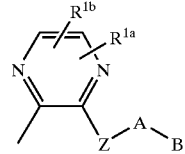

Z is selected from $(CH_2)_rC(O)(CH_2)_r$ and $(CH_2)_rC(O)NR^3(CH_2)_r$; and,

Y is selected from one of the following carbocyclic and heterocyclic systems which are substituted with 0–2 $R^{4a}$;
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole.

[4] In an even more preferred embodiment, the present invention provides novel compounds, wherein;

D-E is selected from the group:
1-aminoisoquinolin-7-yl; 1,3-diaminoisoquinolin-7-yl; 1,4-diaminoisoquinolin-7-yl; 1,5-diaminoisoquinolin-7-yl; 1,6-diaminoisoquinolin-7-yl; 1-aminophthalaz-7-yl; 1,4-diaminophthalaz-7-yl; 1,5-diaminophthalaz-7-yl; 1,6-diaminophthalaz-7-yl; 4-aminopterid-6-yl; 8-amino-1,7-naphthyrid-2-yl; 5-amino-1,6-naphthyrid-3-y; 5-amino-2,6-naphthyrid-3-yl; 3-amino-benzisoxazol-5-yl; 1-amino-3,4-dihydroisoquinolin-7-yl; and, 1-aminoisoindol-6-yl;

M is selected from the group:

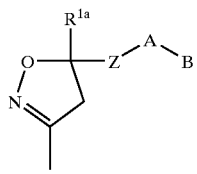 a

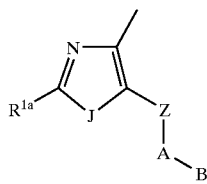 j

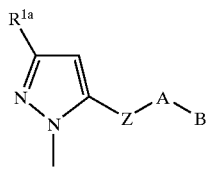 t₁

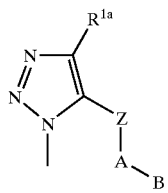 v

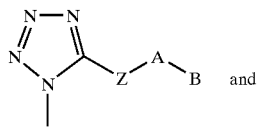 y  and

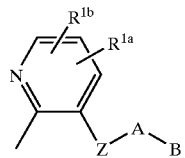 bb

A is selected from:
$C_{5-6}$ carbocyclic residue substituted with 0–2 $R^4$, and 5–6 membered heterocyclic system containing from 1–4 heteroatoms selected from the group consisting of N, O, and S substituted with 0–2 $R^4$;

Y is selected from one of the following carbocyclic and heterocyclic systems which are substituted with 0–2 $R^{4a}$;
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole;

$R^2$, at each occurrence, is selected from H, $CF_3$, $C_{1-6}$ alkyl, benzyl, $C_{5-6}$ carbocyclic residue substituted with 0–2 $R^{4b}$, and 5–6 membered heterocyclic system containing from 1–4 heteroatoms selected from the group consisting of N, O and S substituted with 0–2 $R^{4b}$;

$R^{2a}$, at each occurrence, is selected from H, $CF_3$, $C_{1-6}$ alkyl, benzyl, phenethyl, $C_{5-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{5-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{5-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$, together with the atom to which they are attached, combine to form a ring selected from imidazolyl, morpholino, piperazinyl, pyridyl, and pyrrolidinyl, substituted with 0–2 $R^{4b}$;

$R^4$, at each occurrence, is selected from H, =O, $OR^2$, $CH_2OR^2$, F, Cl, $C_{1-4}$ alkyl, $NR^2R^{2a}$, $CH_2NR^2R^{2a}$, $C(O)R^{2c}$, $CH_2C(O)R^{2c}$, $C(O)NR^2R^{2a}$, $CH(=NR^2)NR^2R^{2a}$, $CH(=NS(O)_2R^5)NR^2R^{2a}$, $SO_2NR^2R^{2a}$, $NR^2SO_2$—$C_{1-4}$ alkyl, $S(O)_2R^5$, and $CF_3$ provided that if B is H, then $R^4$ is other than tetrazole, C(O)-alkoxy, and $C(O)NR^2R^{2a}$;

$R^{4a}$, at each occurrence, is selected from H, =O, $(CH_2)_rOR^2$, F, Cl, $C_{1-4}$ alkyl, $NR^2R^{2a}$, $CH_2NR^2R^{2a}$, $NR^2R^{2b}$, $CH_2NR^2R^{2b}$, $(CH_2)_rC(O)R^{2c}$, $NR^2C(O)R^{2b}$, $C(O)NR^2R^{2a}$, $C(O)NH(CH_2)_2NR^2R^{2a}$, $NR^2C(O)NR^2R^{2a}$, $SO_2NR^2R^{2a}$, $S(O)_2R^5$, and $CF_3$; and, $R^{4b}$, at each occurrence, is selected from H, =O, $(CH_2)_rOR^3$, F, Cl, $C_{1-4}$ alkyl, $NR^3R^{3a}$, $CH_2NR^3R^{3a}$, $C(O)R^3$, $CH_2C(O)R^3$, $C(O)OR^{3c}$, $C(O)NR^3R^{3a}$, $CH(=NR^3)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_2CF_3$, $S(O)_2$—$C_{1-4}$ alkyl, $S(O)_2$-phenyl, and $CF_3$.

[5] In a further preferred embodiment, the present invention provides novel compounds wherein:

D-E is selected from the group:
1-aminoisoquinolin-7-yl; 1,3-diaminoisoquinolin-7-yl; 1,4-diaminoisoquinolin-7-yl; 1,5-diaminoisoquinolin-7-yl; 1,6-diaminoisoquinolin-7-yl; 8-amino-1,7-naphthyrid-2-yl; 5-amino-1,6-naphthyrid-3-y; 5-amino-2,6-naphthyrid-3-yl; 3-aminobenzisoxazol-5-yl; 1-amino-3,4-dihydroisoquinolin-7-yl; and, 1-aminoisoindol-6-yl.

[6] In an even further preferred embodiment, the present invention provides a novel compound selected from:

1-(1'-Amino-isoquinol-7'-yl)-3-methyl-5-[(2'-aminosulfonyl-[1,1']-biphen-4-yl)carbonylamino]pyrazole;

1-(1'-Amino-isoquinol-7'-yl)-3-methyl-5-[(2'-methylsulfonyl-[1,1']-biphen-4-yl)carbonylamino]pyrazole;

1-(4'-Amino-isoquinol-7'-yl)-3-methyl-5-[(2'-aminosulfonyl-[1,1']-biphen-4-yl)carbonylamino]pyrazole;

1-(Isoquinol-7'-yl)-3-methyl-5-[(2'-aminosulfonyl-[1,1']-biphen-4-yl)carbonylamino]pyrazole;

3-(1'-Amino-isoquinol-7'-yl)-5-[(2'-aminosulfonyl-[1,1']-biphen-4-yl)carbonylamino]-5-methylisoxazoline;

3-(Isoquinol-5'-yl)-5-[(2'-aminosulfonyl-[1,1']-biphen-4-yl)carbonylamino]-5-methylisoxazoline;

3-(Isoquinol-7'-yl)-5-[(2'-aminosulfonyl-[1,1']-biphen-4-yl)carbonylamino]-5-methylisoxazoline;

3-(2'-Aminobenzimidazol-5'-yl)-5-[(2'-aminosulfonyl-[1,1']-biphen-4-yl)aminocarbonyl]-5-methylisoxazoline;

3-(3'-Aminoindazol-5'-yl)-5-[(2'-aminosulfonyl-[1,1']-biphen-4-yl)aminocarbonyl]-5-methylisoxazoline;

3-(3'-Aminobenzisoxazol-5'-yl)-5-[(2'-aminosulfonyl-[1,1']-biphen-4-yl)aminocarbonyl]-5-methylisoxazoline;

1-(3'-Aminobenzisoxazol-5'-yl)-3-methyl-5-[(2'-aminosulfonyl-[1,1']-biphen-4-yl)aminocarbonyl]pyrazole;

3-(1-Amino-isoquinol-7-yl)-4-[(2'-aminosulfonyl-[1,1']-biphen-4-yl)aminocarbonyl]-1,2,3-triazole;

3-(4-amino-isoquinol-7-yl)-4-[(2'-aminosulfonyl-[1,1']-biphen-4-yl)aminocarbonyl]-1,2,3-triazole;

3-(isoquinol-7-yl)-4-[(2'-aminosulfonyl-[1,1']-biphen-4-yl)aminocarbonyl]-1,2,3-triazole;

1-(Quinol-2-ylmethyl)-3-methyl-5-[(2'-aminosulfonyl-[1,1']-biphen-4-yl)aminocarbonyl]pyrazole;

1-(Quinol-2-yl)-3-methyl-5-[(2'-aminosulfonyl-[1,1']-biphen-4-yl)aminocarbonyl]pyrazole;

1-(3'-Aminoindazol-5'-yl)-3-methyl-5-[(2'-aminosulfonyl-[1,1 ]-biphen-4-yl)aminocarbonyl]pyrazole;

1-(3-Aminoindazole-5'-yl)-3-methyl-5-[(2'-aminosulfonyl-[1,1']-biphen-4-yl)aminocarbonyl]pyrazole;

1-(3'-Aminobenzisoxazol-5'-yl)-3-methyl-5-[(2'-aminosulfonyl-(phenyl)pyrid-2-ylaminocarbonyl]pyrazole;

1-(3'-Aminobenzisoxazol-5'-yl)-3-methyl-5-[isoquinol-7-yl)aminocarbonyl]pyrazole;

1-(1'-Aminoisoquinol-7'-yl)-3-ethyl-5-[(2'-aminosulfonyl-[1,1']-biphen-4-yl)aminocarbonyl]pyrazole;

1-(1'-Aminoisoquinol-7'-yl)-3-isopropyl-5-[(2'-aminosulfonyl-[1,1']-biphen-4-yl)aminocarbonyl]pyrazole;

1-(2',4'-Diaminoquinazol-6'-yl)-3-methyl-5-[(2'-aminosulfonyl-[1,1']-biphen-4-yl)aminocarbonyl]pyrazole;

1-(4'-Aminoquinazol-6'-yl)-3-methyl-5-[(2'-aminosulfonyl-[1,1]'-biphen-4-yl)aminocarbonyl]pyrazole;

1-(1'-Aminoisoquinol-7'-yl)-3-methyl-5-[4-(N-pyrrolidinylcarbonyl)phenylaminocarbonyl]pyrazole;

1-(3'-Aminobenzisoxazol-5'-yl)-3-trifluoromethyl-5-[(2'-methylsulfonyl-3-fluoro-[1,1']-biphen-4-yl)aminocarbonyl]pyrazole;

1-(1'-Aminopthalazin-7'-yl)-3-methyl-5-[(2'-aminosulfonyl-[1,1']-biphen-4-yl)carbonylamino]pyrazole;

3-(3'-Aminobenzisoxazol-5'-yl)-5-[[5-[(2'-aminosulfonyl)phenyl]pyrid-2-yl]aminocarbonyl]-5-(methylsulfonylaminomethyl)isoxazoline;

1-(3'-Aminobenzisoxazol-5'-yl)-3-trifluoromethyl-5-[(2-fluoro-4-morpholinophenyl)aminocarbonyl]pyrazole;

1-(3'-Aminobenzisoxazol-5'-yl)-3-trifluoromethyl-5-[[4-(2'-isopropylimidazol-1-yl)phenyl]aminocarbonyl]pyrazole;

1-(3'-Aminobenzisoxazol-5'-yl)-3-trifluoromethyl-5-[[4-(2'-ethylimidazol-1-yl)phenyl]aminocarbonyl]pyrazole;

1-(3'-Aminobenzisoxazol-5'-yl)-3-trifluoromethyl-5-[[4-[(2'-dimethylaminomethyl)imidazol-1'-yl]phenyl]aminocarbonyl]pyrazole;

1-(3'-Aminobenzisoxazol-5'-yl)-3-trifluoromethyl-5-[[4-[(2'-methoxymethyl)imidazol-1'-yl]phenyl]aminocarbonyl]pyrazole;

1-(3'-Aminobenzisoxazol-5'-yl)-3-trifluoromethyl-5-[[4-[(2'-dimethylaminomethyl)imidazol-1'-yl]-2-fluorophenyl]aminocarbonyl]pyrazole;

1-(3'-Aminobenzisoxazol-5'-yl)-3-trifluoromethyl-5-[[(2-methoxy-4-(2'-methylimidazol-1'-yl)phenyl]aminocarbonyl]pyrazole;

1-(3'-Aminobenzisoxazol-5'-yl)-3-trifluoromethyl-5-[[4-(2'-isopropylimidazol-1'-yl)-2-fluorophenyl]aminocarbonyl]pyrazole;

1-(3'-Aminobenzisoxazol-5'-yl)-3-trifluoromethyl-5-[[4-(2'-ethylimidazol-1'-yl)-2-fluorophenyl]aminocarbonyl]pyrazole;

1-(3'-Aminobenzisoxazol-5'-yl)-3-ethyl-5-[[4-(2'-ethylimidazol-1'-yl)-2-fluorophenyl]aminocarbonyl]pyrazole;

1-(3'-Aminobenzisoxazol-5'-yl)-3-ethyl-5-[[4-[(2'-methoxymethyl)imidazol-1'-yl]phenyl]aminocarbonyl]pyrazole;

1-(3'-Aminobenzisoxazol-5'-yl)-3-ethyl-5-[[4-[(2'-dimethylaminomethyl)imidazol-1'-yl]phenyl]aminocarbonyl]pyrazole;

1-(3'-Aminobenzisoxazol-5'-yl)-3-ethyl-5-[[4-[(2'-methyl)benzimidazol-1'-yl]phenyl]aminocarbonyl]pyrazole;

1-(3'-Aminobenzisoxazol-5'-yl)-3-ethyl-5-[(2'-ethylimidazol-1'-ylphenyl)aminocarbonyl]pyrazole;

1-(3'-Aminobenzisoxazol-5'-yl)-3-ethyl-5-[[4-(2'-ethylimidazol-1'-yl)-2,5-difluorophenyl]aminocarbonyl]pyrazole;

1-(3'-Aminobenzisoxazol-5'-yl)-3-ethyl-5-[(2-fluoro-4-morpholinophenyl)aminocarbonyl]pyrazole;

1-(3'-Aminobenzisoxazol-5'-yl)-3-ethyl-5-[(2'-isopropylimidazol-1'-ylphenyl)aminocarbonyl]pyrazole;

1-(3'-Aminobenzisoxazol-5'-yl)-3-ethyl-5-[[4-(2'-methylimidazol-1'-yl)-2-fluorophenyl]aminocarbonyl]pyrazole;

1-(3'-Aminobenzisoxazol-5'-yl)-3-ethyl-5-[(2'-aminosulfonyl-3-amino-[1,1']-biphen-4-yl)aminocarbonyl]pyrazole;

1-(3'-Aminobenzisoxazol-5'-yl)-3-ethyl-5-[(2'-aminosulfonyl-3-nitro-[1,1']-biphen-4-yl)aminocarbonyl]pyrazole;

1-(3'-Aminobenzisoxazol-5'-yl)-3-ethyl-5-[[4-(2'-methylimidazol-1'-yl)phenyl]aminocarbonyl]pyrazole;

1-(3'-Aminobenzisoxazol-5'-yl)-3-ethyl-5-[[2-dimethyl-4-(N-pyrrolidinocarbonyl)phenyl]aminocarbonyl]pyrazole;

1-(3'-Aminobenzisoxazol-5'-yl)-3-ethyl-5-[[2-pyrrolidino-4-(N-pyrrolidinocarbonyl)phenyl]-aminocarbonyl]pyrazole;

1-(3'-Aminobenzisoxazol-5'-yl)-3-ethyl-5-[[2-fluoro-4-(N-pyrrolidinocarbonyl)phenyl]aminocarbonyl]pyrazole;

1-(3'-Aminobenzisoxazol-5'-yl)-3-ethyl-5-[(2'-aminosulfonyl-3-fluoro-[1,1']-biphen-4-yl)aminocarbonyl]pyrazole;

1-(3'-Aminobenzisoxazol-5'-yl)-3-ethyl-5-[[5-[(2'-methylsulfonyl)phenyl]pyrimid-2-yl]aminocarbonyl]pyrazole;

1-(3'-Aminobenzisoxazol-5'-yl)-3-ethyl-5-[[(2'-methylsulfonyl)-3-fluoro-[1,1']-biphen-4-yl]aminocarbonyl]pyrazole;

1-(3'-Aminobenzisoxazol-5'-yl)-3-ethyl-5-[[5-[(2'-aminosulfonyl)phenyl]pyrid-2-yl]aminocarbonyl]pyrazole;

1-(3'-Aminobenzisoxazol-5'-yl)-5-[[(2'-methylsulfonyl)-3-fluoro-[1,1']-biphen-4-yl]aminocarbonyl]tetrazole;

1-(3'-Aminobenzisoxazol-5'-yl)-5-[[4-(2'-methylimidazol-1'-yl)phenyl]aminocarbonyl]tetrazole;

1-(3'-Aminobenzisoxazol-5'-yl)-5-[(2'-aminosulfonyl-[1,1']-biphen-4-yl)aminocarbonyl]tetrazole;

1-(3'-Aminobenzisoxazol-5'-yl)-5-[(2-fluoro-4-(N-pyrrolidinocarbonyl)phenyl)aminocarbonyl]tetrazole;

1-(3'-Aminobenzisoxazol-5'-yl)-5-[(2-(N-pyrrolidino)-4-(N-pyrrolidinocarbonyl)phenyl)aminocarbonyl]tetrazole;

1-(1'-Amino-isoquinol-7'-yl)-5-[[(2'-aminosulfonyl)-3-fluoro-[1,1']-biphen-4-yl]aminocarbonyl]tetrazole;

1-(1'-Amino-isoquinol-7'-yl)-5-[[(2'-methylsulfonyl)-3-fluoro-[1,1']-biphen-4-yl]aminocarbonyl]tetrazole;

1-(3'-Aminobenzisoxazol-5'-yl)-3-trifluoromethyl-5-[(2'aminosulfonylphenyl)pyrimidin-2-yl)aminocarbonyl]pyrazole;

1-(3'-Aminobenzisoxazol-5'-yl)-3-trifluoromethyl-5-[4-(2'-methylimidazol-1'-yl)phenyl)aminocarbonyl]pyrazole;

1-(3'-Aminobenzisoxazol-5'-yl)-3-trifluoromethyl-5-[4-(2'-methylimidazol-1'-yl)-2-fluorophenyl)aminocarbonyl]pyrazole;

1-(3'-Aminobenzisoxazol-5'-yl)-3-trifluoromethyl-5-[4-(1'-methylimidazol-2'-yl)-2-fluorophenyl)aminocarbonyl]pyrazole;

1-(3'-Aminobenzisoxazol-5'-yl)-3-trifluoromethyl-5-[4-(2'-aminoimidazol-1'-yl)phenyl)aminocarbonyl]pyrazole;

1-(3'-Aminobenzisoxazol-5'-yl)-3-trifluoromethyl-5-[(2'-dimethylaminomethyl-3-fluoro-[1,1']-biphen-4-yl)aminocarbonyl]pyrazole;

Ethyl 1-(3'-aminobenzisoxazol-5'-yl)-5-[(2'-aminosulfonyl-3-fluoro-[1,1']-biphen-4-yl)aminocarbonyl]pyrazole-3-carboxylate;

1-(3'-Aminobenzisoxazol-5'-yl)-5-[(2'-aminosulfonyl-3-fluoro-[1,1']-biphen-4-yl)aminocarbonyl]pyrazole-3-carboxylic acid;

1-(3'-Aminobenzisoxazol-5'-yl)-5-[(2'-aminosulfonyl-3-fluoro-[1,1']-biphen-4-yl)aminocarbonyl]pyrazole-3-carboxamide;

Ethyl 1-(3'-aminobenzisoxazol-5'-yl)-5-[(2'-methylsulfonyl-3-fluoro-[1,1']-biphen-4-yl)aminocarbonyl]pyrazole-3-carboxylate;

1-(3'-Aminobenzisoxazol-5'-yl)-5-[(2'-methylsulfonyl-3-fluoro-[1,1']-biphen-4-yl)aminocarbonyl]pyrazole-3-carboxylic acid;

1-(3'-Aminobenzisoxazol-5'-yl)-3-(hydroxymethyl)-5-[(2'-methylsulfonyl-3-fluoro-[1,1']-biphen-4-yl)aminocarbonyl]pyrazole;

1-(3'-Aminobenzisoxazol-5'-yl)-3-[dimethylaminomethyl]-5-[(2'-methylsulfonyl-3-fluoro-[1,1']-biphen-4-yl)aminocarbonyl]pyrazole;

Ethyl 1-(3'-aminobenzisoxazol-5'-yl)-5-[(2'-methylsulfonyl-3-fluoro-[1,1]-biphen-4-yl)aminocarbonyl]pyrazole-4-carboxylate;

1-(3'-Aminobenzisoxazol-5'-yl)-5-[(2'-methylsulfonyl-3-fluoro-[1,1']-biphen-4-yl)aminocarbonyl]pyrazole-4-carboxylic acid;

1(1',2',3',4'-Tetrahydroisoquinol-7'-yl)-3-methyl-5-[(2'-aminosulfonyl-[1,1']-biphen-4-yl)carbonylamino]pyrazole;

1-(1'-Amino-isoquinol-7'-yl)-3-[(2'-methylaminosulfonyl-[1,1']-biphen-4-yl)carbonylamino]-5-methylpyrazole;

1-(4'-Amino-isoquinol-7'-yl)-3-methyl-5-[(2'-methylsulfonyl-[1,1']-biphen-4-yl)carbonylamino]pyrazole;

1-(1'-Amino-isoquinol-7'-yl)-3-trifluoromethyl-5-[(2'-methylsulfonyl-[1,1']-biphen-4-yl)carbonylamino]pyrazole;

1-(1'-Amino-isoquinol-7'-yl)-3-trifluoromethyl-5-[(2-fluoro-4-(N-pyrrolidinocarbonyl)-phenyl)carbonylamino]pyrazole;

1-(1'-Amino-isoquinol-7'-yl)-3-trifluoromethyl-5-[(2'-methylsulfonyl-3-fluoro-[1,1']-biphen-4-yl)carbonylamino]pyrazole;

1-(1'-Amino-isoquinol-7'-yl)-3-trifluoromethyl-5-[(2'-aminosulfonyl-[1,1']-biphen-4-yl)carbonylamino]pyrazole;

1-(1'-Amino-isoquinol-7'-yl)-3-trifluoromethyl-5-[(2'-aminosulfonyl-3-fluoro-[1,1']-biphen-4-yl)carbonylamino]pyrazole;

1-(1'-Amino-isoquinol-7'-yl)-3-trifluoromethyl-5-[(5-(2'-methylsulfonylphenyl)pyrid-2-yl)carbonylamino]pyrazole;

1-(1'-Amino-isoquinol-7'-yl)-3-methyl-5-[(2'-aminosulfonyl-3-fluoro-[1,1']-biphen-4-yl)carbonylamino]pyrazole;

1-(1'-Amino-isoquinol-7'-yl)-3-methyl-5-[(2'-methylsulfonyl-3-fluoro-[1,1']-biphen-4-yl)carbonylamino]pyrazole;

1-(1'-Amino-isoquinol-7'-yl)-3-trifluoromethyl-5-[(2'-aminosulfonyl-3-chloro-[1,1]-biphen-4-yl)carbonylamino]pyrazole;

1-(1'-Amino-isoquinol-7'-yl)-3-trifluoromethyl-5-[(2'-aminosulfonyl-3-methyl-[1,1']-biphen-4-yl)carbonylamino]pyrazole;

1-(1'-Amino-isoquinol-7'-yl)-3-trifluoromethyl-5-[(2'-methylaminosulfonyl-[1,1']-biphen-4-yl)carbonylamino]pyrazole;

1-(1'-Aminoisoquinol-7'-yl)-3-ethyl-5-[(2'-methylaminosulfonyl-[1,1']-biphen-4-yl)aminocarbonyl]pyrazole;

1-(1'-Aminoisoquinol-7'-yl)-3-ethyl-5-[(2'-methylsulfonyl-[1,1']-biphen-4-yl)aminocarbonyl]pyrazole;

1-(1'-Aminoisoquinol-7'-yl)-3-propyl-5-[(2'-aminosulfonyl-[1,1']-biphen-4-yl)aminocarbonyl]pyrazole;

1-(1'-Aminoisoquinol-7'-yl)-3-propyl-5-[(2'-methylaminosulfonyl-[1,1']-biphen-4-yl)aminocarbonyl]pyrazole;

1-(1'-Aminoisoquinol-7'-yl)-3-propyl-5-[(2'-methylsulfonyl-[1,1']-biphen-4-yl)aminocarbonyl]pyrazole;

1-(1'-Aminoisoquinol-7'-yl)-3-ethyl-5-[(2'-aminosulfonyl-3-fluoro-[1,1']-biphen-4-yl)aminocarbonyl]pyrazole;

1-(1'-Aminoisoquinol-7'-yl)-3-ethyl-5-[(2'-methylsulfonyl-3-fluoro-[1,1']-biphen-4-yl)aminocarbonyl]pyrazole;

1-(1'-Aminoisoquinol-7'-yl)-3-ethyl-5-[4-(N-pyrrolidinocarbonyl-1-yl)phenylaminocarbonyl]pyrazole;

1-(1'-Aminoisoquinol-7'-yl)-3-trifluoromethyl-5-[4-(imidazol-1'-yl)phenylaminocarbonyl]pyrazole;
1-(1'-Aminoisoquinol-7'-yl)-3-trifluoromethyl-5-[3-fluoro-4-(2-methylimidazol-1'-yl)phenylaminocarbonyl] pyrazole;
1-(1'-Aminoisoquinol-7'-yl)-3-trifluoromethyl-5-[4-(2-methylimidazol-1'-yl)phenylaminocarbonyl]pyrazole;
1-(1'-Aminoisoquinol-7'-yl)-3-trifluoromethyl-5-[2-fluoro-4-(2-methylimidazol-1'-yl)phenylaminocarbonyl] pyrazole;
1-(3'-Aminobenzisoxazol-5'-yl)-3-methyl-5-[(2'-methylsulfonyl-[1,1']-biphen-4-yl)aminocarbonyl] pyrazole;
1-(3'-Aminobenzisoxazol-5'-yl)-3-trifluoromethyl-5-[(2'-aminosulfonyl-3-fluoro-[1,1']-biphen-4-yl) aminocarbonyl]pyrazole;
1-(3'-Aminobenzisoxazol-5'-yl)-3-trifluoromethyl-5-[2-fluoro-4-(N-pyrrolidinocarbonyl)phenyl-aminocarbonyl] pyrazole;
1-(3'-Aminobenzisoxazol-5'-yl)-3-trifluoromethyl-5-[(5-(2'-aminosulfonylphenyl)pyrid-2-yl)aminocarbonyl] pyrazole;
1-(3'-Aminobenzisoxazol-5'-yl)-3-trifluoromethyl-5-[(5-(2'-methylsulfonylphenyl)pyrimid-2-yl)aminocarbonyl] pyrazole;
1-(3'-Aminobenzisoxazol-5'-yl)-3-methyl-5-[(4-(pyrid-3'-yl)phenyl)aminocarbonyl]pyrazole;
1-(3'-Aminobenzisoxazol-5'-yl)-3-trifluoromethyl-5-[(4-(pyrid-3'-yl-3-fluorophenyl)aminocarbonyl]pyrazole;
1-(3'-Aminoindazol-5'-yl)-3-trifluoromethyl-5-[(2'-aminosulfonyl-3-fluoro-[1,1']-biphen-4-yl) aminocarbonyl]pyrazole;
1-(3'-Aminoindazol-5'-yl)-3-trifluoromethyl-5-[(2'-methylsulfonyl-3-fluoro-[1,1']-biphen-4-yl) aminocarbonyl]pyrazole;
1-(3'-Aminoindazol-5'-yl)-3-trifluoromethyl-5-[2-fluoro-4-(N-pyrrolidinocarbonyl)phenylaminocarbonyl]pyrazole;
1-(3'-Aminoindazol-5'-yl)-3-methyl-5-[(4-(pyrid-3'-yl) phenyl)aminocarbonyl]pyrazole;
1-(3'-Aminoindazol-5'-yl)-3-trifluoromethyl-5-[(4-(pyrid-3'-yl-3-fluorophenyl)aminocarbonyl]pyrazole;
1-(3'-Aminomethylnaphth-2'-yl)-3-trifluoromethyl-5-[(2'-methylsulfonyl-3-fluoro-[1,1']-biphen-4-yl) aminocarbonyl]pyrazole;
1-(3'-Aminobenzisoxazol-5'-yl)-3-trifluoromethyl-5-[(3-fluoro-2'-hydroxymethyl-[1,1']-biphen-4-yl) aminocarbonyl]pyrazole;
1-(3'-Aminobenzisoxazol-5'-yl)-3-trifluoromethyl-5-[(3-fluoro-2'-methylaminomethyl-[1,1']-biphen-4-yl) aminocarbonyl]pyrazole;
1-(3'-Aminobenzisoxazol-5'-yl)-3-trifluoromethyl-5-[(2'-bromomethyl-3-fluoro-[1,1']-biphen-4-yl) aminocarbonyl]pyrazole;
1-(3'-Aminobenzisoxazol-5'-yl)-3-trifluoromethyl-5-[(3-fluoro-2'-pyridiniummethyl-[1,1']-biphen-4-yl) aminocarbonyl]pyrazole;
1-(3'-Aminobenzisoxazol-5'-yl)-3-trifluoromethyl-5-[(2'-aminomethyl-3-fluoro-[1,1']-biphen-4-yl)aminocarbonyl] pyrazole;
1-(3'-Aminobenzisoxazol-5'-yl)-3-trifluoromethyl-5-[(3-fluoro-2'-N-pyrrolidinylmethyl-[1,1']-biphen-4-yl) aminocarbonyl]pyrazole;
1-(3'-Aminobenzisoxazol-5'-yl)-3-trifluoromethyl-5-[(3-fluoro-2'-imidazol-1"-yl-[1,1']-biphen-4-yl) aminocarbonyl]pyrazole;
1-(3'-Aminobenzisoxazol-5'-yl)-3-trifluoromethyl-5-[((2'-(4"-t-butoxycarbonyl)piperazin-1"-ylmethyl)-3-fluoro-[1, 1']-biphen-4-yl)aminocarbonyl]pyrazole;
1-(3'-Aminobenzisoxazol-5'-yl)-3-trifluoromethyl-5-[((2'-(N,N-dimethylamino)pyridiniummethyl)-3-fluoro-[1,1']-biphen-4-yl)aminocarbonyl]pyrazole;
1-(3'-Aminobenzisoxazol-5'-yl)-3-trifluoromethyl-5-[(3-fluoro-2'-piperazin-1"-ylmethyl-[1,1']-biphen-4-yl) aminocarbonyl]pyrazole;
1-(3'-Aminobenzisoxazol-5'-yl)-3-trifluoromethyl-5-[(3-fluoro-2'-N-methylmorpholiniummethyl-[1,1']-biphen-4-yl)aminocarbonyl]pyrazole;
1-(3'-Aminobenzisoxazol-5'-yl)-3-trifluoromethyl-5-[(3-fluoro-2'-morpholinomethyl-[1,1']-biphen-4-yl) aminocarbonyl]pyrazole;
1-(3'-Aminobenzisoxazol-5'-yl)-3-trifluoromethyl-5-[(3-fluoro-2'-(N-methyl-N-methoxyamino)-[1,1']-biphen-4-yl)aminocarbonyl]pyrazole;
1-(3'-Aminobenzisoxazol-5'-yl)-5-[(2'-methylsulfonyl-3-fluoro-[1,1']-biphen-4-yl)aminocarbonyl]triazole;
1-(3'-Aminobenzisoxazol-5'-yl)-5-[(2'-aminosulfonyl-3-fluoro-[1,1']-biphen-4-yl)aminocarbonyl]triazole;
1-(3'-Aminobenzisoxazol-5'-yl)-3-trifluoromethyl-5-[(2'-methylaminosulfonyl-3-fluoro-[1,1']-biphen-4-yl) aminocarbonyl]pyrazole;
1-(3'-Aminobenzisoxazol-5'-yl)-5-[(2'-dimethylaminomethyl-3-fluoro-[1,1']-biphen-4-yl) aminocarbonyl]tetrazole;
1-(3'-Aminobenzisoxazol-5'-yl)-3-ethyl-5-[(2'-dimethylaminomethyl-3-fluoro-[1,1']-biphen-4-yl) aminocarbonyl]pyrazole; and,
1-(3'-Aminobenzisoxazol-5'-yl)-3-ethyl-5-[4'-(2"-dimethylaminomethylimidazol-1"-yl)-2'-fluorophenyl) aminocarbonyl]pyrazole;
or a pharmaceutically acceptable salt thereof.

In a second embodiment, the present invention provides novel pharmaceutical compositions, comprising: a pharmaceutically acceptable carrier and a therapeutically effective amount of a compound of formula (I) or a pharmaceutically acceptable salt form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt form thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1991). All references cited herein are hereby incorporated in their entirety herein by reference.

One general synthesis of compounds of Formula I where ring M is N-linked is shown in Scheme 1a. Q, B' and $R^f$ are protected functional groups that can be converted to R, B and $R^{1a}$ respectively. D-E can also be called P1, the sidechain that fits into the S1 pocket of fXa. The compounds can also be obtained by changing the sequences of the reaction steps as described in Scheme 1a. For N-linked M ring, the appropriate heterocyclic aniline is treated under conditions described in "The Chemistry of Heterocyclic Compounds, Weissberger, A. and Taylor, E. C. Ed., John Wiley & Sons" or as described later in the synthesis section to give N-linked ring M. Further modifications and deprotections give N-linked ring M with R, Z-A-B and $R^{1a}$ substitutents.

SCHEME 1a

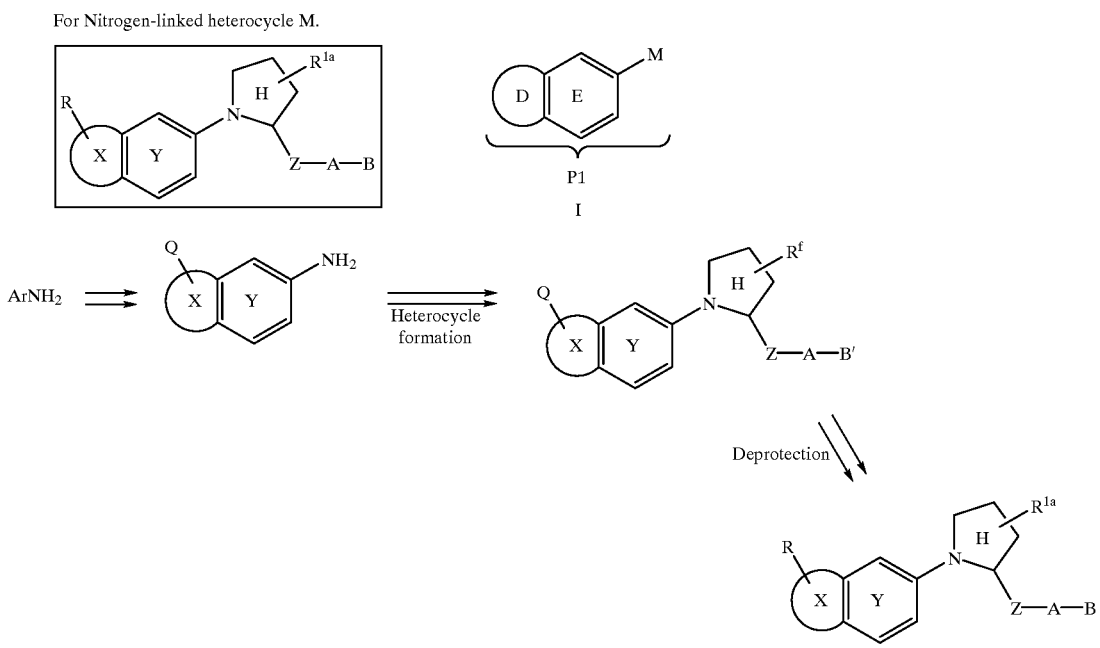

In Scheme 1b is shown how to obtain compounds wherein ring M is C-linked and is either five- or six-membered. The aniline from Scheme 1a is diazotized with nitrous acid and treated with NaBr to give the heterocyclic bromide. Treatment with n-BuLi followed by DMF gives an aldehyde which can be converted to ring M as described in "The Chemistry of Heterocyclic Compounds, Weissberger, A. and Taylor, E. C. Ed., John Wiley & Sons" or as will be described. Other precursor functional groups like acid, cyanide, methylketone, etc. can also be used to form the ring M. Further modifications and deprotections can yield five-membered ring M substituted with R, Z-A-B and $R^{1a}$. The corresponding C-linked six-membered ring M can be obtained by converting the above bromide with n-butyl lithium and triisopropyl borate to give the heterocyclic boronic acid. Suzuki coupling with the appropriate heterocyclic bromide, followed by modifications and deprotections gives the C-linked six-membered ring M with R, Z-A-B and $R^{1a}$ substitutents.

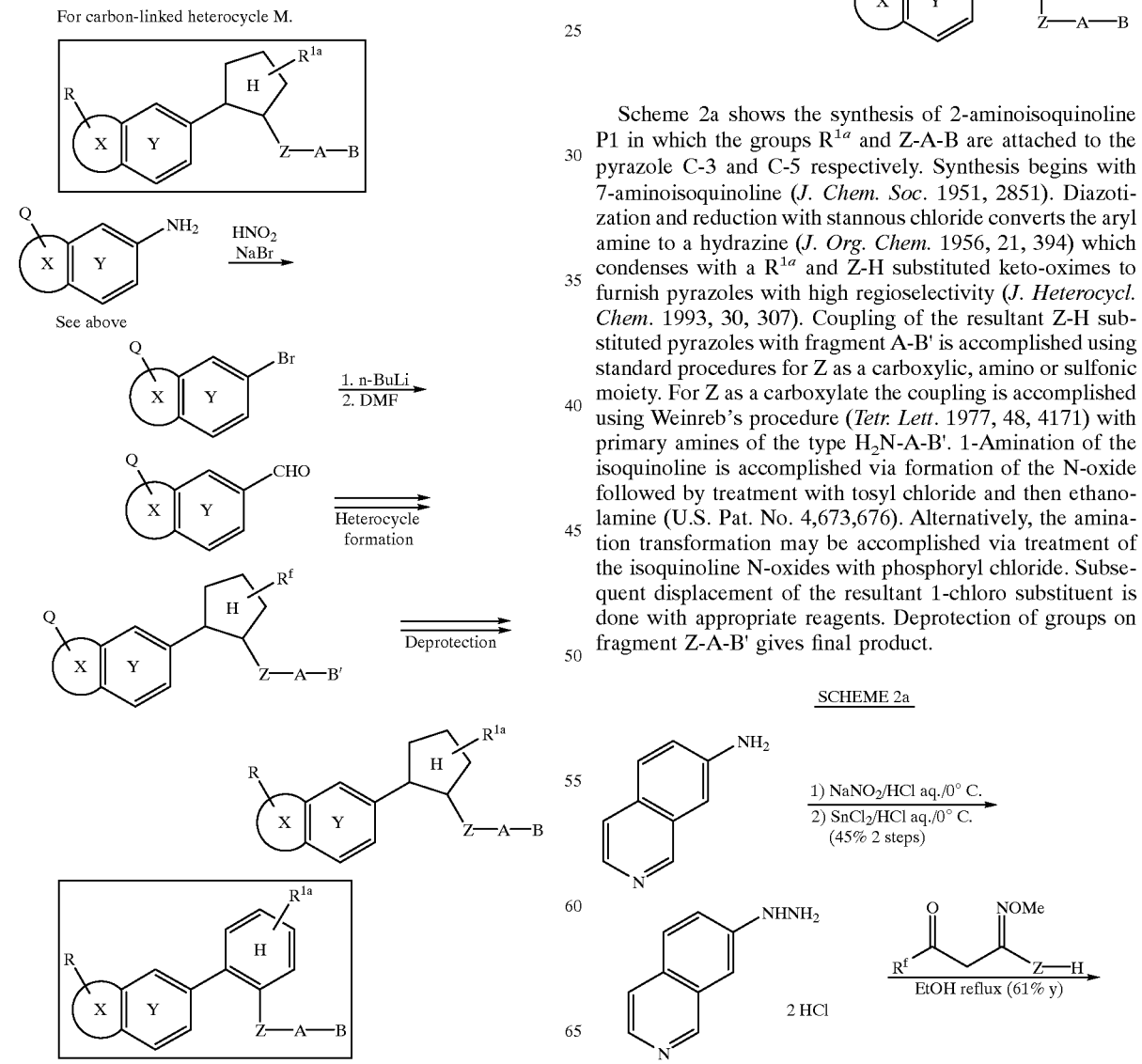

Scheme 2a shows the synthesis of 2-aminoisoquinoline P1 in which the groups $R^{1a}$ and Z-A-B are attached to the pyrazole C-3 and C-5 respectively. Synthesis begins with 7-aminoisoquinoline (J. Chem. Soc. 1951, 2851). Diazotization and reduction with stannous chloride converts the aryl amine to a hydrazine (J. Org. Chem. 1956, 21, 394) which condenses with a $R^{1a}$ and Z-H substituted keto-oximes to furnish pyrazoles with high regioselectivity (J. Heterocycl. Chem. 1993, 30, 307). Coupling of the resultant Z-H substituted pyrazoles with fragment A-B' is accomplished using standard procedures for Z as a carboxylic, amino or sulfonic moiety. For Z as a carboxylate the coupling is accomplished using Weinreb's procedure (Tetr. Lett. 1977, 48, 4171) with primary amines of the type $H_2N$-A-B'. 1-Amination of the isoquinoline is accomplished via formation of the N-oxide followed by treatment with tosyl chloride and then ethanolamine (U.S. Pat. No. 4,673,676). Alternatively, the amination transformation may be accomplished via treatment of the isoquinoline N-oxides with phosphoryl chloride. Subsequent displacement of the resultant 1-chloro substituent is done with appropriate reagents. Deprotection of groups on fragment Z-A-B' gives final product.

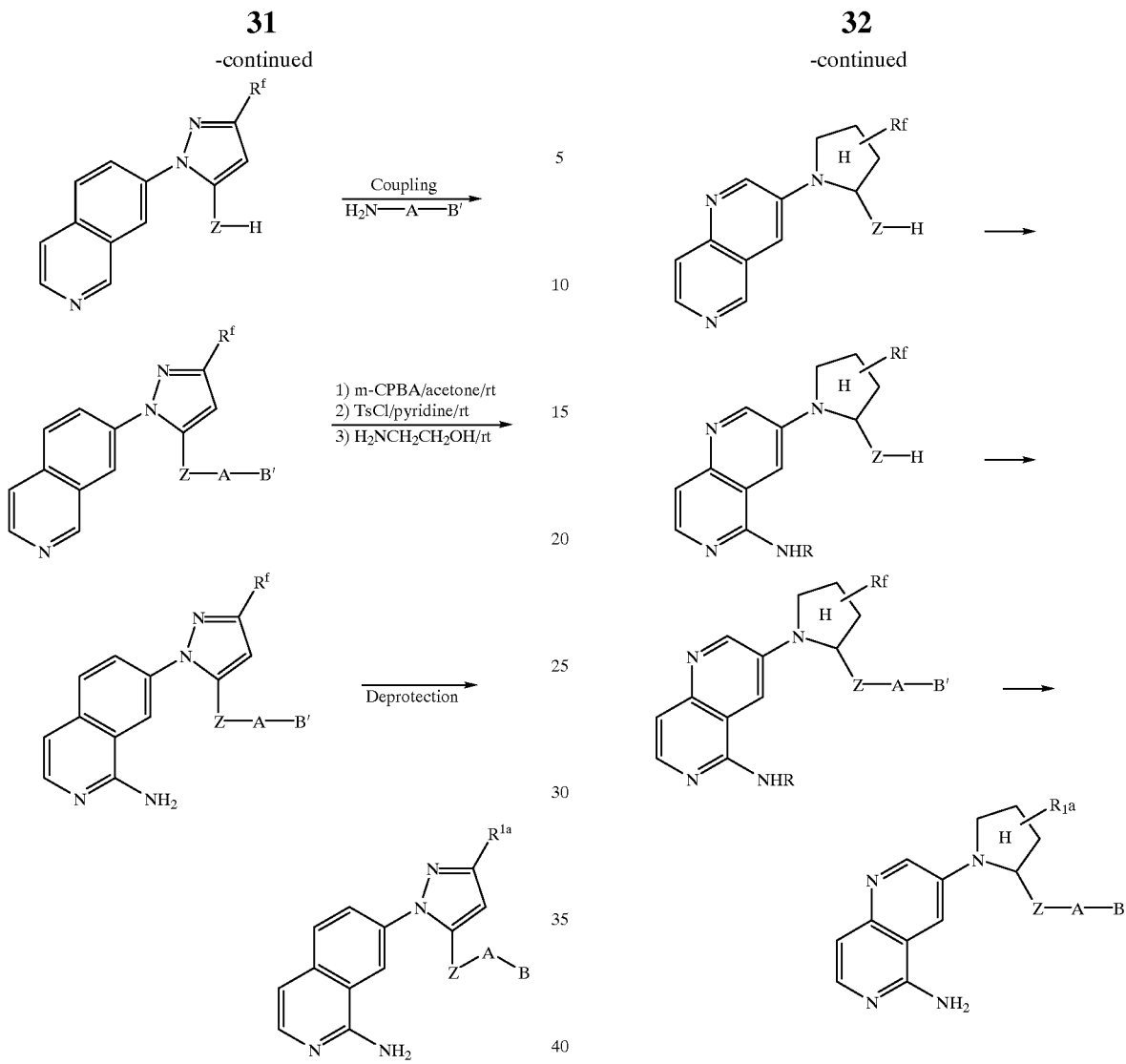

In Scheme 2b is illustrated the preparation of 5-amino substituted 1,6-naphthrydine compounds. Compounds of this type can be prepared from 3-nitro-1,6-naphthrydine (*Tetr.* 1989, 45, 2693). Reduction to the corresponding amine will allow for transformation to the desired 5-membered nitrogen containing heterocycle with $R^f$ and Z-H substitution. Introduction of a 5-amino moiety may be accomplished through the 5-chloro compound (*Chem. Pharm. Bull.* 1969, 17, 1045) as previously described in Scheme 2a. Suitable protection of the amino substituent is employed before introduction of fragment A-B'. Conversion to the final product may be accomplished in an analogous fashion to that described in Scheme 2a.

In Scheme 2c is shown how to prepare isoquinolines, which contain a 1,5-diamine substituent, from 7-aminoisoquinoline by suitable protection of the amine as an amide, directed nitration, and deprotection of the amine a 5-nitro-7-aminoisoquinoline may be obtained. The desired 5-membered nitrogen containing heterocycle with $R^f$ and Z-H substitution may be synthesized as previously shown in Scheme 2a. The addition of fragment A-B' and the 1-aminoisoquinoline portion would be accomplished as described earlier. The transformation of A-B', $R^f$, and the 4-nitro substituent to A-B, $R^{1a}$, and a 4-amino group, respectively, is accomplished by previously outlined methods.

SCHEME 2b

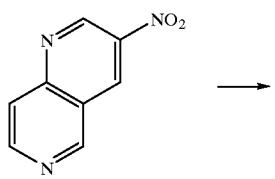

SCHEME 2c

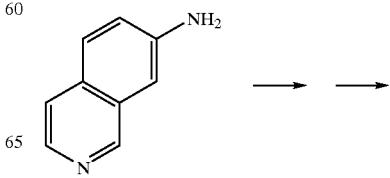

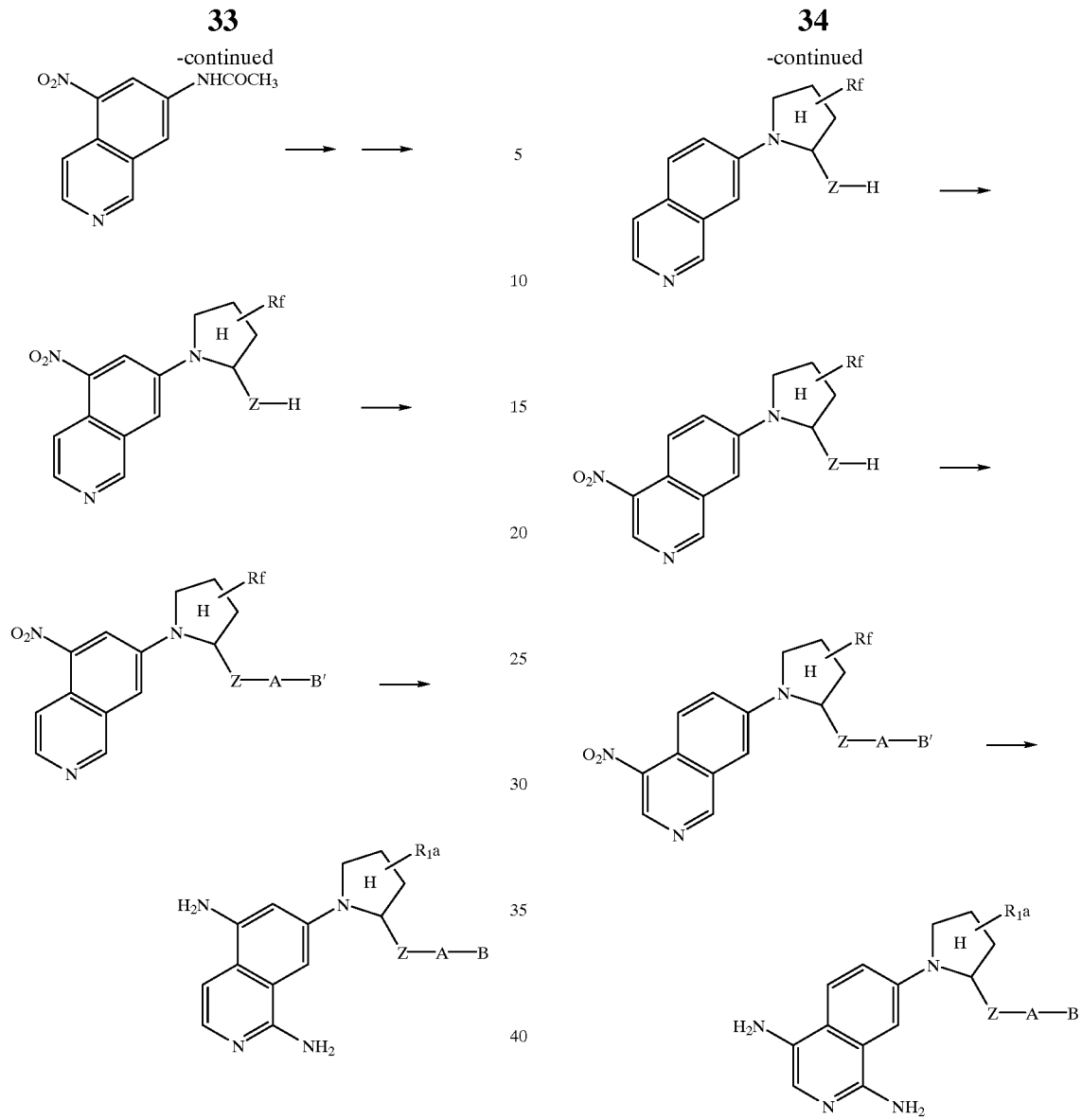

In Scheme 2d is shown how to prepare isoquinolines which contain 1,4-diamine substitution. From 7-aminoisoquinoline, the desired 5-membered nitrogen containing heterocycle with $R^f$ and Z-H substitution may be synthesized as previously shown in Scheme 2a. Nitration to the isoquinoline 4 position may be accomplished using standard conditions to afford a 4-nitro moiety. The addition of fragment A-B' and the 1-aminoisoquinoline portion can be accomplished as described earlier. The transformation of A-B', $R^f$, and the 4-nitro substituent to A-B, $R^{1a}$, and a 4-amino group, respectively, is accomplished by previously outlined methods.

SCHEME 2d

Scheme 3 illustrates the preparation of an intermediate for 3-aminobenzisoxazole and 3-aminoindazole. Compounds of this general type can be obtained from a fluorocyanobenzaldehyde prepared from commercially available 2-fluoro-5-methylbenzonitrile by first bis-bromination in a nonprotic solvent in the presence of AIBN or other suitable free radical initiator at a temperature ranging from ambient temperature to the reflux temperature of the selected solvent or under a UV light. The bis-bromo compound may then be converted to an aldehyde using a protic solvent in strong acidic or basic conditions at ambient temperature or higher. The aldehyde or the acid equivalent can then be converted to various C-linked ring H by methods which will be described later.

SCHEME 3

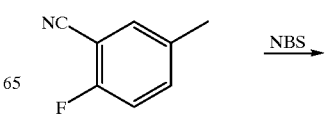

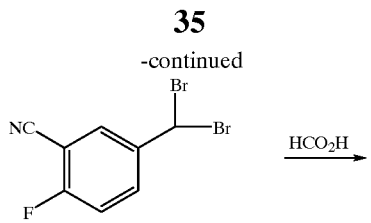

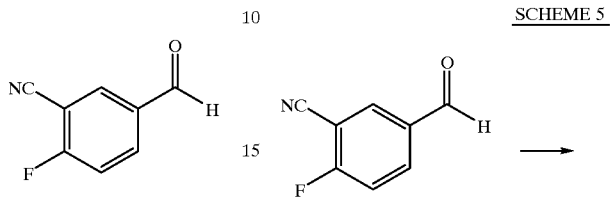

Scheme 4 outlines the formation of C-linked aminobenzisoxazoles. The aminobenzisoxazole P1 can be obtained by first treating the oxime of acetone with potassium t-butoxide in an aprotic polar solvent, followed by the addition of the fluorocyanophenylheterocycle H and then treatment with a protic solvent under strongly acidic conditions (*J. Heterocycl. chem.* 1989, 26, 1293). Coupling and deprotection as described previously gives 3-aminobenzisoxazoles of Formula I.

ketal. Protection of the amino group with CBZCl and deprotection of the ketal with HCl/MeOH gives the aldehyde. The aldehyde or the acid equivalent can be converted to various C-linked heterocycles as described later. Coupling and deprotection as described previously gives 3-aminoindazoles of Formula I.

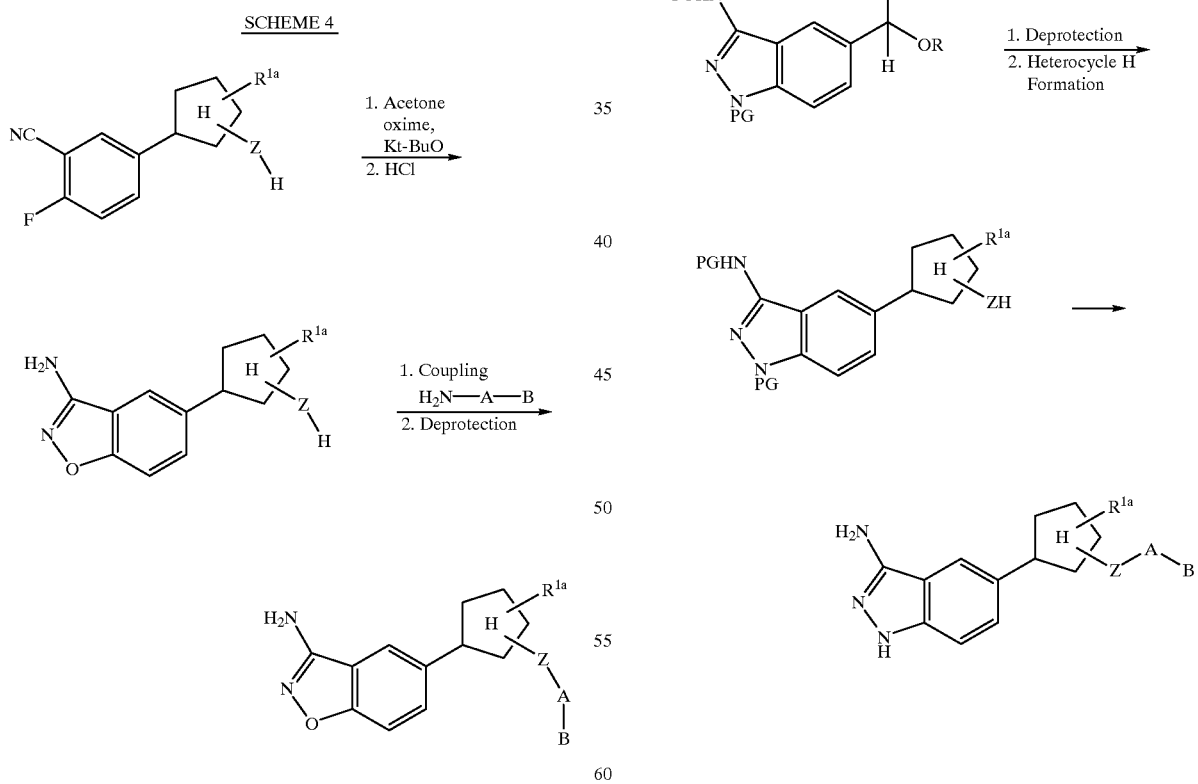

Scheme 5 outlines the formation of the C-linked 3-aminoindazoles of Formula I. Protection of the aldehyde as propylene ketal by standard conditions followed by refluxing with hydrazine in ethanol gives 3-aminoindazole Scheme 6 illustrates the preparation of aminobenzimidazole aldehyde which can be carried onto the C-linked or N-linked heterocycles by the methods described later in the synthesis section. Cyclization of 3,4-diaminobenzoate to give cbz-protected 2-aminobenzimidazole followed by DIBAL reduction and oxidation gives the desired aldehyde.

SCHEME 6

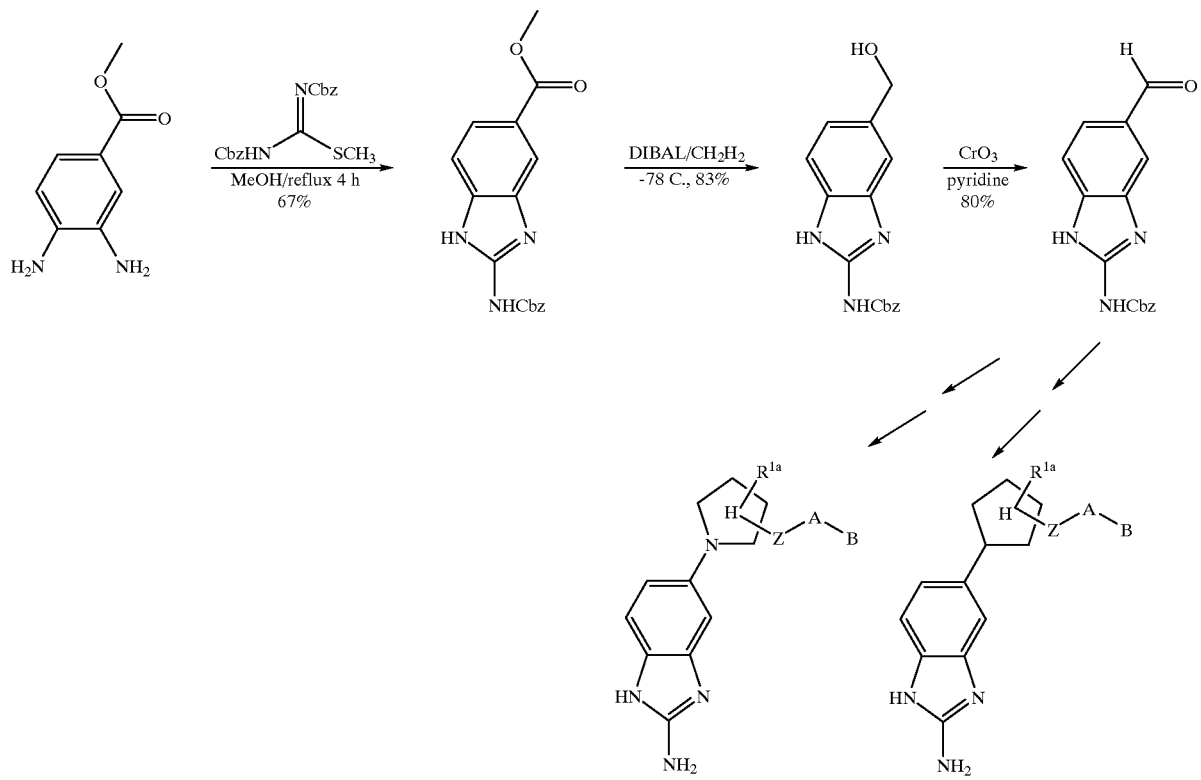

Scheme 7 illustrates the preparation of N-linked aminobenzisoxazoles, aminoindazoles, diaminoquinazolines and aminoquinazolines of Formula I. Compounds of this type can be made from the aniline derivative prepared from commercially available 2-fluoro-5-nitrobenzonitrile using tin(II) chloride or other compatible reducing agents in a protic or an aprotic solvent with or without a miscible co-solvent at from ambient temperature to reflux temperature of the selected solvent.

The N-linked 3-aminobenzisoxazoles and 3-amino-indazoles can be obtained as described previously. The N-linked aminoquinazoline and diaminoquinazoline P1's can be obtained by condensing the fluorocyano compound with formamidine acetate or guanidine hydrochloride (*J. Heterocycl. Chem.* 1988, 25, 1173).

SCHEME 7

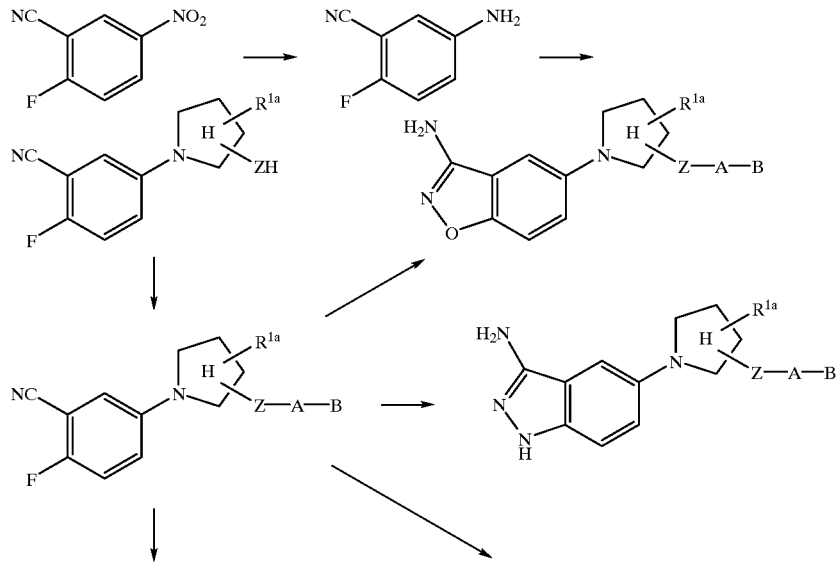

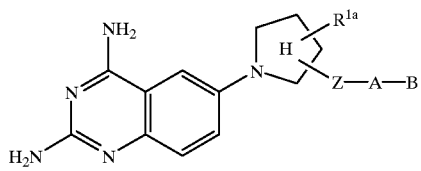
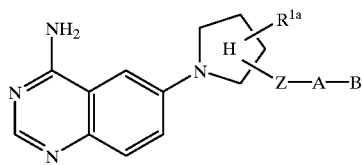

Scheme 8 illustrates the preparation of 1-amino-2-benzopyrazine P1 heterocyclic intermediates leading to compounds of Formula I. Compounds of this general type can be obtained from an aminostilbene prepared from commercially available 2-cyano-4-nitrotoluene by first condensing the nitrotoluene with benzaldehyde or one of its analogs in an alcoholic solvent in the presence of an alkoxide base at a temperature ranging from −10° C. to the reflux temperature of the selected solvent. The nitrostilbene may then be reduced to aminostilbene by reaction with tin(II) chloride or another compatible reducing agent in a protic solvent with or without a miscible co-solvent at ambient temperature or higher. The aniline may then be carried on to the N-linked or C-linked heterocycles H by the methods previously described.

SCHEME 8

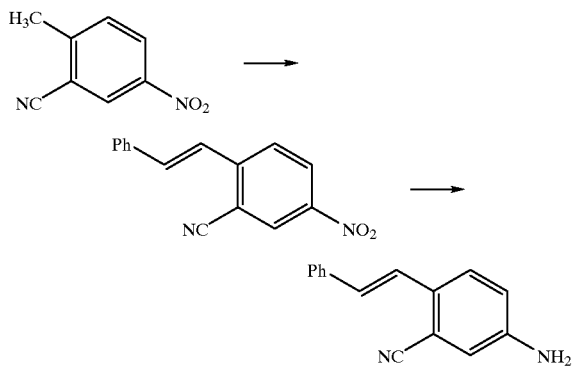

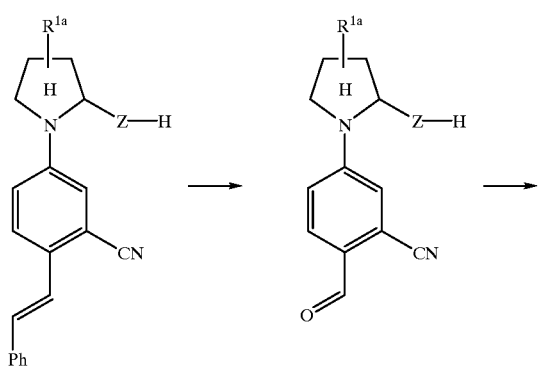

-continued

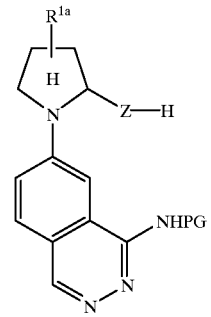

Scheme 8 also further outlines transformation of the N-linked and C-linked (not shown) heterocyclic stilbenes to give 1-aminophthalazines of Formula I. Oxidative cleavage of the stilbene double bond according to the method of Narasimhan et al (*Synth. Commun* 1985, 15(9), 769) or Sheu et al (*J. Am Chem. Soc.* 1990, 112, 879) or their equivalent should give an aldehyde. The aldehyde can be treated with hydrazine neat or in a polar or apolar solvent at ambient temperature or up to the reflux temperature of the solvent selected to cause ring closure. Group Z-H can then be coupled with group H₂N-A-B according to the methods outlined in Scheme 2a.

The N-linked and C-linked heterocyclic 2-cyanobenzaldehydes prepared in Scheme 8 can also be used as convenient starting materials for the preparation of N-linked 1,3-diaminoisoquinoline intermediate of Scheme 9 and C-linked (not shown) 1,3-diaminoisoquinoline intermediate of Scheme 9 by appropriate adaptation of the chemistry outlined below. The 2-cyanobenzaldehyde can be reduced to the benzylic alcohol by a hydride reducing agent, preferably sodium borohydride, then treated with a sulfonylchloride, methane sulfonyl chloride as suggested by Scheme 9 or an equivalent, using a trialkylamine base and a dry chlorocarbon solvent with cooling. The mesylate and biscyano intermediates can also be converted to the corresponding 1-aminoisoindole P1 and 1-amino-3,4-dihydroisoqunoline P1 respectively.

SCHEME 9

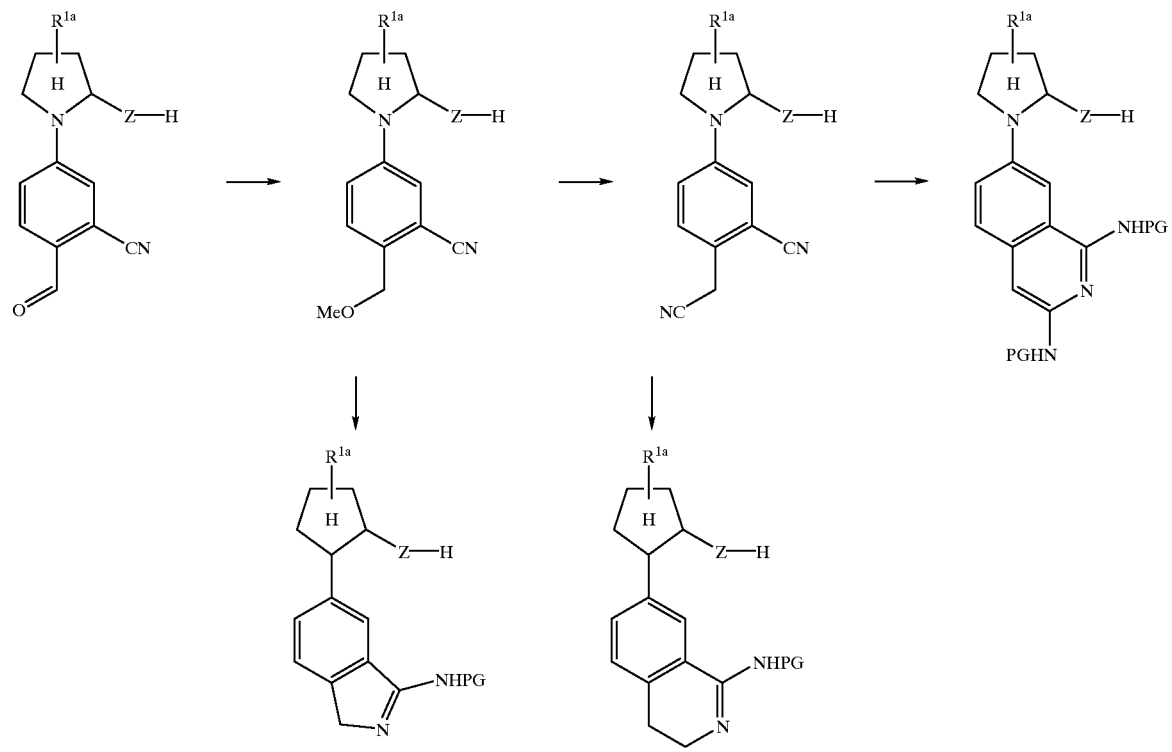

Scheme 10 illustrates another approach to preparing the N-linked and C-linked heterocyclic benzylic alcohols intermediates. These compounds may be obtained from 2-cyano-4-nitro-toluene by photochemical benzylic bromination with N-bromosuccinimide in carbon tetrachloride with a sun lamp and at reflux in the presence of a catalytic amount of a radical initiator such as AIBN or dibenzoylperoxide. The benzylic bromide is then readily displaced with potassium acetate under phase transfer conditions using 18-crown-6 as the phase transfer agent along with water and a non-miscible organic co-solvent with or without heating. The resulting acetate is then hydrolyzed with aqueous acid or by transesterification with anhydrous acid in an alcoholic solvent to give a benzylic alcohol. Depending upon the further demands of the chemistry involved in heterocycle formation step(s) the benzylic alcohol may be protected according to the methodology recommended by Greene and Wuts. The nitro group of the resulting product can then be reduced to the aniline according to the methods outlined above for Scheme 8 and then carried on to N-linked and C-linked heterocyclic benzylic alcohols of Scheme 10. It should be recognized that these benzylic alcohols can be readily transformed into the benzylic sulfonate ester intermediates of Scheme 9 or oxidized to the benzaldehyde of Scheme 8 by methods known to the skilled practitioner.

SCHEME 10

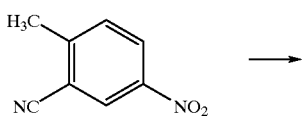

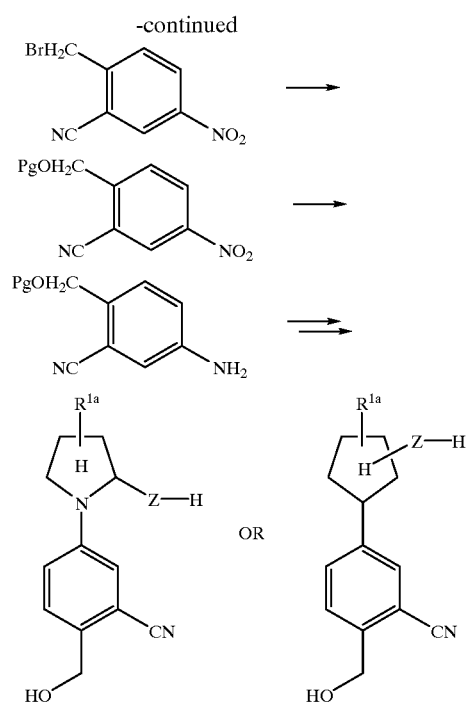

The compounds of the present invention in which the D-E residue is isoquinazolin-1-one can be prepared as described in Scheme 11. For compounds which are N-linked to heterocycle M, the reaction of 5-nitroisatoic anhydride with formamide at 150° C. affords 7-nitroisoquinazolin-1-one which can be reduced to the corresponding 7-aminoisoquinazolin-1-one by a variety of reducing agents. Diazotization, reduction to the hydrazine and N-heterocycle formation can be carried out to afford the isoquinazolin-1-one N-linked to the appropriate heterocycle. For compounds which are C-linked to heterocycle M, the reaction of 5-bromoanthranilic acid with formamide at 150° C. affords the 7-bromoisoquinazolin-1-one. This bromide can be converted into an aldehyde or acetyl group which can be then converted into the appropriate C-linked heterocycle.

anhydride and then hydroxide will produce the desired 7-nitroisoquinolin-1-one. This transformation can be carried out with other reagents as well. Reduction of the nitro group and subsequent formation of the N-heterocycle will afford the isoquinolin-1-one N-linked to the appropriate heterocycle. For compounds which are C-linked to heterocycle M, analogous chemistry can be used to prepare desired 7-bromoisoquinolin-1-one, which can then be converted into the appropriate aldehyde or acetyl group for subsequent

SCHEME 11

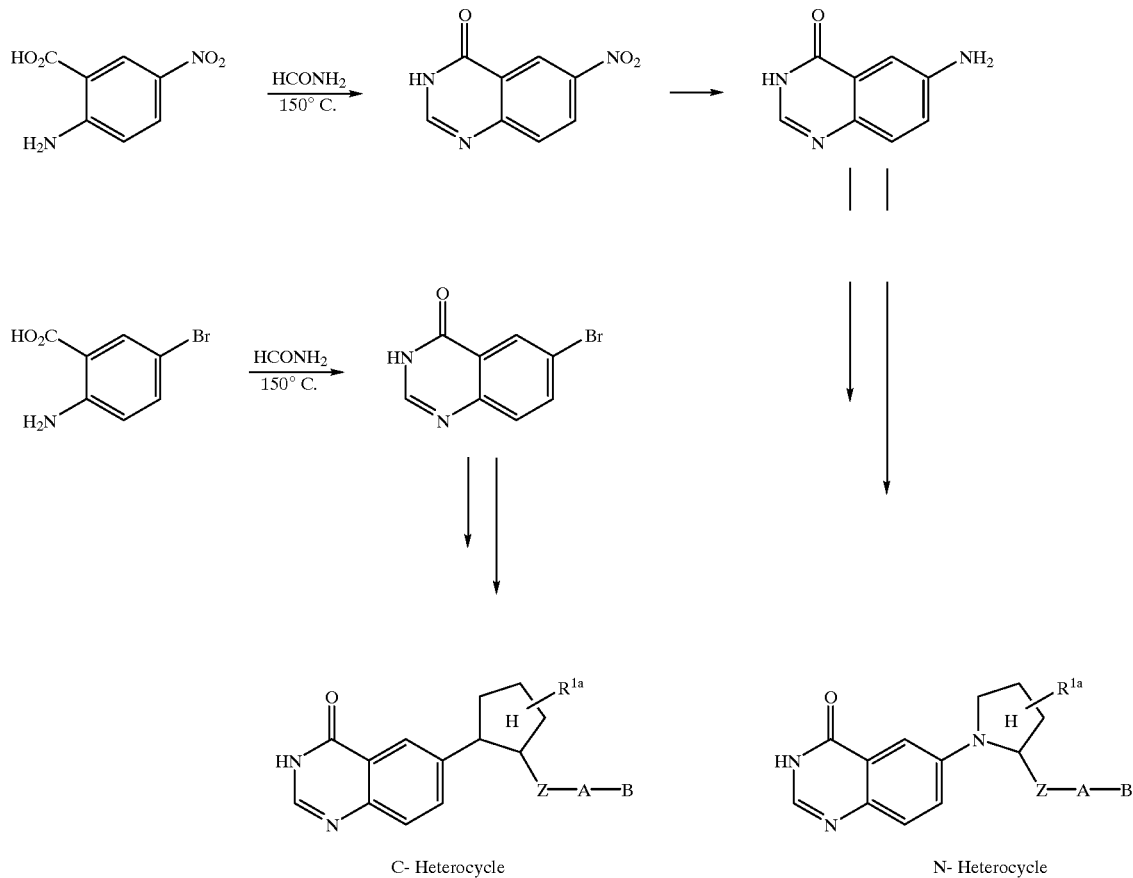

The compounds of the present invention in which the D-E residue is isoquinolin-1-one can be prepared as described in Scheme 12. For compounds which are N-linked to heterocycle M, oxidation of 7-nitroisoquinoline to its corresponding N-oxide followed by sequential treatment with acetic conversion to the C-linked heterocycle. One method for conversion of the bromide to an acetyl group employs palladium catalysed coupling with (ethoxyvinyl)tributyltin followed by acid hydrolysis of the intermediate vinyl ether residue.

SCHEME 12

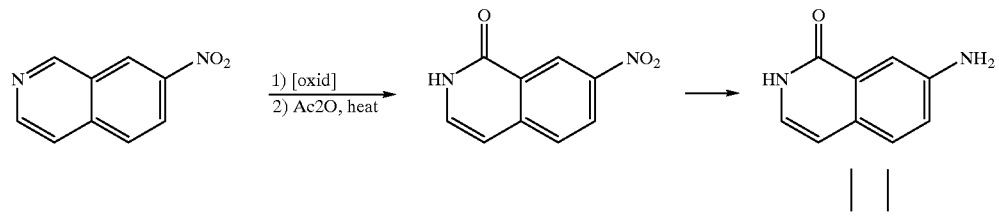

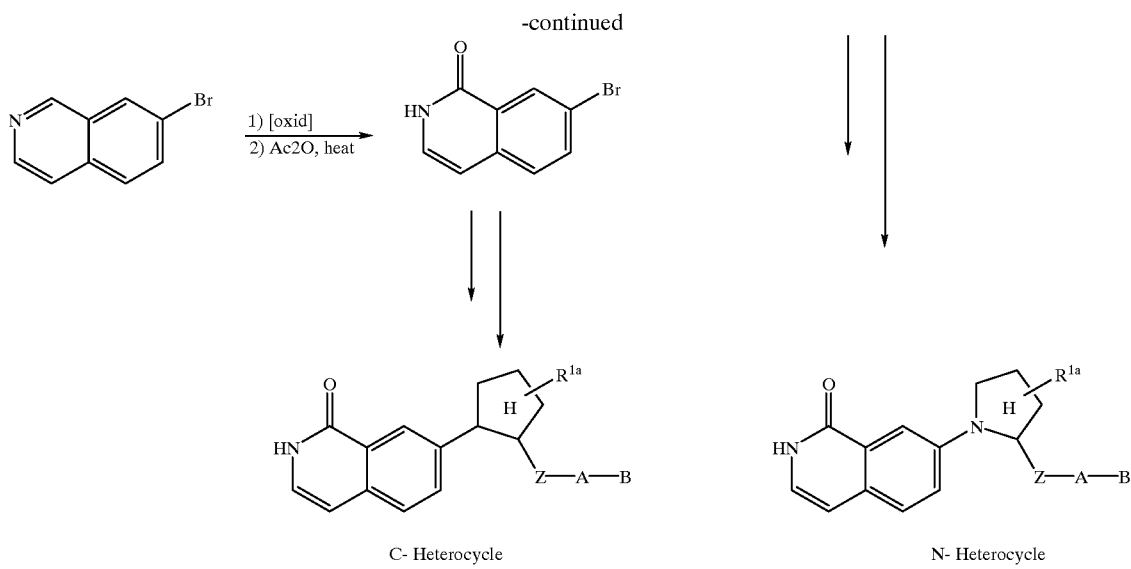

C- Heterocycle

N- Heterocycle

Compounds wherein D-E is 3-aminobenzisothiazole are exemplified by synthesis on the pyrazole core as shown in Scheme 13. The 4-fluoro-3-cyano-pyrazole intermediate as described previously can be used. Displacement of the fluoro substituent via nucleophilic aromatic substitution methodology with a thio nucleophile followed by the standard Weinreb coupling methodology should afford the desired coupled thiobenzyl intermediate. The nitrile can be converted to the amidine via standard conditions. Oxidation of the sulfide to the sulfoxide with MCPBA followed by the standard closure adopted by Wright et al for the isothiazolones with trichloroacetic anhydride should afford the desired amino-isothiazolones.

SCHEME 13

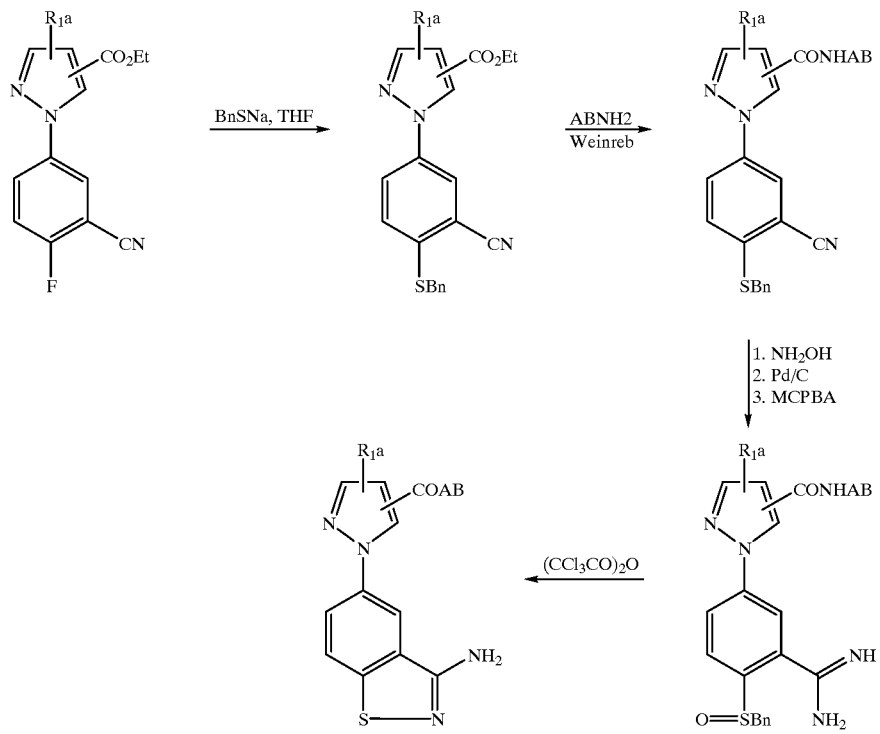

Compounds in which the M-heterocycle is thiazole can be prepared according to the procedures described in Scheme 14. The appropriate Q-D-E bromide can be converted into a beta-keto ester in several ways. One preferred method involves transmetallation with an alkyllithium reagent followed by quenching with DMF to afford the corresponding aldehyde. Addition of ethyl diazoacetate in the presence of tin (II) chloride affords the beta-keto ester directly. Other methods are available for this conversion, one of which involves Reformatsky reaction of the aldehyde followed by oxidation to the beta-keto ester.

such as sodium hydride or lithium diisopropylamide. The beta-keto ester can be converted into the corresponding thiazole derivatives by bromination with NBS followed by cyclization with an appropriate thiourea or thioamide in a

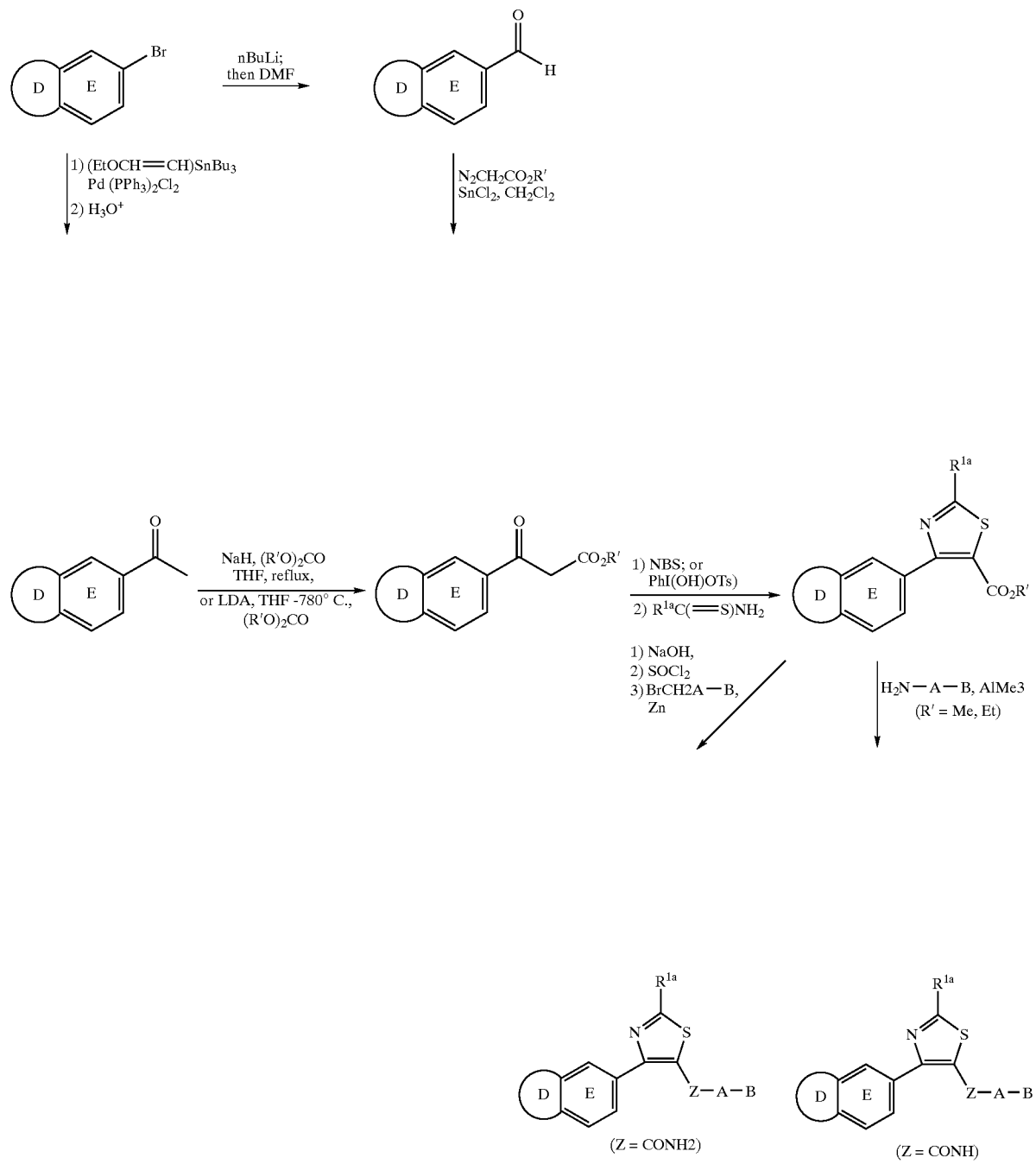

SCHEME 14

A second method for converting the bromide into a beta-keto ester involves palladium catalysed coupling with (ethoxyvinyl)tributyltin followed by acidic hydrolysis to afford the corresponding acetyl derivative. Many methods exist for conversion of the acetyl derivative to the beta-keto ester, one preferred method involves reacting the acetyl derivative with a dialkyl carbonate in the presence of a base solvent such as ethanol or tetrahydrofuran. A one pot method for this conversion involves treating the beta-keto ester with hydroxytosyloxyiodobenzene in acetonitrile, which forms an intermediate alpha-tosyloxy-beta-keto ester, followed by addition of a thiourea or thioamide to effect cyclization to the corresponding thiazole. Manipulation of the ester group of these thiazoles can then afford the compounds containing an appropriate Z-A-B group. Where Z=CONH, standard methods of peptide coupling with an appropriate amine can be employed, such as reaction of the ester with an aluminum reagent derived from the amine. Where Z=COCH$_2$, formation of the acid chloride by standard methods can be followed by addition of an appropriate zinc reagent. The R$^{1a}$ group on the thiazole ring can also be manipulated to provide a variety of different groups. For example, when thiourea is used as the cyclization partner, a 2-aminothiazole is produced. This amino group can be readily diazotized and displaced with the appropriate copper halide to afford 2-halothiazoles. The halogen atom can then be readily displaced by a variety of carbon, nitrogen, oxygen and sulfur nucleophiles to produce a wide variety of alkyl, aryl, heteroatom, and heterocyclic derivatives of R$^{1a}$.

The tetrazole compounds of this invention where Z is —CONH— can be prepared as exemplified in Scheme 15. An appropiately substituted amine (D-ENH$_2$) is acylated with ethyl oxalyl chloride. The resulting amide can be converted to the tetrazole either by the methods described by Duncia (*J. Org. Chem.* 1991, 2395–2400) or Thomas (*Synthesis* 1993, 767–768, 1993). The amide can be converted to the iminoyl chloride first and the reacted with NaN$_3$ to form the 5-carboethoxytetrazole (*J. Org. Chem.* 1993, 58, 32–35 and *Bioorg. & Med. Chem. Lett.* 1996, 6, 1015–1020). The 5-carboethoxytetrazole is then coupled with an appropriate amine (BANH$_2$) by the method described by Weinreb (*Tetr. Lett.* 1977, 48, 4171–4174). Final deprotection as described before yields the desire product.

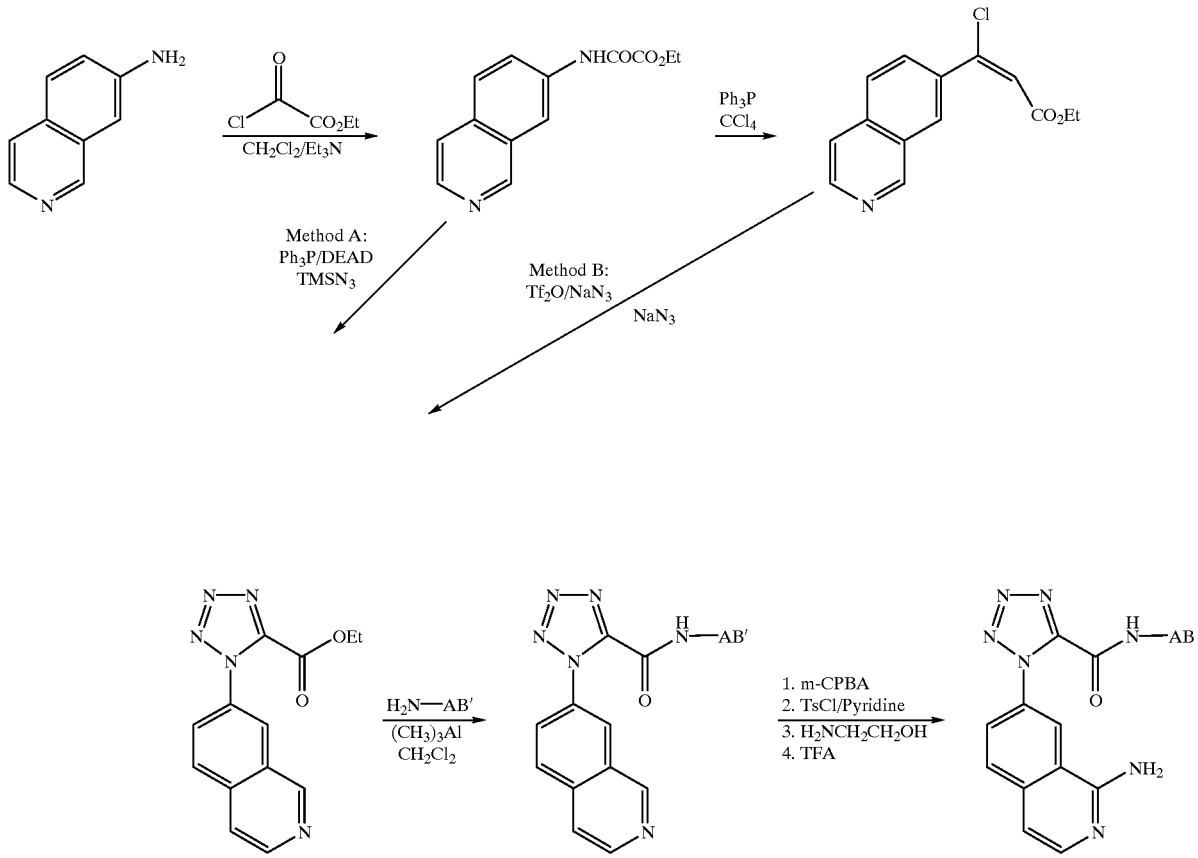

SCHEME 15

The tetrazole compounds of this invention where Z is —CO— can also be prepared via iminoyl chloride (*Chem. Ber.* 1961, 94, 1116 and *J. Org. Chem.* 1976, 41, 1073) using an appropriately substituted acyl chloride as starting material. The ketone-linker can be reduced to compounds where Z is alkyl.

The tetrazole compounds of this invention where Z is —SO$_2$NH—, —S—, —S(O), SO$_2$— can be prepared as exemplified in Scheme 16. Appropiately substituted thioisocyanate is reacted with sodium azide to give the 5-thiotetrazole (*J. Org. Chem.* 1967, 32, 3580–3592). The thio-compound can be alkylated (*J. Org. Chem.* 1978, 43, 1197–1200) and then oxidized to the sulfoxide and sulfone. The thio-compound can also be converted to the sulfonyl chloride and the reacted with an amine to give the desired sulfonamide. The tetrazole compounds of this invention where Z is —O— can be prepared via the same method described in Scheme 16 by using appropiately substituted isocyanate as the startimg material.

SCHEME 16

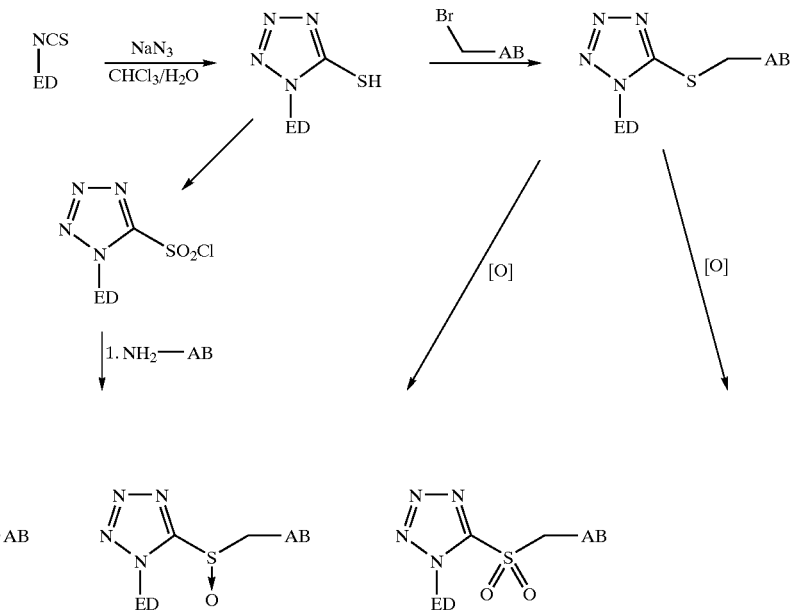

The tetrazole compounds of this invention where Z is —NH—, —NHCO—, —NHSO$_2$— can be prepared from 5-aminotetrazole, which can be prepared by Smiles Rearrangement as shown in Scheme 17. The thio-compound prepared as described in Scheme 3 is alkylated with 2-chloroacetamide. The resulting compound is then refluxed in ethanolic sodium hydroxide to give the corresponding 5-amino-tetrazole (*Chem. Pharm. Bull.* 1991, 39, 3331–3334). The resulting 5-amino-tetrazole can then be alkylated or acylated to form the desired products.

SCHEME 17

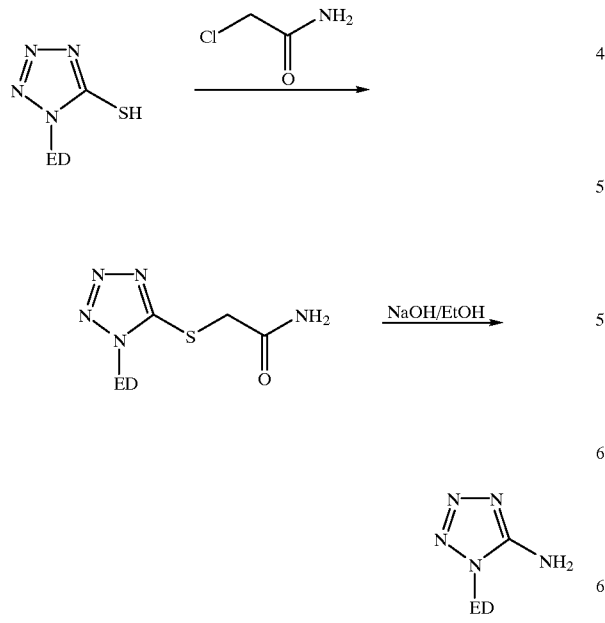

The N-linked imidazole ring M can be synthesized by the synthetic route shown in Scheme 18. Alkylation of D-E-NH$_2$ with 2-bromoethylacetate followed by reaction with Gold's reagent in the presence of a base, such as NaOMe or LDA, form imidazole ring M.

SCHEME 18

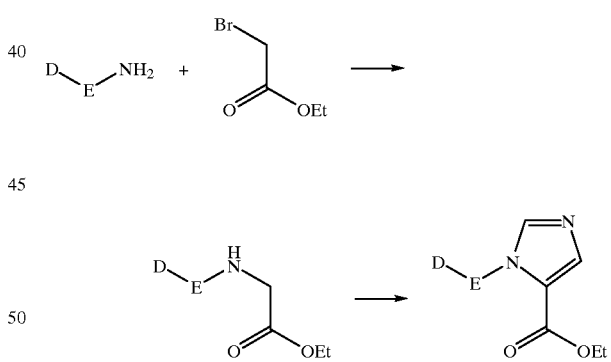

Additional imidazole derivatives can be made by the general procedures as described in Scheme 18a. Here, P is a protective group for amino group. E is a substituted group or groups. G is an aromatic ring (six, six-six or five-six ring). R$_1$ and/or R$_2$ is H, a substituted alkyl group, or either V or a precusor of (CH$_2$)$_n$V. V is nitro, amino, thio, hydroxy, sulfone, sulfonic ester, sulfoxide, ester, acid, or halide. n is 0 and 1. U is aldehyde, ester, acid, amide, amino, thiol, hydroxy, sulfonic acid, sulfonic ester, sulfonyl chloride, or methylene halide. Z, A, and B are the same as those described for formula I.

SCHEME 18a

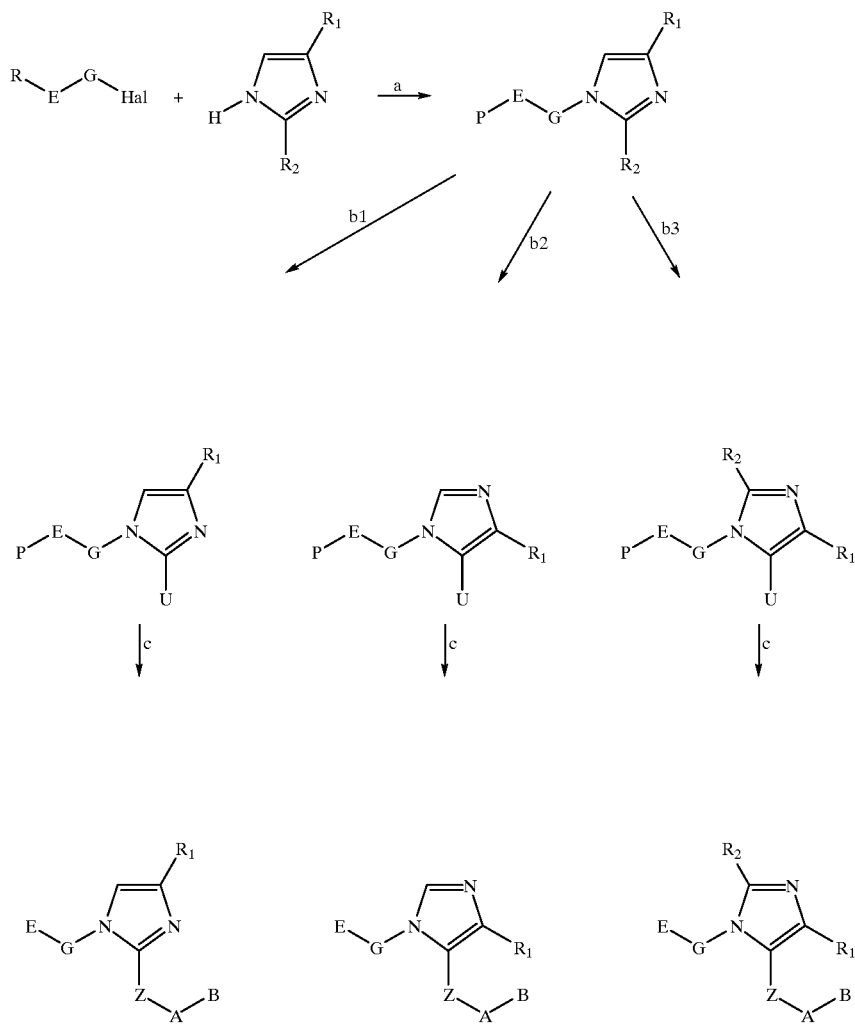

A general procedure to make 2,4,5-trisubstituted or 4,5-disubstituted imidazole derivatives is described in Scheme 18b. The starting ester b can be obtained by acylation of N,O-dimethylhydroxyamine with ethyl malonyl chloride. After metalation with a lithium reagent, compound a can react with b to give compound c. Compound c can also be directly made from coupling reaction of a with zinc reagent of ethyl malonyl chloride. Compound c can be brominated with NBS to form compound d, which can react with excess $NH_3$ and $R_1CO_2H$ to afford compound e. The ester group in e can be transferred to other functionalities, which can be further reacted to give compound f.

Scheme 18b

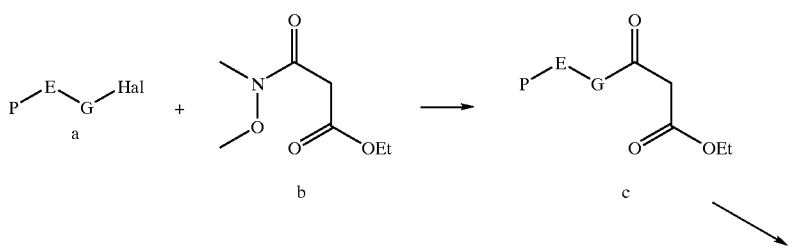

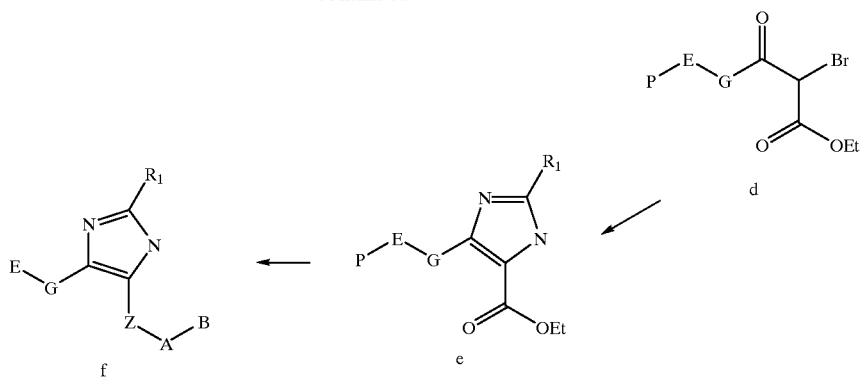

The general procedure to make C-linked imidazole ring M is described in Scheme 19. Aldehyde D-E-CHO from Scheme 1 can be converted into cyano compound by treatment with hydroxyamine and then dehydration with POCl$_3$. The amidine can be obtained from cyano compound by Pinner reaction, which can be cyclized with alpha-halo ester, ketone or aldehyde to form imidazole ring M.

of an appropriately substituted hydrazine with a variety of diketo esters. Condensations of this type typically afford a mixture of pyrazole regioisomers which can be effectively separated via silica gel column chromatography (Scheme 20). Hydrolysis of the esters followed by coupling with an appropriate amine can afford the desired amide intermediate. Various substituents on the pyrazole can then be manipu-

SCHEME 19

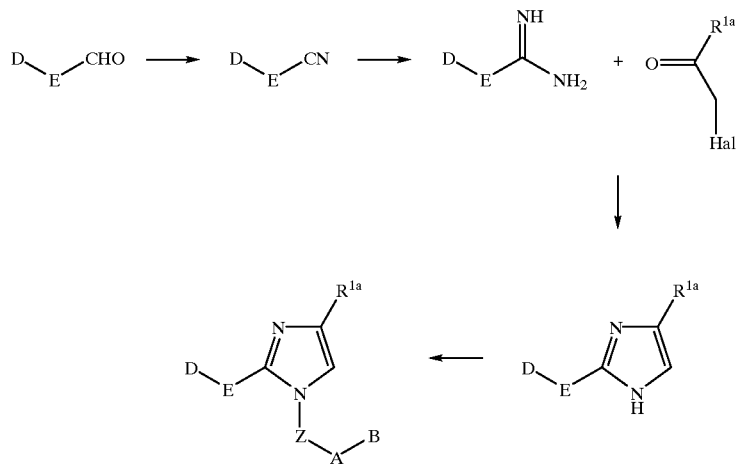

Pyrazole ring M of the general Formula I such as those described in Scheme 1 can be prepared by the condensation lated to afford a variety of benzo, heterocyclic and bicylic compounds.

SCHEME 20

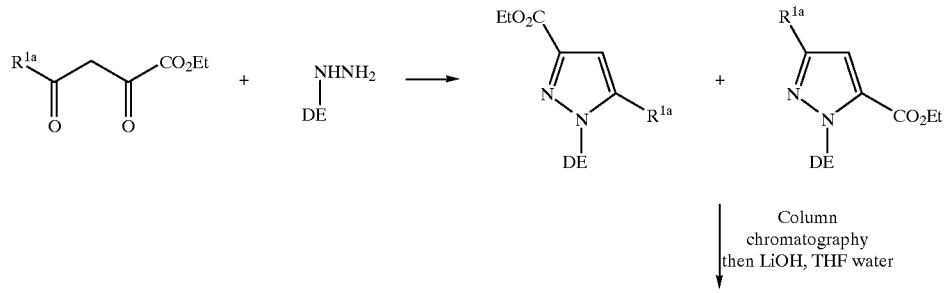

Column chromatography then LiOH, THF water

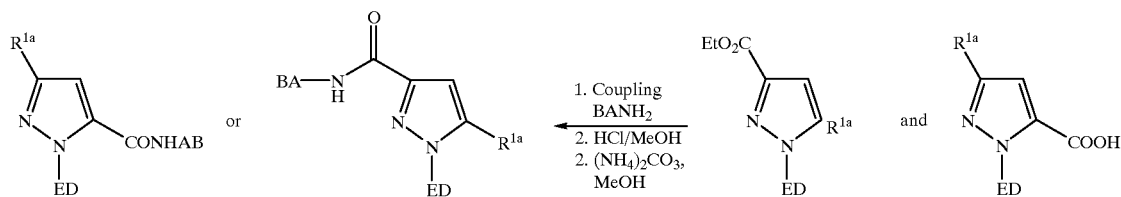

The above methodology when applied to diketo derivatives also affords a mixture of pyrazole regioisomers. These can be further manipulated to afford the compounds of Formula I as shown in Scheme 21.

intermediates to the final compounds of formula I can then be accomplished by the protection of the amino functionality with a suitable protecting group commonly known to those in the art or by derivatization

SCHEME 21

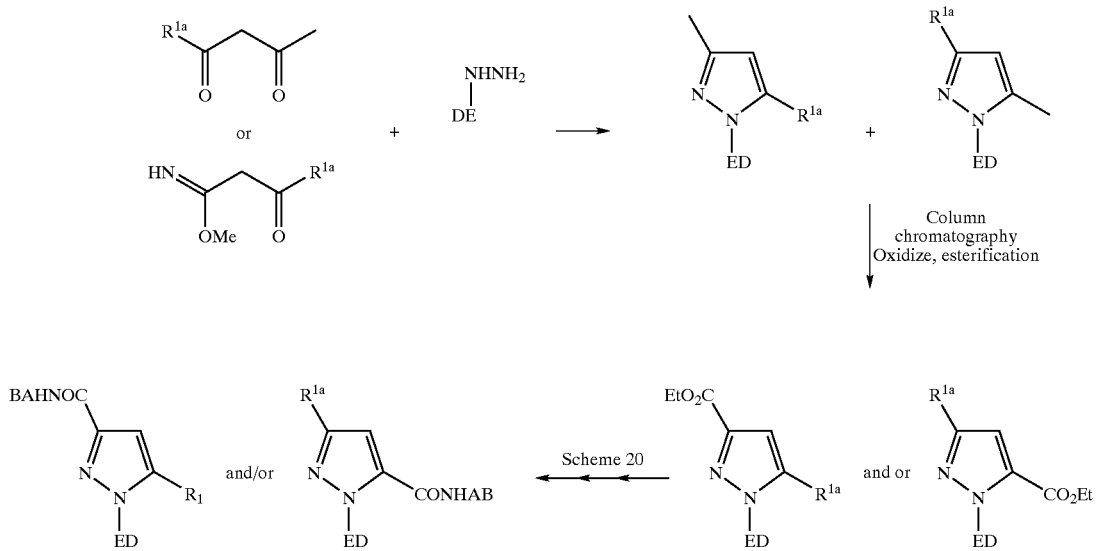

When ketoimidates are used for condensations with hydrazines the corresponding pyrazole amino esters regioadducts are obtained (Scheme 22). Conversion of these (e.g. sulfonamide) then following the general synthetic strategy to prepare the compounds of this invention.

SCHEME 22

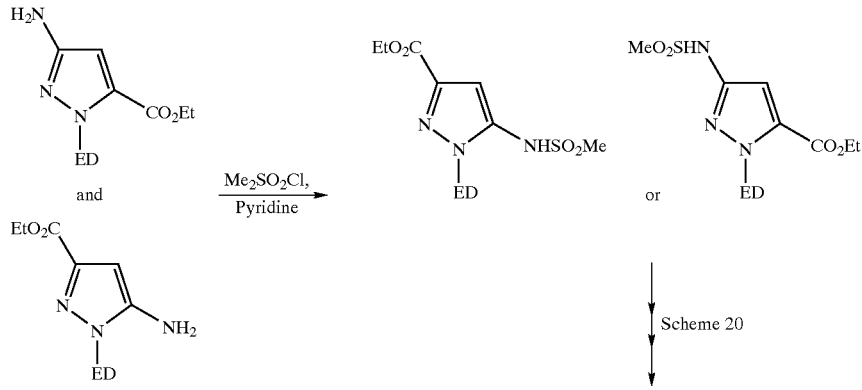

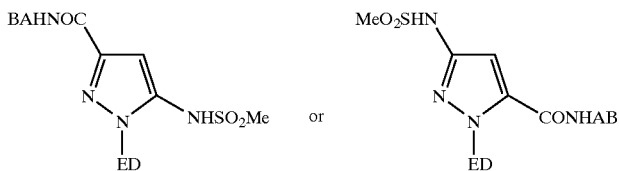

The pyrazole ester intermediate can be further manipulated to the ketones by the cuprate methodology described by Knochel et al (Scheme 23). Alternatively the ester can be reduced to either the alcohol or aldehyde via methods known to those in the art followed by either a reductive amination with an appropriate amine to an alkyl amine or by converting the alcohol to a leaving group which in turn can be displaced with a number of nucleophiles to provide the intermediates which on further manipulations should afford the compounds of this invention.

SCHEME 23

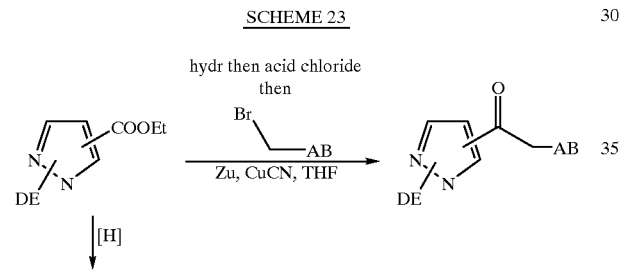

-continued

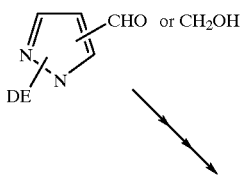

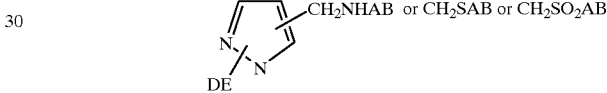

Thio compounds such as those described in Scheme 24 can be easily prepared by the conversion of 5-hydroxy pyrazole to its thiol by treatment with Lawesson's reagent in refluxing toluene.

SCHEME 24

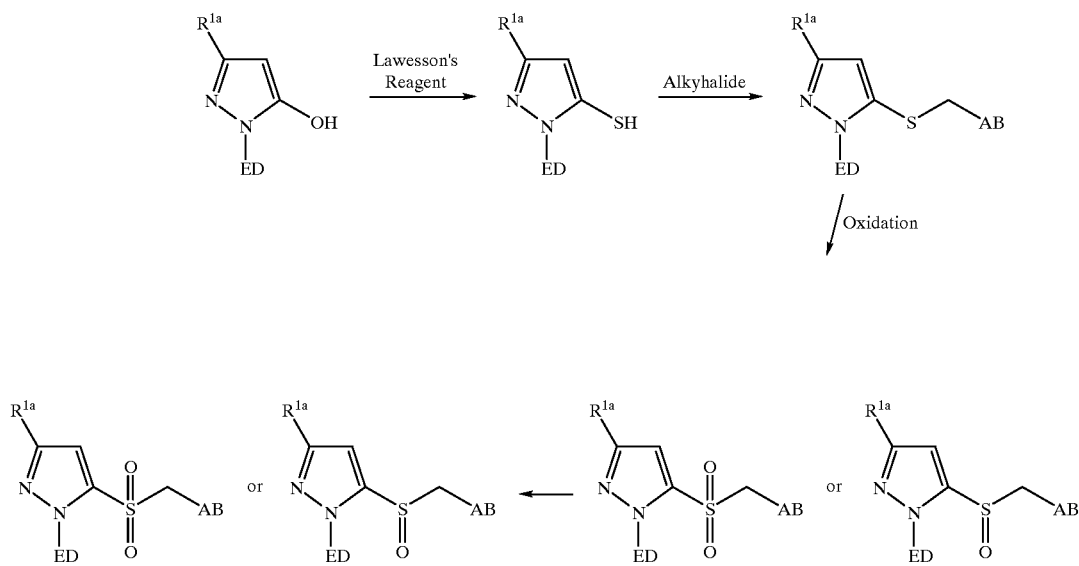

Compounds of this invention wherein the pyrazole ring M is replaced with a 1,2,3-triazole can be prepared as outlined in Scheme 25.

Alternatively the 1,2,4 triazoles can also be prepared by the methodology of Zecchi et al (*Synthesis* 1986, 9, 772) via an aza Wittig condensation (Scheme 27).

SCHEME 25

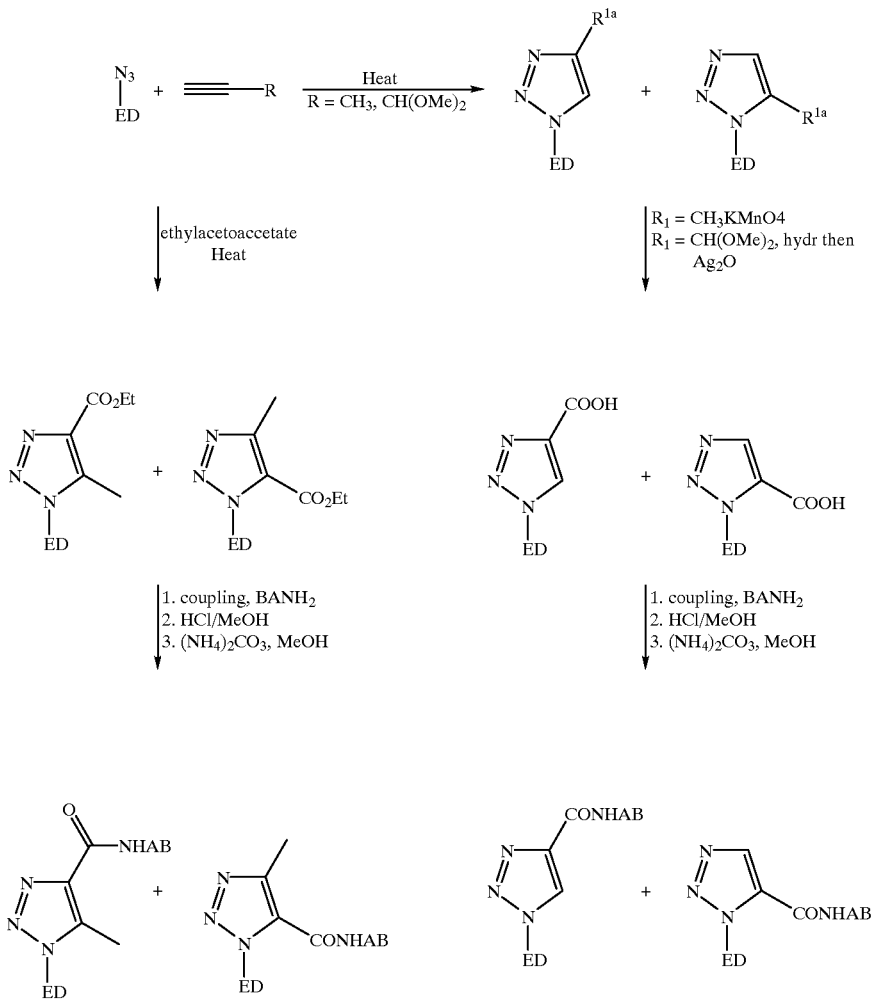

The compounds of this invention where the ring M is 1,2,4-triazole can be easily obtained by the methodology of Huisgen et. al. (*Liebigs Ann. Chem.* 1962, 653, 105) by the cycloaddition of nitriliminium species (derived from the treatment of triethylamine and chloro hydrazone) and an appropriate nitrile dipolarophile as in Scheme 26.

SCHEME 26

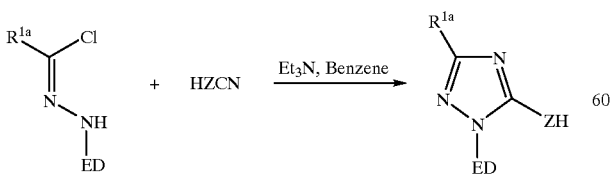

This methodology provides a wide variety of 1,2,4 triazoles with a varied substitution pattern at the 1,3 and 5 positions.

SCHEME 27

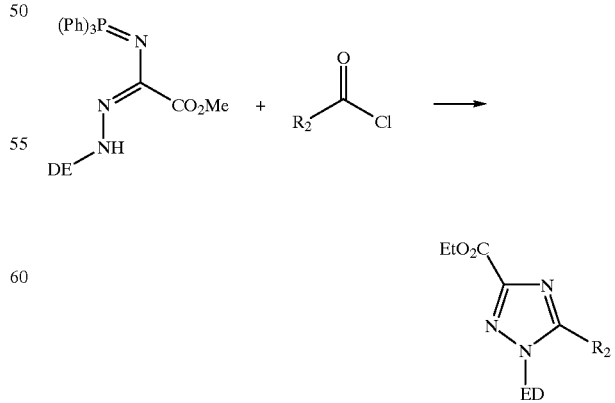

$R_2$ = alkyl or aryl

Alternatively the 1,2,4 triazoles can also be prepared via the methodology of Sauer et al (*Tetr. Lett.* 1968, 325) by the photolysis of a cyclic carbonate with an appropriate nitile (Scheme 28).

SCHEME 28

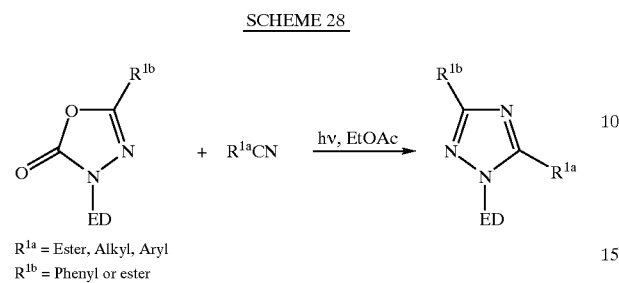

$R^{1a}$ = Ester, Alkyl, Aryl
$R^{1b}$ = Phenyl or ester

For compounds of this invention the esters can be converted to the amide intermediates via the Weinreb methodology (*Tetr. Lett.* 1977, 48, 4171), i.e., the condensation of an appropriate amine aluminum complex with the ester (Scheme 29).

SCHEME 29

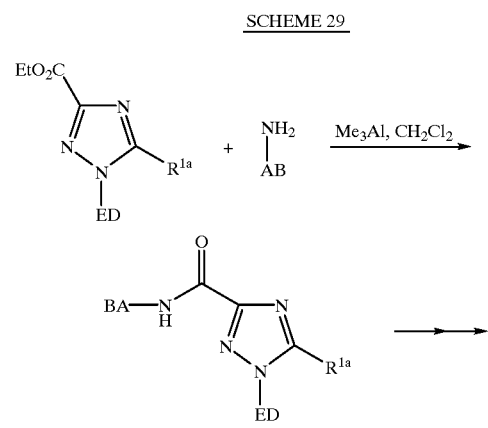

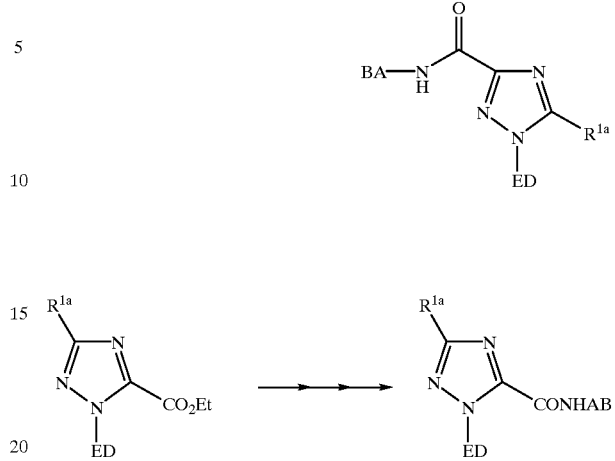

Isoxazoline ring M of formula I wherein the 4 and 5 positions are substituted can be prepared following the 1,3-dipolar cycloaddition methodology outlined in Scheme 30. An appropriate benzhydroximinoyl chloride or heterocyclic oximinoylchloride or oxime when subjected to 1,3-dipolar cycloaddition protocol with a suitable 1,2-disubstituted olefin as a dipolarophile should afford a mixture of regioisomers. Separation of the regioisomers by column chromatography followed by the sequence of reactions as described previously should then afford the compounds of choice. Optically active isoxazolines can also be obtained by enzymatic resolution on the regioisomeric esters or by the use of an appropriate chiral auxilliary on the dipolarophile as described by Olsson et al (*J. Org. Chem.* 1988, 53, 2468).

SCHEME 30

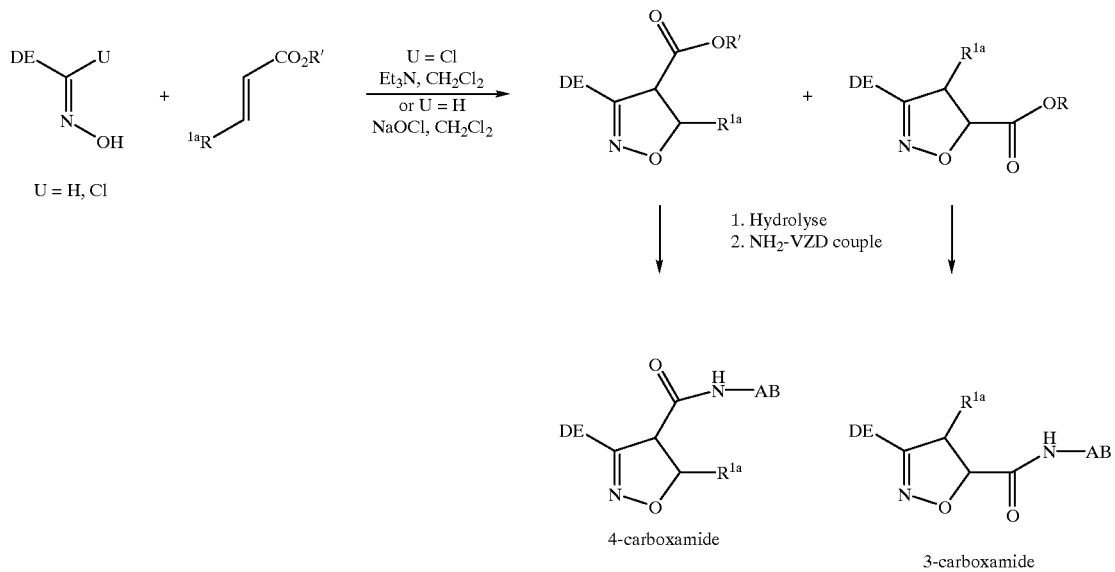

4-carboxamide 3-carboxamide

In the case of compounds with general formula I wherein Z is an amide the cycloaddition process described in Scheme 30 utilizes an appropriately substituted crotonate ester. The crotonate esters can be obtained from commercial sources or can be obtained from ethyl-4-bromocrotonate by nucleophilic displacement reactions shown in Scheme 31.

SCHEME 31

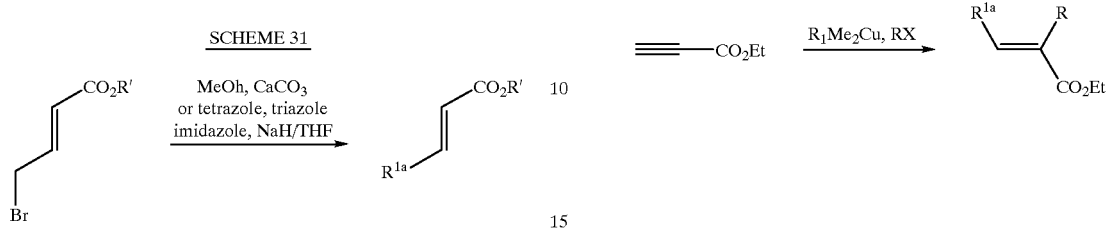

Trisubstituted olefins as dipolarophiles can be obtained from ethylpropiolate by the cuprate chemistry (Scheme 32) according to the method described by Deslongchamps et al (*Synlett* 1994, 660).

SCHEME 32

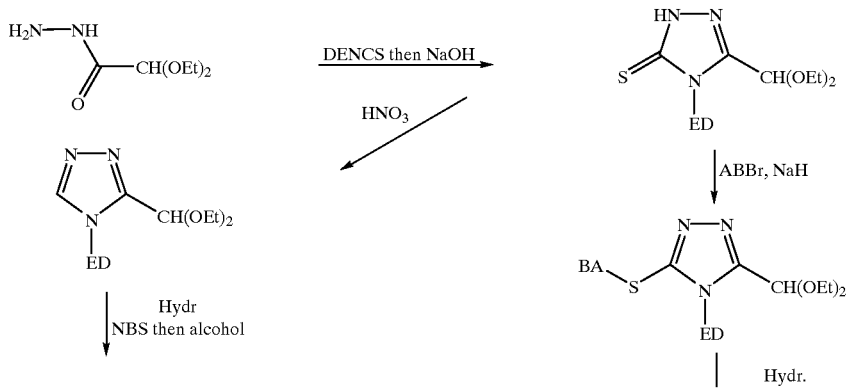

Compounds of this invention with 1,3,4-triazole ring M can be easily obtained via the methodology of Moderhack et al (*J. Prakt. Chem.* 1996, 338, 169) as in Scheme 33.

SCHEME 33

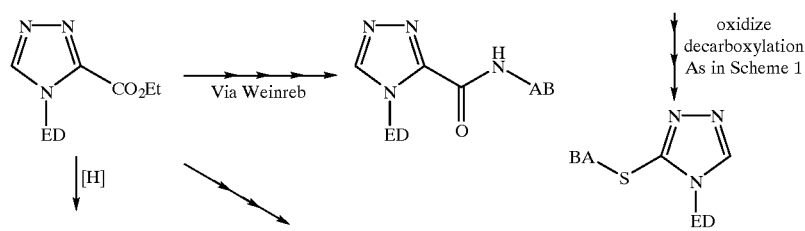

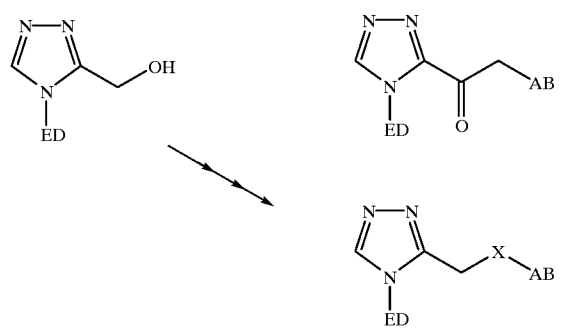

X = Nothing or H or alkyl or heteroatom

This reaction involves the condensation of a carbazide with an appropriately substituted commercially available thioisocyanate to the cyclic thiourea derivative as described previously. Alkylation or nucleophilic displacement reactions on the thiono intermediate then affords a thio alkyl or aryl intermediate which can be hydrolysed, oxidized and decarboxylated to the 5-H-2-thio-triazole intermediate which can be effectively converted to the compounds of this invention. Alternatively the thiono urea intermediate can be oxidized directly to the 2-H-triazole which can then be converted to the ester and then subjected to a variety of reactions shown above to obtain the compounds of this invention. The esters can also be converted to the amine via the Hoffmann rearrangement and this methodology provides a variety of analogs similar to those shown previously. The cyclic thiono urea intermediate can also be oxidized to the sulfonyl chloride by methods shown previously. This in turn can provide the sulfonamides shown in Scheme 34.

SCHEME 34

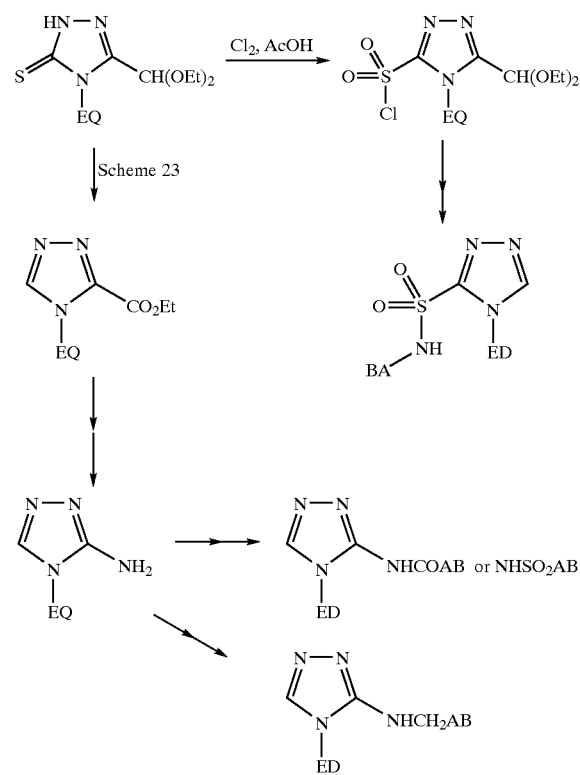

SCHEME 35

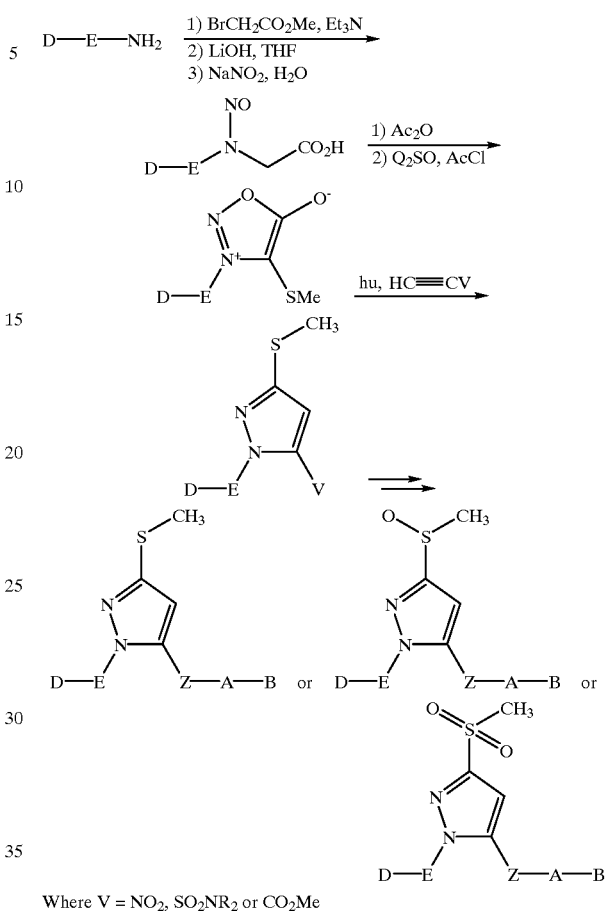

Where V = NO$_2$, SO$_2$NR$_2$ or CO$_2$Me

Scheme 35 describes the general synthesis for pyrazoles which have thio and oxidized sulfur derivatives. An appropriately substituted amine is alkylated with ethyl bromoacetate and hydrolyzed to the glycine derivative. Preparation of the N-nitroso compound was easily achieved with sodium nitrite (*J. Chem. Soc.* 1935, 899). Cyclization to the syndone using acetic anhydride (*J. Chem. Soc.* 1935, 899) was following by the introduction of the sulfide unit using a sulfoxide as solvent and acetyl chloride as a activating reagent (*Tetr.* 1974, 30, 409). Photolytic cleavage of the sydnone in the presence of an acetylenic compound the 1,3,5 trisubstituted pyrazole as the major regioisomer (*Chem. Ber.* 1979, 112, 1206). These can be carried on, as described before, to the final compounds containing the sulfide, sulfoxide or sulfone functionality.

Scheme 36 shows one possible synthesis of isoxazoles. Substituted benzaldehydes are reacted with hydroxyl amine then chlorinated to give the hydroximinoyl chloride according to the procedure of (*J. Org. Chem.* 1980, 45, 3916). Preparation of the nitrile oxide in situ with triethylamine and cycloaddition with a substituted alkyne gives a mixture of regioisomeric isoxazoles as shown by H. Kawakami (*Chem. Lett.* 1987, 1, 85). Preparation of the disubstituted alkyne is achieved by nucleophilic attack of the alkynyl anion on an electrophile as shown by Jungheim et al (*J. Org. Chem.* 1987, 57, 4007).

Alternatively, one could make the hydroxyiminoyl chloride of the R$^{1a}$ piece and react it with an appropriately substituted alkyne to give another set of regioisomeric isoxazoles which can be separated chromatographically.

SCHEME 36

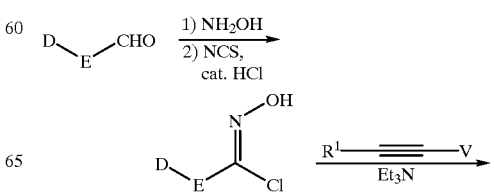

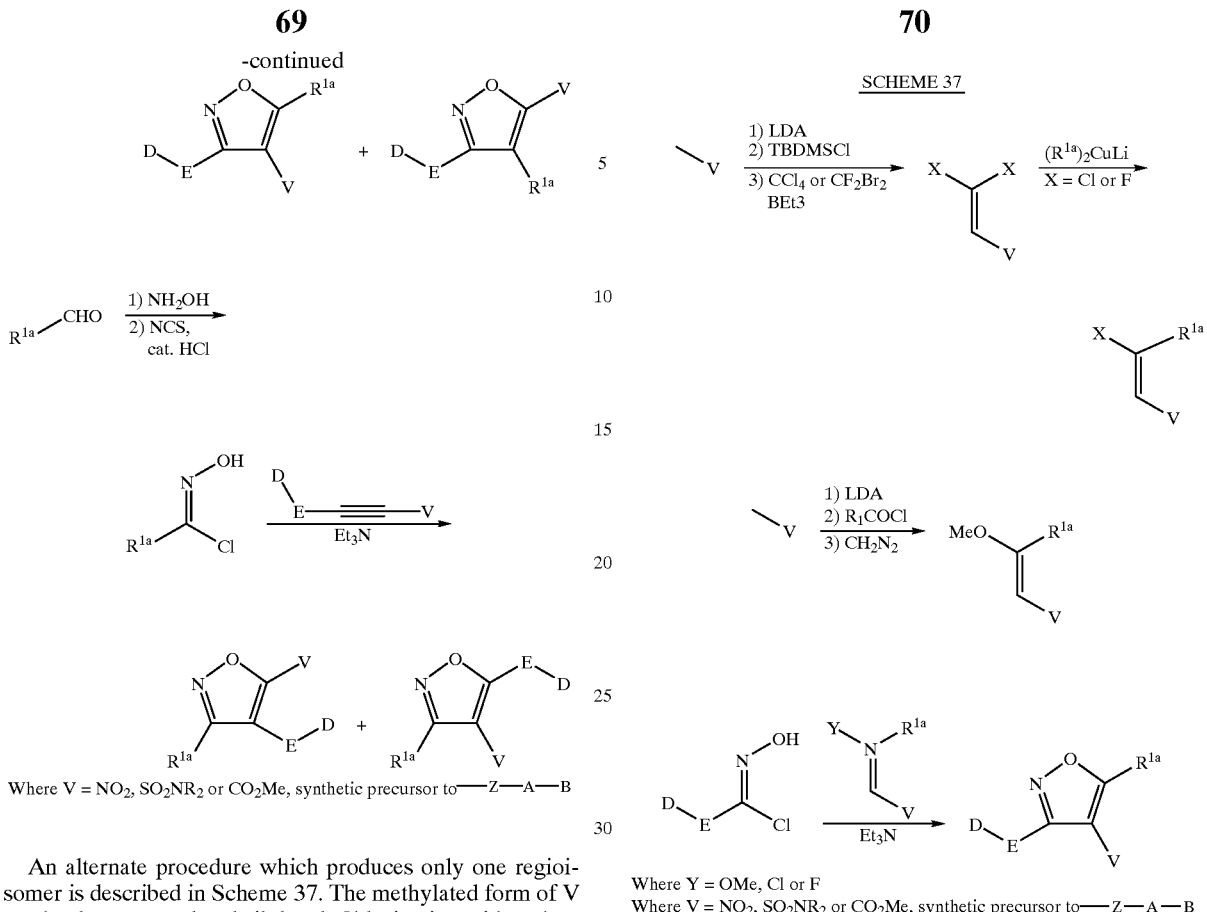

Where V = NO₂, SO₂NR₂ or CO₂Me, synthetic precursor to—Z—A—B

An alternate procedure which produces only one regioisomer is described in Scheme 37. The methylated form of V can be deprotonated and silylated. Chlorination with carbon tetrachloride or fluorination with difluorodibromomethane under triethylborane catalysis give the geminal dihalo compound as shown by Sugimoto (*Chem. Lett.* 1991, 1319). Cuprate-mediated conjugate addition-elimination give the desired alkene as in Harding (*J. Org. Chem.* 1978, 43, 3874).

Alternatively, one can acylate with an acid chloride to form a ketone as in Andrews (*Tetr. Lett.* 1991, 7731) followed by diazomethane to form the enol ether. Each of these compounds can be reacted with a hydroximinoyl chloride in the presence of triethylamine to give one regioisomeric isoxazole as shown by Stevens (*Tetr. Lett.* 1984, 4587).

Where Y = OMe, Cl or F
Where V = NO₂, SO₂NR₂ or CO₂Me, synthetic precursor to——Z—A—B When core substitutent $R^{1a}$ is $CH_2$—$R^{1'}$, the synthesis is shown in Scheme 38. After being treated with LDA, the ketone starting material reacts with PhSSO₂Ph to give the phenylthiolated compound which reacts with hydrazine in acetic acid to form pyrazole derivative. The pyrazole ester reacts with an amine or aniline (previously treated with AlMe₃) to provide amide. Oxidation of the sulfide with mCPBA gives the corresponding sulfone. Deprotonation of the sulfone with base, followed by trapping with an electrophile(E-X) and treatment with SmI₂ provided the desired compound after deprotection.

SCHEME 38

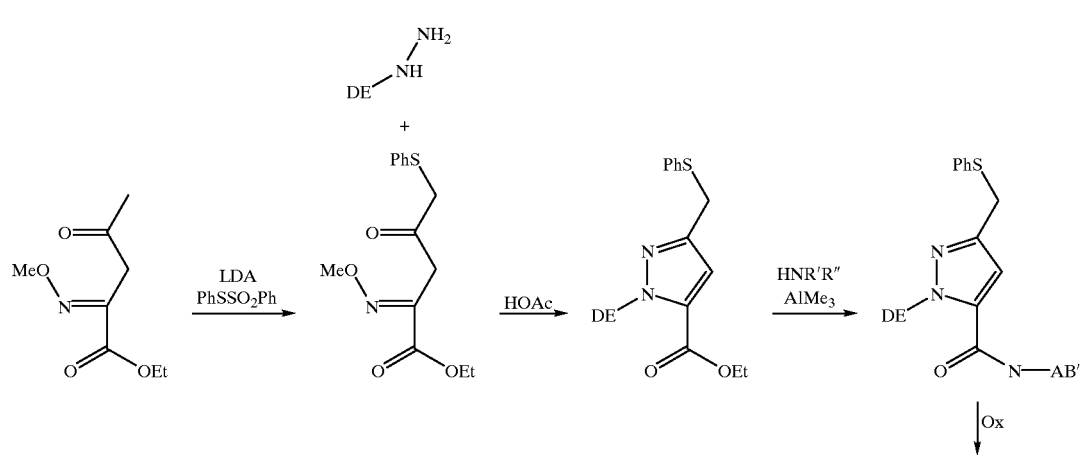

-continued

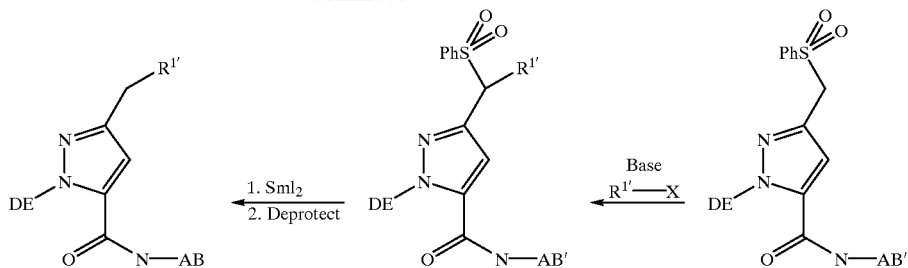

Scheme 39 shows other methods of synthesis for $R^{1a}$=$CH_2R^{1'}$ or $COR^{1'}$. Protection of the hydroxyl group of hydroxyacetone with a benzyl halide and treatment with a base and $CO(CO_2Et)_2$ gives the tricarbonyl compound. Refluxing with $NH_2OMe\cdot HCl$ in pyridine and ethanol in the presence of molecular sieve 3 Å gives the oxime. Cyclization of oxime with $D$-$E$-$NHNH_2$ provided pyrazole, which can be converted into the corresponding amide by reacting with an amine or aniline (previously activated with $AlMe_3$).

Debenzylation by catalytic hydrogenation provides the alcohol. The alcohol is converted into the tosylate with TsCl, followed by replacement with a nucleophile to provide the desired compound. The alcohol can also be oxidized to the corresponding aldehyde or acid, or further converted to ester or amide.

SCHEME 39

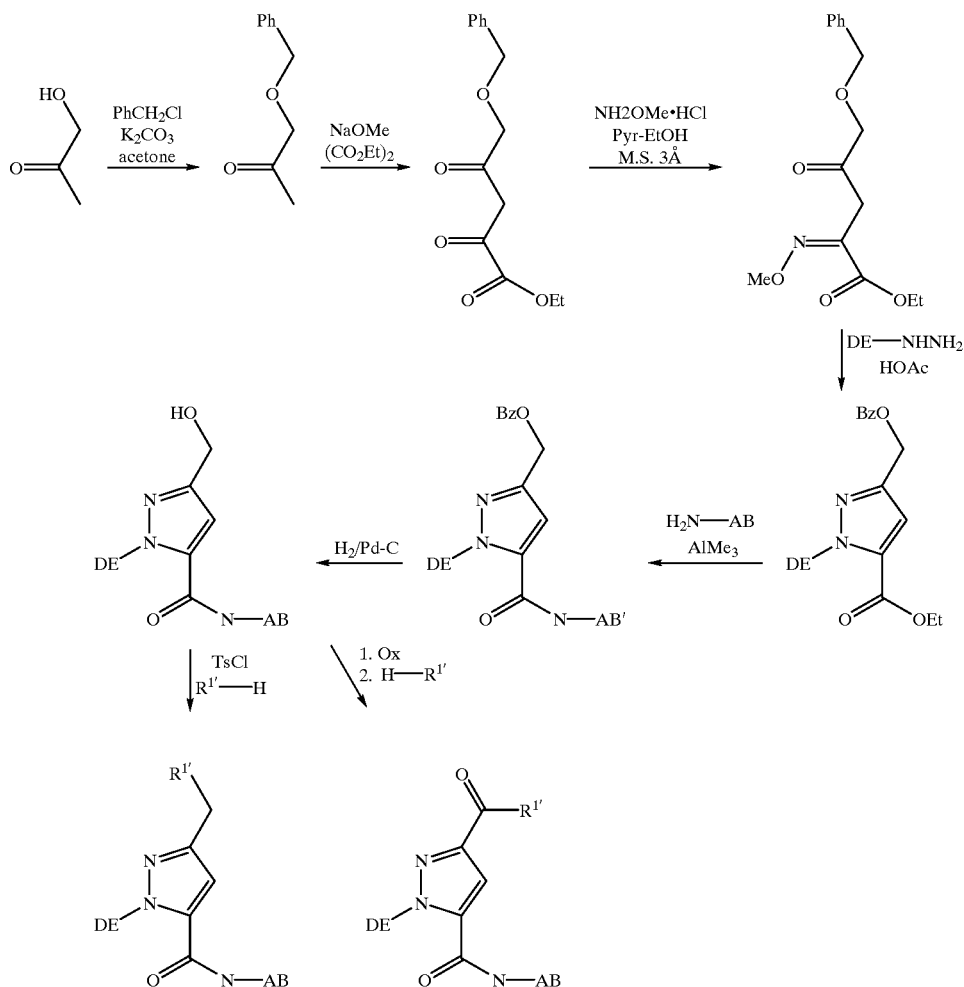

Scheme 40 shows the synthesis of pyrazole ring with a chloride group. Chlorination of pyrazole starting material obtained previously in Scheme 2a with NCS formed chloropyrazole. The chloropyrazole can be reacted with an aniline in the presence of AlMe₃ followed by amination as described in Scheme 2a to give the desired product.

SCHEME 40

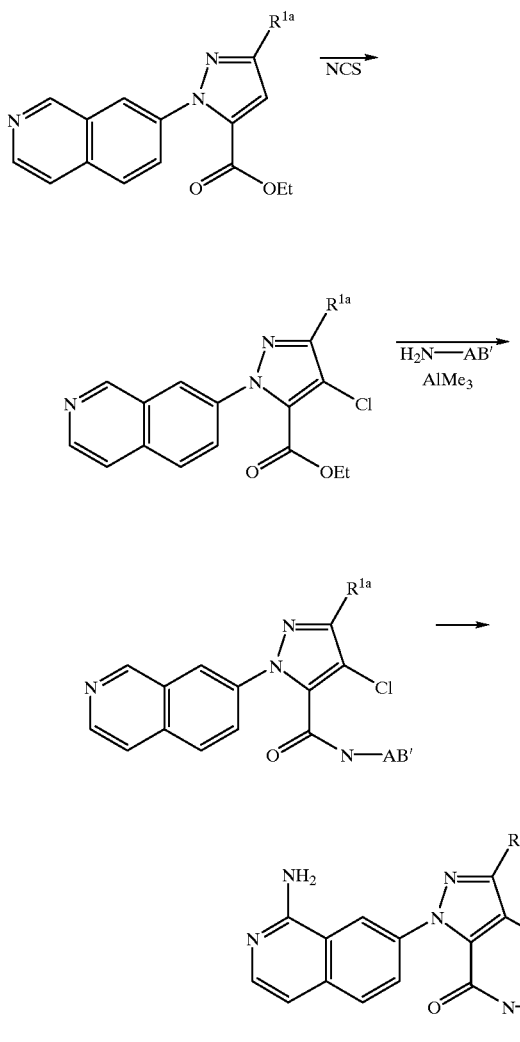

Scheme 41 describes the synthesis of compounds wherein M is a benzene ring and V is a nitro, protected sulfonamide or ester group and precursor of group Z of Formula I. The V group is placed on an appropriately substituted phenol either via nitration as shown by Poirier et al. (*Tetrahedron* 1989, 45(5), 1415), sulfonylation as shown by Kuznetsov (*Akad. Nauk SSSR Ser. Khim* 1990, 8, 1888) or carboxylation by Sartori et al. (*Synthesis* 1988, 10, 763). Bromination with triphenylphosphine and bromine (*J. Am. Chem. Soc.* 1964, 86, 964) gives the desired bromide. Suzuki coupling with the appropriate boronic acid provides the desired substituted pyridine.

Scheme 41

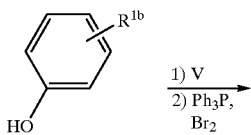

-continued

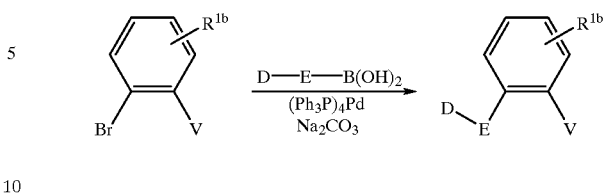

Schemes 42–45 describe the synthesis of compounds wherein M is pyridine. Each scheme represents a different substitution pattern for the pyridine ring. In Scheme 42, a suitably protected aldehyde is subjected to base-catalyzed condensation with an activated ester to give after deprotection the desired aldehyde. Refluxing with ammonium chloride as shown by Dornow and Ische (*Chem. Ber.* 1956, 89, 876) provides the pyridinol which is brominated with POBr₃ (Tjeenk et al. *Rec. Trav. Chim.* 1948, 67, 380) to give the desired 2-bromopyridine. Suzuki coupling with the appropriate boronic acid provides the desired substituted pyridine.

Scheme 42

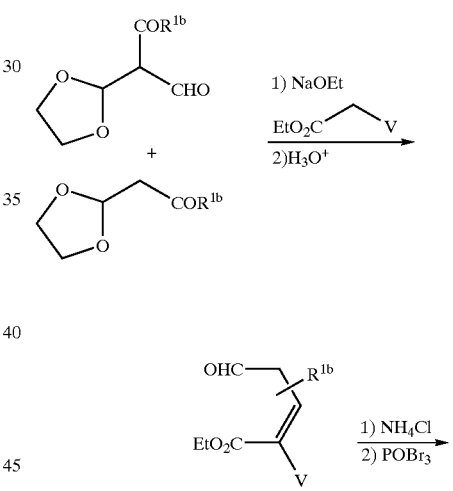

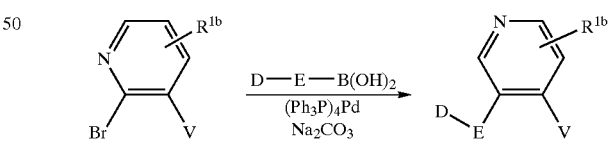

Treatment of an appropriately substituted 5-ethoxyoxazole with an alkene as shown by Kondrat'eva et al. (*Dokl. Akad. Nauk SSSR* 1965, 164, 816) provides a pyridine with the V substituent at the para position. Bromination at the 3-position as shown by van der Does and Hertog (*Rec. Trav. Khim. Pays-Bas* 1965, 84, 951) followed by palladium-catalyzed boronic acid coupling provides the desired substituted pyridine.

Scheme 43

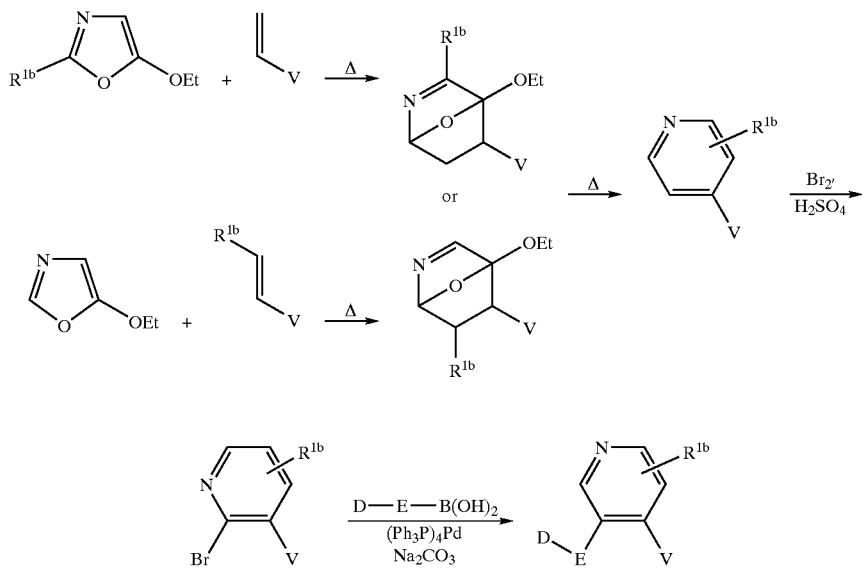

Scheme 44 describes a synthesis of a third substitution pattern on a pyridine ring. The appropriate tricarbonyl compound which can be prepared by methods described in Scheme 42 is treated with ammonium chloride to form the pyridinol which is subsequently brominated. Palladium-catalyzed coupling provides the desired substituted pyridine.

Scheme 44

Scheme 45

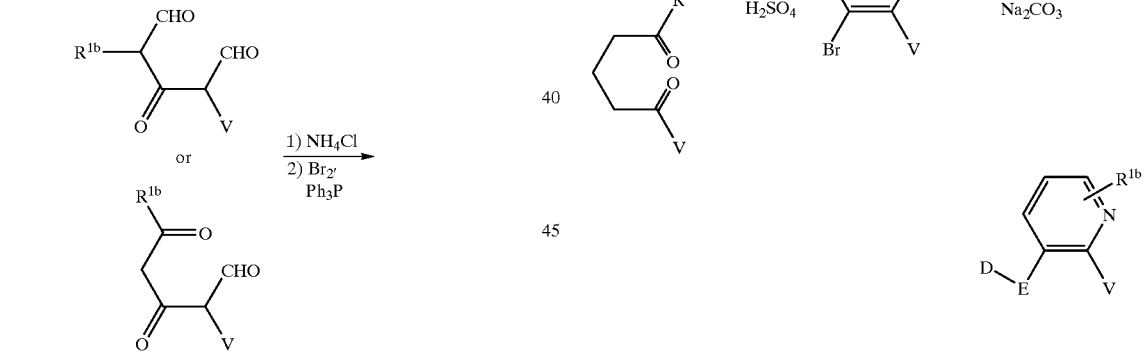

Scheme 45 takes a suitably substituted dicarbonyl compound and by chemistry illustrated in Schemes 42 and 44, reacts it with ammonium chloride. Bromination gives the 3-bromopyridine which upon palladium-catalyzed coupling provides the desired substituted pyridine.

Schemes 46–48 describe the synthesis of compounds wherein M is pyridazine. Each scheme represents a different substitution pattern for the pyridine ring. In Scheme 46 an activated ester is reacted with an appropriately substituted α-keto aldehyde and hydrazine as shown by Schmidt and Druey (*Helv. Chim. Acta* 1954, 37, 134 and 1467). Conversion of the pyridazinone to the bromide using $POBr_3$ and palladium-catalyzed coupling provides the desired substituted pyridazine.

Scheme 46

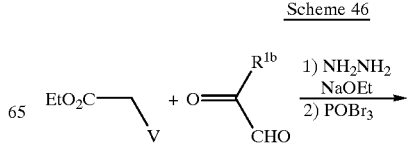

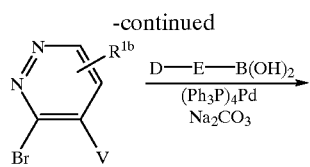

In Scheme 47, glyoxal can react under basic conditions with an activated ketone and subsequently brominated/dehydrobrominated to give the desired ketoaldehyde. Alternatively, a protected ketone can react with an activated aldehyde, undergo bromination/dehydrobromination, be deprotected and oxidized to give the regioisomeric ketoaldehyde. Cyclization as shown by Sprio and Madonia (*Ann. Chim.* 1958, 48, 1316) with hydrazine followed by palladium-catalyzed coupling provides the desired substituted pyridazine.

Scheme 47

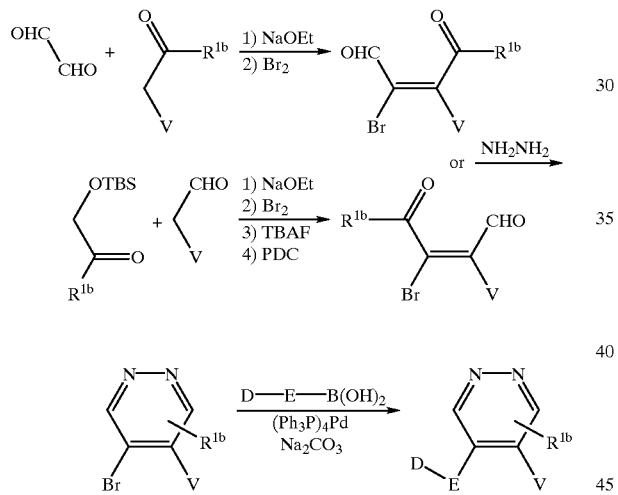

By analogy to Scheme 47, in Scheme 48, a aldehyde can be reacted with an activated ketone, brominated, dehydro-brominated and deprotected to give the desired diketone. Alternatively, a regioisomeric ketone can be placed through the same reaction sequence to produce an isomeric keto aldehyde. Reaction with hydrazine followed by palladium-catalyzed coupling provides the desired substituted pyridazine.

Scheme 48

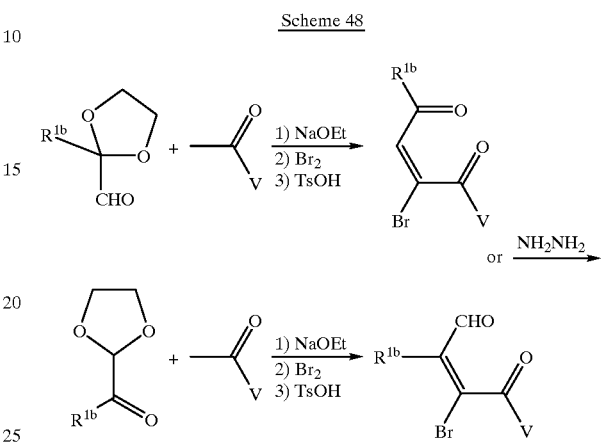

Schemes 49 and 50 describe the synthesis of compounds wherein M is pyrimidine. Each scheme represents a different substitution pattern for the pyrimidine ring. In Scheme 49, a condensation with an appropriately substituted acid chloride and an activated ester followed by conjugate reduction by tin hydride (Moriya et al. *J. Org. Chem.* 1986, 51, 4708) gives the desired 1,4 dicarbonyl compound. Cyclization with formamidine or a substituted amidine followed by bromination gives the desired regioisomeric pyrimidine. Palladium-catalyzed coupling provides the desired substituted pyrimidine.

Scheme 49

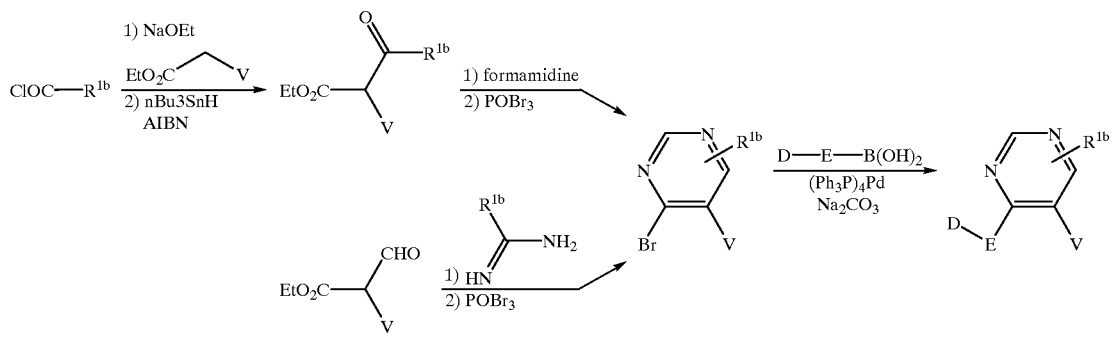

Using similar chemistry, Scheme 50 shows how an amidine can be condensed with a 1,3-dicarbonyl compound and subsequently brominated in the 5-position (*J. Het. Chem.* 1973, 10, 153) to give a specific regioisomeric bromopyrimidine. Palladium-catalyzed coupling provides the desired substituted pyrimidine.

the 1-aminopyrazole which is subsequently brominated with N-bromosuccimide. Lead tetraacetate mediated rearrangement as shown by Neunhoeffer et al. (*Ann.* 1985, 1732) provides the desired regioisomeric 1,2,3-triazine. Palladium-catalyzed coupling provides the substituted triazine.

Scheme 50

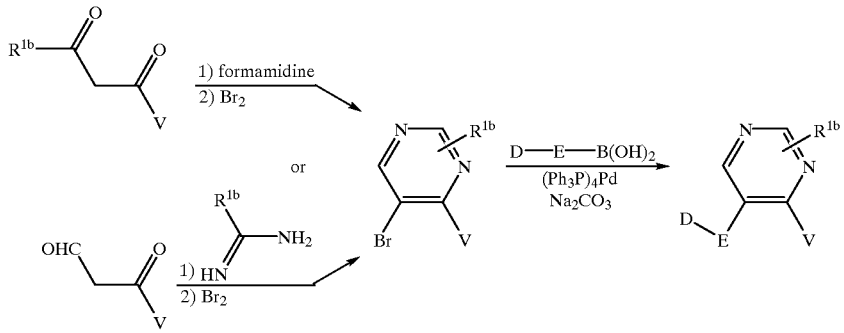

Using the same ketoaldehyde from Scheme 50, cyclization with an appropriately substituted 1,2-diamine (*Chimia* 1967, 21, 510) followed by aromatization (*Helv. Chim. Acta* 1967, 50, 1754) provides a regioisomeric mixture of pyrazines as illustrated in Scheme 51. Bromination of the hydrobromide salt (U.S. Pat. No. 2,403,710) yields the intermediate for the palladium-catalyzed coupling step which occurs as shown above.

Scheme 51

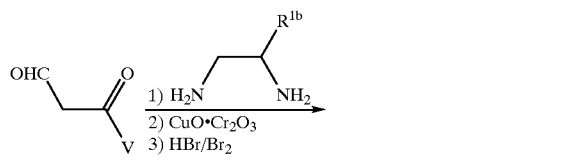

Schemes 52 and 53 describe the synthesis of compounds wherein M is a 1,2,3-triazine. In Scheme 52, a vinyl bromide is palladium coupled to a molecule containing the substituent R$^{1b}$. Allylic bromination followed by azide displacement provide the cyclization precursor. Triphenylphosphine-mediated cyclization (*J. Org. Chem.* 1990, 55, 4724) give Scheme 52

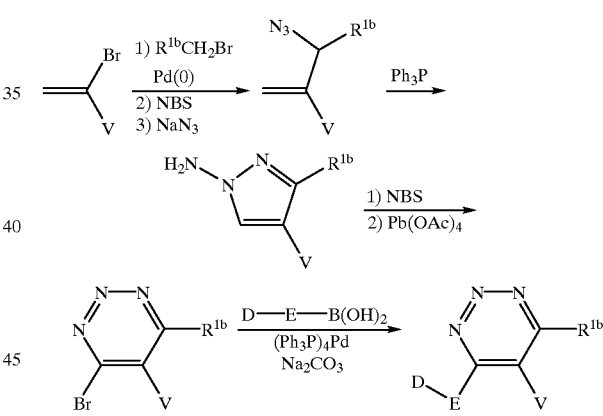

In Scheme 53, an alkene is allylically brominated and the bromide is displaced to give a regioisomer of the azide in Scheme 52. Following the same reaction sequence as shown above, cyclization provides the 1-aminopyrazole. Bromination followed by lead tetraacetate mediated rearrangement give the 1,2,3-triazine. Palladium-catalyzed coupling provides the other desired triazine.

Scheme 53

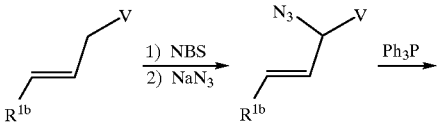

-continued

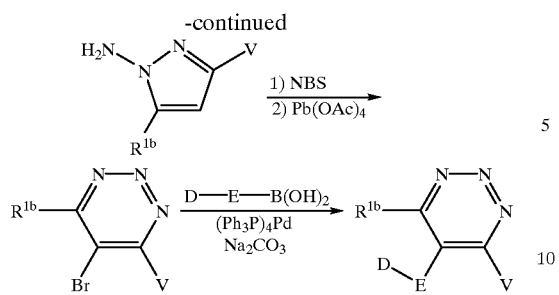

Schemes 54 and 55 describe the synthesis of compounds wherein M is a 1,2,4-triazine. In Scheme 54, a nitrile is converted using hydrazine to give the amidrazone which is condensed with a α-ketoester to give the triazinone as shown by Paudler and Lee (*J. Org. Chem.* 1971, 36, 3921). Bromination as shown by Rykowski and van der Plas (*J. Org. Chem.* 1987, 52, 71) followed by palladium-catalyzed coupling provides the desired 1,2,4-triazine.

Scheme 54

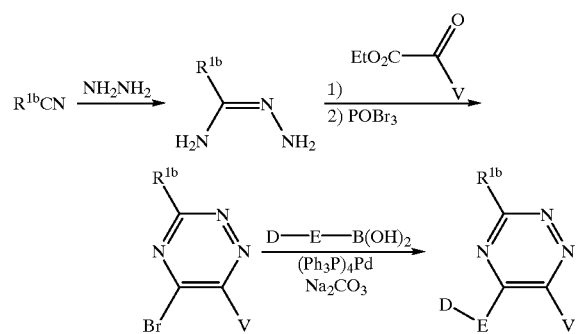

In Scheme 55, to achieve the opposite regioisomer the reaction scheme shown above is modify by the substituting a protect α-ketoester. This allows the most nucleophilic nitrogen to attack the ester functionality setting up the opposite regiochemistry. Deprotection and thermal cyclization gives the triazinone which is brominated as shown above. Palladium-catalyzed coupling provides the other desired 1,2,4-triazine.

Scheme 55

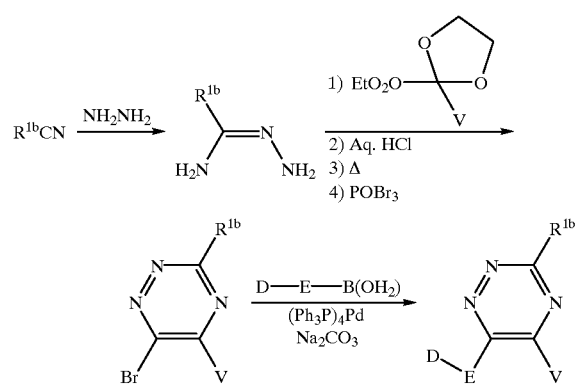

Scheme 56 describes the synthesis of compounds wherein M is a 1,2,3,4-tetrazine. Lithiation of a vinyl bromide, transmetallation with tin, palladium catalyzed carbonylation and hydrazone formation provides a diene for a subsequent Diels-Alder reaction as shown by Carboni and Lindsey (*J. Am. Chem. Soc.* 1959, 81, 4342). Reaction with dibenzyl azodicarboxylate followed by catalytic hydrogenation to debenzylate and decarboxylate should give after bromination the desired 1,2,3,4-tetrazine. Palladium-catalyzed coupling provides the desired substitution.

Scheme 56

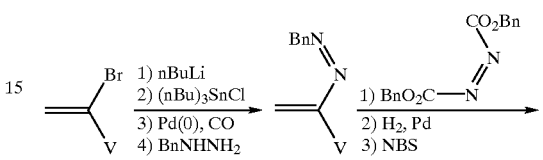

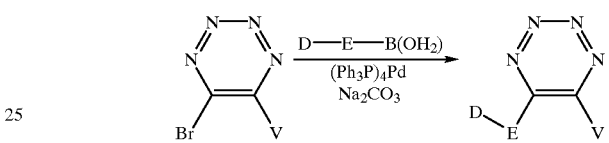

Compounds of this invention where B is either a carbocyclic or heterocyclic residue as defined in Formula I are coupled to A as shown generically and by specific example in Scheme 57, either or both of A and B may be substituted with 0–2 $R^4$. W is defined as a suitable protected nitrogen, such as $NO_2$ or NHBOC; a protected sulfur, such as S-tBu or SMOM; or a methyl ester. Halogen-metal exchange of the bromine in bromo-B with n-butyl lithium, quenching with triisopropyl borate and acidic hydrolysis should give the required boronic acid, B'—B(OH)2. The W-A-Br subunit may be already linked to ring M before the Susuki coupling reaction. Deprotection can provide the complete subunit.

Scheme 57

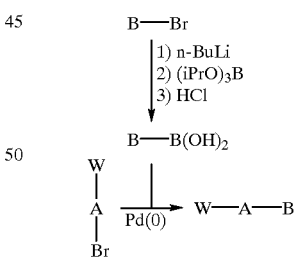

Scheme 58 describes a typical example of how the A-B subunit can be prepared for attachment to ring M. 4-Bromoaniline can be protected as Boc-derivative and the coupled to 2-(t-butylamino)sulfonylphenylboronic acid under Suzuki conditions. 2-(t-Butylamino) sulfonylphenylboronic acid can be prepared by the method described by Rivero (*Bioorg. Med. Chem. Lett.* 1994, 189). Deprotection with TFA can provide the aminobiphenyl compound. The aminobiphenyl can then be coupled to the core ring structures as described below.

Scheme 58

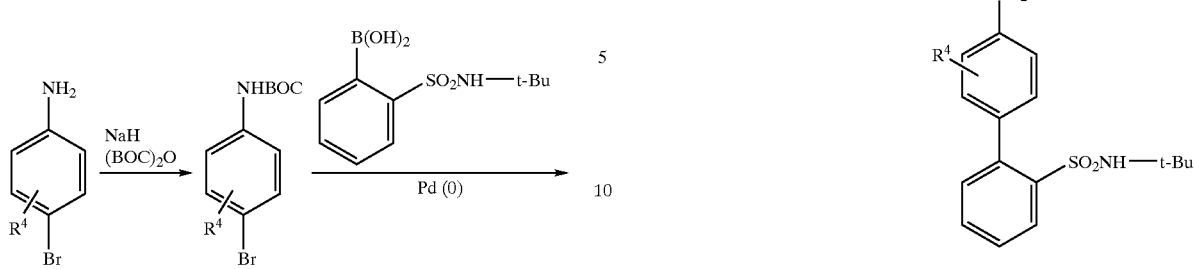

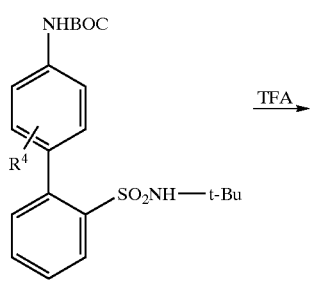

For N-substituted heterocycles, Scheme 59 shows how the boronic acid can be formed by a standard literature procedure (Ishiyama, T.; Murata, M.; and Miyaura, N. *J. Org. Chem.* 1995, 60, 7508–7510). Copper-promoted C—N bond coupling of the boronic acid and heterocycle can be performed as described (Lam, P. Y. S.; et. al., *Tet. Lett.* 1998, 39, 2941–2944). It is preferrable to use boroxine or unhindered borate as the boron source. The acid obtained can be condensed with H-A-B' and after deprotection yields the desired product.

Scheme 59

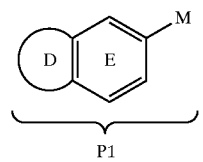

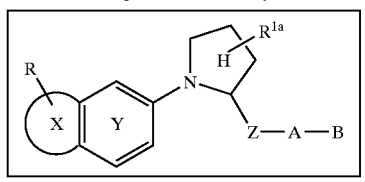

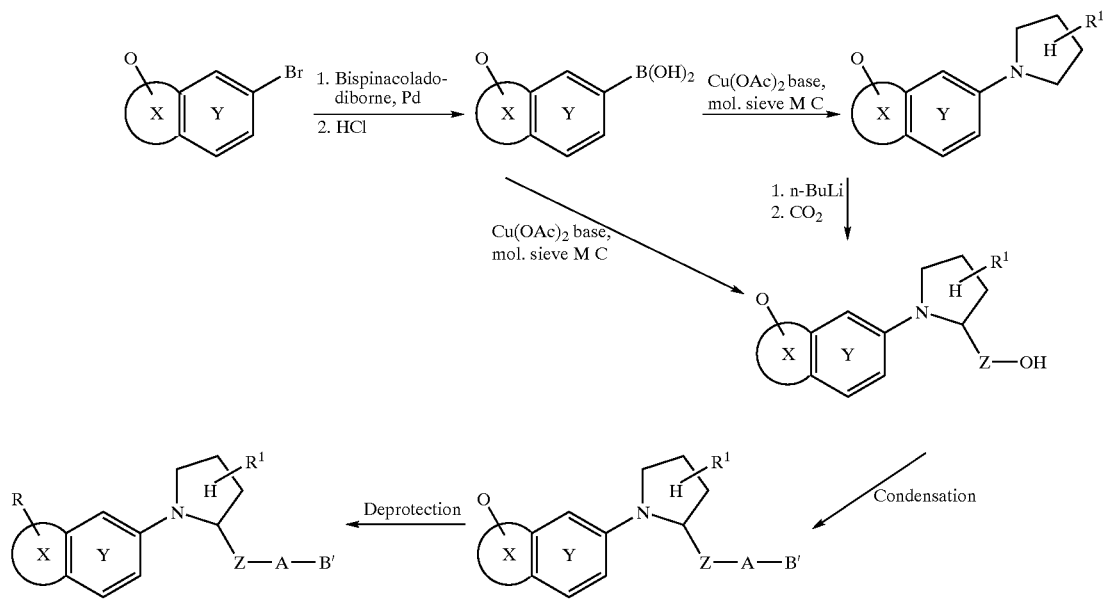

A synthetic route for making aminobenzisoxazole derivatives with an imidazole core is shown in Scheme 60. Palladium(0)-catalyzed cross-coupling reaction of an alkoxydiboron (pinacol diborate) with a haloarene (see, Ishiyama et al, *J. Org. Chem.* 1995, 60, 7508–7510) should afford an arylborate intermediate, which can be hydrolyzed with 4M HCl (10 eq.) in a minimum amount of THF at room temperature to give arylboronic acid. 4-Imidazolecarboxylic acid can be converted to 4-trifluoromethylimidazole by reacting with $SF_4$ (3 eq.) and HF (7.5 eq.) in a shaker tube at 40° C. Copper(II)-catalyzed coupling reaction of arylboronic acid with 4-trifluoromethylimidazole in the presence of pyridine (5 eq.) and 4 Å molecular sieves in THF should provide 1-aryl-4-trifluoromethylimidazole. Lithiation of the imidazole with n-BuLi, followed by quenching with methylchloroformate, can give 1-aryl-4-trifluoromethyl-1H-imidazole-5-methylcarboxylate. Nucleophilic replacement of fluorobenzene with pre-mixed potassium tert-butoxide and acetone oxime followed by treatment with 20% HCl in ethanol can form 1-aminobenzisoxazole-4-trifluoromethyl-1H-imidazole-5-methylcarboxylate. The ester may then be converted to an amide by a Weinreb coupling reaction. Alternatively, after the saponification of the ester in aqueous NaOH in THF, the resulting acid can be converted to the corresponding acyl chloride upon treatment with $SOCl_2$ or oxalyl chloride, followed by reacting with aniline containing an o-substituent to form an amide. Fluorobenzene can similarly be converted to aminobenzisoxazole derivative by treatment with pre-mixed potassium tert-butoxide and acetone oxime, followed by reaction with 20% HCl in ethanol. The ester can also be saponified in aqueous NaOH in THF to give an acid, which then can be coupled with aniline to give amide via a coupling reagent (ex. PyBrop) under basic conditions.

Scheme 60

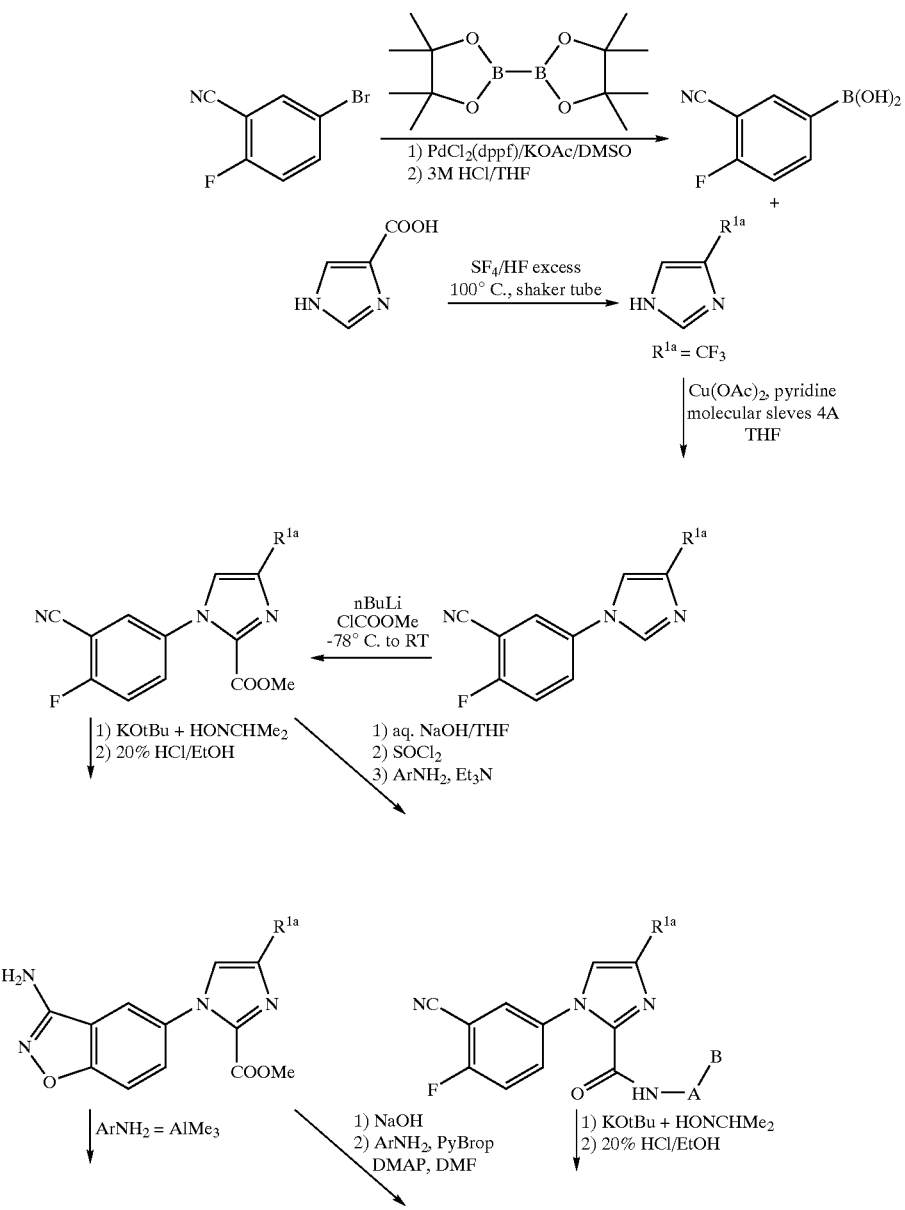

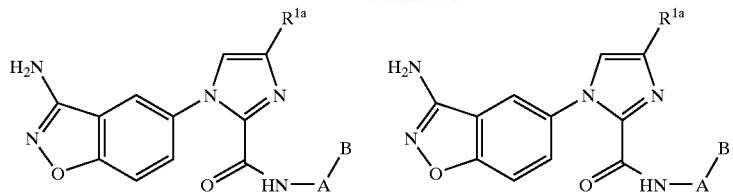

o-Fluorobenzonitrile derivatives with imidazole core can be converted to 1-aminoquinazoline-1H-imidazole derivatives by treatment with formamidine salt in pyridine and ethanol (Scheme 61).

Scheme 61

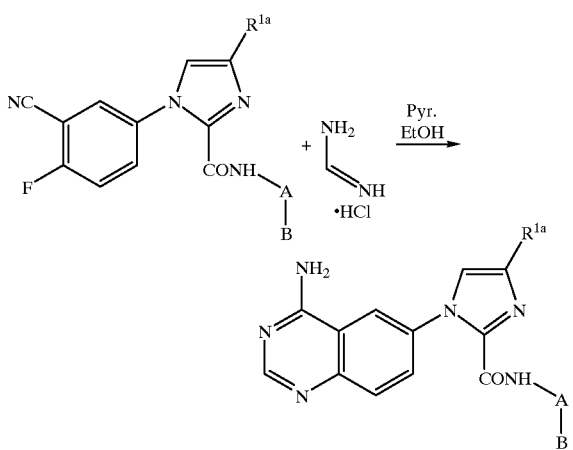

Scheme 62 illustrates the preparation of bicyclic core intermediates leading to compounds with indazole and indole cores. Compounds of the general type can be obtained by the method outlined in Chem. Ber. (1926) 35–359. The pyrazole N-oxide can be reduced by any number of methods including triphenylphosphine in refluxing toluene followed by the hydrolysis of the nitrile substituent to a carboxylic acid with basic hydrogen peroxide to give indazole intermediate which may be coupled in the usual way to give indazole product. Indole intermediate may be obtained via the Fischer Indole Synthesis (Org. Syn, Col. Vol. III 725) from an appropriately substituted phenylhydrazine and acetophenone. Further elaboration using standard synthetic methods including the introduction of a 3-formyl group by treatment with $POCl_3$ in DMF, the optional protection of the indole NH with the Sem group ($TMSCH_2CH_2OCH2Cl$, NaH, DMF) and oxidation of the aldehyde to a carboxylic acid which is now ready for transformation to indole product.

Scheme 62

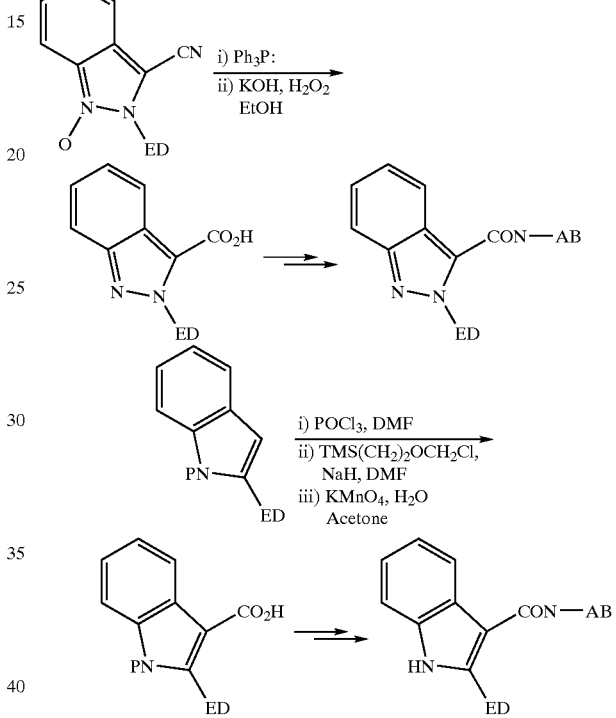

When B is defined as X—Y, the following description applies. Groups A and B are available either through commercial sources, known in the literature or readily synthesized by the adaptation of standard procedures known to practioners skilled in the art of organic synthesis. The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE A

Preparation of Amide, Ester, Urea, Sulfonamide and Sulfamide linkages between A and B.

| Rxn. No. | if A contains: | then the reactive substituent of Y is: | to give the following product A—X—Y: |
|---|---|---|---|
| 1 | A—$NHR^2$ as a substituent | ClC(O)—Y | A—$NR^2$—C(O)—Y |

TABLE A-continued

Preparation of Amide, Ester, Urea, Sulfonamide and Sulfamide linkages between A and B.

| Rxn. No. | if A contains: | then the reactive substituent of Y is: | to give the following product A—X—Y: |
|---|---|---|---|
| 2 | a secondary NH as part of a ring or chain | ClC(O)—Y | A—C(O)—Y |
| 3 | A—OH as a substituent | ClC(O)—Y | A—O—C(O)—Y |
| 4 | A—NHR$^2$ as a substituent | ClC(O)—CR$^2$R$^{2a}$—Y | A—NR$^2$—C(O)—CR$^2$R$^{2a}$—Y |
| 5 | a secondary NH as part of a ring or chain | ClC(O)—CR$^2$R$^{2a}$—Y | A—C(O)—CR$^2$R$^{2a}$—Y |
| 6 | A—OH as a substituent | ClC(O)—CR$^2$R$^{2a}$—Y | A—O—C(O)—CR$^2$R$^{2a}$—Y |
| 7 | A—NHR$^3$ as a substituent | ClC(O)NR$^2$—Y | A—NR$^2$—C(O)NR$^2$—Y |
| 8 | a secondary NH as part of a ring or chain | ClC(O)NR$^2$—Y | A—C(O)NR$^2$—Y |
| 9 | A—OH as a substituent | ClC(O)NR$^2$—Y | A—O—C(O)NR$^2$—Y |
| 10 | A—NHR$^2$ as a substituent | ClSO$_2$—Y | A—NR$^2$SO$_2$—Y |
| 11 | a secondary NH as part of a ring or chain | ClSO$_2$—Y | A—SO$_2$—Y |
| 12 | A—NHR$^2$ as a substituent | ClSO$_2$—CR$^2$R$^{2a}$—Y | A—NR$^2$—SO$_2$—CR$^2$R$^{2a}$—Y |
| 13 | a secondary NH as part of a ring or chain | ClSO$_2$—CR$^2$R$^{2a}$—Y | A—SO$_2$—CR$^2$R$^{2a}$—Y |
| 14 | A—NHR$^2$ as a substituent | ClSO$_2$—NR$^2$—Y | A—NR$^2$—SO$_2$NR$^2$—Y |
| 15 | a secondary NH as part of a ring or chain | ClSO$_2$—NR$^2$—Y | A—SO$_2$—NR$^2$—Y |
| 16 | A—C(O)Cl | HO—Y as a substituent | A—C(O)—O—Y |
| 17 | A—C(O)Cl | NHR$^2$—Y as a substituent | A—C(O)—NR$^2$—Y |
| 18 | A—C(O)Cl | a secondary NH as part of a ring or chain | A—C(O)—Y |
| 19 | A—CR$^2$R$^{2a}$C(O)Cl | HO—Y as a substituent | A—CR$^2$R$^{2a}$C(O)—O—Y |
| 20 | A—CR$^2$R$^{2a}$C(O)Cl | NHR$^2$—Y as a substituent | A—CR$^2$R$^{2a}$C(O)—NR$^2$—Y |
| 21 | A—CR$^2$R$^{2a}$C(O)Cl | a secondary NH as part of a ring or chain | A—CR$^2$R$^{2a}$C(O)—Y |
| 22 | A—SO$_2$Cl | NHR$^2$—Y as a substituent | A—SO$_2$—NR$^2$—Y |
| 23 | A—SO$_2$Cl | a secondary NH as part of a ring or chain | A—SO$_2$—Y |
| 24 | A—CR$^2$R$^{2a}$SO$_2$Cl | NHR$^2$—Y as a substituent | A—CR$^2$R$^{2a}$SO$_2$NR$^2$—Y |
| 25 | A—CR$^2$R$^{2a}$SO$_2$Cl | a secondary NH as part of a ring or chain | A—CR$^2$R$^{2a}$SO$_2$—Y |

The chemistry of Table A can be carried out in aprotic vents such as a chlorocarbon, pyridine, benzene or toluene, temperatures ranging from −20° C. to the reflux point of the vent and with or without a trialkylamine base.

TABLE B

Preparation of ketone linkages between A and B.

| Rxn. No. | if A contains: | then the reactive substituent of Y is: | to give the following product A—X—Y: |
|---|---|---|---|
| 1 | A—C(O)Cl | BrMg—Y | A—C(O)—Y |
| 2 | A—CR$^2$R$^{2a}$C(O)Cl | BrMg—Y | A—CR$^2$R$^{2a}$$_2$C(O)—Y |
| 3 | A—C(O)Cl | BrMgCR$^2$R$^{2a}$—Y | A—C(O)CR$^2$R$^{2a}$—Y |
| 4 | A—CR$^2$R$^{2a}$C(O)Cl | BrMgCR$^2$R$^{2a}$—Y | A—CR$^2$R$^{2a}$C(O)CR$^2$R$^{2a}$—Y |

The coupling chemistry of Table B can be carried out by a variety of methods. The Grignard reagent required for Y is prepared from a halogen analog of Y in dry ether, dimethoxyethane or tetrahydrofuran at 0° C. to the reflux point of the solvent. This Grignard reagent can be reacted directly under very controlled conditions, that is low temeprature (−20° C. or lower) and with a large excess of acid chloride or with catalytic or stoichiometric copper bromide.dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al. (*Tetr. Lett.* 1984, 4805), or a coupling mediated by manganese (II) catalysis (Cahiez and Laboue, *Tetr. Lett.* 1992, 33(31), 4437).

TABLE C

Preparation of ether and thioether linkages between A and B

| Rxn. No. | if A contains: | then the reactive substituent of Y is: | to give the following product A—X—Y: |
|---|---|---|---|
| 1 | A—OH | Br—Y | A—O—Y |
| 2 | A—CR$^2$R$^{2a}$—OH | Br—Y | A—CR$^2$R$^{2a}$O—Y |
| 3 | A—OH | Br—CR$^2$R$^{2a}$—Y | A—OCR$^2$R$^{2a}$—Y |
| 4 | A—SH | Br—Y | A—S—Y |
| 5 | A—CR$^2$R$^{2a}$—SH | Br—Y | A—CR$^2$R$^{2a}$S—Y |
| 6 | A—SH | Br—CR$^2$R$^{2a}$—Y | A—SCR$^2$R$^{2a}$—Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE D

Preparation of —SO— and —SO2— linkages from thioethers of Table 3.

| Rxn. No. | if the starting material is: | and it is oxidized with Alumina (wet)/Oxone (Greenhalgh, Synlett, (1992) 235) the product is: | and it is oxidized with m-chloroperbenzoic acid (Satoh et al., Chem. Lett. (1992) 381), the product is: |
|---|---|---|---|
| 1 | A—S—Y | A—S(O)—Y | A—SO$_2$—Y |
| 2 | A—CR$^2$R$^{2a}$S—Y | A—CR$^2$R$^{2a}$S(O)—Y | A—CR$^2$R$^{2a}$SO$_2$—Y |
| 3 | A—SCR$^2$R$^{2a}$—Y | A—S(O)CR$^2$R$^{2a}$—Y | A—SO$_2$CR$^2$R$^{2a}$—Y |

The thioethers of Table C serve as a convenient starting material for the preparation of the sulfoxide and sulfone analogs of Table D. A combination of wet alumina and oxone can provide a reliable reagent for the oxidation of the thioether to the sulfoxide while m-chloroperbenzoic acid oxidation will give the sulfone.

Other features of the invention will become apparent in the course of the following descriptions of exemplary embodiments which are given for illustration fo the invention and are not intended to be limiting thereof.

EXAMPLES

Example 1

1-(1'-Amino-isoquinol-7'-yl)-3-methyl-5-[(2'-aminosulfonyl-[1,1']-biphen-4-yl)carbonylamino] pyrazole, mesylate salt 7-Aminoisoquinoline (6.26 g, 43.4 mmol) (*J. Chem. Soc.* 1951, 2851) is added to 40 mL of concentrated hydrochloric acid at 0° C. Sodium nitrite (3.0 g, 43.4 mmol) is dissolved in 15 mL water, cooled to 0° C., and added dropwise to the isoquinoline solution. The reaction is stirred for 30 min at 0° C. Stannous chloride dihydrate (29.3 g, 130.2 mmol, 3 eq) is dissolved in 25 mL concentrated hydrochloric acid, the solution cooled to 0° C., and added dropwise to the isoquinoline solution. The reaction is placed in the refrigerator overnight. The next day the precipitate is isolated by filtration, washed with 100 mL ice cold brine followed by 100 mL of a 2:1 petroleum ether/ethyl ether solution. The brown solid is dried under dynamic vacuum overnight. The tin double salt of the isoquinoline (9.0 g, 26 mmol) is suspended in 100 mL glacial acetic acid and ethyl 2,4-dioxopentanoate oxime (4.0 g, 21.3 mmol) added dropwise. The reaction was brought to reflux overnight. The next day the acetic acid was evaporated and to the residue was added 100 mL water, cooled to 0° C. and neutralized with solid sodium bicarbonate. The solution was extracted with ethyl acetate (6×50 mL), dried over sodium sulfate, and evaporated to give the title compound as a brownish solid (5.15 g, 86% yield) which was >85% of the desired pyazole regioisomer. The material may be purified by silica gel flash chromatography eluting with 5% methanol in chloroform: $^1$H NMR (CDCl$_3$) δ 1.24 (t, 3H, J=7.1 Hz, OCH$_2$CH$_3$), 2.40 (s, 3H, pyrazole CH$_3$), 4.24 (q, 2H, J=7.1 Hz, OCH$_2$CH$_3$), 6.89 (s, 1H pyrazole H), 7.70 (d, 1H, J=5.9 Hz, H$_4$), 7.75 (dd, 1H, J=8.8 Hz, J=2.2 Hz, H6), 7.89 (d, 1H, J=8.8 Hz, H5), 8.05 (d, 1H, J=2.0 Hz, H7), 8.58 (s, 1H, J=5.9 Hz, H3), 9.29 (s, 1H, H1), MS (ES+): 282.1 (M+H)$^+$ (100%), C$_{30}$H$_{29}$N$_5$O$_3$S 539.65.

To a solution of 2'-tert-butylaminosulfonyl-[1,1']-biphenyl-4-ylamine (2.19 g, 7.19 mmol) in 100 mL of anhydrous dichloromethane under an atmosphere of nitrogen was added dropwise trimethyl aluminium (10.9 mL, 21.6 mmol, 2M in hexane). The solution was stirred for 30 min at ambient temperature. Ethyl 1-(isoquinolyn-7'-yl)-3-methyl-5-pyrazole carboxylate (2.02 g, 7.19 mmol) in 70 mL of anhydrous dichloromethane was added dropwise and the reaction warmed to 40° C. and allowed to stir for 15 hours. The reaction was quenched with 50 mL 1N hydrochloric acid at 0° C., diluted with 50 mL water and made basic with solid sodium carbonate. The phases are separated and the aqueous extracted with dichloromethane (3×30 mL), dried over sodium sulfate, and evaporated to give the amide (3.50 g, 90% yield) as a brown solid and of sufficient purity for the next step. The material may be purified by silica gel flash chromatography eluting with 5% methanol in chloroform. MS (ES+): 540.22 (M+H)$^+$ (100%). The amide was dissolved in 60 mL acetone to which was added meta-chloroperbenzoic acid (70%) (1.86 g, 7.55 mmol) and the reaction allowed to stir overnight at ambient temperature. The next day the solvent was removed under reduced pressure and the residue taken up in 100 mL each of ethyl acetate and saturated sodium bicarbonate. The phases are separated and the organic dried over sodium sulfate, and evaporated to give the N-oxide as a pale red solid in quantitative yield and of sufficient purity for the next step. MS (ES+): 556.20 (M+H)$^+$ (15%); 578.21 (M+Na)$^+$ (100%).

The N-oxide was dissolved in 110 mL of anhydrous pyridine and tosyl chloride (1.64 g, 8.63 mmol) was added in three equal portions and the reaction allowed to stir at ambient temperature overnight. The pyridine was removed under reduced pressure and to the residue was added 45 mL ethanolamine and the reaction stirred at ambient temperature for 2 days. The reaction was poured onto cracked ice and the solids isolated by filtration and dried under vacuum to yield 2.33 g (65% yield) of a mixture of 1-aminoisoquinoline (major) and 4-aminoisoquinoline (minor) products as a tan solid. MS (ES+) 555.22 (M+H)$^+$ (100%), HRMS (FAB+) for $C_{30}H_{30}N_6O_3S$ calc. (M+H)$^+$ 555.217836; found 555.21858.

To 20 mL of trifluoroactic acid was added the 1-aminoisoquinoline compound and the reaction brought to reflux overnight. The next day the solvent was removed under reduced pressure and the residue made basic with aqueous sodium carbonate cooled to 0° C., extracted with ethyl acetate (3×40 mL), dried over sodium sulfate, and evaporated. The tan solid was purified by silica gel flash column chromatography eluting with 15% MeOH/CHCl$_3$ to give 1.60 g (76% yield) of the title compound as a light tan solid. MS (ES+) 499.14 (M+H)$^+$ (100%), HRMS (FAB+) for $C_{26}H_{22}N_6O_3S$ calc. (M+H)$^+$ 499.155236; found 499.153551.

The product was then treated with one equivalent of methane sulfonic acid in THF. Evaporation of the solvent gave Example 1, MS (ES+) 499.0 (M+H)$^+$ (100%), mp 195° C.

Example 2

1-(1'-Amino-isoquinol-7'-yl)-3-methyl-5-[(2'-methylsulfonyl-[1,1']-biphen-4-yl)carbonylamino]pyrazole mesylate The title compound was prepared analogously to Example 1. MS (ES+) 498.0 (M+H)$^+$ (100%), mp 175° C.

Example 3

1-(4'-Amino-isoquinol-7'-yl)-3-methyl-5-[(2'-aminosulfonyl-[1,1']-biphen-4-yl)carbonylamino]pyrazole The title compound was prepared analogously to Example 1. MS (ES+) 499.0 (M+H)$^+$ (100%), mp 204° C.

Example 4

1-(Isoquinol-7'-yl)-3-methyl-5-[(2'-aminosulfonyl-[1,1']-biphen-4-yl)carbonylamino]pyrazole The title compound was prepared analogously to Example 1. MS (ES+) 484.1 (M+H)$^+$ (100%).

Example 5

3-(1'-Amino-isoquinol-7'-yl)-5-[(2'-aminosulfonyl-[1,1']-biphen-4-yl)carbonylamino]-5-methylisoxazoline The title compound was prepared analogously to Example 1. MS (ES+) 502.3 (M+H)$^+$ (100%).

Example 6

3-(Isoquinol-5'-yl)-5-[(2'-aminosulfonyl-[1,1']-biphen-4-yl)carbonylamino]-5-methylisoxazoline The title compound was prepared analogously to Example 1. MS (ES+) 487.3 (M+H)$^+$ (100%).

Example 7

3-(Isoquinol-7'-yl)-5-[(2'-aminosulfonyl-[1,1']-biphen-4-yl)carbonylamino]-5-methylisoxazoline The title compound was prepared analogously to Example 1. MS (ES+) 487.3 (M+H)$^+$ (100%).

Example 8

3-(2'-Aminobenzimidazol-5'-yl)-5-[(2'-aminosulfonyl-[1,1']-biphen-4-yl)aminocarbonyl]-5-methylisoxazoline To a solution of methyl 3,4-diaminobenzoate (7.50 g) in methanol (225 mL) was added N,N'-dicarbobenzyloxy methyl isothiourea (16.20 g). The reaction mixture was brought to reflux for 4 h. Heat was removed and the mixture was allowed to cool. The stirring was continued at rt for overnight. The precipitate was filtered and washed with ether (40 mL) and air dried to give 2-benzyloxycarbonyl-amino-5-methoxycarbonylbenzimidazole (9.80 g) as a purple solid. ESI mass spectrum z (rel. intensity) 326 (M+H. 100).

A suspension of benzimidazole (1.58 g) in methylene chloride (40 mL) was cooled to −78° C. DIBAL (1.0 M in CH$_2$Cl$_2$, 21.87 mL) was added via syringe. The reaction mixture was stirred at −78° C. for 1.5 h. and slowly warmed up to rt. The reaction was quenched with methanol (2 mL), HCl (5%, 2 mL). The solvent was removed and the residue partitioned between ethyl acetate (60 mL) and water (60 mL), washed with water (2×40 mL), brine (40 mL); dried over sodium sulfate, to give 2-benzyloxycarbonylamino-5-hydroxymethylbenzimidazole (1.2 g). ESI mass spectrum z (rel. intensity) 298 (M+H, 100).

To a solution of pyridine (3.83 g) in methylene chloride (30 mL) was added CrO$_3$ (2.42 g). The mixture was stirred at rt for 45 minutes followed by addition of a solution of 2-benzyloxycarbonylamino-5-hydroxymethylbenzimida-zole (1.2 g) in methylene chloride (20 mL) and DMF (10 mL). The reaction mixture was stirred at rt for 2.5 h. Two thirds of the solvent was removed and the residue was partitioned between ethyl acetate and sodium bicarbonate (sat.), washed with KHSO$_4$ (5% in H$_2$O), water and brine; dried over sodium sulfate to give aldehyde (0.95 g). ESI mass spectrum z (rel. intensity) 296 (M+H, 100).

To a solution of aldehyde (0.50 g) in ethanol was added a solution of hydroxyamine hydrochloride (0.15 g) in water(5 mL) and a solution of sodium acetate (0.28 g) in water (5 mL). The reaction nixture was stirred at rt overnight. Next day, ethanol was removed and the white precipitate was filtered, washed with water and air dried to give the oxime (0.50 g). ESI mass spectrum z (rel. intensity) 311 (M+H, 100).

To a solution of 2-benzyloxycarbonylamino-5-oximebenzimidazole (0.31 g) in THF (50 mL) was added methyl acrylic acid (0.11 g), to this mixture was added bleach (5.25%, 2.4 mL) dropwise at 0° C. under stirring. After addition of bleach, the stirring was continued at rt overnight. Most of the solvent was removed and the mixture was partitioned between ethyl acetate and water. The organic was separated and washed with water, brine; dried over sodium sulfate. The resulting solid was recrystallized using methylene chloride/hexane (1:1) to give isoxazoline (0.25 g) as a pure compound. ESI mass spectrum z (rel. intensity) 395 (M+H, 100).

To a solution of isoxazoline (100 mg) in DMF (5 mL) was added triethylamine (39 mg), (2'-tert-butylaminosulfonyl-[1,1']-biphenyl-4-yl)amine (115 mg) and BOP (168 mg). The reaction mixture was stirred at 55° C. overnight. Next day, the mixture was partitioned between ethylacetate (25 mL) and water (25 mL), washed with HCl (5%, 4×10 mL), sodium bicarbonate (5%, 2×10 mL), water (2×10 mL) and brine (10 mL); dried over sodium sulfate, filtered and concentrated to leave 3-(2-benzyloxycarbonylamino-5-yl)-5-[(2'-tert-butylaminosulfonyl-[1,1']-biphenyl-4-yl) aminocarbonyl]-5-methylisoxazoline (120 mg). ESI mass spectrum z (rel. intensity) 681 (M+H, 100).

3-(2-Benzyloxycarbonylamino-5-yl)-5-[(2'-tert.butylaminosulfonyl-[1,1']-biphen-4-yl)aminocarbonyl]-5-methylisoxazoline (100 mg) was dissolved in TFA (4 mL). The resulting solution was brought to reflux for 3 h., cooled to room temperature, stripped off TFA, partitioned between ethylacetate and sodium bicarbonate (5%), washed with water, dried over sodium sulfate, filtered and concentrated. Prep. TLC gave pure title compound (35 mg). ESI mass spectrum z (rel. intensity) 491 (M+H, 100), mp 162° C.

Example 9

3-(3'-Aminoindazol-5'-yl)-5-[(2'-aminosulfonyl-[1,1']-biphen-4-yl)aminocarbonyl]-5-methylisoxazoline To a solution of 2-fluoro-5-methylbenzonitrile (13.50 g) in $CCl_4$ (500 mL) was added NBS (35.60 g) and benzoylperoxide (2.40 g). The reaction mixture was brought to reflux for 16 h. Heat was removed and allow it to cool. The mixture was filtered through silic gel, filtrate was concentrated to give a 5:1 mixture (25 g) of 2-fluoro-5-bis-bromomethylbenzonitrile and 2-fluoro-5-bromomethylbenzonitrile.

The mixture (25 g) was dissolved in formic acid (85% in water, 200 mL). The resulting solution was refluxed for 4.5 h. After allowing the reaction mixture to cool to room temperature, most of the formic acid was stripped off, sodium bicarbonate was added to quench the remaining acid, it was partitioned between ethylacetate and sodium bicarbonate (sat.), washed with water and brine, dried over sodium sulfate, filtered and concentrated, flash chromatography (10% EtOAc in hexane) to give 3-cyano-4-fluorobenzaldehyde (12 g) as a white crystal. $^1$H NMR ($CDCL_3$) δ 10.0 (s,1H), 8.15–8.24 (m, 2H), 7.42 (t, 1H) ppm; CI mass spectrum z (rel. intensity) 150 (M+H, 100).

To a solution of 3-cyano-4-fluorobenzaldehyde (1.49 g) in benzene was added 1,3-propanediol (0.91 g) and toluenesulfonic acid (0.20 g). The mixture was brought to reflux for 3 hr. with a water trap. After cooling, it was partitioned between ethylacetate and water, washed with sodium bicarbonate (15% in water), water, brine and water; dried over sodium sulfate, filtered and concentrated to give ketal (1.80 g); $^1$H NMR ($CDCL_3$) δ 7.69–7.80 (m, 2H), 7.20 (t, 1H), 5.48 (s, 1H), 4.24–4.30 (m, 2H), 3.95–4.04 (m, 2H), 2.12–2.28 (m, 1H), 1.45–1.52 (m, 1H) ppm; CI mass spectrum z (rel. intensity) 207 (M+H, 100).

To a solution of ketal (0.6 g) in n-butanol (10 mL) was added hydrazine monohydrate (1.45 g). The reaction mixture was brought to reflux for 3 hr, cooled to room temperature, quenched with pH 5 buffer solution, partitioned between methylene chloride and water. The organic phase was separated and washed with $NH_4Cl$ (sat.), 3×$H_2O$, dried over sodium sulfate, filtered and concentrated to give ketal (0.45 g). CI mass spectrum z (rel. intensity) 220 (M+H, 100).

To a solution of ketal (0.42 g) in methylene chloride was added TEA (1.6 mL) and di-tert-butyl-dicarbonate (2.4 g). The mixture was stirred at room temperature overnight. The mixture was partitioned between methylene chloride and water, washed with pH 5 buffer solution, water and brine; dried over sodium sulfate and concentrated to give 1-tert-butoxycarbonyl-3-tert-butoxyaminoindazole-5-aldehydedioxane (0.55 g). CI mass spectrum z (rel. intensity) 420 (M+H, 100).

To a solution of indazole (0.55 g) in acetone (10 mL) was added toluene sulfonic acid (100 mg). The reaction mixture was stirred at rt for 2 h. Acetone was removed and the residue was partitioned between ethyl acetate and water, washed with 2×$H_2O$, brine and dried over sodium sulfate. Flash chromatography gave 1-tert-butoxycarbonyl-3-tert-butoxycarbonylamino-5-hydrogencarbonylindazole (0.3 g). CI mass spectrum z (rel. intensity) 362 (M+H, 100).

To a solution of indazole (0.30 g) in ethanol (6 mL) was added a solution of hydroxyamine hydrochloride (0.07 g) in water (1 mL) and another solution of sodium acetate (0.14 g) in water (1 mL). The mixture was stirred at rt overnight. Ethanol was removed and the resulting solid was filtered, washed with water and air dried to give aldoxime.

To a solution of aldoxime (0.22 g) in THF was added 2-methyacrylic acid (0.06 g) followed by dropwise addition of bleach (1.4 mL) at 0° C. with vigorous stirring. After the addition, reaction mixture was slowly warmed to rt and stirred at rt overnight. Partitioned between ethylacetate and HCl (5%), washed with 3×$H_2O$, dried over sodium sulfate, filtered and concentrated, flash chromatography to give isoxazoline (0.14 g).

To a solution of isoxazoline (0.14 g) in DMF (6 mL) was added 2'-tert-butylaminosulfonyl-[1,1']-biphenyl-4-ylamine (0.14 mg), TEA (0.05 g) and BOP reagent (0.2 g). The mixture was stirred at 50° C. overnight; partitioned between ethylacetate and water, washed with brine, 4×water, dried over sodium sulfate, filtered, concentrated and flash chromatographed to give an isoxazoline (0.06 g). ESI mass spectrum z (rel. intensity) 747 (M+H, 100).

The isoxazoline (0.06 g) was dissolved in TFA (5 mL). The resulting solution was brought to reflux for 1.5 h. The mixture was stripped off TFA, partitioned between ethylacetate and sodium bicarbonate (5%), washed with 2×water, dried over sodium sulfate, filtered and concentrated. Prep. TLC afforded example 9 (5 mg). ESI mass spectrum z (rel. intensity) 491 (M+H, 100), mp 157–159° C.

Example 10

3-(3'-Aminobenzisoxazol-5'-yl)-5-[(2'-aminosulfonyl-[1,1']-biphen-4-yl)aminocarbonyl]-5-methylisoxazoline To a solution of 3-cyano-4-fluorobenzaldehyde (2.50 g) in ethanol (40 mL) was added a solution of hydroxyamine (1.46 g) in water (10 mL), a solution of sodium acetate (2.75 g) in water (10 mL). The mixture was stirred at rt, overnight. Ethanol was removed and the white precipitate was filtered, washed with water and air dried to leave 3-cyano-4-fluorobenzaldehydeoxime (2.05 g). CI mass spectrum z (rel. intensity) 165 (M+H, 100).

To a solution of 3-cyano-4-fluorobenzaldoxime (2.50 g) in THF (100 mL) was added 2-methylacrylic acid (1.64 g). The mixture was cooled to 0° C. on an ice bath followed by dropwise addition of NaOCl (5.25% in water) (37 mL) with vigourous stirring. After the addition, the reaction mixture was slowly warmed up to rt and stirred at rt overnight. The mixture was partitioned between ethylacetate and HCl (5% in water), washed with brine, $2\times H_2O$, dried over sodium sulfate, filtered and concentrated. The resulting solid was recrystalized to give 3-(4-fluoro-3-cyanophenyl-1-yl)-5-methyl-5-hydroxycarbonylisoxazoline (3.30 g) as a pure compound. $^1$H NMR (DMSO-$d_6$) δ 13.6 (br, 1H), 8.20 (dd, 1H), 8.10 (td, 1H), 3.84 (d, 1H), 3.41 (d, 1H), 1.57 (s, 3H) ppm; ESI mass spectrum z (rel. intensity) 247 (M–H, 100).

To a solution of acetone oxime (2.60 g) in DMF (10 mL) was added potassium tert-butoxide (1.0 M in THF, 2.6 mL) via syringe. The mixture was stirred at rt 10 minutes, a solution of 3-(4-fluoro-3-cyanophen-1-yl)-5-methyl-5-hydroxycarbonylisoxazoline (0.5 g) in DMF (5 mL) was added. The reaction mixture was stirred at rt overnight. HCl (5% in water) was added to quench the reaction solution, partitioned between ethylacetate and water, washed with $2\times H_2O$, brine, $2\times H_2O$, dried over sodium sulfate, filtered and concentrated to leave isoxazoline (0.51 g) as white crystals. $^1$H NMR (CDCl$_3$) δ 9.09 (br, 1H), 7.86 (dd, 1H), 7.78 (d, 1H), 7.59 (d, 1H), 3.87 (d, 1H), 3.27 (d, 1H), 2.19 (s, 3H), 2.05 (s, 3H), 1.78 (s, 3H) ppm. CI mass spectrum z (rel. intensity) 302 (M+H, 100).

To a solution of isoxazoline (0.51 g) in ethanol (10 mL) was added HCl (20% in water, 3 mL). The mixture was brought to reflux for 1.5 h. Ethanol was removed and the residue was partitioned between ethyl acetate and water, washed with 2×water, dried over sodium sulfate, filtered and concentrated to 3-(3-aminobenzisoxazol-5-yl)-5-methyl-5-ethoxycarbonylisoxazoline (0.42 g) as white solid. $^1$H NMR (CDCl$_3$) δ 7.90 (s, 1H), 7.79 (d, 1H), 7.35, (d, 1H), 4.25 (q, 2H), 3.95 (d, 1H), 3.49 (s, 2H), 3.25 (d, 1H), 1.73, (s, 3H), 1.30 (s, 3H). CI mass spectrum z (rel. intensity) 290 (M+H, 100).

To a solution of isoxazoline (0.42 g) in THF (10 mL) was added NaOH (10% in water) (10 mL). The mixture was stirred at 60° C. for 1.5 h, cooled to rt and HCl (10% in water) was added dropwise untill pH 4–5. The mixture was partitioned between ethylacetate and water, washed with $2\times H_2O$, dried over sodium sulfate, filtered and concentrated to give isoxaoline acid (0.32 g) as a pure compound. $^1$H NMR (DMSO-$d_6$) δ 13.25 (br, 1H), 8.20 (s, 1H), 7.83 (d, 1H), 7.58 (d, 1H), 6.58 (s, 2H), 3.82 (d, 1H), 3.00 (d, 1H), 1.60 (s, 3H) ppm. ESI mass spectrum z (rel. intensity) 262 (M+H, 100).

To a solution of isoxazoline acid (52 mg) in DMF (2 mL) was added TEA (26 mg), 2'-tert-butylaminosulfonyl-[1,1']-biphenyl-4-ylamine (79 mg) and BOP reagent (115 mg). The reaction mixture was stirred at 50° C. overnight. Partitioned between ethylacetate and water, washed with $2\times H_2O$ brine and $2\times H_2O$, dried over sodium sulfate, filtered and flash chromatographed to elute amide (45 mg). ESI mass spectrum z (rel. intensity) 547 (M+H, 100); mp 144° C.

The amide (40 mg) was dissolved in TFA (2 mL). The resulting solution was brought to reflux for 1.5 h., stripped off TFA and flash chromatographed to give the title compound (22 mg) as a pure compound. ESI mass spectrum z (rel. intensity) 492 (M+H, 100), mp 164° C.

Example 11

1-(3'-Aminobenzisoxazol-5'-yl)-3-methyl-5-[(2'-aminosulfonyl-[1,1']-biphen-4-yl)aminocarbonyl]pyrazole To a solution of 2-fluoro-5-nitrobenzonitrile (2.0 g) in ethylacetate (50 mL) was added stannous chloride dihydrate (27.0 g). The mixture was brought to reflux for 1.5 h and allowed to cool. The mixture was partitioned between ethyl acetate and sodium bicarbonate (sat. in water). The aqueous phase was extracted with ethyl acetate four times. The organic phase was washed with $4\times H_2O$, dried over sodium sulfate, filtered and concentrated to leave 4-fluoro-3-cyanoaniline (1.40 g). CI mass spectrum z (rel. intensity) 137 (M+H, 100).

4-Fluoro-3-cyanoaniline (1.4 g) was added to 10 mL of concentrated hydrochloric acid at 0° C. Sodium nitrite (0.71 g) was dissolved in water (3 mL), cooled to 0° C., and added dropwise to the 4-fluoro-3-cyanoaniline solution. The reaction was stirred at 0° C. for 30 minutes. Stannous chloride dihydrate (6.95 g) was dissolved in HCl (conc., 4 mL). The solution was cooled to 0° C., and added dropwise to the 4-fluoro-3-cyanoaniline solution. The reaction was placed in the refrigerator overnight. Next day, the precipitate was isolated by filtration, washed with ice cold brine (30 mL), followed by a 2:1 petrolium ether/ethylether (30 mL) solution. The yellow solid was dried under vacuum overnight to leave 4-fluoro-3-cyanophenylhyrazine tin chloride (2.5 g).

To a suspension of 4-fluoro-3-cyanophenylhyrazine tin chloride (0.9 g) in acetic acid (15 mL) was added the oxime (0.5 g). The reaction was brought to reflux overnight. The next day the acetic acid was evaporated and the residue was partitioned between ethylacetate and sodium bicarbonate (sat.). The equeous was extracted by ethylacetate (4×20 mL). The organic phase was washed with water, brine, dried over sodium sulfate, filtered and concentrated. Flash chromatography gave ethyl 1-(4-fluoro-3-cyanophenyl)-3-methyl-5-pyrazole carboxylate (0.7 g) as pure compound. CI mass spectrum z (rel. intensity) 274 (M+H, 100).

To a solution of acetone oxime (70 mg) in DMF (6 mL) was added potassium tert-butoxide (1.0M in THF, 1.1 mL). The reaction was stirred at rt for 15 minutes. A solution of ethyl 1-(4-fluoro-3-cyanophenyl)-3-methyl-5-pyrazole carboxylate (0.2 g) in DMF (3 mL) was added to the oxime solution. The reaction was stirred at rt overnight. The next day the reaction was partitioned between ethylacetate and amonium chloride (sat. in water), washed with brine, $4\times H_2O$, dried over sodium sulfate, filtered and concentrated. Flash chromatography gave 1-(4-isopropylideneaminooxy-3-cyanophenyl)-3-methyl-5-pyrazole carboxylate (0.18 g). CI mass z (rel. intensity) 327 (M+H, 100).

To a solution of 1-(4-isopropylideneaminooxy-3-cyanophenyl)-3-methyl-5-pyrazole carboxylate (0.18 g) in ethanol (5 mL) was added HCl (20%, 3 mL). The reaction was brought to reflux for 2.5 h, ethanol was evaporated and the residue was partitioned between ethylacetate and water, washed with 2×H$_2$O, dried over sodium sulfate, filtered and concentrated to give 1-(3-aminobenzisoxazole-5-yl)-3-methyl-5-pyrazole carboxylate (0.14 g). CI mass spectrum z (rel. intensity) 287 (M+H, 100).

To a solution of ethyl 1-(3-aminobenzisoxazole-5-yl)-3-methyl-5-pyrazole carboxylate (0.14 g) in THF (5 mL) was added NaOH (10% in water, 5 mL). The reaction was stirred at 600° C. for 2 h, THF was evaporated, HCl (10% in water) was added dropwisely until the pH was between 4–5, partitioned between ethylacetate and water, washed with brine, dried over sodium sulfate, filtered and concentrated to give 1-(3-aminobenzisoxazole-5-yl)-3-methyl-5-pyrazole carboxylic acid (0.11 g). ESI mass spectrum z (rel. intensity) 259 (M+H, 100).

To a solution of the pyrazole carboxylic acid (55 mg) in DMF (5 mL) was added TEA (33 mg), 2'-tert-butylaminosulfonyl-[1,1']-biphenyl-4ylamine (97 mg) and BOP reagent (141 mg). The reaction was stirred at 50° C. overnight. The next day the reaction was partitioned between ethylacetate and water, washed with brine, 4×H$_2$O, dried over sodium sulfate, filtered, concentrated and flash chromatography to give amide (85 mg). ESI mass spectrum z (rel. intensity) 567 (M+Na, 100).

The amide was dissolved in TFA (3 mL). The resulting solution was brought to reflux for 1 h. TFA was evaporated, flash chromatographed to give the title compound (60 mg) as a white solid. ESI mass spectrum z (rel. intensity) 489 (M+H, 100). mp 186° C.

Example 12–14

3-(1-Amino-isoquinol-7-yl)-4-[(2'-aminosulfonyl-[1,1']-biphen-4-yl)aminocarbonyl]-1,2,3-triazole (Example 12), 3-(4-amino-isoquinol-7-yl)-4-[(2'-aminosulfonyl-[1,1']-biphen-4-yl)aminocarbonyl]-1, 2,3-triazole (Example 13), and 3-(isoquinol-7-yl)-4-[(2'-aminosulfonyl-[1,1']-biphen-4-yl) aminocarbonyl]-1,2,3-triazole (Example 14)

To a solution of 7-aminoisoquinoline (7.0 g) in TFA (35 mL) at 0° C. was added sodium nitrite (4.02 g) portionwise over a period of 30 minutes. The reaction was stirred at 0° C. to room temperature for 1.5 h. Water (3.5 mL) was added followed by portionwise addition of sodium azide (3.48 g) at 0° C. over a period of 30 minutes. After the addition, the reaction was slowly warmed up to room temperature and stirred for 1 h. Two third of TFA was evaporated and the residue was cooled to 0° C. Sodium bicarbonate (sat. in water) was added dropwisely to the residue until the pH was abouty 8–9. After extraction with methylene chloride (4×60 mL), the organic phase was combined, washed with water, brine, dried over sodium sulfate, filtered and concentrated to leave 7-azidoisoquinoline (7.5 g) as a dark brown solid. CI mass spectrum z (rel. intensity) 171 (M+H, 100).

7-Azidoisoquinoline (7.20 g) was suspended in toluene (80 mL). Propargyladehyde di-ethyl acetal (6.50 g) was added to the 7-azidoisoquinoline suspension. The reaction was stirred at room temperature overnight. The next day the solvent was evaporated and the residue was put on flash chromatography to give a mixture (10.25 g) of regioisomeric triazole aldehyde di-ethyl acetal in a 3:2 ratio by NMR. The mixture was further purified by recrystalization to give 1,2,3-triazole (6.50 g) as a pale yellow solid. CI mass spectrum z (rel. intensity) 299 (M+H, 100).

The acetal (1.5 g) was dissolved in TFA (50% in water, 15 mL). The resulting solution was stirred at room temperature overnight. The next day the solvent was evaporated and the residue was partitioned between ethyl acetate and sodium bicarbonate (sat. in water), washed with water, brine, dried over sodium sulfate, filtered and concentrated to give aldehyde (1.0 g) as a white solid. CI mass spectrum z (rel. intensity) 225 (M+H, 100).

To a solution of aldehyde (1.0 g) in methanol (25 mL) was added sodium cyanide (0.44 g), manganese (IV) oxide (6.30 g) and acetic acid (0.27 g). The reaction was stirred at room temperature overnight. The next day the reaction was filtered through celite, the pad was washed with a solution of methanol in methylene chloride (50%). The filtrate was concentrated and partitioned between ethylacetate and sodium bicarbonate (sat in water), washed with water, dried over sodium sulfate, filtered and concentrated to give the carboxylate (0.75 g) as a pure compound. CI mass spectrum z (rel. intensity) 255 (M+H, 100).

To a solution of 2'-tert-butylaminosulfonyl-[1,1']-biphenyl-4-ylamine (132 mg) in methylene chloride (8 mL) was added AlMe$_3$ (2.0 M in hexane, 0.6 mL). The resulting solution was stirred at room temperature for 20 minutes. A solution of carboxylate (100 mg) in methylene chloride (5 mL) was added. The reaction was stirred at room temperature overnight. The next day the solvent was removed and HCl (10% in water, 5 mL) was added. The residue then was basified by the addition of sodium carbonate, partitioned between ethyl acetate and water, washed with sodium bicarbonate (sat. in water), water, dried over sodium sulfate, filtered and concentrated. Flash chromatography purification gave amide (110 mg) as a pure compound. ESI mass spectrum z (rel. intensity) 549 (M+Na, 100).

The amide (20 mg) was dissolved in TFA (2 mL). The resulting solution was stirred at 80° C. for 1 h. TFA was evaporated and the residue was purified on a flash chromatograpy to give 3-(isoquinol-7-yl)-4-[(2'-aminosulfonyl-[1,1']-biphen-4-yl)aminocarbonyl]-1,2,3-triazole (Example 14) as a pure compound. ESI mass spectrum z (rel. intensity) 471 (M+H, 100), mp 230° C.

To a suspension of triazole (80 mg) in methylene chloride (8 mL) was added MCPBA (50 mg). The reaction was stirred at reflux for 1 h. The mixture became a clear solution and was cooled to room temperature. The solvent was removed and the residue partitioned between ethylacetate and sodium bicarbonate (sat. in water), washed with water, dried over sodium sulfate, filtered and concentrated to give the desired isoquinoline-N-oxide (65 mg). To a solution of isoquinolne-N-oxide (65 mg) in pyridine (5 mL) was added TsCl (60 mg). The resulting solution was stirred at room temperature overnight. The next day the solvent was stripped off to dryness, ethanol amine (3 mL) was added. The reaction was stirred at room temperature overnight. The next day, the reaction mixture was partitioned between ethylacetate and water, the equeous phase was extracted with ethyl acetate (3×15 mL). The extracts were combined, concentrated and flash chromatographed to give the tert-butylaminosulfonyl compound (50 mg). The tert-butylaminosulfonyl compound (50 mg) was refluxed in TFA (4 mL) for 1 h and the TFA stripped off. The residue was partitioned between ethylacetate and sodium bicarbonate (sat. in water), washed with water, dried over sodium sulfate, filtered and concentrated, prep. TLC to give Example 12: 3-(1-amino-isoquinol-7-yl)-4-[(2'-aminosulfonyl-[1,1']-biphenyl-4-yl)aminocarbonyl]-1,2,3-triazole) (20 mg). ESI mass spectrum z (rel. intensity) 486 (M+H, 100), mp 250° C., and Example 13: 3-(4-amino-isoquinol-7-yl)-4-[(2'-aminosulfonyl-[1,1']-biphenyl-4-yl) aminocarbonyl]-1,2,3-triazole (6 mg). ESI mass spectrum z (rel. intensity) 486 (M+H, 100), mp 245° C.

Example 15

1-(Quinol-2-ylmethyl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 484 (M+H, 100), mp 169° C.

Example 16

1-(Quinol-2-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 484 (M+H, 100), mp 181° C.

Example 17

1-(3'-Aminoindazol-5'-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 488 (M+H, 100), mp 203° C.

Example 18

1-(3-Aminoindazole-5-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 488 (M+H, 100), mp 197° C.

Example 19

1-(3'-Aminobenzisoxazol-5'-yl)-3-methyl-5-[(2'-aminosulfonyl-(phenyl)pyridy-2-ylaminocarbonyl]pyrazole The title compound was prepared analogously to Example 12. ESI mass spectrum z (rel. intensity) 490 (M+H, 100), mp 188° C.

Example 20

1-(3'-Aminobenzisoxazol-5'-yl)-3-methyl-5-[isoquinol-7-yl)aminocarbonyl]pyrazole The title compound was prepared analogously to Example 12. ESI mass spectrum z (rel. intensity) 385 (M+H, 100), mp 210° C.

Example 21

1-(1'-Aminoisoquinol-7'-yl)-3-ethyl-5-[(2'-aminosulfonyl-[1,1']-biphen-4-yl)aminocarbonyl]pyrazole The title compound was prepared analogously to Example 12. ESI mass spectrum z (rel. intensity) 513 (M+H, 100), mp 201° C.

Example 22

1-(1'-Aminoisoquinol-7'-yl)-3-isopropyl-5-[(2'-aminosulfonyl-[1,1']-biphen-4-yl)aminocarbonyl]pyrazole The title compound was prepared analogously to Example 12. ESI mass spectrum z (rel. intensity) 527 (M+H, 100), mp 165° C.

Example 23

1-(2',4'-Diaminoquinazol-6'-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 515 (M+H, 100), mp 215° C.

Example 24

1-(4'-Aminoquinazol-6'-yl)-3-methyl-5-[(2'-aminosulfonyl-[1,1']-biphen-4-yl)aminocarbonyl]pyrazole The title compound was prepared analogously to Example 12. ESI mass spectrum z (rel. intensity) 500 (M+H, 100), mp 205° C.

Example 25

1-(1'-Aminoisoquinol-7'-yl)-3-methyl-5-[4-(N-pyrrolidinylcarbonyl)phenylaminocarbonyl]pyrazole, trifluoroacetic acid salt Standard trimethylaluminum (Weinreb protocol) coupling of 4-carboxamidopyrrolidinophenyl-aniline with ethyl-N1-pyrazole(isoquinol-7-yl)-3-methyl-5-carboxylate, acidic workup and purification via silica gel column chromatography afforded the desired coupled product in 50% yield. $^1$H NMR, (CDCl$_3$) δ: 9.20 (s, 1H), 8.89 (bs, 1H), 8.72 (d, 1H), 8.04 (s, 1H), 7.84 (d, 1H), 7.75 (dd, 1H), 7.66 (d, 1H), 7.45 (d, 2H), 7.37 (d, 2H), 6.80 (s, 1H), 3.60 (t, 2H), 3.39 (t, 2H), 2.40 (s, 1H), 1.84 (m-4H) ppm; ESI mass spectrum m/z (rel intensity) 426 (M+H, 100).

The isoquinoline product was then converted to the desired product following oxidation (MCPBA) and rearrangement (pTsCl/pyridine; ethanolamine) described previously. $^1$H NMR (DMSO d$_6$) δ: 8.70 (s, 1H), 7.98 (bs, 2H), 7.75 (dd, 4H), 7.46 (d, 2H), 7.27 (d, 1H), 7.09 (s, 1H), 3.30 (b, 4H), 2.34 (s, 3H), 7.78 (b, 4H) ppm; ESI mass spectrum m/z (rel intensity) 441 (M+H, 100).

Example 26

1-(3'-Aminobenzisoxazol-5'-yl)-3-trifluoromethyl-5-[(2'-methylsulfonyl-3-fluoro-[1,1']-biphen-4-yl)aminocarbonyl]pyrazole Preparation of 1-(4-fluoro-3-cyanophenyl)-3-trifluoromethyl-5-pyrazolecarboxylic acid.

Method A:

To a suspension of 4-fluoro-3-cyanophenylhydrazine tin chloride (20 g, 53.6 mmol) in ethanol (150 mL) was added 1,1,1-trifluoro-2,4-pentanedione (8.18 g, 53.6 mmol). The reaction was brought to reflux overnight. The next day the ethanol was evaporated and the residue partitioned between ethyl acetate and HCl (1 N). The aqueous phase was extracted with ethyl acetate (4×20 mL). The organic phase is washed with water, brine, dried over sodium sulfate, filtered and concentrated. Flash chromatography gave 1-(4-fluoro-3-cyanophenyl)-3-trifluoromethyl-5-methylpyrazole (8 g, 56% yield) as pure compound: MS (CI): 270 (M+H)$^+$ (100%).

To a solution of 1-(4-fluoro-3-cyanophenyl)-3-trifluoromethyl-5-methylpyrazole (4.0 g, 14.9 mmol) in CCl$_4$ (75 mL) was added NBS (5.3 g, 29.7 mmol) and benzylperoxide (0.2 g, 1.49 mmol). The reaction was brought to reflux overnight. The next day the CCl$_4$ was evaporated and the residue was partitioned between ethyl acetate and sodium bicarbonate (sat.). The organic phase was washed with water, brine, dried over sodium sulfate, filtered and concentrated. Flash chromatography gave 1-(4-fluoro-3-cyanophenyl)-3-trifluoromethyl-5-bromomethylpyrazole (2.6 g, 50% yield) as pure compound: MS (CI): 348 (M+H)$^+$ (100%).

To a solution of 1-(4-fluoro-3-cyanophenyl)-3-trifluoromethyl-5-bromomethylpyrazole (0.6 g, 1.72 mmol) in DMSO (10 mL) was added copper (I) oxide (0.52 g, 3.62 mmol) and water (3 mL). The reaction was stirred at 60° C. overnight. The next day the reaction mixture was filtered through celite. The filtrate was partitioned between ethyl acetate and water. The organic was washed three times with water, brine, dried over sodium sulfate, filtered and concentrated to leave 1-(4-fluoro-3-cyanophenyl)-3-trifluoromethyl-5-hydroxymethyl pyrazole (0.45 g, 92% yield) as pure compound: MS (CI): 286 (M+H)$^+$ (100%).

To a solution of 1-(4-fluoro-3-cyanophenyl)-3-trifluoromethyl-5-hydroxymethylpyrazole (0.45 g, 1.58 mmol) in acetonitrile (10 mL) was added catalytic amount of ruthenium chloride at 0° C. followed by addition of a solution sodium periodate (0.71 g, 3.32 mmol) in water. The reaction was stirred at 0° C. to room temperature overnight. The next day the acetonitrile was evaporated and the residue was partitioned between ethyl acetate and water, washed with brine, dried over sodium sulfate, filtered and concentrated to give 1-(4-fluoro-3-cyanophenyl)-3-trifluoromethyl-5-hydroxycarbonylpyrazole (0.27 g, 57% yield) as pure compound: MS (ES–): 298 (M–H)$^-$ (40%).
Method B:

To a suspension of 4-fluoro-3-cyanophenylhyrazine tin chloride (17 g, 50 mmol) in acetic acid (200 mL) was added 4,4,4-trifluoro-1-(2-furyl)-2,4-butanedione (10.3 g, 50 mmol). The reaction was brought to reflux overnight. The next day the acetic acid was evaporated and the residue was partitioned between ethyl acetate and water, washed with HCl (1N), water and brine, dried over sodium sulfate, filtered and concentrated, flash chromatography to give 1-(4-fluoro-3-cyanophenyl)-3-trifluoromethyl-5-(2-furyl) pyrazole (7.0 g, 44% yield) as pure compound. MS (CI): 322 (M+H)$^+$ (100%).

To a solution of 1-(4-fluoro-3-cyanophenyl)-3-trifluoromethyl-5-(2-furyl)pyrazole (4.0 g, 12.5 mmol) in acetonitrile (30 mL) was added carbon tetrachloride (30 mL), ruthenium chloride (0.4 g) and a solution of sodium periodate (11.9 g, 56.1 mmol) in water (45 mL). The reaction is stirred at room temperature overnight. The next day the reaction mixture was filtered through celite. The filtrate was concentrated and partitioned between ethyl acetate and HCl (1N). The organic phase was washed with water, dried over sodium sulfate, filtered and concentrated to give 1-(4-fluoro-3-cyanophenyl)-3-trifluoromethyl-5-hydroxycarbonyl pyrazole (2.4 g, 64% yield) as pure compound. MS (ES–): 298 (M–H)$^-$ (40%).
Preparation of 1-(4-fluoro-3-cyanophenyl)-3-trifluoromethyl-5-[(2'-methylsulfonyl-3-fluoro-[1,1']-biphen-4-yl)aminocarbonyl]pyrazole.

To a solution of 1-(4-fluoro-3-cyanophenyl)-3-trifluoromethyl-5-hydroxycarbonylpyrazole (0.2 g, 0.67 mmol) in methylene chloride (10 mL) was added oxalyl chloride (0.84 g, 6.7 mmol) and one drop of DMF. The resulting solution was stirred at room temperature overnight. The next day the solvent is evaporated and the residue is redissolved in methylene chloride and to the solution was added (2'-methylsulfonyl-3-fluoro-[1,1']-biphen-4-yl)amine hydrochloride (0.2 g, 0.67 mmol) and DMAP (0.25 g, 2.01 mmol). The reaction was stirred at room temperature overnight. The next day, methylene chloride was evaporated and the residue was partitioned between ethyl acetate and HCl (1N), washed with HCl (1N), sodium bicarbonate (sat.), brine and water, dried over sodium sulfate, filtered and concentrated to leave 1-(4-fluoro-3-cyanophenyl)-3-trifluoromethyl-5-[(2'-methylsulfonyl-3-fluoro-[1,1']-biphen-4-yl)aminocarbonyl]pyrazole (0.32 g, 87% yield) as pure compound. MS (ESI): 547 (M+H) (100%).
Preparation of 1-(3'-aminobenzisoxazol-5'-yl)-3-trifluoromethyl-5-[(2'-methylsulfonyl-3-fluoro-[1,1']-biphen-4-yl)aminocarbonyl]pyrazole To a solution of acetone oxime (86 mg, 1.18 mmol) in DMF (6 mL) was added sodium t-butoxide (1 M in THF, 1.18 mL). The mixture was stirred at room temperature for half hour followed by addition of a solution of 1-(4-fluoro-3-cyanophenyl)-3-trifluoromethyl-5-[(2'-methylsulfonyl-3-fluoro-[1,1']-biphen-4-yl)aminocarbonyl]pyrazole (0.22 g, 0.39 mmol) in DMF (4 mL). The reaction was stirred at room temperature for 5 hours. The reaction mixture was then partitioned between ethyl acetate and HCl (5%), washed with HCl (5%), four times with water, brine, dried over sodium sulfate, filtered and concentrated. Flash chromatography (30% ethyl acetate/hexane) gave 1-(4-isopropylideneaminooxy-3-cyanophenyl)-3-trifluoromethyl-5-[(2'-methylsulfonyl-3-fluoro-[1,1']-biphen-4-yl)aminocarbonyl]pyrazole (0.19 g, 81% yield) as pure compound: MS (ESI): 600 (M+H) (100%).

1-(4-Isopropylideneaminooxy-3-cyanophenyl)-3-trifluoromethyl-5-[(2'-methylsulfonyl-3-fluoro-[1,1']-biphen-4-yl)aminocarbonyl]pyrazole (0.19 g, 0.32 mmol) was dissolved in ethanol (4 mL) and to the solution was added HCl (20%, 4 mL). The reaction mixture was stirred at 80° C. for three hours. The reaction mixture was cooled to room temperature. The white precipitate was filtered and recrystalized in methanol to give the title compound (0.14 g, 80% yield): MS (ESI): 501 (M+H) (100%).

Example 27

1-(1'-Aminopthalazin-7'-yl)-3-methyl-5-[(2'-aminosulfonyl-[1,1']-biphen-4-yl)carbonylamino]pyrazole Preparation of 3-nitro-6-styrylbenzamide.

A mixture of 2-cyano-4-nitrotoluene (10 g, 6.17 mmol), benzaldehyde (6.51 g, 6.17 mmol) and potassium carbonate (20 g) in MeOH (200 mL) was heated at reflux for 10 min. The mixture was cooled to ambient temperature over 30 min, whereupon precipitation of the product was complete. The product was isolated by filtration and washed successively with 1N HCl, water and MeOH then air dried. There was obtained 13.0 g of the benzamide (mp 269.8° C.) as evident from the lack of a nitrile adsorption in the IR and the appearance of peaks at 3357.1, 3193.6 (—NH2) and 1648.7 cm$^{-1}$ (H2NC(=O)—); LRMS (M–NO)$^+$ m/z=238.
Preparation of 3-amino-6-styrylbenzamide.

The nitro compound prepared above (13 g, 48.41 mmol) and SnCl$_2$.H$_2$O (54.7 g, 240 mmol) were combined in EtOH and heated at reflux for 1.5 h. The EtOH was removed by distillation in vacuo then 30% NaOH added. Extraction of this suspension with EtOAc followed by washing the organic extract with brine, drying (MgSO$_4$) and evaporation gave the product aniline (13.39 g); LRMS (M+H)$^+$ m/z=239.
Preparation of 3-hydrazino-6-styrylbenzamide.

The aniline (13 g, 54.6 mmol) from above was dissolved in conc. HCl (90 mL) and cooled to 0° C. A solution of NaNO$_2$ (3.94 g) in water (45 mL) was added dropwise over 10 min and the diazotization mixture left to stir at 0–5° C.

for 1 h. After this time SnCl$_2$.H2O (39 g) in water (170 mL) was added dropwise to the cold mixture over 30 min then allowed to thaw to ambient temperature over 3 h. The solid product was isolated by filtration, then the filter cake was washed with water several times and air-dried to give the hydrazine contaminated with Sn (II) salts (10.9 g).

Preparation of ethyl 3-methyl-1-(3-amido-4-styrylphenyl)-1H-pyrazole-5-carboxylate.

The phenylhydrazine prepared above (3.2 g) and ethyl 2-N-(methoxy)imino-4-oxopentanoate (2.46 g, 13.18 mmol) in AcCN (30 mL) and AcOH (5 mL) were heated at reflux for 4 h. The reaction was cooled and diluted with EtOAc then washed repeatedly with satd. NaHCO3 solution until the washings were basic. The mixture was evaporated and the dark oil left to stand until crystallization was complete. The solidified mass was triturated with 8:2 AcCN:water then filtered and air-dried. There was obtained 1.38 g of pyrazole; mp 162.6° C.; LRMS (M+H)$^+$ m/z=376.

Preparation of ethyl 3-methyl-1-(3-cyano-4-styrylphenyl)-1H-pyrazole-5-carboxylate.

Ethyl 3-methyl-1-(3-amido-4-styrylphenyl)-1H-pyrazole-5-carboxylate (8.36 g, 22.3 mmol) in pyridine (50 mL) was cooled to 0° C. and methanesulfonyl chloride (7.67 g, 66.9 mmol) added dropwise over 10 min. The ice bath was removed and the reaction left to stir for 18 h. The reaction mixture was evaporated and the residue suspended in 1N HCl (200 mL) and MeOH (60 mL). The mixture was stirred vigourously for 15 min then filtered, washed with water and air-dried. There was obtained 6.23 g of nitrile; mp 128.3° C.

Preparation of 3-methyl-1-(3-cyano-4-styrylphenyl)-1H-pyrazole-5-carboxylic acid.

The ethyl ester (7.17 g, 20 mmol) in MeOH (100 mL) with 50% NaOH solution (10 mL) was stirred for 2 h at ambient temperature. After this time TLC (2:1 EtOAc:Hexane) indicated that all of the starting ester was consumed. Water (100 mL) was added and the solution acidified (pH=1) by the addition of conc. HCl. The percipitated product was removed by filtration then washed with water and air-dried. There was obtained 3-methyl-1-(3-cyano-4-styrylphenyl)-1H-pyrazole-5-carboxylic acid (5.9 g); mp 225.9° C.

To 3-methyl-1-(3-cyano-4-styrylphenyl)-1H-pyrazole-5-carboxylic acid (5.6 g, 17 mmol) in CHCl$_3$ (60 mL) and oxalyl chloride (3 mL) was added a few drops DMF. The reaction bubbled vigorously and after 20 min, when the reaction had subsided, the solvent was removed by distillation in vacuo and pumped on for several hours to remove the last traces of HCl. Complete conversion to the acid chloride was demonstrated by TLC (2:1 EtOAc:Hexane) by converting a small sample to the ethyl ester by treatment with EtOH and comparison with a previously prepared sample.

To the acid chloride (17 mmol) in CHCl$_3$ (100 mL) and pyridine (170 mmol) was added 4-(2'-N-t-butylsulfamido)phenyl)aniline (5.2 g, 17.1 mmol). The reaction was stirred for 1 h at ambient temperature, then diluted with 1:1 EtOAc:n-BuCl (300 mL) and washed with 1N HCl until washings were acidic. The organic solution was dried and evaporated to give 8.12 g of 3-methyl-1-(3-cyano-4-styrylphenyl)-1H-pyrazole-5-(N-(4-(2'-t-butylsulfamido)phenyl)phenyl)carboxyamide; mp 130.3° C.; LRMS (M+Na)$^+$ m/z=638.2.

Preparation of 3-methyl-1-(3-cyano-4-formylphenyl)-1H-pyrazole-5-(N-(4-(2'-t-butylsulfamido)phenyl)phenyl)carboxyamide.

A MeOH (200 mL) solution of 3-methyl-1-(3-cyano-4-styrylphenyl)-1H-pyrazole-5-(N-(4-(2'-t-butylsulfamido)phenyl)phenyl)carboxyamide was cooled to −78° C. and saturated with a stream of ozone. The solution was then purged with a stream of N2 for 10 min and dimethylsulfide (3 mL) added. The mixture was allowed to come to ambient temperature than evaporated to dryness. The residue was dissolved in EtOAc, washed with water (4x) dried (MgSO4) and evaporated. There was obtained 3.97 g of the aldehyde; LRMS (M+Na)$^+$ m/z=564.0.

Preparation of Example 27.

The above prepared carboxyamide (0.42 g, 0.78 mmol) with hydrazine hydrate (0.15 g, 3 mmol) and AcOH (0.28 g, 4.68 mmol) in benzene (25 mL) were heated at reflux under a Dean Stark trap for 18 h. The benzene solution was cooled to ambient temperature and washed with water (3x) and dried (MgSO4) then evaporated. The residue was applied to a short column of flash silica and eluted with 1:1:0.078 EtOAc:Hexane:MeOH. The desired pthalazine product (0.1 g) was obtained in a mixture with 3-methyl-1-(3-amido-4-(formylhydrazone)phenyl)-1H-pyrazole-5-(N-(4-(2'-t-butylsulfamido)phenyl)phenyl)carboxyamide.

This mixture was heated at reflux with trifluoroacetic acid (10 mL) for 1 h, then evaporated. The mixture was separated by reverse phase hplc on a C18 column by eluting with a gradient of 20% AcCN:Water with 0.05% TFA to 100% AcCN with 0.05% TFA over 30 min. At 9.83 min 3-methyl-1-(3-amido-4-(formylhydrazone)phenyl)-1H-pyrazole-5-(N-(4-(2'-sulfamido)phenyl)phenyl)carboxyamide (14 mg) was eluted; HRMS (M+H)$^+$ found: 518.1634, calc.: 518.1610. At 10.76 min the target compound, example 27 (2.8 mg) was eluted; HRMS (M+H)$^+$ found: 500.1511, calc.: 500.1505.

Example 28

3-(3'-Aminobenzisoxazol-5'-yl)-5-[[5-[(2'-aminosulfonyl)phenyl]pyrid-2-yl]aminocarbonyl]-5-(methylsulfonylaminomethyl)isoxazoline Preparation of 3-(3-cyano-4-fluorophenyl)-5-(azidomethyl)-5-(carbomethoxy)isoxazoline 3-Cyano-4-fluorobenzaldehyde (5.00 g) and hydroxyamine hydrochloride (2.90 g, 1.25 Eq) were dissolved in ethanol (100 mL) and pyridine (100 mL). The mixture was stirred at RT under N$_2$ for 45 minutes. The solvents were removed and the brown oil was partitioned between ethyl acetate and water. The organic layer was washed with brine, dried over MgSO$_4$, and concentrated to give 3-cyano-4-fluorobenzaldehydeoxime (5.03 g). CI mass spectrum z (rel. intensity) 165 (M+H, 100).

Sodium azide (10.7 g) was added to a solution of methyl (2-bromomethyl)acrylate (20.0 g) in DMSO (200 mL). The mixture was stirred at RT under N$_2$ for 2 h. The reaction mixture was poured into water and extracted with ethyl acetate. The organic layer was washed with brine, dried over MgSO$_4$, and concentrated to give methyl (2-azidomethyl) acrylate (14.1 g).

To a solution of 3-cyano-4-fluorobenzaldoxime (4.30 g) in CH$_2$Cl$_2$ (150 mL) was added methyl (2-azidomethyl) acrylate (4.33 g). The mixture was cooled to 0° C. in an ice bath followed by dropwise addition of NaOCl (66 mL of 0.67 M aqueous solution) with vigorous stirring. After the addition, the reaction mixture was slowly warmed up to RT (2 h). The mixture was washed with water and brine, dried over sodium sulfate, and concentrated. The resulting solid was purified by chromatography on silica gel with CH$_2$Cl$_2$ to give 3-(3-cyano-4-fluorophenyl)-5-(azidomethyl)-5-(carbomethoxy)isoxazoline (2.45 g) as a pure compound. $^1$H NMR (CDCl$_3$) δ 7.97 (m, 1H), 7.88 (m, 1H), 7.31 (t, 1H), 3.87 (s, 3H), 3.87–3.46 (m, 4H) ppm; NH$_3$—CI mass spectrum z (rel. intensity) 321 [(M+NH$_4$)$^+$, 100].

Preparation of 3-(3-cyano-4-fluorophenyl)-5-(aminomethyl)-5-(carbomethoxy)isoxazoline, hydrochloride salt.

To a solution of 3-[3-cyano-4-fluorophenyl]-5-(azidomethyl)-5-(carbomethoxy)isoxazoline (2.14 g) in THF (50 mL) was added triethylphosphite (1.45 mL). The mixture was refluxed under $N_2$ for 5 h. The THF was removed, and the residue was dissolved in EtOAc and washed with water and brine. It was dried over $MgSO_4$ and concentrated to a yellow oil. This oil was then dissolved in 4N HCl in dioxane (30 mL) and refluxed for 4 h. The reaction mixture was cooled, and ether was added. The precipitate formed was filtered and dried to give 1.15 g of the hydrochloride salt. $^1$H NMR (DMSO) δ 8.36 (bs, 2H), 8.21 (m, 1H), 8.09 (m, 1H), 7.68 (t, 1H), 4.02–3.80 (m, 2H), 3.78 (s, 3H), 3.70–3.37 (m, 2H) ppm; ESI mass spectrum z (rel. intensity) 279.9 (M+H, 100).

Preparation of 3-(3-cyano-4-fluorophenyl)-5-(methylsulfonylaminomethyl)-5-(carbomethoxy)isoxazoline.

To a solution of 3-(3-cyano-4-fluorophenyl)-5-(aminomethyl)-5-(carbomethoxy)isoxazoline hydrochloride salt (1.15 g) in $CH_2Cl_2$ (50 mL) was added triethylamine (1.27 mL) and methanesulfonyl chloride (0.31 mL). The mixture was stirred at RT under $N_2$ for 1 h. The solvent was diluted with $CH_2Cl_2$ and washed with water, 1N aqueous HCl, and saturated aqueous $NaHCO_3$. It was dried over $MgSO_4$ and concentrated to a yellow solid (1.13 g). $^1$H NMR ($CDCl_3$) δ 7.92 (m, 2H), 7.30 (t, 1H), 4.82 (t, 1H), 3.84 (s, 3H), 3.76–3.60 (m, 4H), 3.03 (s, 3H) ppm; ESI mass spectrum z (rel. intensity) 377.9 (M+H, 100).

Preparation of 3-(3-cyano-4-fluorophenyl)-5-(methylsulfonylaminomethyl)-5-(hydroxycarbonyl)isoxazoline.

To a solution of 3-(3-cyano-4-fluorophenyl)-5-(methylsulfonylaminomethyl)-5-(carbomethoxy)isoxazoline (1.13 g) in THF (50 mL) was added LiOH (3.50 mL of 1N aqueous solution). The mixture was stirred at RT under $N_2$ for ½ h. The solvent was removed, the resulting material was diluted with water and acidified with concentrated HCl. It was then extracted with EtOAc, and the organic solution was dried over $MgSO_4$ and concentrated to a light yellow foam (0.98 g). $^1$H NMR (DMSO-$d_6$) δ 8.17 (m, 2H), 7.56 (t, 1H), 3.98–3.79 (m, 2H), 3.69 (bs, 2H), 3.01 (s, 3H) ppm; ESI mass spectrum z (rel. intensity) 339.8 (M−H, 100).

Preparation of 3-(3-cyano-4-fluorophenyl)-5-[[5-[(2'-t-butylaminosulfonyl)phenyl]pyrid-2-yl]aminocarbonyl]-5-(methylsulfonylaminomethyl)isoxazoline.

To a solution of 3-(3-cyano-4-fluorophenyl)-5-(methylsulfonylaminomethyl)-5-(hydroxycarbonyl)isoxazoline (0.33 g) in $CH_3CN$ (15 mL) was added oxalyl chloride (0.22 mL), followed by a few drops of DMF. The mixture was refluxed under $N_2$ for 1 h. The solvent was removed, toluene was added and then removed to dryness. The resulting solid was dried under vacuum. It was then dissolved in $CH_2Cl_2$ (20 mL) and [2-(t-butylaminosulfonyl)phenyl]-2-aminopyridine (0.30 g) was added followed by DMAP (0.30 g). The resulting mixture was stirred at RT under $N_2$ for 16 h. It was diluted with $CH_2Cl_2$ and washed with water and brine, dried over $MgSO_4$, and concentrated. The resulting solid was purified by chromatography on silica gel with 1:1 EtOAc/$CH_2Cl_2$ to give 0.11 g of the desired product. $^1$H NMR ($CDCl_3$) δ 9.43 (s, 1H), 8.40 (d, 1H), 8.25 (d, 1H), 8.17 (dd, 1H), 7.98–7.83 (m, 3H), 7.62–7.50 (m, 2H),7.35–7.24 (m, 2H), 5.81 (t, 1H),4.06 (s, 1H), 3.82 (m, 4H), 3.02 (s, 3H), 1.07 (s, 9H) ppm; ESI mass spectrum z (rel. intensity) 629.0 (M+H, 100).

Preparation of 3-(3'-Aminobenzisoxazol-5'-yl)-5-[[5-[(2'-aminosulfonyl)phenyl]pyrid-2-yl]aminocarbonyl]-5-(methylsulfonylaminomethyl)isoxazoline To a solution of acetone oxime (28.0 mg) in DMF (2 mL) was added potassium tert-butoxide (1.0 M in THF, 0.44 mL) via syringe. The mixture was stirred at RT for 15 minutes, a solution of 3-(3-cyano-4-fluorophenyl)-5-[[5-[(2'-t-butylaminosulfonyl)phenyl]pyrid-2-yl]aminocarbonyl]-5-(methylsulfonylaminomethyl)isoxazoline (0.16 g) in DMF (2 mL) was added. The reaction mixture was stirred at RT overnight. Aqueous $NH_4Cl$ was added to quench the reaction solution. The mixture was poured into water and extracted with EtOAc. The organic solution was washed with brine, dried over $MgSO_4$, and concentrated to an oil.

This oil was dissolved in ethanol (8 mL) and methanol (2 mL). Aqueous HCl (18%, 2 mL) was added. The mixture was heated at 80° C. for 2 h. The solvents were removed and the residue was dissolved in $CH_3CN$ and purified by HPLC (C18 reverse phase, eluted with 0.05% of TFA in $H_2O$/$CH_3CN$) to give 50 mg of white solid as TFA salt. ESI mass spectrum z (rel. intensity) 641.9 (M+H, 100).

The above solid was refluxed with 5 mL of TFA under $N_2$ for ½ h. The solvents were removed and the residue was dissolved in $CH_3CN$ and purified by HPLC (C18 reverse phase, eluted with 0.05% of TFA in $H_2O$/$CH_3CN$) to give 31 mg of white solid as TFA salt. $^1$H NMR (DMSO-$d_6$) δ 9.43 (s, 1H), 8.40 (d, 1H), 9.82 (s, 1H), 8.34 (d, 1H), 8.25 (s, 1H), 8.12–8.02 (m, 2H), 7.95–7.84 (m, 2H),7.70–7.51 (m, 2H), 7.38 (m, 2H), 3.98–3.50 (m, 4H), 2.98 (s, 3H) ppm. ESI mass spectrum z (rel. intensity) 585.8 (M+H, 100).

Example 29

1-(3'-Aminobenzisoxazol-5'-yl)-3-trifluoromethyl-5-[(2-fluoro-4-morpholinophenyl)aminocarbonyl]pyrazole Preparation of 2-fluoro-4-morpholinoaniline.

A solution of 2,4-difluoronitrobenzene (10.0 mL) and morpholine (17.4 mL) in THF (100 mL) was stirred at RT under $N_2$ for 2 h. The solvent was removed and the residue was partitioned between EtOAc and water. The organic layer was washed brine, dried over $MgSO_4$, and concentrated. The resulting solid was purified by chromatography on silica gel with 20–50% EtOAc in hexane to give 18.1 g of 4-fluoro-2-morpholinonitrobenzene and 1.81 g of 2-fluoro-4-morpholinonitrobenzene. ESI mass spectrum z (rel. intensity) 227.1 (M+H, 100).

2-Fluoro-4-morpholinonitrobenzene (1.80 g) was dissolved in methanol (100 mL) and 10% Pd/C (94 mg) was added. The mixture was placed in a hydrogenator (45 psi) for 2.5 h. The reaction mixture was filtered through celite and washed with methanol. The filtrate was concentrated to give 1.51 g solid. $^1$H NMR ($CDCl_3$) δ 6.76–6.54 (m, 3H), 3.84 (t, 4H), 3.45 (bs, 2H), 3.02 (t, 4H) ppm. ESI mass spectrum z (rel. intensity) 197.1 (M+H, 100).

Preparation of 1-(3'-Aminobenzisoxazol-5'-yl)-3-trifluoromethyl-5-[(3-fluoro-4-morpholinophenyl)aminocarbonyl]pyrazole.

The title compound was prepared from 1-(3-cyano-4-fluorophenyl)-3-trifluoromethyl-5-pyrazolecarboxylic acid and 2-fluoro-4-morpholinoaniline as a TFA salt by the same procedures described in Example 26. $^1$H NMR (DMSO-$d_6$) δ 9.39 (s, 1H), 8.06 (d, 1H), 7.77–7.48 (m, 4H), 6.81–6.75 (m, 2H), 3.77 (t, 4H), 3.15 (t, 4H) ppm. ESI mass spectrum z (rel. intensity) 491.2 (M+H, 100).

Example 30

1-(3'-Aminobenzisoxazol-5'-yl)-3-trifluoromethyl-5-[[4-(2'-isopropylimidazol-1'-yl)phenyl]aminocarbonyl]pyrazole The title compound was prepared in an analogous fashion as TFA salt. $^1$H NMR (DMSO-d$_6$) δ 10.03 (s, 1H), 8.08 (d, 1H), 8.00 (d, 2H), 7.79–7.56 (m, 7H), 3.28 (m, 1H), 1.39 (d, 6H) ppm. ESI mass spectrum z (rel. intensity) 496.3 (M+H, 100).

Example 31

1-(3'-Aminobenzisoxazol-5'-yl)-3-trifluoromethyl-5-[[4-(2'-ethylimidazol-1'-yl)phenyl]aminocarbonyl]pyrazole The title compound was prepared in an analogous fashion as TFA salt. $^1$H NMR (DMSO-d$_6$) δ 10.48 (s, 1H), 8.08 (d, 1H), 8.00 (d, 2H), 7.79–7.56 (m, 7H), 3.00 (q, 2H), 1.29 (t, 3H) ppm. ESI mass spectrum z (rel. intensity) 482.2 (M+H, 100).

Example 32

1-(3'-Aminobenzisoxazol-5'-yl)-3-trifluoromethyl-5-[[4-[(2'-dimethylaminomethyl)imidazol-1'-yl]phenyl]aminocarbonyl]pyrazole Preparation of 4-[(2'-dimethylaminomethyl)imidazol-1'-yl]aniline.

To a solution of 4-fluoronitrobenzene (7.87 g) and 2-imidazole-carboxaldehyde (5.90 g) in DMF (60 mL) was added K$_2$CO$_3$ (9.26 g). The mixture was heated at 80° C. under N$_2$ for 16 h. The mixture was poured into water, and the precipitate was filtered to give 6.70 g of yellow solid. The filtrate was then extracted with EtOAc, and the organic layer was washed brine, dried over MgSO$_4$, and concentrated to a yellow solid (5.40 g). Both batch were identified as the 4-[(2'-carboxaldehyde)imidazol-1'-yl]nitrobenzene. ESI mass spectrum z (rel. intensity) 218 (M+H, 100).

A mixture of 4-[(2'-carboxaldehyde)imidazol-1'-yl]nitrobenzene (3.00 g) and dimethylamine (32 mL of 40% aqueous solution) in methanol (50 mL) was stirred at RT under N$_2$ for ½ h. NaBH$_4$ (1.56 g) was added portion wise. After the addition was completed, the reaction mixture was heated at 56° C. for 2 h. Brine was added to the reaction mixture, it was then extracted with CH$_2$Cl$_2$. The organic solution was washed with brine, dried over MgSO$_4$, and concentrated to give 1.96 g of 4-[(2'-dimethylaminomethyl)imidazol-1'-yl]nitrobenzene. ESI mass spectrum z (rel. intensity) 247.2 (M+H, 100).

4-[(2'-dimethylaminomethyl)imidazol-1'-yl]nitrobenzene (1.96 g) was dissolved in methanol (100 mL) and 10% Pd/C (0.20 g) was added. The mixture was placed in a hydrogenator (30 psi) for 12 h. The reaction mixture was filtered through celite and washed with methanol. The filtrate was concentrated. It was then purified by chromatography on silica gel with 20% methanol in CH$_2$Cl$_2$ to give 1.30 g of 4-[(2'-dimethylaminomethyl)imidazol-1'-yl]aniline. $^1$H NMR (CDCl$_3$) δ 7.25 (dd, 2H), 7.03 (d, 2H), 6.72 (d, 2H), 3.82 (bs, 2H), 3.36 (s, 2H), 2.24 (s, 6H) ppm. ESI mass spectrum z (rel. intensity) 217.2 (M+H, 100).

Preparation of 1-(3'-Aminobenzisoxazol-5'-yl)-3-trifluoromethyl-5-[[4-[(2'-dimethylaminomethyl)imidazol-1'-yl]phenyl]aminocarbonyl]pyrazole The title compound was prepared from 1-(3-cyano-4-fluorophenyl)-3-trifluoromethyl-5-pyrazolecarboxylic acid and 4-[(2'-dimethylaminomethyl)imidazol-1'-yl]aniline as a TFA salt by the same procedures described in Example 26. $^1$H NMR (acetone-d$_6$) δ 10.39 (s, 1H), 8.07 (d, 1H), 7.93 (d, 2H), 7.76 (m, 1H), 7.56 (m, 5H), 7.36 (d, 1H), 4.59 (s, 2H), 3.00 (s, 6H), ppm. ESI mass spectrum z (rel. intensity) 511.2 (M+H, 100).

Example 33

1-(3'-Aminobenzisoxazol-5'-yl)-3-trifluoromethyl-5-[[4-[(2'-methoxymethyl)imidazol-1'-yl]phenyl]aminocarbonyl]pyrazole Preparation of 4-(2'-methoxymethyl)imidazol-1'-yl]aniline 4-[(2'-Carboxaldehyde)imidazol-1'-yl]nitrobenzene (3.00 g) was dissolved in methanol (50 mL). NaBH$_4$ (1.56 g) was added portion wise. After the addition was completed, the reaction mixture was stirred at RT under N$_2$ for 12 h. The methanol was removed and water was added. The precipitate formed was filtered and dried to give 1.90 g of 4-[(2'-hydroxymethyl)imidazol-1'-yl]nitrobenzene. $^1$H NMR (DMSO-d$_6$) δ 8.39 (d, 2H), 7.91 (d, 2H), 7.58 (s, 1H), 7.06 (s, 1H), 5.60 (t, 1H), 4.48 (d, 2H). AP mass spectrum z (rel. intensity) 220.1 (M+H, 100).

4-[(2'-hydroxymethyl)imidazol-1'-yl]nitrobenzene (1.70 g) was dissolved in CH$_2$Cl$_2$. Triethylamine (1.62 mL) was added followed by methanesulfonyl chloride (0.76 mL). The mixture was stirred at RT under N$_2$ for 2.5 h. The solvent was removed. The residue was dissolved in methanol (100 mL) and NaOMe (10 mL of 20% solution in methanol) was added. The reaction mixture was stirred at RT under N$_2$ for 12 h. The solvent was removed. The residue was partitioned between water and CH$_2$Cl$_2$. The organic solution was washed with brine, dried over MgSO$_4$, and concentrated to give 1.60 g of 4-[(2'-methoxymethyl)imidazol-1'yl]nitrobenzene. $^1$H NMR (CDCl$_3$) δ 8.39 (d, 2H), 7.72 (d, 2H), 7.20 (s, 2H), 4.45 (s, 2H), 3.42 (s, 3H). ESI mass spectrum z (rel. intensity) 234.1 (M+H, 100).

4-[(2'-Methoxymethyl)imidazol-1'-yl]nitrobenzene (1.78 g) was dissolved in methanol (100 mL) and 10% Pd/C (0.20 g) was added. The mixture was placed in a hydrogenator (40 psi) for 20 h. The reaction mixture was filtered through celite and washed with methanol. The filtrate was concentrated. It was then purified by chromatography on silica gel with 5% methanol in CH$_2$Cl$_2$ to give 0.67 g of 4-[(2'-methoxymethyl)imidazol-1'-yl]aniline. $^1$H NMR (CDCl$_3$) δ 7.18 (d, 2H), 7.06 (d, 2H), 6.71 (d, 2H), 4.36 (s, 2H), 3.96 (bs, 2H), 3.35 (s, 3H) ppm. ESI mass spectrum z (rel. intensity) 204.2 (M+H, 100).

Preparation of 1-(3'-Aminobenzisoxazol-5'-yl)-3-trifluoromethyl-5-[[4-[(2'-methoxymethyl)imidazol-1'-yl]phenyl]aminocarbonyl]pyrazole.

The title compound was prepared from 1-(3-cyano-4-fluorophenyl)-3-trifluoromethyl-5-pyrazolecarboxylic acid and 4-[(2'-methoxymethyl)imidazol-1'-yl]aniline as a TFA salt by the same procedures described in Example 26. $^1$H NMR (acetone-d$_6$) δ 10.39 (s, 1H), 8.08 (d, 1H), 7.97 (d, 2H), 7.76 (m, 2H), 7.69 (m, 3H), 7.57 (m, 2H), 4.75 (s, 2H), 3.36 (s, 3H), ppm. ESI mass spectrum z (rel. intensity) 498.2 (M+H, 100).

Example 34

1-(3'-Aminobenzisoxazol-5'-yl)-3-trifluoromethyl-5-[[4-[(2'-dimethylaminomethyl)imidazol-1'-yl]-2-fluorophenyl]aminocarbonyl]pyrazole Preparation of 4-[(2'-dimethylaminomethyl)imidazol-1'-yl]-2-fluoroaniline.

2-Imidazole-carboxaldehyde (1.00 g) and dimethylamine (10 mL of 40% aqueous solution) in methanol (10 mL) was stirred at RT under $N_2$ for ½ h. $NaBH_4$ (1.18 g) was added portion wise. After the addition was completed, the reaction mixture was heated at 56° C. for 2 h. Brine was added to the reaction mixture, it was then extracted with $CH_2Cl_2$. The organic solution was washed with brine, dried over $MgSO_4$, and concentrated to 2-(dimethylaminomethyl)imidazole as a yellow oil. $^1H$ NMR ($CDCl_3$) δ 6.97 (s, 2H), 3.61 (s, 2H), 2.28 (s, 6H) ppm.

The above oil was dissolved in DMF (10 mL) and KO-t-Bu (10.5 mL of 1M solution in THF) was added. The mixture was stirred at RT under $N_2$ for ½ h. It was then added dropwise to a solution of 2,4-difluoronitrobenzene (1.14 mL) in DMF (10 mL). The resulting mixture was stirred at RT under $N_2$ for 2 h. The mixture was poured into water and extracted with EtOAc. The organic layer was washed brine, dried over $MgSO_4$, and concentrated to a yellow oil. The resulting material was purified by chromatography on silica gel with EtOAc to give 1.11 g of a 1:5 mixture of 2-fluoro-4-[(2'-dimethylaminomethyl)imidazol-1'-yl]nitrobenzene and 4-fluoro-2-[(2'-dimethylaminomethyl)imidazol-1'-yl]nitrobenzene. ESI mass spectrum z (rel. intensity) 265.2 (M+H, 100).

The above mixture was dissolved in methanol (100 mL) and 10% Pd/C (0.15 g) was added. The mixture was placed in a hydrogenator (40 psi) for 8 h. The reaction mixture was filtered through celite and washed with methanol. The filtrate was concentrated. The two regioisomers were then separated by HPLC (C18 reverse phase, eluted with 0.05% TFA in $H_2O/CH_3CN$) to give 80 mg of 4-[(2'-dimethylaminomethyl)imidazol-1'-yl]-2-fluoroaniline and 0.48 g of 2-[(2'-dimethylaminomethyl)imidazol-1'-yl]-4-fluoroaniline. ESI mass spectrum z (rel. intensity) 235.2 (M+H, 100).
Preparation of 1-(3'-Aminobenzisoxazol-5'-yl)-3-trifluoromethyl-5-[[4-[(2'-dimethylaminomethyl)imidazol-1'-yl]phenyl]aminocarbonyl]pyrazole.

The title compound was prepared from 1-(3-cyano-4-fluorophenyl)-3-trifluoromethyl-5-pyrazolecarboxylic acid and 4-[(2'-dimethylaminomethyl)imidazol-1'-yl]-2-fluoroaniline as a TFA salt by the same procedures described in Example 26. $^1H$ NMR (acetone-$d_6$) δ 9.95 (s, 1H), 8.20–8.09 (m, 2H), 7.78 (m, 1H), 7.59 (m, 4H), 7.44 (d, 1H), 7.36 (d, 1H), 4.68 (s, 2H), 3.05 (s, 6H), ppm. ESI mass spectrum z (rel. intensity) 529.2 (M+H, 100).

Example 35

1-(3'-Aminobenzisoxazol-5'-yl)-3-trifluoromethyl-5-[[(2-methoxy-4-(2'-methylimidazol-1'-yl)phenyl] aminocarbonyl]pyrazole Preparation of 2-methoxy-4-(2'-methylimidazol-1'-yl) aniline.

A solution of 5-fluoro-2-nitrophenol (2.03 g) and 2-methylimidazole (2.14 g) in $CH_3CN$ (50 mL) was stirred at reflux under $N_2$ for 16 h. The solvent was removed and the residue was purified by chromatography on silica gel with 0–10% MeOH in $CH_2Cl_2$ to give 2.21 g of 5-(2'-methylimdazol-1-yl)-2-nitrophenol. ESI mass spectrum z (rel. intensity) 220.1 (M+H, 100).

5-(2'-Methylimdazol-1-yl)-2-nitrophenol (1.16 g) was dissolved in DMF (30 mL). To this solution was added $K_2CO3$ (0.92 g) and iodomethane (0.33 mL) and the reaction mixture was stirred at RT under $N_2$ for 6 h. The reaction mixture was poured into 100 mL water and extracted with EtOAc (4×50 mL), dried over $MgSO_4$, and concentrated to give 0.25 g of 2-methoxy-4-(2'-methylimidazol-1'-yl) nitrobenzene. ESI mass spectrum z (rel. intensity) 234.2 (M+H, 100).

2-Methoxy-4-(2'-methylimidazol-1'-yl)nitrobenzene (0.25 g) was dissolved in methanol (20 mL) and 10% Pd/C (29.3 mg) was added. The mixture was placed on a hydrogenator (40 psi) for 4 h. The reaction mixture was filtered and washed with methanol. The filtrate was concentrated to give 0.27 g of the title compound. $^1H$ NMR ($CDCl_3$) δ 2.32 (s, 3H, $CH_3$), 3.86 (s, 3H, $OCH_3$), 3.95 (bs, 2H, $NH_2$), 6.68 (t, 1H, J=1.8 Hz, aromatic H), 6.72 (m, 2H, aromatic H), 6.95 (d, 1H, J=1.4 Hz, imidazole H), 6.99 (d, 1H, J=1.1 Hz, imidazole H) ppm. ESI mass spectrum z (rel. intensity) 204.2 (M+H, 100).
Preparation of 1-(3'-Aminobenzisoxazol-5'-yl)-3-trifluoromethyl-5-[[(2'-methoxy-4-(2'-methylimidazol-1'-yl)phenyl]aminocarbonyl]pyrazole.

The title compound was prepared from 1-(3-cyano-4-fluorophenyl)-3-trifluoromethyl-5-pyrazolecarboxylic acid and 2-methoxy-4-(2'-methylimidazol-1'-yl)aniline as a TFA salt by the procedures described in Example 26. $^1H$ NMR (DMSO) δ 2.53 (s, 3H, $CH_3$), 3.82 (s, 3H, $OCH_3$), 7.17 (dd, 1H, J=10.0 Hz, J=1.5 Hz, aromatic H), 7.35 (d, 1H, J=1.4, aromatic H), 7.58 (d, 1H, J=8.8, aromatic H), 7.60 (s, 1H, pyrazole H), 7.65 (d, 1H, J=1.5, aromatic H), 7.76 (d, 1H, J=1.8, imidazole H), 7.87 (d, 1H, J=1.8, imidazole H), 7.90 (bs, 1H, NH), 8.11 (d, 1H J=1.4, aromatic H), 10.15 (bs, 1H, $CF_3CO_2H$) ppm. ESI mass spectrum z (rel. intensity) 498.3 (M+H, 100).

Example 36

1-(3'-Aminobenzisoxazol-5'-yl)-3-trifluoromethyl-5-[[4-(2'-isopropylimidazol-1'-yl)-2-fluorophenyl] aminocarbonyl]pyrazole The title compound was prepared in an analogous fashion as TFA salt. $^1H$ NMR (acetone-$d_6$) δ 10.02 (s, 1H), 8.28 (t, 1H), 8.11 (d, 1H), 7.82–7.56 (m, 7H), 3.33 (m, 1H), 1.40 (d, 6H) ppm. ESI mass spectrum z (rel. intensity) 514.2 (M+H, 100).

Example 37

1-(3'-Aminobenzisoxazol-5'-yl)-3-trifluoromethyl-5-[[4-(2'-ethylimidazol-1'-yl)-2-fluorophenyl] aminocarbonyl]pyrazole The title compound was prepared in an analogous fashion as TFA salt. $^1H$ NMR (acetone-$d_6$) δ 9.99 (s, 1H), 8.27 (t, 1H), 8.10 (d, 1H), 7.80–7.57 (m, 7H), 3.04 (q, 2H), 1.30 (t, 3H) ppm. ESI mass spectrum z (rel. intensity) 500.2 (M+H, 100).

Example 38

1-(3'-Aminobenzisoxazol-5'-yl)-3-ethyl-5-[[4-(2'-ethylimidazol-1'-yl)-2-fluorophenyl]aminocarbonyl] pyrazole The title compound was prepared in an analogous fashion as TFA salt. $^1H$ NMR (acetone-$d_6$) δ 9.63 (s, 1H), 8.28 (t, 1H), 7.98 (d, 1H), 7.72–7.48 (m, 6H), 7.03 (s, 1H), 3.04 (q, 2H), 2.73 (q, 2H), 1.31 (tt, 6H) ppm. ESI mass spectrum z (rel. intensity) 460.2 (M+H, 100).

Example 39

1-(3'-Aminobenzisoxazol-5'-yl)-3-ethyl-5-[[4-[(2'-methoxymethyl)imidazol-1'-yl]phenyl] aminocarbonyl]pyrazole The title compound was prepared in an analogous fashion as TFA salt. $^1H$ NMR (DMSO) δ 10.82 (s, 1H), 8.02–7.75

(m, 5H), 7.62–7.48 (m, 4H), 7.04 (s, 1H), 4.59 (s, 2H), 3.30 (s, 3H) ppm. ESI mass spectrum z (rel. intensity) 458.3 (M+H, 100).

Example 40

1-(3'-Aminobenzisoxazol-5'-yl)-3-ethyl-5-[[4-[(2'-dimethylaminomethyl)imidazol-1'-yl]phenyl]aminocarbonyl]pyrazole The title compound was prepared in an analogous fashion as TFA salt. $^1$H NMR (CD$_3$OD) δ 7.89 (d, 1H), 7.82 (d, 2H), 7.58 (dd, 2H), 7.50–7.48 (m, 3H), 7.28 (d, 5H), 6.96 (s, 1H), 4.35 (s, 2H), 2.81 (S, 6H), 2.78 (q, 2H), 1.37 (t, 3H) ppm. ESI mass spectrum z (rel. intensity) 471.3 (M+H, 100).

Example 41

1-(3'-Aminobenzisoxazol-5'-yl)-3-ethyl-5-[[4-[(2'-methyl)benzimidazol-1'-yl]phenyl]aminocarbonyl]pyrazole The title compound was prepared in an analogous fashion as TFA salt. $^1$H NMR (acetone-d$_6$) δ 10.10 (s, 1H), 8.09 (d, 2H), 7.99 (d, 1H), 7.93 (d, 1H), 7.76–7.67 (m, 3H), 7.57–7.30 (m, 5H), 7.00 (S, 1H), 2.76 (q, 2H), 1.31 (t, 3H) ppm. ESI mass spectrum z (rel. intensity) 478.2 (M+H, 100).

Example 42

1-(3'-Aminobenzisoxazol-5'-yl)-3-ethyl-5-[(2'-ethylimidazol-1'-ylphenyl)aminocarbonyl]pyrazole The title compound was prepared in an analogous fashion as TFA salt. $^1$H NMR (acetone-d$_6$) δ 10.10 (s, 1H), 7.98 (m, 3H), 7.64 (m, 5H), 7.50 (d, 1H), 6.98 (S, 1H), 3.02 (q, 2H), 2.75 (q, 2H), 1.30 (tt, 6H) ppm. ESI mass spectrum z (rel. intensity) 442.2 (M+H, 100).

Example 43

1-(3'-Aminobenzisoxazol-5'-yl)-3-ethyl-5-[[4-(2'-ethylimidazol-1'-yl)-2,5-difluorophenyl]aminocarbonyl]pyrazole The title compound was prepared in an analogous fashion as TFA salt. $^1$H NMR (acetone-d$_6$) δ 9.80 (S, 1H), 8.30–8.24 (m, 1H), 7.99 (d, 1H), 7.85–7.63 (m, 4H), 7.51 (d, 1H), 7.06 (s, 1H), 4.40 (bs, 2H), 2.70 (q, 2H), 2.68 (S, 3H), 1.26 (t, 3H) ppm. ESI mass spectrum z (rel. intensity) 464.2 (M+H, 100).

Example 44

1-(3'-Aminobenzisoxazol-5'-yl)-3-ethyl-5-[(2-fluoro-4-morpholinophenyl)aminocarbonyl]pyrazole The title compound was prepared in an analogous fashion as TFA salt. $^1$H NMR (acetone-d$_6$) δ 9.08 (s. 1H), 7.94 (d, 1H), 7.64 (m, 2H), 7.47 (d, 1H), 6.92 (S, 1H), 6.78 (m, 2H), 4.07 (bs, 2H), 3.77 (t, 4H), 3.14 (t, 4H), 2.70 (q, 2H), 1.28 (t, 3H) ppm. ESI mass spectrum z (rel. intensity) 451.2 (M+H, 100).

Example 45

1-(3'-Aminobenzisoxazol-5'-yl)-3-ethyl-5-[(2'-isopropylimidazol-1'-ylphenyl)aminocarbonyl]pyrazole The title compound was prepared in an analogous fashion as TFA salt. $^1$H NMR (acetone-d$_6$) δ 10.15 (s, 1H),7.98 (m, 3H), 7.70–7.59 (m, 5H), 7.48 (d, 1H), 6.99 (s, 1H), 3.26 (m, 1H), 2.74 (q, 2H), 1.39 (d, 6H), 1.30 (t, 3H) ppm. ESI mass spectrum z (rel. intensity) 456.3 (M+H, 100).

Example 46

1-(3'-Aminobenzisoxazol-5'-yl)-3-ethyl-5-[[4-(2'-methylimidazol-1'-yl)-2-fluorophenyl]aminocarbonyl]pyrazole The title compound was prepared in an analogous fashion as TFA salt. $^1$H NMR (acetone-d$_6$) δ 9.67 (s, 1H), 8.25 (t, 1H), 7.98 (dd, 1H), 7.71–7.48 (m, 6H), 7.04 (s, 1H), 2.72 (q, 2H), 2.69 (s, 3H), 1.31 (t, 3H) ppm. ESI mass spectrum z (rel. intensity) 446.2 (M+H, 100).

Example 47

1-(3'-Aminobenzisoxazol-5'-yl)-3-ethyl-5-[(2'-aminosulfonyl-3-amino-[1,1']-biphen-4-yl)aminocarbonyl]pyrazole The title compound was prepared in an analogous fashion as TFA salt. $^1$H NMR (DMSO-d$_6$) δ 10.02 (s, 1H), 8.01 (d, 1H), 7.99 (s, 1H), 7.58 (m, 3H), 7.49 (t, 1H), 7.26 (tt, 2H), 7.17 (s, 1H), 7.06 (s, 1H), 6.91 (s, 1H), 6.82 (d, 1H), 2.71 (q, 2H), 1.28 (t, 3H) ppm. ESI mass spectrum z (rel. intensity) 540.2 (M+Na, 100).

Example 48

1-(3'-Aminobenzisoxazol-5'-yl)-3-ethyl-5-[(2'-aminosulfonyl-3-nitro-[1,1']-biphen-4-yl)aminocarbonyl]pyrazole The title compound was prepared in an analogous fashion as TFA salt. $^1$H NMR (DMSO-d$_6$) δ 10.91 (s, 1H), 8.01 (m, 1H), 7.92 (m, 1H), 7.70 (s, 1H), 7.62 (m, 2H), 7.47 (m, 4H), 7.36 (m, 2H), 7.04 (s, 1H), 6.50 (bs, 2H), 2.71 (q, 2H), 1.25 (t, 3H) ppm. ESI mass spectrum z (rel. intensity) 548.2 (M+H, 100).

Example 49

1-(3'-Aminobenzisoxazol-5'-yl)-3-ethyl-5-[[4-(2'-methylimidazol-1'-yl)phenyl]aminocarbonyl]pyrazole The title compound was prepared in an analogous fashion as TFA salt. $^1$H NMR (acetone-d$_6$) δ 10.13 (s, 1H), 8.00–7.95 (m, 3H), 7.68–7.61 (m, 5H), 7.48 (d, 1H), 6.99 (s, 1H), 2.74 (q, 2H), 2.67 (s, 3H), 1.29 (t, 3H) ppm. ESI mass spectrum z (rel. intensity) 428.2 (M+H, 100).

Example 50

1-(3'-Aminobenzisoxazol-5'-yl)-3-ethyl-5-[[2-dimethyl-4-(N-pyrrolidinocarbonyl)phenyl]aminocarbonyl]pyrazole The title compound was prepared in an analogous fashion as TFA salt. $^1$H NMR (acetone-d$_6$) δ 9.31 (bs, 1H), 8.27 (d, 1H), 7.99 (d, 1H), 7.72 (dd, 1H), 7.51 (m, 2H), 7.36 (d, 1H), 6.94 (s, 1H), 4.70 (bs, 2H), 3.53 (bs, 4H), 2.73 (q, 2H), 2.62 (s, 6H),1.92 (bs, 4H), 1.30 (t, 3H) ppm. ESI mass spectrum z (rel. intensity) 488.0 (M+H, 100).

Example 51

1-(3'-Aminobenzisoxazol-5'-yl)-3-ethyl-5-[[2-pyrrolidino-4-(N-pyrrolidinocarbonyl)phenyl]aminocarbonyl]pyrazole The title compound was prepared in an analogous fashion as TFA salt. $^1$H NMR (DMSO-d$_6$) δ 9.90 (s, 1H), 7.90 (s, 1H), 7.46 (m, 2H), 7.18 (d, 1H), 6.93 (s, 1H), 6.83 (m, 2H), 3.38 (m, 4H), 3.19 (bs, 4H), 2.64 (q, 2H), 1.78 (m, 8H), 1.24 (t, 3H) ppm. ESI mass spectrum z (rel. intensity) 513.9 (M+H, 100).

Example 52

1-(3'-Aminobenzisoxazol-5'-yl)-3-ethyl-5-[[2-fluoro-4-(N-pyrrolidinocarbonyl)phenyl]aminocarbonyl]pyrazole The title compound was prepared in an analogous fashion as TFA salt. $^1$H NMR (CDCl$_3$) δ 8.35 (m, 1H), 8.06 (m, 1H), 7.68 (s, 1H), 7.57 (dd, 1H), 7.43 (d, 1H), 7.25 (m, 2H), 6.85 (s, 1H), 4.64 (bs, 2H), 3.61 (t, 2H), 3.40 (t, 2H), 2.76 (q, 2H), 1.9o (m, 4H), 1.28 (t, 3H) ppm. ESI mass spectrum z (rel. intensity) 463.0 (M+H, 100).

Example 53

1-(3'-Aminobenzisoxazol-5'-yl)-3-ethyl-5-[(2'-aminosulfonyl-3-fluoro-[1,1']-biphen-4-yl)aminocarbonyl]pyrazole The title compound was prepared in an analogous fashion as TFA salt. $^1$H NMR (DMSO-d$_6$) δ 10.32 (s, 1H), 8.01–7.94 (m, 2H), 7.63–7.44 (m, 5H), 7.40–7.23 (m, 4H), 7.15 (dd, 1H), 7.01 (s, 1H), 2.67 (q, 2H), 1.25 (t, 3H) ppm. ESI mass spectrum z (rel. intensity) 542.9 (M+Na, 100).

Example 54

1-(3'-Aminobenzisoxazol-5'-yl)-3-ethyl-5-[[5-[(2'-methylsulfonyl)phenyl]pyrimid-2-yl]aminocarbonyl]pyrazole The title compound was prepared in an analogous fashion as TFA salt. $^1$H NMR (DMSO-d$_6$) δ 11.34 (s, 1H), 8.68 (s, 2H), 8.13 (dd, 1H), 7.96 (d, 1H), 7.80 (m, 2H), 7.64 (m, 2H), 7.10 (s, 1H), 3.05 (s, 3H), 2.70 (q, 2H), 1.29 (t, 3H) ppm. ESI mass spectrum z (rel. intensity) 525.9 (M+Na, 100).

Example 55

1-(3'-Aminobenzisoxazol-5'-yl)-3-ethyl-5-[[(2'-methylsulfonyl)-3-fluoro-[1,1']-biphen-4-yl]aminocarbonyl]pyrazole The title compound was prepared in an analogous fashion as TFA salt. $^1$H NMR (DMSO-d$_6$) δ 10.33 (s, 1H), 8.07 (d, 1H), 7.96 (s, 1H), 7.78–7.61 (m, 3H), 7.55–7.47 (m, 2H), 7.41 (d, 1H), 7.21 (s, 1H), 7.04 (s, 1H),2.90 (s, 3H), 2.70 (q, 2H), 1.28 (t, 3H) ppm. ESI mass spectrum z (rel. intensity) 541.9 (M+Na, 100).

Example 56

1-(3'-Aminobenzisoxazol-5'-yl)-3-ethyl-5-[[5-[(2'-aminosulfonyl)phenyl]pyrid-2-yl]aminocarbonyl]pyrazole The title compound was prepared in an analogous fashion as mesylate salt. $^1$H NMR (CD$_3$OD) δ 8.51 (dd, 1H), 8.36 (d, 1H), 8.15 (d, 1H), 7.93 (d, 1H), 7.81 (d, 1H), 7.70 (m, 3H), 7.48 (m, 2H), 7.32 (s, 1H), 2.83 (q, 2H), 1.39 (t, 3H) ppm. ESI mass spectrum z (rel. intensity) 502.0 (M–H, 100).

Example 57

1-(3'-Aminobenzisoxazol-5'-yl)-5-[[(2'-methylsulfonyl)-3-fluoro-[1,1']-biphen-4-yl]aminocarbonyl]tetrazole Preparation of ethyl 1-(3-cyano-4-fluorophenyl)-5-tetrazole carboxylate.

To a suspension of 2-fluoro-5-nitrobenzonitrile (5.20 g) in ethanol (150 mL) was added 5% Pd/C (1.00 g). The reaction was placed on a hydrogenator (50 psi) for 10 minutes. The reaction mixture was filtered through celite and the filtrate evaporated to give 4.25 g of 5-amino-2-fluorobenzonitrile. $^1$H NMR (CDCl$_3$) δ 3.75 (bs, 2H, NH$_2$), 6.83 (m, 2H, aromatic H), 6.99 (m, 1H, aromatic H). GC mass spectrum z (rel. intensity) 137 (M+H, 100).

To a solution of 5-amino-2-fluorobenzonitrile (3.75 g) and Et$_3$N (4.22 mL) in CH$_2$Cl$_2$ (100 mL) was added ethyloxalyl chloride (3.08 mL) in a dropwise fashion over 10 minutes. The reaction was stirred at RT under N$_2$ for 1.5 h. The reaction mixture was washed with water (2×50 mL) and brine (1×50 mL), filtered through phase separatory paper and evaporated. The residue was dissolved in 20 mL of CH$_2$Cl$_2$ and 100 mL of hexane was added. The solution was allowed to stand at RT for the weekend. The precipitate was filtered, rinsed with hexane, and dried under vacuum to give 5.43 g of 1-(3-cyano-4-fluorophenyl)-oxoacetic acid ethyl ester. $^1$H NMR (CDCl$_3$) δ 1.44 (t, 3H, J=7.2 Hz, OCH$_2$CH$_3$), 4.44 (q, 2H, J=7.0 Hz, OCH$_2$CH$_3$), 7.26 (t, 1H, J=3.8 Hz, aromatic H), 7.82 (m, 1H, aromatic H), 8.04 (m, 1H, aromatic H), 8.97 (bs, 1H, NH). DCI mass spectrum z (rel. intensity) 237.1 (M+H, 6.6), 254.0 (M+Na, 100).

A solution of triphenylphosphine (10.89 g) in CCl$_4$ (100 mL) was stirred at 0° C. for 30 minutes. 1-(3-Cyano-4-fluorophenyl)-oxoacetic acid ethyl ester (4.86 g) in CCl$_4$ (50 mL) was added and the reaction was stirred at reflux under N$_2$ for 16 h. The reaction was cooled to RT and the precipitate was filtered off. The filtrate was evaporated and dissolved in CH$_3$CN (200 mL). Sodium azide (1.34 g) was added and the reaction stirred at RT under N$_2$ for 16 h. The solvent was evaporated and the residue was taken up in EtOAc (100 mL). The organic solution was washed with water (2×50 mL) and brine (1×50 mL), dried over MgSO$_4$, and evaporated. The crude material was purified by silica gel chromatography eluting with CH$_2$Cl$_2$ to give 1.85 g of the title compound. $^1$H NMR (CDCl$_3$) δ 1.44 (t, 3H, J=7.1 Hz, OCH$_2$CH$_3$), 4.50 (q, 2H, J=7.1 Hz, OCH$_2$CH$_3$), 7.47 (t, 1H, J=3.8 Hz, aromatic H), 7.81 (m, 1H, aromatic H), 7.87 (m, 1H, aromatic H).

Preparation of 1-(3'-Aminobenzisoxazol-5'-yl)-5-[[(2'-methylsulfonyl)-3-fluoro-[1,1']-biphen-4-yl]aminocarbonyl]tetrazole.

To a solution of [(2'-methylaminosulfonyl)-3-fluoro-[1,1']-biphen-4-yl]amine (0.23 g) in anhydrous CH$_2$Cl$_2$ (15 mL) was added trimethylaluminum (1.60 mL, 2M in heptane). The reaction was stirred at RT under N$_2$ for 15 minutes. A solution of ethyl 1-(3-cyano-4-fluorophenyl)-5-tetrazole carboxylate (0.20 g) in anhydrous CH$_2$Cl$_2$ (10 mL) was added and the reaction was stirred at RT under N$_2$ for 16 h. The reaction was quenched with 5 mL of 1N HCl and diluted with CH$_2$Cl$_2$ (30 mL). The organic solution was washed with water (2×25 mL) and brine (1×25 mL), filtered through phase separatory paper, and evaporated to give 0.21 g of 1-(3'-cyano-4'-fluorophenyl)-5-[[(2'-methylsulfonyl)-3-fluoro-[1,1']-biphen-4-yl]aminocarbonyl]tetrazole. ESI mass spectrum z (rel. intensity) 479.1 (M–H, 100).

To a solution of acetone oxime (59.3 mg) in 5 mL of anhydrous DMF was added potassium tert-butoxide (1.20 mL, 1M in THF) and the mixture stirred at RT under N$_2$ for 15 minutes. A solution of 1-(3'-cyano-4'-fluorophenyl)-5-[[(2'-methylsulfonyl)-3-fluoro-[1,1']-biphen-4-yl]aminocarbonyl]tetrazole (0.19 g) in 10 mL of anhydrous DMF was added and the reaction was stirred at RT under N$_2$ for 16 h. The reaction was quenched with saturated aqueous NH$_4$Cl, poured into 50 mL of water, and extracted with EtOAc (3×50 mL). The combined organic solution was washed with water (2×25 mL) and brine (1×25 mL), dried over MgSO$_4$, and evaporated. The crude material was purified by silica gel chromatography eluting with 2% MeOH in CH$_2$Cl$_2$ to give 0.11 g of a white solid. To a suspension of this solid (0.10 g) in 10 mL of EtOH was added 4 mL of 18% aqueous HCl. The solution was stirred at 80° C. under N$_2$ for 1 h, then cooled to RT. The resulting precipitate was filtered and dried under vacuum to give 71.7 mg of 1-(3'-Aminobenzisoxazol-5'-yl)-5-[[(2'-methylsulfonyl)-3-fluoro-[1,1']-biphen-4-yl]aminocarbonyl]tetrazole. $^1$H NMR (DMSO-d$_6$) δ 2.93 (s, 3H, CH$_3$), 6.66 (bs, 2H, NH$_2$), 7.25 (d, 1H, J=9.8 Hz, aromatic H), 7.41 (t, 2H, J=8.0 Hz, aromatic H), 7.70 (m, 3H, aromatic H), 7.77 (t, 1 H, J=6.2 Hz, aromatic H), 7.89 (d, 1H, J=9.0 Hz, aromatic H), 8.09 (d, 1H, J=6.6 Hz, aromatic H), 8.20 (s, 1H, aromatic H), 11.26 (s, 1H, NH). ESI mass spectrum z (rel. intensity) 492.1 (M–H, 100).

1-(3'-Aminobenzisoxazol-5'-yl)-5-[[(2'-methylsulfonyl)-3-fluoro-[1,1']-biphen-4-yl]aminocarbonyl]tetrazole (58.2 mg) was dissolved in 20 mL of MeOH and a solution of methanesulfonic acid (1.18 mL, 0.1M in THF) was added. The reaction was stirred at RT under N$_2$ for 2 h and evaporated. The residue was dissolved in water and evaporated to give 55.6 mg of the title compound as the mesylate salt. $^1$H NMR (DMSO-d$_6$) δ 2.37 (s, 3H, CH$_3$SO$_3$H), 2.93 (s, 3H, CH$_3$), 7.26 (d, 1H, J=7.6 Hz, aromatic H), 7.40 (d, 1H, J=9.2 Hz, aromatic H), 7.42 (d, 1H, J=11.1 Hz, aromatic H), 7.72 (m, 3H, aromatic H), 7.78 (m, 1 H, aromatic H), 7.89 (dd, 1H, J=9.0 Hz, J=2.0 Hz, aromatic H), 8.10 (d, 1H, J=7.9 Hz, aromatic H), 8.21 (d, 1H, J=1.9 Hz, aromatic H), 11.27 (s, 1H, CH$_3$SO$_3$H). APCI mass spectrum z 494.1 (M+H). HRMS (Q-TOF) calc. 494.104677, obs. 494.105900.

Example 58

1-(3'-Aminobenzisoxazol-5'-yl)-5-[[4-(2'-methylimidazol-1'-yl)phenyl]aminocarbonyl] tetrazole The title compound was prepared in an analogous fashion as the TFA salt. $^1$H NMR (DMSO-d$_6$) δ 6.65 (bs, 2H, NH$_2$), 7.62 (d, 2H, J=9.1 Hz, aromatic H), 7.70 (d, 1H, J=8.8 Hz, aromatic H), 7.75 (d, 1H, J=2.2 Hz, aromatic H), 7.86 (d, 1 H, J=2.2 Hz, imidazole H), 7.93 (dd, 1H, J=9.0 Hz, J=2.0 Hz, imidazole H), 8.00 (d, 2H, J=9.1 Hz, aromatic H), 8.19 (d, 1H, J=2.2 Hz, aromatic H), 11.72 (s, 1H, CF$_3$CO$_2$H). ESI mass spectrum z (rel. intensity) 402.2 (M+H, 100).

Example 59

1-(3'-Aminobenzisoxazol-5'-yl)-5-[(2'-aminosulfonyl-[1,1']-biphen-4-yl)aminocarbonyl] tetrazole The title compound was prepared in an analogous fashion as the TFA salt. $^1$H NMR (DMSO-d$_6$) δ 6.65 (bs, 2H, NH$_2$), 7.27 (bs, 2H, NH$_2$), 7.30 (d, 1H, J=7.3 Hz, aromatic H), 7.38 (d, 2H, J=8.4 Hz, aromatic H), 7.59 (m, 2H, aromatic H), 7.71 (d, 1 H, J=9.1 Hz, aromatic H), 7.77 (d, 2H, J=8.4 Hz, aromatic H), 7.90 (d, 1H, J=8.8 Hz, aromatic H), 8.20 (s, 1H, aromatic H), 11.49 (s, 1H, CF$_3$CO$_2$H). ESI mass spectrum z (rel. intensity) 474.9 (M–H, 100).

Example 60

1-(3'-Aminobenzisoxazol-5'-yl)-5-[(2-fluoro-4-(N-pyrrolidinocarbonyl)phenyl)aminocarbonyl]tetrazole The title compound was prepared in an analogous fashion as the TFA salt. $^1$H NMR (DMSO-d$_6$) δ 1.83 (m, 4H, CH$_2$), 3.39 (t, 2H, J=6.2 Hz, CH$_2$), 3.45 (t, 2H, J=6.4 Hz, CH$_2$), 6.65 (bs, 2H, NH$_2$), 7.39 (d, 1H, J=8.5 Hz, aromatic H), 7.47 (dd, 1H, J=11.0 Hz, J=1.8 Hz, aromatic H), 7.70 (d, 2H, J=8.7 Hz, aromatic H), 7.86 (dd, 2H, J=9.2 Hz, J=1.8 Hz, aromatic H), 8.20 (d, 1H, J=1.8 Hz, aromatic H), 11.25 (s, 1H, CF$_3$CO$_2$H). ESI mass spectrum z (rel. intensity) 436.8 (M+H, 100). HRMS (Q-TOF) calc. 437.148590, obs. 437.149700.

Example 61

1-(3'-Aminobenzisoxazol-5'-yl)-5-[(2-(N-pyrrolidino)-4-(N-pyrrolidinocarbonyl)phenyl) aminocarbonyl]tetrazole The title compound was prepared in an analogous fashion as the TFA salt. $^1$H NMR (DMSO-d$_6$) δ 1.84 (m, 8H, CH$_2$), 3.17 (m, 4H, CH$_2$), 3.41 (m, 4H, CH$_2$), 6.95 (d, 1H, J=7.7 Hz, aromatic H), 7.02 (s, 1H, aromatic H), 7.46 (t, 1H, J=8.4 Hz, aromatic H), 7.71 (d, 2H, J=8.7 Hz, aromatic H), 7.86 (dd, 2H, J=8.8 Hz, J=1.8 Hz, aromatic H), 8.20 (d, 1H, J=2.2 Hz, aromatic H), 10.69 (s, 1H, CF$_3$CO$_2$H). ESI mass spectrum z (rel. intensity) 488.1 (M+H, 100).

Example 62

1-(1'-Amino-isoquinol-7'-yl)-5-[[(2'-aminosulfonyl)-3-fluoro-[1,1']-biphen-4-yl]aminocarbonyl]tetrazole, trifluoroacetate salt Preparation of Ethyl 1-(isoquinol-7'-yl)-5-tetrazole carboxylate.

7-Aminoisoquinoline (4.81 g, 33.4 mmol) (*J. Chem. Soc.* 1951, 2851) was dissolved in 100 mL of dichloromethane under a nitrogen atmosphere. Triethylamine (5.60 mL, 40.2 mmol, 1.2 eq.) was added to the isoquinoline solution. Ethyl oxalylchloride (4.10 mL, 36.7 mmol, 1.1 eq.) was added dropwise over 30 minutes and the reaction was stirred for 60 min. at ambient temperature. The solution was diluted with 100 mL of dichloromethane, washed with water (2×50 mL) and brine (1×50 mL), filtered through phase separatory paper, and evaporated to give a pale yellow solid. This solid was dissolved in 50 mL of dichloromethane and hexanes (100 mL) was added. The resulting precipitate was isolated by filtration and dried under vacuum to give [(isoquinol-7'-yl)amino]-oxoacetic acid, ethyl ester as an off-white solid (7.60 g, 93% yield). $^1$H NMR (CDCl$_3$) δ 1.47 (t, 3H, J=7.1 Hz, OCH$_2$CH$_3$), 4.47 (q, 2H, J=7.2 Hz, OCH$_2$CH$_3$), 7.63 (d, 1H, J=5.5 Hz, aromatic H), 7.78 (dd, 1H, J=8.9 Hz, J=2.0 Hz, aromatic H), 7.86 (d, 1H, J=8.8 Hz, aromatic H), 8.50 (d, 1H, J=1.9 Hz, aromatic H), 8.52 (d, 1H, J=5.8 Hz, aromatic H), 9.13 (bs, 1H, NH), 9.27 (s, 1H, aromatic H). C$_{13}$H$_{12}$N$_2$O$_3$ 244.25.

A solution of triphenylphosphine (17.65 g, 67.3 mmol, 2 eq.) in 500 mL of carbon tetrachloride was stirred at 0° C. for 60 minutes. [(Isoquinol-7'-yl)amino]-oxoacetic acid, ethyl ester (8.15 g, 33.4 mmol) was added and heated at reflux for 16 hours. The solution was cooled to ambient temperature and the precipitate was filtered off. The filtrate was evaporated to dryness and dissolved in 125 mL of acetonitrile. Sodium azide (2.17 g, 33.4 mmol) was added and the reaction mixture was stirred for 16 hours at ambient temperature. The solvent was evaporated and the resulting residue was dissolved in 200 mL of ethyl acetate. The ethyl acetate solution was washed with water (2×100 mL) and brine (1×50 mL), dried over magnesium sulfate, and evaporated. The crude material was purified by silica gel flash chromatography eluting with 1:1 ethyl acetate to hexane to give the title compound as an off-white solid (3.85 g, 43% yield). $^1$H NMR (CDCl$_3$) δ 1.23 (t, 3H, J=7.7 Hz, OCH$_2$CH$_3$), 4.39 (q, 2H, J=7.1 Hz, OCH$_2$CH$_3$), 7.98 (d, 1H, J=5.5 Hz, aromatic H), 8.07 (dd, 1H, J=8.8 Hz, J=2.2 Hz, aromatic H), 8.24 (d, 1H, J=8.7 Hz, aromatic H), 8.55 (d, 1H, J=1.4 Hz, aromatic H), 8.69 (d, 1H, J=5.5 Hz, aromatic H), 9.47 (s, 1H, aromatic H). C$_{13}$H$_{11}$N$_5$O$_2$ 269.26.

Preparation of 1-(1'-Amino-isoquinol-7'-yl)-5-[[(2'-aminosulfonyl)-3-fluoro-[1,1']-biphen-4-yl]aminocarbonyl]tetrazole, trifluoroacetate salt.

To a solution of (2'-tert-butylaminosulfonyl-3-fluoro-[1,1']-biphen-4-yl)amine (0.40 g, 1.24 mmol) in 15 mL of anhydrous dichloromethane under nitrogen was added trimethyl aluminum (3.00 mL, 6.00 mmol, 2M in heptane). The solution was stirred for 15 minutes at ambient temperature. Ethyl 1-(isoquinol-7'-yl)-5-tetrazole carboxylate (0.35 g, 1.30 mmol) in 15 mL of anhydrous dichloromethane was added slowly and the reaction mixture was allowed to stir for 16 hours at ambient temperature. The reaction was quenched with 5 mL 1N hydrochloric acid and diluted with 20 mL dichloromethane. The phases were separated and the dichloromethane phase was washed with water (2×20 mL) and brine (1×20 mL), dried over magnesium sulfate, and evaporated. The crude material was purified by silica gel flash chromatography eluting with 0–30% ethyl acetate in dichloromethane to give 1-(isoquinol-7'-yl)-5-[(2'-butylaminosulfonyl-3-fluoro-[1,1']-biphen-4-yl)carbonylamino]tetrazole as a pale yellow solid (0.23 g, 33% yield). $^1$H NMR (CDCl$_3$) δ 1.05 (s, 9H, tert-butyl), 7.29 (d, 3H, J=1.6 Hz, aromatic H), 7.42 (dd, 1H, J=11.3 Hz, J=1.8 Hz, aromatic H), 7.52 (td, 1H, J=4.0 Hz, J=1.4 Hz, aromatic H), 7.56 (td, 1H, J=7.4 Hz, J=1.5 Hz, aromatic H), 7.81 (d, 1H, J=5.8 Hz, aromatic H), 7.89 (dd, 1H, J=8.8 Hz, J=2.2 Hz, aromatic H), 8.07 (d, 1H, J=8.8 Hz, aromatic H), 8.16 (dd, 1H, J=7.7 Hz, J=1.5 Hz, aromatic H), 8.31 (bs, 1H, NH), 8.34 (t, 1H, J=8.0 Hz, aromatic H), 8.72 (d, 1H, J=5.9 Hz, aromatic H), 9.42 (s, 1H, aromatic H), 9.47 (bs, 1H, NH). MS (ES+): 546.3 (M+H)$^+$. C$_{27}$H$_{24}$FN$_7$O$_3$S 545.57.

1-(Isoquinol-7'-yl)-5-[(2'-butylaminosulfonyl-3-fluoro-[1,1']-biphen-4-yl)carbonylamino]tetrazole (0.12 g, 0.220 mmol) was dissolved in 50 mL of dichloromethane. meta-Chloroperbenzoic acid (≧60%) (90.1 mg, 0.313 mmol, 1.4 eq) was added and the reaction mixture was refluxed for 4 hours. The solution was poured into 20 mL of saturated sodium bicarbonate. The phases were separated and the aqueous layer was extracted with dichloromethane (2×25 mL). The combined organic solution was washed with water (2×20 mL) and brine (1×25 mL), filtered through phase separatory paper, and evaporated to give the N-oxide as an off-white solid. MS (ES+): 584.2 (M+Na)$^+$. The N-oxide was dissolved in 10 mL of anhydrous pyridine and tosyl chloride (63.3 mg, 0.332 mmol) was added. The reaction was stirred at ambient temperature for 3 hours. The pyridine was removed under reduced pressure and to the residue was added 10 mL ethanolamine and the reaction mixture was stirred at ambient temperature for 3 hours. The reaction mixture was poured onto cracked ice and extracted with ethyl acetate (3×50 mL). The combined organic solution was washed with brine (1×50 mL), dried over magnesium sulfate, and evaporated to give a yellow foam. This foam was dissolved in 20 mL of dichloromethane and evaporated to give the 1-aminoisoquinoline product as a pale yellow solid (0.07 g, 57% yield). $^1$H NMR (CDCl$_3$) δ 1.06 (s, 9H, tert-butyl), 4.01 (bs, 1H, NH), 5.42 (bs, 2H, NH$_2$), 7.13 (d, 1H, J=5.8 Hz, aromatic H), 7.26 (m, 2H, aromatic H), 7.38 (dd, 1H, J=11.4 Hz, J=1.8 Hz, aromatic H), 7.50 (td, 1H, J=7.3 Hz, J=1.5 Hz, aromatic H), 7.58 (td, 1H, J=7.3 Hz, J=1.5 Hz, aromatic H), 7.78 (dd, 1H, J=8.7 Hz, J=2.2 Hz, aromatic H), 7.88 (d, 1H, J=8.8 Hz, aromatic H), 8.05 (d, 1H, J=5.9 Hz, aromatic H), 8.16 (d, 1H, J=8.1 Hz, aromatic H), 8.18 (s, 1H, aromatic H), 8.30 (t, 1H, J=8.2 Hz, aromatic H). MS (ES+) 561.2 (M+H)$^+$. C$_{27}$H$_{25}$FN$_8$O$_3$S 560.59.

The 1-aminoisoquinoline compound was dissolved in 5 mL of trifluoroacetic acid and the reaction brought to reflux for 90 minutes. The solvent was removed and the residue was dissolved in acetonitrile and purified by HPLC (C$_{18}$ reverse phase, eluting with acetonitrile and water with 0.05% trifluoroacetic acid added). Evaporation of the solvents gave the title compound as a white solid (45.4 mg, 59% yield). $^1$H NMR (DMSO-d$_6$) δ 7.22 (d, 1H, J=8.0 Hz, aromatic H), 7.34 (d, 3H, J=6.9 Hz, aromatic H), 7.44 (bs, 1H, NH), 7.62 (m, 4H, aromatic H), 7.82 (d, 1H, J=7.0 Hz, aromatic H), 8.02 (d, 1H, J=6.6 Hz, aromatic H), 8.18 (d, 1H, J=8.8 Hz, aromatic H), 8.28 (d, 1H, J=8.4 Hz, aromatic H), 8.96 (bs, 1H, NH), 11.38 (bs, 1H, CF$_3$CO$_2$H). MS (APCI+) 505.3 (M+H)$^+$. HRMS (ES+) for C$_{23}$H$_{17}$FN$_8$O$_3$S calc. (M+H)$^+$ 505.1206; found 505.1221.

Example 63

1-(1'-Amino-isoquinol-7'-yl)-5-[[(2'-methylsulfonyl)-3-fluoro-[1,1']-biphen-4-yl)aminocarbonyl]tetrazole, mesylate salt The title compound was prepared in an analogous fashion as the mesylate salt. $^1$H NMR (DMSO-d$_6$) δ 2.30 (s, 3H, CH$_3$), 2.94 (s, 3H, CH$_3$), 7.26 (d, 1H, J=9.9 Hz, aromatic H), 7.36 (d, 1H, J=8.7 Hz, aromatic H), 7.42 (d, 2H, J=5.8 Hz, aromatic H), 7.65 (t, 1H, J=7.7 Hz, aromatic H), 7.72 (d, 1H, J=7.7 Hz, aromatic H), 7.77 (d, 1H, J=5.9 Hz, aromatic H), 8.08 (d, 1H, J=6.6 Hz, aromatic H), 8.20 (d, 1H, J=8.8 Hz, aromatic H), 8.32 (dd, 1H, J=5.8 Hz, J=1.8 Hz, aromatic H), 8.98 (bs, 1H, NH), 11.42 (bs, 1H, CH$_3$SO$_3$H). MS (APCI) 504.2 (M+H)$^+$. HRMS (Q-TOF) for C$_{24}$H18FN$_7$O$_3$S calc. (M+H)$^+$ 504.125413; found 504.124200.

Example 64

1-(3'-Aminobenzisoxazol-5'-yl)-3-trifluoromethyl-5-[(2'aminosulfonylphenyl)pyrimidin-2-yl)aminocarbonyl]pyrazole The pyrazole carboxylic acid obtained in example 11 was subjected to the standard acid chloride coupling protocol with amino-2'-t-butylaminosulfonylphenyl-pyrimidin-2-yl to afford the coupled pyrimidyl amide precursor. This compound was then treated with acetoneoxime (NaH/DMF) followed by acid hydrolysis as per example 11 to afford the amino benzisoxazole derivative. Removal of the tert-butyl group by treatment with TFA (1 mL) at 100° C. followed by purification via reverse phasew preparation HPLC (acetonitrile/water: 2% TFA) and lyophilization afforded the titled compound as colorless crystals. ESI mass spectrum m/z (relative intensity) 545 (M+H, 100).

Example 65

1-(3'-Aminobenzisoxazol-5'-yl)-3-trifluoromethyl-5-[4'(2"-methylimidazol-1"-yl)phenyl)aminocarbonyl]pyrazole, TFA salt To a suspension of NaH (4.8 g, 120 mmol, prewashed with THF (3×5 mL) in THF (100 mL) was added a solution of 1-fluoro-4-nitrobenzene (14.1 g, 100 mmol) and 2-methylimidazole (8.2 g, 100 mmol) in THF (50 mL) at 0° C. The mixture was refluxed for 16 hours and cooled to room temperature. To it was added EtOAc (200 mL) and water (100 mL). The organic layer was separated, washed with water and brine, dried over $MgSO_4$, and concentrated to give the crude nitro intermediate. A solution of the nitro intermediate in MeOH (200 mL) was treated with hydrogen gas in a balloon in the presence of 5% Pd on carbon (1.5 g) at room temperature for 24 hours. The mixture was filtered and the filtrate was concentrated to give 4-(2'-methylimidazol-1'-yl) aniline (16.5 g, 95.4% for the two steps) as a pale yellow solid. $^1H$ NMR ($CDCl_3$) δ 7.05 (dd, J=6.4 Hz, J=2.1 Hz, 2H), 6.98 (d, J=1.1 Hz, 1H), 6.93 (d, J=1.1 Hz, 1H), 6.73 (dd, J=6.4 Hz, J=2.1 Hz, 2H), 3.85 (bs, 2H), 2.31 (s, 3H); MS(CI) m/z 174 (M+H, 100).

To a solution of 1-(4'-fluoro-3'-cyanophenyl)-3-trifluoromethyl-5-pyrazolecarboxylic acid (2 g, 6.39 mmol) in $CH_3CN$ (30 mL) was added $SOCl_2$ (5.1 g, 42.8 mmol) and the resulting solution was refluxed for 2 hours. The mixture was concentrated on an evaporator and the residue was dissolved in MeOH (20 mL). The resulting solution was refluxed for 30 minutes, and then concentrated and purified by silica gel chromatography with $CH_2Cl_2$ to give methyl 1-(4'-fluoro-3'-cyanophenyl)-3-trifluoromethyl-5-pyrazolecarboxylic ester (1.93 g, 92%). $^1H$ NMR ($CDCl_3$) δ 7.78 (dd, J=5.6 Hz, J=2.6 Hz, 1H), 7.73 (dd, J=8.4 Hz, J=3.4 Hz, 1H), 7.36 (t, J=8.4 Hz, 1H), 7.30 (s, 1H), 3.88 (s, 3H); $^{19}F$ NMR ($CDCl_3$) δ -63.01, -104.60; MS(CI) m/z 331 (M+$NH_4$, 100).

To a solution of acetone oxime (0.67 g, 9.2 mmol) in DMF (20 mL) was added potassium tert-butoxide (1.0 M in THF, 9.2 mL) and the mixture was stirred at room temperature for 15 minutes. To it was added a solution of methyl 1-(4'-fluoro-3'-cyanophenyl)-3-trifluoromethyl-5-pyrazolecarboxylic ester (1.92 g, 6.15 mmol) in DMF (20 mL) and the resulting mixture was stirred at room temperature for 20 hours and quenched with water (10 mL). The mixture was extracted with EtOAc (100 mL) and the EtOAc layer was washed with brine (10 mL×5), dried over $MgSO_4$, concentrated, and purified by silica gel chromatography eluted with 80% $CH_2Cl_2$ in hexane to give methyl 1-(4'-isopropylideneaminooxy-3'-cyanophenyl)-3-trifluoromethyl-5-pyrazolecarboxylic ester (1.53 g, 68%) as a white solid. $^1H$ NMR ($CDCl_3$) δ 7.69 (d, J=9.1 Hz, 1H), 7.66 (d, J=2.2 Hz, 1H), 7.60 (dd, J=9.1 Hz, J=2.5 Hz, 1H), 7.26 (s, 1H), 3.85 (s, 3H), 2.19 (s, 3H), 2.08 (s, 3H); $^{19}F$ NMR ($CDCl_3$) δ -62.88; MS(ES+) m/z 367 (M+H, 100).

To a solution of methyl 1-(4'-isopropylideneaminooxy-3'-cyanophenyl)-3-trifluoromethyl-5-pyrazolecarboxylic ester (1.53 g, 4.18 mmol) in MeOH (13 mL) and $CH_2Cl_2$ (6 mL) was added 18% HCl (13 mL) and the mixture was refluxed for 3 hours and then concentrated to remove organic solvents. The resulting aqueous solution was neutralized with 2N NaOH to pH 7 and extracted with EtOAc. The EtOAc layer was washed with brine, dried over $MgSO_4$, and concentrated to give methyl 1-(3'-aminobenzisoxozol-5-yl)-3-trifluoromethyl-5-pyrazolecarboxylic ester (1.32 g, 96%) as a white solid. $^1H$ NMR ($CD_3OD$) δ 7.89 (d, J=2.1 Hz, 1H), 7.63 (dd, J=8.8 Hz, J=2.2 Hz, 1H), 7.50 (d, J=8.8 Hz, 1H), 7.40 (s, 1H), 3.79 (s, 3H); $^{19}F$ NMR ($CD_3OD$) δ -64.36; MS(ES+) m/z 327 (M+H, 100).

A solution of methyl 1-(3'-aminobenzisoxozol-5-yl)-3-trifluoromethyl-5-pyrazolecarboxylic ester (260 mg, 0.8 mmol) in THF (10 mL) was treated with 2N NaOH (10 mL) at room temperature for 16 hours. The mixture was acidified with conc. HCl to pH 3 and extracted with EtOAc. The EtOAc layer was dried over $Na_2SO_4$ and concentrated to give 1-(3'-aminobenzisoxozol-5-yl)-3-trifluoromethyl-5-pyrazolecarboxylic acid (240 mg, 96%). $^1H$ NMR ($CD_3OD$) δ 7.90 (d, J=1.9 Hz, 1H), 7.62 (dd, J=8.8 Hz, J=2.4 Hz, 1H), 7.49 (d, J=8.8 Hz, 1H), 7.35 (s, 1H); $^{19}F$ NMR ($CD_3OD$) δ -64.32; MS(ES+) m/z 311 (M−H, 100).

To a solution of 1-(3'-aminobenzisoxozol-5-yl)-3-trifluoromethyl-5-pyrazolecarboxylic acid (240 mg, 0.77 mmol) in DMF (5 mL) was added 4-(2'-methylimidazol-1'-yl)aniline (133 mg, 0.77 mmol), DMAP (99.5 mg, 0.79 mmol), and PyBrop (372 mg, 0.79 mmol). The resulting mixture was stirred at 60° C. for 16 hours, and quenched with EtOAc (100 ml) and water (20 mL). The EtOAc layer was washed with 1N HCl (10 mL), 1N NaOH (10 mL), water (10 mL), and brine (10 mL×3), dried over $MgSO_4$, and concentrated. The residue was purified by HPLC ($CH_3CN$—$H_2O$–0.05% TFA) to give the title compound (281 mg, 63%) as a white solid. $^1H$ NMR ($CD_3OD$) δ 7.97 (d, J=0.8 Hz, 1H), 7.89 (d, J=9.1 Hz, 2H), 7.65 (dd, J=9.1 Hz, J=2.2 Hz, 1H), 7.64 (d, J=2.2 Hz, 1H), 7.58 (d, J=2.2 Hz, 1H), 7.52 (d, J=8.8 Hz, 2H), 7.50 (d, J=8.4 Hz, 1H), 7.45 (s, 1H), 2.54 (s, 3H); $^{13}C$ NMR ($CD_3OD$) δ 163.74, 160.46, 158.79, 146.51, 141.45, 140.03, 135.89, 131.89, 129.10, 127.59, 124.51, 122.77, 122.39 (TFA-$CF_3$), 120.04, 119.62, 118.22, 110.87, 108.24, 11.29; $^{19}F$ NMR ($CD_3OD$) δ -64.21, -77.51 (TFA); MS(ES+) m/z 468.2 (M+H, 100); HRMS: calcd. 468.1396; obs. 468.1381; Anal. ($C_{22}H_{16}N_7O_2F_3$+1.33 TFA+0.11 HCl+1.4 $H_2O$): C, H, N, F, Cl.

Example 66

1-(3'-Aminobenzisoxazol-5'-yl)-3-trifluoromethyl-5-[4'(2"-methylimidazol-1'-yl)-2'-fluorophenyl) aminocarbonyl]pyrazole, TFA salt To a solution of 4-bromo-2-fluoroaniline (19.2 g, 100 mmol) in THF (100 mL) at 0° C. was slowly added $LiN(TMS)_2$ (1M in THF, 200 mL) over 30 minutes. After the resulting solution was warmed to room temperature, a solution of di-tert-butyl dicarbonate (21.8 g, 100 mmol) in THF (50 mL) was slowly added, stirred for 15 minutes, and filtered through a pad of silica gel. The filtrate was concentrated and recrystalized from hexane to give 4-bromo-2-fluoro-1-tert-butoxycarbonylaniline (27.7 g, 95%). $^1H$ NMR ($CDCl_3$) δ 8.00 (t, J=8.8 Hz, 1H), 7.25–7.20 (m, 2H), 6.66 (bs, 1H), 1.52 (s, 9H); $^{19}F$ NMR ($CDCl_3$) δ -130.42; MS(ES+) m/z 290/292 (M+H, 100).

To a solution of 4-bromo-2-fluoro-1-tert-butoxycarbonylaniline (2.9 g, 10 mmol) in THF (20 mL) at −78° C. was slowly added n-BuLi (2.5 M, 10 mL). After the solution was stirred at that temperature for 30 minutes, $B(OMe)_3$ (4.68 g, 45 mmol) was added and the resulting mixture was warmed to room temperature over 2 hours. The mixture was concentrated and the residue was dissolved in EtOAc (150 mL) and water (50 mL), acidified with 1N HCl to pH 4 and filtered through a pad of Celite. The organic layer was separated, washed with water and brine, dried over $Na_2SO_4$, concentrated, and purified by silica gel chromatography eluted with gradient solvents ($CH_2Cl_2$ to EtOAc) to give 3-fluoro-4-tert-butoxycarbonylaminophenylboronic acid (1.45 g, 56.9%) as a white solid. $^1H$ NMR ($CD_3OD$) δ 7.80 (s, 1H), 7.47 (d, J=8.4 Hz, 1H), 7.40 (d, J=12.8 Hz, 1H), 1.52 (s, 9H); $^{19}F$ NMR ($CD_3OD$) δ -132.66; MS(ES−) m/z 254 (M−H, 100).

To a solution of 3-fluoro-4-tert-butoxycarbonylaminophenylboronic acid (1.1 g, 4.35 mmol) in THF (10 mL) was added 2-methylimidazole (0.36 g, 4.33 mmol), pyridine (3.4 g, 43 mmol), $Cu(OAc)_2$ (0.79 g, 4.33 mmol), and 4 Å molecular sieves. After being stirred at room temperature for 16 hours, the resulting mixture was diluted with EtOAc (100 mL) and filtered through a pad of silica gel.

The filtrate was concentrated and treated with 3M HCl in EtOAc (10 mL) at room temperature for 1 hour, and then water (20 mL) was added. The aqueous layer was neutralized with 1N NaOH to pH 8 and extracted with EtOAc. The organic layer was dried over $Na_2SO_4$ and concentrated to give 2-fluoro-4-(2'-methylimidazol-1'-yl)aniline (0.4 g, 48.5% for the two steps). $^1$H NMR (CD$_3$OD) δ 7.25 (dd, J=12.1 Hz, J=1.8 Hz, 1H), 7.20 (d, J=1.4 Hz, 1H), 7.17 (dd, J=8.5 Hz, J=1.8 Hz, 1H), 7.09 (d, J=1.5 Hz, 1H), 6.91 (t, J=8.8 Hz, 1H), 3.74 (s, 3H); $^{19}$F NMR (CD$_3$OD) δ −135.71; MS(ES+) m/z 192 (M+H, 100);

To a solution of 1-(3'-aminobenzisoxozol-5-yl)-3-trifluoromethyl-5-pyrazolecarboxylic acid (130 mg, 0.42 mmol) in DMF (15 mL) was added 2-fluoro-4-(2'-methylimidazol-1'-yl)aniline (80 mg, 0.42 mmol), diisopropylethylamine (0.2 mL), PyBrop (194 mg, 0.42 mmol), and 4 Å molecular sieves. The resulting mixture was stirred at room temperature for 30 minutes and at 75° C. for 16 hours and EtOAc (100 ml) was added. The mixture was filtered through a pad of Celite, and the filtrate was washed with 1N HCl (5 mL×2), 1N NaOH (5 mL×2), water (10 mL), and brine (5 mL×4), dried over MgSO$_4$, and concentrated. The residue was purified by silica gel TLC plates eluted with 10% MeOH in EtOAc, followed by further purification by HPLC (CH$_3$CN—H$_2$O–0.05% TFA) to give the title compound (75 mg, 37%) as a white solid. $^1$H NMR (CD$_3$OD) δ 8.09 (t, J=8.4 Hz, 1H), 7.97 (d, J=1.9 Hz, 1H), 7.66 (dd, J=8.8 Hz, J=2.2 Hz, 1H), 7.67 (d, J=2.1 Hz, 1H), 7.58 (d, J=2.2 Hz, 1H), 7.55 (dd, J=9.1 Hz, J=2.1 Hz, 1H), 7.50 (d, J=9.1 Hz, 1H), 7.46 (s, 1H), 7.40 (d, J=8.8 Hz, 1H), 2.56 (s, 3H); $^{13}$C NMR (CD$_3$OD) δ 163.76, 160.43, 159.05, 157.17, 154.67, 146.80, 143.78, 139.61, 135.74, 129.10, 127.30, 124.48, 123.35, 121.03, 120.08, 119.77, 118.23, 115.47, 115.23, 110.92, 108.65, 11.33; $^{19}$F NMR (CD$_3$OD) δ −64.21, −77.62 (TFA), −121.45; MS(ES+) m/z 486.2 (M+H, 100); Anal. (C$_{22}$H$_{15}$N$_7$O$_2$F$_4$+1.3 TFA+1 H$_2$O): C, H, N, F.

Example 67

1-(3'-Aminobenzisoxazol-5'-yl)-3-trifluoromethyl-5-[4'(1"-methylimidazol-2"-yl)-2'-fluorophenyl)aminocarbonyl]pyrazole, TFA salt To a solution of 1N-methylimidazole (1.64 g, 20 mmol) in THF 40 mL) at −78° C. was added nBuLi (2.5 M, 9.6 mL) and the resulting solution was stirred at −78° C. for 30 minutes. After Bu$_3$SnCl (7.18 g, 22 mmol) was added, the resulting mixture was slowly warmed to room temperature over 2 hours and was stirred for an additional 16 hours. To 4-bromo-2-fluoro-1-tert-butoxycarbonylaniline (0.58 g, 2 mmol) and Pd(PPh$_3$)$_4$ (92 mg, 0.08 mmol) was added the above solution (15 mL) and the resulting mixture was degassed and filled with nitrogen three times. The mixture was refluxed under nitrogen for 18 hours, and was cooled to room temperature. After saturated aqueous KF (10 mL) was added, the resulting mixture was stirred for 1 hour and filtered through a pad of Celite. The filtrate was washed with water and brine, dried over MgSO$_4$, concentrated, and purified by silica del chromatography with EtOAc to give 2-fluoro-4-(1'-methylimidazol-2'-yl)-1-tert-butoxycarbonylaniline (0.35 g, 60%) as a white solid. $^1$H NMR (CDCl$_3$) δ 8.19 (t, J=8.0 Hz, 1H), 7.42 (dd, J=12.1 Hz, J=1.8 Hz, 1H), 7.36 (d, J=9.1 Hz, 1H), 7.10 (d, J=1.1 Hz, 1H), 6.96 (s, 1H), 6.80 (bs, 1H), 3.75 (s, 3H), 1.54 (s, 9H); $^{19}$F NMR (CDCl$_3$) δ −132.59; MS(ES+) m/z 292.2 (M+H, 100).

To a solution of 2-fluoro-4-(1'-methylimidazol-2'-yl)-1-tert-butoxycarbonylaniline (0.33 g, 1.13 mmol) in EtOAc (10 mL) was added 3M HCl (5 mL) and the resulting solution was stirred at room temperature for 30 minutes. The solution was cooled to 0° C., neutralized with 50% NaOH to pH 8, and extracted with EtOAc (50 mL×3). The EtOAc layer was concentrated and purified by silica gel chromatography eluted with 5% MeOH in EtOAc to give 2-fluoro-4-(1'-methylimidazol-2'-yl)aniline (0.18 g, 83%). $^1$H NMR (CD$_3$OD) δ 7.54 (d, J=2.2 Hz, 1H), 7.51 (d, J=2.2 Hz, 1H), 7.37 (dd, J=11.8 Hz, J=2.2 Hz, 1H), 7.27 (dd, J=8.4 Hz, J=2.2 Hz, 1H), 6.97 (t, J=8.8 Hz, 1H), 3.88 (s, 3H) $^{19}$F NMR (CD$_3$OD) δ −136.77 (dd, J=90.1 Hz, J=9.1 Hz); MS(ES+) m/z 192 (M+H, 100).

To a solution of 1-(3'-aminobenzisoxozole-5-yl)-3-trifluoromethyl-5-pyrazolecarboxylic acid (30 mg, 0.096 mmol) in DMF (2 mL) was added 2-fluoro-4-(1'-methylimidazol-2'-yl)aniline (20.4 mg, 0.106 mmol), diisopropylethylamine (0.2 mL), and PyBrop (49.4 mg, 0.106 mmol). The resulting mixture was stirred at 60° C. for 16 hours and quenched with EtOAc (75 ml) and water (5 mL). The EtOAc layer was washed with 1N HCl (5 mL), 1N NaOH (5 mL), and brine (5 mL×4), dried over MgSO$_4$, and concentrated. The residue was purified on silica gel TLC plates with 10% MeOH in EtOAc, followed by further purification by HPLC (CH$_3$CN—H$_2$O–0.05% TFA) to give the title compound (19 mg, 40.8%) as a white solid. $^1$H NMR (CD$_3$OD) δ 8.21 (t, J=8.1 Hz, 1H), 7.99 (dd, J=2.2 Hz, J=0.6 Hz, 1H), 7.70–7.66 (m, 3H), 7.64 (d, J=2.2 Hz, 1H), 7.57 (dt, J=8.3 Hz, J=1.0 Hz, 1H), 7.52 (dd, J=8.8 Hz, J=0.5 Hz, 1H), 7.48 (s, 1H), 3.93 (s, 3H); $^{13}$C NMR (CD$_3$OD) δ 163.78, 160.43, 159.02, 156.71, 154.22, 144.84, 143.78 (CF$_3$), 139.64, 135.73, 129.09, 127.05, 126.51, 126.08, 120.52, 120.08, 118.23, 117.99, 110.93, 108.71, 36.16; $^{19}$F NMR (CD$_3$OD) δ −64.21, −77.58 (TFA), −123.46; MS(ES+) m/z 486.2 (M+H, 100).

Example 68

1-(3'-Aminobenzisoxazol-5'-yl)-3-trifluoromethyl-5-[4'(2"-aminoimidazol-1"-yl)phenyl)aminocarbonyl]pyrazole, TFA salt To a solution of 2-aminoimidazole sulfate (2.24 g, 17 mmol) in DMF (30 mL) was added 4-bromo-1-nitrobenzene (3.4 g, 17 mmol), K$_2$CO$_3$ (4.69 g, 34 mmol) and 18-crown-6 (50 mg), and the resulting mixture was stirred at 80° C. for 16 hours. The mixture was cooled to room temperature, and was diluted with EtOAc (150 mL) and water (50 mL). The organic layer was washed with brine (20 mL×5), dried over MgSO$_4$, and concentrated to give 4-(2'-amino-imidazol-1'-yl)nitrobenzene (3.23 g, 98%). $^1$H NMR (CD$_3$OD) δ 8.38 (d, J=9.1 Hz, 2H), 7.73 (d, J=9.1 Hz, 2H), 6.90 (d, J=1.9 Hz, 1H), 6.66 (d, J=1.9 Hz, 1H); MS(ES+) m/z 205 (M+H, 100).

A solution of 4-(2'-amino-imidazol-1'-yl)nitrobenzene (0.5 g, 2.45 mmol) in methanol (15 mL) was treated with hydrogen in a balloon in the presence of 5% Pd on carbon (70 mg) at room temperature for 16 hours and then filtered. The filtrate was concentrated to give 4-(2'-amino-imidazol-1'-yl)aniline (0.35 g, 82%). $^1$H NMR (CD$_3$OD) δ 7.08 (dd, J=6.6 Hz, J=2.2 Hz, 2H), 6.77 (dd, J=6.6 Hz, J=2.2 Hz, 2H), 6.64 (d, J=1.8 Hz, 1H), 6.58 (d, J=1.8 Hz, 1H); MS(ES+) m/z 175 (M+H, 100).

To a solution of 1-(3'-aminobenzisoxozol-5-yl)-3-trifluoromethyl-5-pyrazolecarboxylic acid (110 mg, 0.35 mmol) in DMF (5 mL) was added freshly prepared 4-(2'-amino-imidazol-1'-yl)aniline (110 mg, 0.63 mmol), iPrNEt$_2$ (1 mL), PyBrop (260 mg, 0.56 mmol), and 4 Å molecular sieves. The resulting mixture was stirred at room temperature for 16 hours and quenched with EtOAc (100 mL). The mixture was filtered and the filtrate was washed with brine (5 mL×5) and 1N HCl ((10 mL×3). The combined HCl layers were neutralized with 50% NaOH to pH 14 and extracted with EtOAc. The EtOAc layer was dried over $Na_2SO_4$, concentrated, and purified by HPLC ($CH_3CN$—$H_2O$–0.05% TFA) to give the title compound (81 mg, 50%) as a white solid. $^1H$ NMR ($CD_3OD$) δ 7.77 (d, J=1.5 Hz, 1H), 7.49 (dd, J=8.8 Hz, J=2.2 Hz, 1H), 7.33 (d, J=8.4 Hz, 1H), 7.18 (s, 1H), 7.16 (dd, J=6.6 Hz, J=2.2 Hz, 2H), 7.12 (d, J=2.5 Hz, 1H), 7.07 (d, J=2.5 Hz, 1H), 6.96 (dd, J=6.6 Hz, J=2.2 Hz, 2H); $^{19}F$ NMR ($CD_3OD$) δ –64.23, –77.76 (TFA); MS(ES+) m/z 469 (M+H, 100).

Example 69

1-(3'-Aminobenzisoxazol-5'-yl)-3-trifluoromethyl-5-[4'(2"-N,N-dimethylaminomethylphenyl)-2'-fluorophenyl)aminocarbonyl]pyrazole, TFA salt To a solution of 2-formylphenylboronic acid (5 g, 33.3 mmol) in THF (80 mL) was added 4-bromo-2-fluoroaniline (4.2 g, 22.2 mmol) and $Na_2CO_3$ (2M, 80 mL) and then was bubbled with nitrogen for 10 minutes. After $Pd(PPh_3)_4$ (1.54 g, 1.33 mmol) was added, the resulting mixture was refluxed under nitrogen for 4 hours. The THF layer was separated, filtered through a pad of silica gel, and washed with THF to give 80 mL solution of 4(2'-formylphenyl)-2-fluoroaniline in THF. MS(CI) m/z 233 (M+$NH_4$, 100%). To the filtrate (15 mL from total 80 mL) was added $Me_2NH.HCl$ (0.68 g, 8.33 mmol) and the resulting mixture was refluxed for 2 hours. The mixture was cooled to room temperature, and to it was added MeOH (5 mL) and then $NaBH_4$ (0.32 g, 8.33 mmol). After being stirred at 50° C. for 1 hour, the mixture was cooled to room temperature again and quenched with 1N HCl to pH 1. The aqueous layer was separated, neutralized with 50% NaOH to pH 12, and extracted with EtOAc. The EtOAc layer was dried over $MgSO_4$, concentrated, and purified by silica gel chromatography eluted with EtOAc to give 4-(2'-N,N-dimethylaminomethylphenyl)-2-fluoroaniline (0.89 g, 87.5%). $^1H$ NMR ($CDCl_3$) δ 7.49 (dd, J=8.8 Hz, J=1.8 Hz, 1H), 7.31–7.21 (m, 3H), 7.14 (dd, J=12.1 Hz, J=1.8 Hz, 1H), 6.97 (dd, J=8.1 Hz, J=1.5 Hz, 1H), 6.80 (t, J=8.8 Hz, 1H), 3.76 (bs, 2H), 3.34 (s, 2H), 2.17 (s, 6H); $^{19}F$ NMR ($CDCl_3$) δ –136.19; MS(ES+) m/z 245.2 (M+H, 100).

To a solution of 1-(4'-fluoro-3'-cyanophenyl)-3-trifluoromethyl-5-pyrazolecarboxylic acid (0.299 g, 1 mmol) in $CH_3CN$ (20 mL) was added $SOCl_2$ (0.74 g, 6 mmol). The resulting mixture was refluxed for 2 hours and then concentrated. To a solution of the residue in THF (25 mL) was added 4-(2'-N,N-dimethylaminomethylphenyl)-2-fluoroaniline (0.29 g, 1.19 mmol) and N,N-diisopropylethylamine (1 mL). The resulting solution was stirred at room temperature for 16 hours and quenched with EtOAc (100 mL) and 1N HCl (50 mL). The organic layer was separated and washed with 1N NaOH (20 mL) and brine, dried over $MgSO_4$, concentrated, and purified on silica gel TLC plates eluted with 10% MeOH in $CH_2Cl_2$ to give 1-(4'-fluoro-3'-cyanophenyl)-3-trifluoromethyl-5-[4'(2"-N,N-dimethylaminomethylphenyl)-2'-fluorophenyl)aminocarbonyl]pyrazole (0.31 g, 59%). $^1H$ NMR ($CDCl_3$) δ 8.18 (t, J=8.4 Hz, 1H), 8.06 (bs, 1H), 7.87–7.79 (m, 2H), 7.50 (dd, J=8.8 Hz, 1H), 7.42–7.30 (m, 5H), 7.24 (d, J=7.0 Hz, 1H), 7.19 (s, 1H), 3.33 (s, 2H), 2.19 (s, 6H); $^{19}F$ NMR ($CDCl_3$) δ –62.85, –104.83, –135.2; MS(ES+) m/z 526.3 (M+H, 100).

To a solution of acetone oxime (0.129 g, 1.77 mmol) in DMF (5 mL) was added potassium tert-butoxide (1.0 M in THF, 1.77 mL), and the mixture was stirred at room temperature for 15 minutes. To it was then added a solution of 1-(4'-fluoro-3'-cyanophenyl)-3-trifluoromethyl-5-[4'(2"-N,N-dimethylaminomethylphenyl)-2'-fluorophenyl) aminocarbonyl]pyrazole (0.31 g, 0.59 mmol) in DMF (5 mL), and the resulting mixture was stirred at room temperature for 20 hours and quenched with water (10 mL). The mixture was extracted with EtOAc (100 mL), and the EtOAc layer was washed with brine (10 mL×5), dried over $MgSO_4$, and concentrated to give a residue. The residue was treated with 4M HCl in dioxane (10 mL) under reflux for 2 hours and concentrated. The resulting residue was dissolved in EtOAc and water, and the EtOAc layer was dried over $Na_2SO_4$, concentrated, and purified on silica gel TLC plates eluted with 5% MeOH in $CH_2Cl_2$, followed by purification by HPLC ($CH_3CN$—$H_2O$–0.05% TFA) to give the title compound (37 mg, 11% for the two steps) as a white solid. $^1H$ NMR ($CD_3OD$) δ 7.99 (dd, J=2.2 Hz, J=0.5 Hz, 1H), 7.83 (t, J=8.1 Hz, 1H), 7.68 (dd, J=8.8 Hz, J=2.0 Hz, 1H), 7.63–7.61 (m, 1H), 7.57–7.54 (m, 1H), 7.52 (dd, J=8.8 Hz, J=0.6 Hz, 1H), 7.45 (s, 1H), 7.42–7.40 (m, 1H), 7.24 (dd, J=11.2 Hz, J=1.9 Hz, 1H), 7.15 (dd, J=8.2 Hz, J=1.2 Hz, 1H), 4.71 (s, 2H), 2.63 (s, 6H); $^{13}C$ NMR ($CD_3OD$) δ 162.33, 159.00, 142.07, 138.89, 138.40, 134.41, 130.78, 130.47, 129.96, 128.80, 127.76, 127.32, 125.99, 125.40, 124.24, 124.11, 118.73, 116.92, 116.80, 116.71, 109.43, 106.93, 57.68, 41.77; $^{19}F$ NMR ($CD_3OD$) δ –64.20, –77.57 (TFA), –123.93; MS(ES+) m/z 539.2 (M+H, 100).

Example 70

Ethyl 1-(3'-aminobenzisoxazol-5'-yl)-5-[(2'-aminosulfonyl-3-fluoro-[1,1']-biphen-4-yl) aminocarbonyl]pyrazole-3-carboxylate Preparation of ethyl 4-(2-furyl)-2,4-dioxobutyrate.

To a suspension of sodium hydride (5.4 g of 60% dispersion in mineral oil, 136 mmol, mineral oil was removed by washing twice with hexanes) in 100 mL of tetrahydrofuran at ambient temperature was added diethyl oxalate (12.3 mL, 91 mmol). To this mixture was added 2-acetylfuran (5.0 g, 45 mmol) as a solution in 25 mL of tetrahydrofuran. The resulting mixture was stirred at 70° C. for 1 h. The reaction was cooled to room temperature and then 10% HCl was added slowly until the solution was acidic. The tetrahydrofuran was removed in vacuo and the residue was taken up in ethyl acetate. The organics were washed with brine, dried ($MgSO_4$) and concentrated to afford 5.5 g (58%) of the title compound which was used without purification.

Preparation of ethyl 1-(3-cyano-4-fluorophenyl)-5-(2-furyl) pyrazole-3-carboxylate.

To ethyl 4-(2-furyl)-2,4-dioxobutyrate (3.5 g, 16.7 mmol) in 50 mL of glacial acetic acid was added 4-fluoro-3-cyanophenylhydrazine tin chloride (6.3 g, 16.7 mmol). The reaction was stirred at 100° C. for 4 h. The reaction was allowed to cool to room temperature and the acetic acid was removed in vacuo. The residue was diluted with ethyl acetate and the organics were washed with saturated aq $NaHCO_3$ and brine, dried ($MgSO_4$) and concentrated. The residue was purified by recrystallization from hexane/ethyl acetate to afford 2.5 g (46%) of the title compound. LRMS (ES+): 326.1 (M+H)$^+$.

Preparation of ethyl 1-(3-cyano-4-fluorophenyl)-pyrazole-3-carboxylate-5-carboxylic acid.

To a solution of ethyl 1-(3-cyano-4-fluorophenyl)-5-(2-furyl)pyrazole-3-carboxylate (1.30 g, 4.0 mmol) in 8:8:12 carbon tetrachloride/acetonitrile/water was added sodium periodate (3.85 g, 18 mmol) and ruthenium (III) chloride monohydrate (20 mg, 0.09 mmol). The resulting biphasic reaction was stirred vigorously at ambient temperature for 24 h. The reaction was quenched with 10% aq HCl and diluted with ethyl acetate. The organics were washed with brine, dried (MgSO$_4$), filtered through a pad of Celite and concentrated. The residue was dissolved in 1:1 hexanes/ethyl acetate and extracted with sat'd aq Na$_2$CO$_3$ (2 times). The combined aqueous extracts were acidified and extracted with ethyl acetate. The ethyl acetate extracts were washed with brine, dried (MgSO$_4$) and concentrated to afford 0.70 g (58%) of the title compound as a solid. LRMS (AP+): 304.1 (M+H)$^+$.

Preparation of ethyl 1-(3-cyano-4-fluorophenyl)-5-[(2'-tert-butylaminosulfonyl-3-fluoro-[1,1']-biphen-4-yl)aminocarbonyl]pyrazole-3-carboxylate.

To a solution of ethyl 1-(3-cyano-4-fluorophenyl)pyrazole-3-carboxylate-5-carboxylic acid (0.44 g, 1.45 mmol) in 10 mL of methylene chloride was added oxalyl chloride (0.19 mL, 2.18 mmol) and 2 drops of dimethylformamide. The reaction was stirred at ambient temperature for 6 h and then the volatiles were removed in vacuo. The residue was dissolved in 10 mL of methylene chloride and then there was added 4-dimethylaminopyridine (0.53 g, 4.35 mmol). The reaction was stirred for 10 min and then there was added (2'-tert-butylaminosulfonyl-3-fluoro-[1,1']-biphen-4-yl) amine hydrochloride (0.47 g, 1.45 mmol). The resulting mixture was allowed to stir at ambient temperature for 16 h. The reaction was diluted with ethyl acetate and the organics were washed with 10% aq HCl, sat'd aq NaHCO$_3$ and brine, dried (MgSO$_4$), filtered through a pad of silica gel and concentrated to afford 0.35 g (40%) of the title compound as a solid. LRMS (ES−): 606.1 (M−H)$^−$.

Preparation of ethyl 1-(4-isopropylideneaminooxy-3-cyanophenyl)-5-[(2'-tert-butylaminosulfonyl-3-fluoro-[1,1']-biphen-4-yl)aminocarbonyl]pyrazole-3-carboxylate.

To a solution of acetone oxime (40 mg, 0.52 mmol) in 2 mL of DMF at ambient temperature was added potassium tert-butoxide (1.2 mL of a 1.0 M solution in tetrahydrofuran, 1.2 mmol). The reaction was stirred for 15 min and then ethyl 1-(3-cyano-4-fluorophenyl)-5-[(2'- tert-butylaminosulfonyl-3-fluoro-[1,1']-biphen-4-yl)aminocarbonyl]pyrazole-3-carboxylate (243 mg, 0.40 mmol) was added as a solution in 3 mL of DMF. The resulting mixture was allowed to stir at ambient temperature for 18 h. The reaction was partitioned between ethyl acetate and sat'd aq ammonium chloride and the organics were washed with brine, dried (MgSO$_4$), and concentrated. The residue was purified by flash chromatography (elution with 2:1 hexanes/ethyl acetate) to afford 0.15 g (57%) of the title compound. LRMS (AP−): 658.9 (M−H)$^−$.

Preparation of ethyl 1-(3'-aminobenzisoxazol-5'-yl)-5-[(2'-aminosulfonyl-3-fluoro-[1,1']-biphen-4-yl)aminocarbonyl]pyrazole-3-carboxylate.

To a solution of ethyl 1-(4-isopropylideneaminooxy-3-cyanophenyl)-5-[(2'-tert-butylaminosulfonyl-3-fluoro-[1,1']-biphen-4-yl)aminocarbonyl]pyrazole-3-carboxylate (0.14 g, 0.21 mmol) in 5 mL of absolute ethanol was added 4 mL of 6N HCl. The reaction was stirred at 80° C. for 1 h and then was cooled to room temperature. The reaction was diluted with ethyl acetate and the organics were washed with water and brine, dried (MgSO$_4$) and concentrated. The residue was dissolved in 5 mL of trifluoroacetic acid and stirred at 80° C. for 30 min. The reaction was cooled and concentrated and the residue was purified by prep HPLC (C18 reverse phase column, elution with a H$_2$O/CH$_3$CN gradient with 0.5% TFA) and lyophilized to afford 34 mg (29%) of the compound of Example 70 as a white powder. LRMS (AP+): 565.2 (M+H)$^+$.

Example 71

1-(3'-Aminobenzisoxazol-5'-yl)-5-[(2'-aminosulfonyl-3-fluoro-[1,1']-biphen-4-yl) aminocarbonyl]pyrazole-3-carboxylic acid To a solution of ethyl 1-(3'-aminobenzisoxazol-5'-yl)-5-[(2'-aminosulfonyl-3-fluoro-[1,1']-biphen-4-yl)aminocarbonyl]pyrazole-3-carboxylate (0.20 g, 0.32 mmol) in 10 mL of 1:1 methanol/water was added potassium hydroxide (20 mg, 0.35 mmol). The reaction was stirred at 60° C. for 2 h and then was cooled to room temperature and acidified with 10% aq HCl. The mixture was diluted with ethyl acetate, washed with brine, dried (MgSO$_4$) and concentrated. A portion of the residue (25 mg) was dissolved in 5 mL of trifluoroacetic acid and stirred at 80° C. for 30 min. The reaction was cooled and concentrated and the residue was purified by prep HPLC (C18 reverse phase column, elution with a H$_2$O/CH$_3$CN gradient with 0.5% TFA) and lyophilized to afford 10 mg (40%) of the compound of Example 71 as a white powder. LRMS (ES+): 537.2 (M+H)$^+$.

Example 72

1-(3'-Aminobenzisoxazol-5'-yl)-5-[(2'-aminosulfonyl-3-fluoro-[1,1']-biphen-4-yl) aminocarbonyl]pyrazole-3-carboxamide To a solution of 1-(3'-aminobenzisoxazol-5'-yl)-5-[(2'-tert-butylaminosulfonyl-3-fluoro-[1,1']-biphen-4-yl)aminocarbonyl]pyrazole-3-carboxylic acid (0.15 g, 0.25 mmol) in 50 mL of acetonitrile at 0° C. was added triethylamine (0.05 mL, mmol) and iso-butyl chloroformate (0.03 mL, mmol). This mixture was stirred for 30 min and then there was added methanolic ammonia (0.50 mL of a 2.0 M solution of ammonia in methanol, mmol). The reaction was allowed to stir with warming to room temperature for 18 h. The volatiles were removed in vacuo and the residue was diluted with ethyl acetate. The organics were washed with sat'd aq NaHCO$_3$ and brine, dried (MgSO$_4$) and concentrated. A portion of the residue (25 mg) was dissolved in 5 mL of trifluoroacetic acid and stirred at 80° C. for 30 min. The reaction was cooled and concentrated and the residue was purified by prep HPLC (C18 reverse phase column, elution with a H$_2$O/CH$_3$CN gradient with 0.5% TFA) and lyophilized to afford 12 mg (50%) of the compound of Example 72 as a white powder. LRMS (ES+): 536.2 (M+H)+.

Example 73

Ethyl 1-(3'-aminobenzisoxazol-5'-yl)-5-[(2'-methylsulfonyl-3-fluoro-[1,1']-biphen-4-yl) aminocarbonyl]pyrazole-3-carboxylate Preparation of ethyl 1-(3-cyano-4-fluorophenyl)-5-[(2'-methylsulfonyl-3-fluoro-[1,1']-biphen-4-yl)aminocarbonyl]pyrazole-3-carboxylate.

To a solution of ethyl 1-(3-cyano-4-fluorophenyl)pyrazole-3-carboxylate-5-carboxylic acid (4.55 g, 15 mmol) in 100 mL of methylene chloride was added oxalyl chloride (2.0 mL, 22.5 mmol) and 2 drops of dimethylformamide. The reaction was stirred at ambient temperature for 6 h and then the volatiles were removed in vacuo. The residue was dissolved in 100 mL of methylene chloride and then there was added 4-dimethylaminopyridine (5.5 g, 45 mmol). The reaction was stirred for 10 min and then there was added 2'-methylsulfonyl-3-fluoro-[1,1']-biphen-4-yl)amine hydrochloride (4.52 g, 15 mmol). The resulting mixture was allowed to stir at ambient temperature for 16 h. The reaction was diluted with ethyl acetate and the organics were washed with 10% aq HCl, sat'd aq NaHCO$_3$ and brine, dried (MgSO$_4$) and concentrated. The residue was purified by flash chromatography (elution with 3:1 hexane/ethyl acetate) to afford 1.55 g (18%) of the title compound as a solid. LRMS (AP+): 551.2 (M+H)$^+$.

Preparation of ethyl 1-(4-isopropylideneaminooxy-3-cyanophenyl)-5-[(2'-methylsulfonyl-3-fluoro-[1,1']-biphen-4-yl)aminocarbonyl]pyrazole-3-carboxylate.

To a solution of acetone oxime (0.26 g, 3.6 mmol) in 20 mL of DMF at ambient temperature was added potassium tert-butoxide (8.3 mL of a 1.0 M solution in tetrahydrofuran, 8.3 mmol). The reaction was stirred for 15 min and then ethyl 1-(3-cyano-4-fluorophenyl)-5-[(2'-methylsulfonyl-3-fluoro-[1,1']-biphen-4-yl)aminocarbonyl]pyrazole-3-carboxylate (1.53 g, 2.77 mmol) was added as a solution in 10 mL of DMF. The resulting mixture was allowed to stir at ambient temperature for 18 h. The reaction was partitioned between ethyl acetate and sat'd aq ammonium chloride and the organics were washed with brine, dried (MgSO$_4$), and concentrated. The residue was purified by flash chromatography (elution with 2:1 hexanes/ethyl acetate) to afford 1.28 g (77%) of the title compound. LRMS (ES−): 602.2 (M−H)$^−$.

Preparation of ethyl 1-(3'-aminobenzisoxazol-5'-yl)-5-[(2'-methylsulfonyl-3-fluoro-[1,1']-biphen-4-yl)aminocarbonyl]pyrazole-3-carboxylate.

To a solution of ethyl 1-(4-isopropylideneaminooxy-3-cyanophenyl)-5-[(2'-methylsulfonyl-3-fluoro-[1,1']-biphen-4-yl)aminocarbonyl]pyrazole-3-carboxylate (1.3 g, 2.1 mmol) in 40 mL of absolute ethanol was added 40 mL of 6N HCl. The reaction was stirred at 80° C. for 1 h and then was cooled to room temperature. The reaction was diluted with ethyl acetate and the organics were washed with water and brine, dried (MgSO$_4$) and concentrated. A portion (100 mg) of the residue was purified by prep HPLC (C18 reverse phase column, elution with a H$_2$O/CH$_3$CN gradient with 0.5% TFA) and lyophilized to afford 30 mg of the compound of Example 73 as a white powder. LRMS (ES+): 564.2 (M+H)$^+$.

Example 74

1-(3'-Aminobenzisoxazol-5'-yl)-5-[(2'-methylsulfonyl-3-fluoro-[1,1']-biphen-4-yl)aminocarbonyl]pyrazole-3-carboxylic acid To a solution of ethyl 1-(3'-aminobenzisoxazol-5'-yl)-5-[(2'-methylsulfonyl-3-fluoro-[1,1']-biphen-4-yl)aminocarbonyl]pyrazole-3-carboxylate (0.43 g, 0.76 mmol) in 20 mL of 1:1 methanol/water was added potassium hydroxide (50 mg, 0.84 mmol). The reaction was stirred at 60° C. for 2 h and then was cooled to room temperature and acidified with 10% aq HCl. The mixture was diluted with ethyl acetate, washed with brine, dried (MgSO$_4$) and concentrated. A 25 mg portion of the residue was purified by prep HPLC (C18 reverse phase column, elution with a H$_2$O/CH$_3$CN gradient with 0.5% TFA) and lyophilized to afford 10 mg of the compound of Example 74 as a white powder. LRMS (ES−): 534.1 (M−H)$^−$.

Example 75

1-(3'-Aminobenzisoxazol-5'-yl)-3-(hydroxymethyl)-5-[(2'-methylsulfonyl-3-fluoro-[1,1']-biphen-4-yl)aminocarbonyl]pyrazole To a solution of 1-(3'-aminobenzisoxazol-5'-yl)-5-[(2'-methylsulfonyl-3-fluoro-[1,1']-biphen-4-yl)aminocarbonyl]pyrazole-3-carboxylic acid (0.41 g, 0.77 mmol) in tetrahydrofuran at −20° C. was added triethylamine (0.12 mL, 0.84 mmol) and iso-butyl chloroformate (0.11 mL, 0.84 mmol). This mixture was stirred for 30 min and then there was added sodium borohydride (60 mg, 1.54 mmol) in a minimal amount of water. The reaction mixture was stirred with slow warming to room temperature for 1 h and then was quenched with 10% aq HCl. After diluting with ethyl acetate, the organics were washed with brine, dried (MgSO$_4$) and concentrated in vacuo to afford 0.29 g of the title compound. A portion (25 mg) of the residue was purified by prep HPLC (C18 reverse phase column, elution with a H$_2$O/CH$_3$CN gradient with 0.5% TFA) and lyophilized to afford 10 mg of the compound of Example 75 as a white powder. MS (AP+): 522.2 (M+H)$^+$.

Example 76

1-(3'-Aminobenzisoxazol-5'-yl)-3-[dimethylaminomethyl]-5-[(2'-methylsulfonyl-3-fluoro-[1,1']-biphen-4-yl)aminocarbonyl]pyrazole, trifluoroacetic acid salt To a solution of 1-(3'-aminobenzisoxazol-5'-yl)-3-hydroxymethyl-5-[(2'-methylsulfonyl-3-fluoro-[1,1']-biphen-4-yl)aminocarbonyl]pyrazole (0.10 g, 0.19 mmol) in 25 mL of acetonitrile was added 1,1,1-triacetoxy-1,1-dihydro-1,2-benziodoxol-3 (1H)-one (Dess-Martin periodinane) (0.19 g, 0.44 mmol) in 10 mL of acetonitrile and 2 drops of acetic acid. The resulting mixture was stirred at ambient temperature for 1 h. The reaction was poured into sat'd aq NaHCO$_3$ and extracted with methylene chloride. The organics were washed with water and brine, dried (MgSO$_4$) and concentrated in vacuo. The residue was dissolved in 10 mL of methanol and then there was added dimethylamine hydrochloride (0.07 g, 0.9 mmol) and sodium cyanoborohydride (0.011 g, 0.18 mmol). The resulting mixture was allowed to stir at ambient temperature for 18 h. The methanol was removed in vacuo and the residue was quenched with 5 mL of 10% aq HCl. The mixture was extracted with ether to remove unreacted starting materials. The aqueous layer was then made basic and extracted with ethyl acetate. The ethyl acetate layer was washed with brine, dried (MgSO$_4$) and concentrated in vacuo. The residue was purified by prep HPLC (C18 reverse phase column, elution with a H$_2$O/CH$_3$CN gradient with 0.5% TFA) and lyophilized to afford 10 mg (8%) of the compound of Example 76 as a white powder. MS (ES+): 549.2 (M+H)$^+$.

Example 77

Ethyl 1-(3'-aminobenzisoxazol-5'-yl)-5-[(2'-methylsulfonyl-3-fluoro-[1,1']-biphen-4-yl)aminocarbonyl]pyrazole-4-carboxylate Preparation of ethyl 1-(3-cyano-4-fluorophenyl)-5-(2-furyl)pyrazole-4-carboxylate.

To a solution of ethyl 3-(2-furyl)-3-ketopropionate (2.1 g, 11.5 mmol) in 20 mL of benzene was added dimethylformamide dimethylacetal (2.3 mL, 17.3 mmol). The resulting solution was stirred at 80° C. for 2 h. The reaction was cooled, filtered through a pad of silica gel and concentrated in vacuo. A portion of the residue (0.60 g, 2.54 mmol) was dissolved in 20 mL of glacial acetic acid and then there was added 4-fluoro-3-cyanophenylhydrazine tin chloride (1.05 g, 2.8 mmol). The reaction mixture was stirred at 100° C. for 4 h. The reaction was allowed to cool to room temperature and the acetic acid was removed in vacuo. The residue was diluted with ethyl acetate and the organics were washed with saturated aq NaHCO₃ and brine, dried (MgSO₄) and concentrated. The residue was purified by flash chromatography (elution with gradient of 6:1→3:1 hexanes/ethyl acetate) to afford 0.32 g (39%) of the title compound. LRMS (ES+): 326.2 (M+H)⁺.

Preparation of ethyl 1-(3-cyano-4-fluorophenyl)-pyrazole-4-carboxylate-5-carboxylic acid.

To a solution of ethyl 1-(3-cyano-4-fluorophenyl)-5-(2-furyl)pyrazole-4-carboxylate (0.3 g, 0.92 mmol) in 6:6:9 carbon tetrachloride/acetonitrile/water was added sodium periodate (0.89 g, 4.15 mmol) and ruthenium (III) chloride monohydrate (20 mg, 0.09 mmol). The resulting biphasic reaction was stirred vigorously at ambient temperature for 6 h. An additional portion of sodium periodate was added (0.45 g, 2.08 mmol) and the reaction was allowed to stir an additional 16 h. The reaction was quenched with 10% aq HCl and diluted with ethyl acetate. The organics were washed with brine, dried (MgSO₄), filtered through a pad of Celite and concentrated to afford 0.28 g (100%) of the title compound as a solid, which was sufficiently pure to be used without purification. LRMS (ES−): 302.0 (M−H)⁻.

Preparation of ethyl 1-(3-cyano-4-fluorophenyl)-5-[(2'-methylsulfonyl-3-fluoro-[1,1']-biphen-4-yl)aminocarbonyl]pyrazole-5-carboxylate.

To a solution of ethyl 1-(3-cyano-4-fluorophenyl) pyrazole-4-carboxylate-5-carboxylic acid (0.28 g, 0.92 mmol) in 10 mL of methylene chloride was added oxalyl chloride (0.19 mL, 2.18 mmol) and 2 drops of dimethylformamide. The reaction was stirred at ambient temperature for 6 h and then the volatiles were removed in vacuo. The residue was dissolved in 10 mL of methylene chloride and then there was added 4-dimethylaminopyridine (0.34 g, 2.76 mmol). The reaction was stirred for 10 min and then there was added (2'-methylsulfonyl-3-fluoro-[1,1']-biphen-4-yl) amine hydrochloride (0.28 g, 0.92 mmol). The resulting mixture was allowed to stir at ambient temperature for 16 h. The reaction was diluted with ethyl acetate and the organics were washed with 10% aq HCl, sat'd aq NaHCO₃ and brine, dried (MgSO₄), filtered through a pad of silica gel and concentrated to afford 0.4 g (80%) of the title compound as a solid. LRMS (ES+): 573.1 (M+Na)⁺.

Preparation of ethyl 1-(4-isopropylideneaminooxy-3-cyanophenyl)-5-[(2'-methylsulfonyl-3-fluoro-[1,1']-biphen-4-yl)aminocarbonyl]pyrazole-4-carboxylate.

To a solution of acetone oxime (70 mg, 0.94 mmol) in 5 mL of DMF at ambient temperature was added potassium tert-butoxide (1.1 mL of a 1.0 M solution in tetrahydrofuran, 1.1 mmol). The reaction was stirred for 15 min and then ethyl 1-(3-cyano-4-fluorophenyl)-5-[(2'-methylsulfonyl-3-fluoro-[1,1']-biphen-4-yl)aminocarbonyl]pyrazole-4-carboxylate (200 mg, 0.36 mmol) was added as a solution in 4 mL of DMF. The resulting mixture was allowed to stir at ambient temperature for 18 h. The reaction was partitioned between ethyl acetate and sat'd aq ammonium chloride and the organics were washed with brine, dried (MgSO₄), filtered through a pad of silica gel and concentrated to afford 0.14 g (65%) of the title compound, which was sufficiently pure to be used without purification. LRMS (ES+): 626.2 (M+Na)⁺.

Preparation of ethyl 1-(3'-aminobenzisoxazol-5'-yl)-5-[(2'-methylsulfonyl-3-fluoro-[1,1']-biphen-4-yl)aminocarbonyl]pyrazole-4-carboxylate.

To a solution of ethyl 1-(4-isopropylideneaminooxy-3-cyanophenyl)-5-[(2'-methylsulfonyl-3-fluoro-[1,1']-biphen-4-yl)aminocarbonyl]pyrazole-4-carboxylate (0.14 g, 0.21 mmol) in 5 mL of absolute ethanol was added 4 mL of 6N HCl. The reaction was stirred at 80° C. for 1 h and then was cooled to room temperature. The reaction was diluted with ethyl acetate and the organics were washed with water and brine, dried (MgSO₄) and concentrated. The residue was purified by prep HPLC (C18 reverse phase column, elution with a H₂O/CH₃CN gradient with 0.5% TFA) and lyophilized to afford 40 mg (30%) of the compound of Example 77 as a white powder. LRMS (AP+): 564.3 (M+H)⁺.

Example 78

1-(3'-Aminobenzisoxazol-5'-yl)-5-[(2'-methylsulfonyl-3-fluoro-[1,1']-biphen-4-yl) aminocarbonyl]pyrazole-4-carboxylic acid To a solution of ethyl 1-(3'-aminobenzisoxazol-5'-yl)-5-[(2'-methylsulfonyl-3-fluoro-[1,1']-biphen-4-yl) aminocarbonyl]pyrazole-4-carboxylate (30 mg, 0.053 mmol) in 10 mL of 1:1 methanol/water was added potassium hydroxide (20 mg, 0.36 mmol). The reaction was stirred at 60° C. for 1 h and then was cooled to room temperature and concentrated. The residue was purified by prep HPLC (C18 reverse phase column, elution with a H₂O/CH₃CN gradient with 0.5% TFA) and lyophilized to afford 18 mg (64%) of the compound of Example 78 as a white powder. LRMS (ES−): 534.1 (M−H)⁻.

Example 79

1-(1',2',3',4'-tetrahydroisoquinol-7'-yl)-3-methyl-5-[(2'-aminosulfonyl-[1,1']-biphen-4-yl) carbonylamino]pyrazole mesylate The title compound is prepared in an analogous fashion. MS (ES+) 488.0 (M+H)⁺ (100%).

Example 80

1-(1'-Amino-isoquinol-7'-yl)-3-[(2'-methylaminosulfonyl-[1,1']-biphen-4-yl) carbonylamino]-5-methyl-pyrazole mesylate The title compound is prepared in an analogous fashion. MS (ES+) 513.0 (M+H)⁺ (100%).

Example 81

1-(4'-amino-isoquinol-7'-yl)-3-methyl-5-[(2'-methylsulfonyl-[1,1']-biphen-4-yl)carbonylamino] pyrazole mesylate The title compound is prepared in an analogous fashion. MS (ES+) 498.0 (M+H)⁺ (100%).

Example 82

1-(1'-Amino-isoquinol-7'-yl)-3-trifluoromethyl-5-[(2'-methylsulfonyl-[1,1']-biphen-4-yl)carbonylamino]pyrazole trifluoroacetate Preparation of 1-(isoquinol-7-yl)-3-trifluoromethyl-5-pyrazole-crboxylic acid.

An acetic acid (500 mL) solution of the 7-hydrazino-isoquinoline-tin salt (50.93 g, 146 mmol) (prepared as discussed in Example 1) and 4,4,4-trifluoromethyl-1-(2-furyl)-1,3-butanedione (20.1 g, 97.57 mmoL) were gently refluxed overnight. The reaction was cooled and concentrated to a small volume. The mixture was quenched with sat. sodium bicarbonate (100 mL) and the organics were extracted with ethyl acetate (4×100 mL), dried (MgSO₄), and evaporated to a brown oil. Chromatography on silica gel (hexane:ethylacetate 1:1) afforded the desired pyrazole compound (40 g). ¹HNMR (CDCl₃) δ: 8.33 (s, 1H), 8.15 (d, 2H), 7.87 (dd, 1H), 7.51 (s, 1H), 7.08 (s, 4H), 6.44 (m, 1H), 6.32 (d, 1H)ppm. ESI (+ve) mass spectrum analysis m/z (relative intensity) 330 (M+H, 100).

The product from above (40 g, 121 mmol) was dissolved in acetone (1L). The solution was gently heated to 60° C., followed by the addition of KMnO₄ (141 g, 890 mmoL) portionwise while maintaining the internal temperature of the reaction to 60° C. Care should be taken to prevent the reaction from taking off. The reaction was judged to be completed by TLC within 10 min. The solution was cooled and gradually quenched with a saturated sodium bisulfite solution (1L). The clear solution was extracted with ethyl acetate (3×200 mL) to remove by-products. The aqueous layer was carefully adjusted to pH 4 whereby the desired compound precipitated out and was filtered and dried over nitrogen (35 g obtained). ¹HNMR (DMSO d₆) δ: 9.50 (bs, 1H), 8.64 (bs, 1H), 8.44 (s, 1H), 8.14 (m, 1H), 8.00 (m, 2H), 7.60 (s, 1H)ppm. ESI (−ve) mass spectrum analysis m/z (relative intensity) 306 (M−H, 100).

Preparation of 1-(1'-Amino-isoquinol-7'-yl)-3-trifluoromethyl-5-[(2'-methylsulfonyl-[1,1']-biphen-4-yl)carbonylamino]pyrazole trifluoroacetate.

The product is prepared in an analogous fashion as Example 1. MS (ES+) 551.8 (M+H)⁺ (100%); mp 173° C.

Example 83

1-(1'-Amino-isoquinol-7'-yl)-3-trifluoromethyl-5-[(2-fluoro-4-(N-pyrrolidinocarbonyl)-phenyl)carbonylamino]pyrazole trifluoroacetate The title compound is prepared in an analogous fashion. MS (ES+) 512.9 (M+H)⁺ (100%); mp 225° C.

Example 84

1-(1'-Amino-isoquinol-7'-yl)-3-trifluoromethyl-5-[(2'-methylsulfonyl-3-fluoro-[1,1']-biphen-4-yl)carbonylamino]pyrazole trifluoroacetate The title compound is prepared in an analogous fashion. MS (ES+) 570.1 (M+H)⁺ (100%).

Example 85

1-(1'-Amino-isoquinol-7'-yl)-3-trifluoromethyl-5-[(2'-aminosulfonyl-[1,1']-biphen-4-yl)carbonylamino]pyrazole trifluoroacetate The title compound is prepared in an analogous fashion. MS (ES+) 553.1 (M+H)⁺ (100%).

Example 86

1-(1'-Amino-isoquinol-7'-yl)-3-trifluoromethyl-5-[(2'-aminosulfonyl-3-fluoro-[1,1']-biphen-4-yl)carbonylamino]pyrazole trifluoroacetate The title compound is prepared in an analogous fashion. MS (ES+) 571.1 (M+H)⁺ (100%); mp 248–250° C.

Example 87

1-(1'-Amino-isoquinol-7'-yl)-3-trifluoromethyl-5-[(5-(2'-methylsulfonylphenyl)pyrid-2-yl)carbonylamino]pyrazole bistrifluoroacetate The title compound is prepared in an analogous fashion. MS (ES+) 553.1 (M+H)⁺ (100%).

Example 88

1-(1'-Amino-isoquinol-7'-yl)-3-methyl-5-[(2'-aminosulfonyl-3-fluoro-[1,1']-biphen-4-yl)carbonylamino]pyrazole trifluoroacetate The title compound is prepared in an analogous fashion. MS (ES+) 517.3 (M+H)⁺ (100%); mp 175–177° C.

Example 89

1(1'-Amino-isoquinol-7'-yl)-3-methyl-5-[(2'-methylsulfonyl-3-fluoro-[1,1']-biphen-4-yl)carbonylamino]pyrazole trifluoroacetate The title compound is prepared in an analogous fashion. MS (AP+) 516.2 (M+H)⁺ (100%); mp 203° C.

Example 90

1-(1-Amino-isoquinol-7'-yl)-3-trifluoromethyl-5-[(2'-aminosulfonyl-3-chloro-[1,1']-biphen-4-yl)carbonylamino]pyrazole trifluoroacetate The title compound is prepared in an analogous fashion. MS (ES+) 587.1 (M+H)⁺ (100%); mp 194° C.

Example 91

1-(1'-Amino-isoquinol-7'-yl)-3-trifluoromethyl-5-[(2'-aminosulfonyl-3-methyl-[1,1']-biphen-4-yl)carbonylamino]pyrazole trifluoroacetate The title compound is prepared in an analogous fashion. MS (ES+) 567.3 (M+H)⁺ (100%).

Example 92

1-(1'-Amino-isoquinol-7'-yl)-3-trifluoromethyl-5-[(2'-methylaminosulfonyl-[1,1']-biphen-4-yl)carbonylamino]pyrazole trifluoroacetate The title compound is prepared in an analogous fashion. MS (ES+) 567.2 (M+H)⁺ (100%); mp 166° C.

Example 93

1(1'-Aminoisoquinol-7'-yl)-3-ethyl-5-[(2'-methylaminosulfonyl-[1,1']-biphen-4-yl)aminocarbonyl]pyrazole trifluoroacetate The title compound was prepared in an analogous fashion. ESI mass spectrum z (rel. intensity) 527 (M+H, 100).mp 173° C.

Example 94

1-(1'-Aminoisoquinol-7'-yl)-3-ethyl-5-[(2'-methylsulfonyl-[1,1']-biphen-4-yl)aminocarbonyl]pyrazole mesylate The title compound was prepared in an analogous fashion. ESI mass spectrum z (rel. intensity) 512 (M+H, 100).mp 185° C.

Example 95

1-(1'-Aminoisoquinol-7'-yl)-3-propyl-5-[(2'-aminosulfonyl-[1,1']-biphen-4-yl)aminocarbonyl]pyrazole trifluoroacetate The title compound was prepared in an analogous fashion. ESI mass spectrum z (rel. intensity) 527 (M+H, 100).

Example 96

1(1'-Aminoisoquinol-7'-yl)-3-propyl-5-[(2'-methylaminosulfonyl-[1,1']-biphen-4-yl)aminocarbonyl]pyrazole trifluoroacetate The title compound was prepared in an analogous fashion. ESI mass spectrum z (rel. intensity) 541 (M+H, 100).

Example 97

1-(1'-Aminoisoquinol-7'-yl)-3-propyl-5-[(2'-methylsulfonyl-[1,1']-biphen-4-yl)aminocarbonyl]pyrazole trifluoroacetate The title compound was prepared in an analogous fashion. ESI mass spectrum z (rel. intensity) 526 (M+H, 100).mp 175° C.

Example 98

1-(1'-Aminoisoquinol-7'-yl)-3-ethyl-5-[(2'-aminosulfonyl-3-fluoro-[1,1']-biphen-4-yl)aminocarbonyl]pyrazole trifluoroacetate The title compound was prepared in an analogous fashion. ESI mass spectrum z (rel. intensity) 531 (M+H, 100); mp 161° C.

Example 99

1-(1'-Aminoisoquinol-7'-yl)-3-ethyl-5-[(2'-methylsulfonyl-3-fluoro-[1,1']-biphen-4-yl)aminocarbonyl]pyrazole trifluoroacetate The title compound was prepared in an analogous fashion. ESI mass spectrum z (rel. intensity) 530 (M+H, 100); mp 135° C.

Example 100

1-(1'-Aminoisoquinol-7'-yl)-3-ethyl-5-[4-(N-pyrrolidinocarbonyl-1-yl)phenylaminocarbonyl]pyrazole mesylate The title compound was prepared in an analogous fashion. ESI mass spectrum z (rel. intensity) 455 (M+H, 100).

Example 101

1-(1'-Aminoisoquinol-7'-yl)-3-trifluoromethyl-5-[4-(imidazol-1'-yl)phenylaminocarbonyl]pyrazole bistrifluoroacetate The title compound was prepared in an analogous fashion. ESI mass spectrum z (rel. intensity) 464 (M+H, 100); mp 115° C.

Example 102

1-(1'-Aminoisoquinol-7'-yl)-3-trifluoromethyl-5-[3-fluoro-4-(2-methylimidazol-1'-yl)phenylaminocarbonyl]pyrazole bistrifluoroacetate The title compound was prepared in an analogous fashion. ESI mass spectrum z (rel. intensity) 496 (M+H, 100); mp 115° C.

Example 103

1-(1'-Aminoisoquinol-7'-yl)-3-trifluoromethyl-5-[4-(2-methylimidazol-1'-yl)phenylaminocarbonyl]pyrazole bistrifluoroacetate The title compound was prepared in an analogous fashion. ESI mass spectrum z (rel. intensity) 478 (M+H, 100); mp 148° C.

Example 104

1-(1'-Aminoisoquinol-7'-yl)-3-trifluoromethyl-5-[2-fluoro-4-(2-methylimidazol-1'-yl)phenylaminocarbonyl]pyrazole bistrifluoroacetate The title compound was prepared in an analogous fashion. ESI mass spectrum z (rel. intensity) 496 (M+H, 100).

Example 105

1-(3'-Aminobenzisoxazol-5'-yl)-3-methyl-5-[(2'-methylsulfonyl-[1,1']-biphen-4-yl)aminocarbonyl]pyrazole trifluoroacetate The title compound was prepared in an analogous fashion. ESI mass spectrum z (rel. intensity) 488 (M+H, 100).

Example 106

1-(3'-Aminobenzisoxazol-5'-yl)-3-trifluoromethyl-5-[(2'-aminosulfonyl-3-fluoro-[1,1']-biphen-4-yl)aminocarbonyl]pyrazole The title compound was prepared in an analogous fashion. ESI mass spectrum z (rel. intensity) 561 (M+H, 100); mp 155° C.

Example 107

1-(3'-Aminobenzisoxazol-5'-yl)-3-trifluoromethyl-5-[2-fluoro-4-(N-pyrrolidinocarbonyl)phenyl-aminocarbonyl]pyrazole trifluoroacetate The title compound was prepared in an analogous fashion. ESI mass spectrum z (rel. intensity) 503 (M+H, 100); mp 150° C.

Example 108

1-(3'-Aminobenzisoxazol-5'-yl)-3-trifluoromethyl-5-[(5-(2'-aminosulfonylphenyl)pyrid-2-yl)aminocarbonyl]pyrazole bistrifluoroacetate The title compound was prepared in an analogous fashion. ESI mass spectrum z (rel. intensity) 544 (M+H, 100); mp 222° C.

Example 109

1-(3'-Aminobenzisoxazol-5'-yl)-3-trifluoromethyl-5-[(5-(2'-methylsulfonylphenyl)pyrimid-2-yl)aminocarbonyl]pyrazole trifluoroacetate The title compound was prepared in an analogous fashion. ESI mass spectrum z (rel. intensity) 544 (M+H, 100); mp 175° C.

Example 110

1-(3'-Aminobenzisoxazol-5'-yl)-3-methyl-5-[(4-(pyrid-3'-yl)phenyl)aminocarbonyl]pyrazole bistrifluoroacetate The title compound was prepared in an analogous fashion. ESI mass spectrum z (rel. intensity) 411 (M+H, 100); mp 142° C.

Example 111

1-(3'-Aminobenzisoxazol-5'-yl)-3-trifluoromethyl-5-[(4-(pyrid-3'-yl-3-fluorophenyl)aminocarbonyl]pyrazole bistrifluoroacetate The title compound was prepared in an analogous fashion. ESI mass spectrum z (rel. intensity) 483 (M+H, 100); mp 201° C.

Example 112

1-(3'-Aminoindazol-5'-yl)-3-trifluoromethyl-5-[(2'-aminosulfonyl-3-fluoro-[1,1']-biphen-4-yl)aminocarbonyl]pyrazole The title compound was prepared in an analogous fashion. ESI mass spectrum z (rel. intensity) 560 (M+H, 100).

Example 113

1-(3'-Aminoindazol-5'-yl)-3-trifluoromethyl-5-[(2'-methylsulfonyl-3-fluoro-[1,1']-biphen-4-yl)aminocarbonyl]pyrazole The title compound was prepared in an analogous fashion. ESI mass spectrum z (rel. intensity) 559 (M+H, 100).

Example 114

1-(3'-Aminoindazol-5'-yl)-3-trifluoromethyl-5-[2-fluoro-4-(N-pyrrolidinocarbonyl)phenylaminocarbonyl]pyrazole The title compound was prepared in an analogous fashion. ESI mass spectrum z (rel. intensity) 502 (M+H, 100); mp 166° C.

Example 115

1-(3'-Aminoindazol-5'-yl)-3-methyl-5-[(4-(pyrid-3'-yl)phenyl)aminocarbonyl]pyrazole The title compound was prepared in an analogous fashion. ESI mass spectrum z (rel. intensity) 410 (M+H, 100); mp 301° C.

Example 116

1-(3'-Aminoindazol-5'-yl)-3-trifluoromethyl-5-[(4-(pyrid-3'-yl-3-fluorophenyl)aminocarbonyl]pyrazole trifluoroacetate The title compound was prepared in an analogous fashion. ESI mass spectrum z (rel. intensity) 482 (M+H, 100); mp 190° C.

Example 117

1-(3'-Aminomethylnaphth-2'-yl)-3-trifluoromethyl-5-[(2'-methylsulfonyl-3-fluoro-[1,1']-biphen-4-yl)aminocarbonyl]pyrazole 3-Hydrazino-2-naphthoic acid: To 3-amino-2-naphthoic acid (15 g, 66.8 mmol) in conc. HCl (100 ml) and water (100 ml) at 0° C. was added NaNO$_2$ (9.22 g, 69 mmol) in 1 g portions while maintaing the reaction temperature below 0° C. After 30 min below 0° C., SnCl$_2$.H$_2$O (75 g) was added in portions over 20 min. The ice bath was removed and stirred at ambient temperature for 1 h. Reaction was filtered and the filter cake washed with water and air dried. The crude material containing tin (II) salts was used as is and gave a mp>300° C.

5-(Furan-2-yl)-3-trifluoromethyl-1-(3-carboxynaphth-2-yl)-1H-pyrazole: A mixture of 1,1,1-trifluoro-4-(furan-2-yl)-2,4-butadione (4.2 g, 20.4 mmol) and the hydrazine prepared above (6.66 g) in MeOH (150 ml) and TFA (2.32 g, 20.4 mmol) was stirred at ambient temperature for 5 days. The reaction was evaporated and redissolved in EtOAc and washed with 1N HCl. The EtOAc solution was dried (MgSO$_4$) and evaporated to give 5.0 g of material. The desired product was isolated by MPLC on 300 g of flash silica gel using a gradient of 1% MeOH in CHCl$_3$ to 3% MeOH in CHCl$_3$. Fractions were collected in 25 mL portions with fractions 1–100 eluted with 1% MeOH in CHCl$_3$, fractions 101–300 eluted with 2% MeOH in CHCl$_3$ and fractions 301–500 eluted with 3% MeOH in CHCl$_3$. The title compound (1.52 g) was recovered from fractions 201–500; LRMS (M+H)$^+$ m/z: 373.2.

5-(Furan-2-yl)-3-trifluoromethyl-1-(3'-hydroxymethylnaphth-2'-yl)-1H-pyrazole: To 1.52 g of 5-(furan-2-yl)-3-trifluoromethyl-1-(3'-carboxynaphth-2'-yl)-1H-pyrazole (4.1 mmol) in THF (100 ml) at 0° C. was added N-methylmorpholine (4.5 mmol, 0.46 g) followed by isobutylchloroformate (4.5 mmol, 0.62 g). The reaction was maintained at 0° C. for 1 h then filtered into a solution of NaBH$_4$ (12.3 mmol, 0.47 g) in water (50 ml) at 0° C. The THF was removed by evaporation, then the residue partioned between EtOAc and 1N HCl. The EtOAc layer was dried and evaporated to give 1.57 g of the benzyl alcohol; LRMS (M+Na)$^+$ m/z: 381.1.

5-(Furan-2-yl)-3-trifluoromethyl-1-(3'-azidomethylnaphth-2'-yl)-1H-pyrazole: To 5-(furan-2-yl)-3-trifluoromethyl-1-(3'-hydroxymethylnaphthal-2'-yl)-1H-pyrazole (4.4 mmol, 1.57 g) and N-methylmorpholine (4.8 mmol, 0.49 g) in CH$_2$Cl$_2$ (100 ml) at 0° C. was added methanesulfonyl chloride (4.8 mmol, 0.55 g) in CH$_2$Cl$_2$ (20 ml). The reaction was allowed to thaw to ambient temperature over 5 h. The reaction was then washed with cold 1N HCl, dried (MgSO$_4$) and evaporated to give 1.82 g of the mesylate. This material was immediately dissolved in DMF (20 ml) and sodium azide (13.2 mmol, 0.92 g) added. The reaction was stirred for 18 h, then diluted with brine and extracted with EtOAc. The EtOAc extract was washed with brine (5×'s), dried (MgSO$_4$) and evaporated to give 1.37 g of crude product. This material was purified to homogeneity by MPLC on a 360 g column of flash silica by eluting with 10:1 hexane:EtOAc. Fractions were collected in 25 ml portions and 0.75 g of 5-(furan-2-yl)-3-trifluoromethyl-1-(3'-azidomethylnaphth-2'-yl)-1H-pyrazole was recovered from fractions 68–100; LRMS (M+H)$^+$ m/z: 384.0, (M+Na)$^+$ m/z: 406.1.

3-Trifluoromethyl-1-(3'-azidomethylnaphth-2'-yl)-1H-pyrazole-5-carboxylic acid: To an acetone (50 ml) solution of 5-(furan-2-yl)-3-trifluoromethyl-1-(3'-azidomethylnaphth-2'-yl)-1H-pyrazole (1.98 mmol, 0.75 g) heated to 60° C. was added dropwise KMnO$_4$ (13.8 mmol, 2.2 g) in water (40 ml). After TLC (5:1 Hexane:EtOAc) indicated that all of the starting material was consumed (ca. 4 h) the reaction was cooled to ambient temperature and filtered through a pad of Celite®. The pad was washed thoroughly with acetone then the combined filtrate was condensed to remove the acetone. The remaining water suspension was made basic with 1N NaOH (pH 11) and the resulting solution washed with Et$_2$O. The basic solution was acidified with 1N HCl (pH 2) and extracted with EtOAc. The extracts were dried and evaporated to give the title acid (0.54 g); LRMS (M−H)$^-$ m/z: 360.

1-(3'-Azidomethylnaphth-2'-yl)-3-trifluoromethyl-5-[(2'-methylsulfonyl-3-fluoro-[1,1']-biphen-4-yl)aminocarbonyl]pyrazole: 1-(3'-azidomethylnaphth-2'-yl)-3-trifluoromethyl-1H-pyrazole-5-carboxylic acid (1.5 mmol, 0.54 g) in CH$_2$Cl$_2$ (25 ml) was stirred with 1.5 ml of a 2M solution of oxalyl chloride in CH$_2$Cl$_2$ (3 mmol) and a 2 drops of DMF for 18 h. The reaction was evaporated and pumped on for several hours to remove the last traces of reagent to give 0.59 g of acid chloride. The acid chloride was combined with 2-fluoro-4-(2-methanesulfonylphenyl)aniline (1.7 mmol, 0.50 g) and DMAP (4.5 mmol, 0.55 g) in CH$_2$Cl$_2$ (25 ml)

and stirred at ambient temperature for 18 h. The reaction mixture was evaporated and applied to a column of flash silica gel (200 g) and eluted with 3:1 hexane:EtOAc. There was obtained 0.19 g of the title compound; LRMS (M−H)− m/z: 607.

1-(3'-Aminomethylnaphth-2'-yl)-3-trifluoromethyl-5-[(2'-methylsulfonyl-3-fluoro-[1,1']-biphen-4-yl)aminocarbonyl]pyrazole: 3-Trifluoromethyl-1-(3'-azidomethylnaphth-2'-yl)-1H-pyrazole-5-(N-(3-fluoro-2-methylsulfonyl-[1,1']-biphen-4-yl)carboxyamide (0.31 mmol, 0.19 g) and $SnCl_2.H_2O$ (1.25 mmol, 0.28 g) in MeOH (20 ml) was stirred at ambient temperature 18 h. The reaction was evaporated, taken up in 1N NaOH (50 ml), then extracted with EtOAc. The extracts were dried ($MgSO_4$) and evaporated. Purification of the final product was by hplc utilizing gradient elution with a mixture of water:acetonitrile with 0.05% trifluoroacetic acid on a reverse phase C18 (60 Å) column gave a pure sample of the title compound; LRMS (M+H)+ m/z: 583.

Example 118

1-(3'-Aminobenzisoxazol-5'-yl)-3-trifluoromethyl-5-[(3-fluoro-2'-hydroxymethyl-[1,1']-biphen-4-yl)aminocarbonyl]pyrazole trifluoroacetate The title compound is prepared in an analogous fashion. ESI mass spectrum z (rel. intensity) 510 (M−H).

Example 119

1-(3'-Aminobenzisoxazol-5'-yl)-3-trifluoromethyl-5-[(3-fluoro-2'-methylaminomethyl-[1,1']-biphen-4-yl)aminocarbonyl]pyrazole trifluoroacetate The title compound is prepared in an analogous fashion. ESI mass spectrum z (rel. intensity) 525 (M+H, 100).

Example 120

1-(3'-Aminobenzisoxazol-5'-yl)-3-trifluoromethyl-5-[(2'-bromomethyl-3-fluoro-[1,1']-biphen-4-yl)aminocarbonyl]pyrazole trifluoroacetate The title compound is prepared in an analogous fashion. ESI mass spectrum z (rel. intensity) 493 (M+H, 100).

Example 121

1-(3'-Aminobenzisoxazol-5'-yl)-3-trifluoromethyl-5-[(3-fluoro-2'-pyridiniummethyl-[1,1']-biphen-4-yl)aminocarbonyl]pyrazole trifluoroacetate The title compound is prepared in an analogous fashion. ESI mass spectrum z (rel. intensity) 573 (M+H, 100).

Example 122

1-(3'-Aminobenzisoxazol-5'-yl)-3-trifluoromethyl-5-[(2'-aminomethyl-3-fluoro-[1,1']-biphen-4-yl)aminocarbonyl]pyrazole trifluoroacetate The title compound is prepared in an analogous fashion. ESI mass spectrum z (rel. intensity) 511 (M+H, 100).

Example 123

1-(3'-Aminobenzisoxazol-5'-yl)-3-trifluoromethyl-5-[(3-fluoro-2'-N-pyrrolidinylmethyl-[1,1']-biphen-4-yl)aminocarbonyl]pyrazole trifluoroacetate The title compound is prepared in an analogous fashion. ESI mass spectrum z (rel. intensity) 565 (M+H, 100).

Example 124

1-(3'-Aminobenzisoxazol-5'-yl)-3-trifluoromethyl-5-[(3-fluoro-2'-imidazol-1"-yl-[1,1']-biphen-4-yl)aminocarbonyl]pyrazole trifluoroacetate The title compound is prepared in an analogous fashion. ESI mass spectrum z (rel. intensity) 562 (M+H, 100).

Example 125

1-(3'-Aminobenzisoxazol-5'-yl)-3-trifluoromethyl-5-[((2'-(4"-t-butoxycarbonyl)piperazin-1"-ylmethyl)-3-fluoro-[1,1']-biphen-4-yl)aminocarbonyl]pyrazole trifluoroacetate The title compound is prepared in an analogous fashion. ESI mass spectrum z (rel. intensity) 680 (M+H, 100).

Example 126

1-(3'-Aminobenzisoxazol-5'-yl)-3-trifluoromethyl-5-[((2'-(N,N-dimethylamino)pyridiniummethyl)-3-fluoro-[1,1']-biphen-4-yl)aminocarbonyl]pyrazole trifluoroacetate The title compound is prepared in an analogous fashion. ESI mass spectrum z (rel. intensity) 616 (M+H, 100).

Example 127

1-(3'-Aminobenzisoxazol-5'-yl)-3-trifluoromethyl-5-[(3-fluoro-2'-piperazin-1"-ylmethyl-[1,1']-biphen-4-yl)aminocarbonyl]pyrazole trifluoroacetate The title compound is prepared in an analogous fashion. ESI mass spectrum z (rel. intensity) 580 (M+H, 100).

Example 128

1-(3'-Aminobenzisoxazol-5'-yl)-3-trifluoromethyl-5-[(3-fluoro-2'-N-methylmorpholiniummethyl-[1,1']-biphen-4-yl)aminocarbonyl]pyrazole trifluoroacetate The title compound is prepared in an analogous fashion. ESI mass spectrum z (rel. intensity) 695 (M+H, 100).

Example 129

1-(3'-Aminobenzisoxazol-5'-yl)-3-trifluoromethyl-5-[(3-fluoro-2'-morpholinomethyl-[1,1']-biphen-4-yl)aminocarbonyl]pyrazole trifluoroacetate The title compound is prepared in an analogous fashion. ESI mass spectrum z (rel. intensity) 581 (M+H, 100).

Example 130

1-(3'-Aminobenzisoxazol-5'-yl)-3-trifluoromethyl-5-[(3-fluoro-2'-(N-methyl-N-methoxyamino)-[1,1']-biphen-4-yl)aminocarbonyl]pyrazole trifluoroacetate The title compound is prepared in an analogous fashion. ESI mass spectrum z (rel. intensity) 555 (M+H, 100).

Example 131

1-(3'-Aminobenzisoxazol-5'-yl)-5-[(2'-methylsulfonyl-3-fluoro-[1,1']-biphen-4-yl)aminocarbonyl]triazole trifluoroacetate The title compound is prepared in an analogous fashion. ESI mass spectrum z (rel. intensity) 493 (M+H, 100).

Example 132

1-(3'-Aminobenzisoxazol-5'-yl)-5-[(2'-aminosulfonyl-3-fluoro-[1,1']-biphen-4-yl)aminocarbonyl]triazole trifluoroacetate The title compound is prepared in an analogous fashion. ESI mass spectrum z (rel. intensity) 494 (M+H, 100).

Example 133

1-(3'-Aminobenzisoxazol-5'-yl)-3-trifluoromethyl-5-[(2'-methylaminosulfonyl-3-fluoro-[1,1']-biphen-4-yl)aminocarbonyl]pyrazole trifluoroacetate The title compound is prepared in an analogous fashion. ESI mass spectrum z (rel. intensity) 575 (M+H, 100).

Example 134

1-(3'-Aminobenzisoxazol-5'-yl)-5-[(2'-dimethylaminomethyl-3-fluoro-[1,1']-biphen-4-yl)aminocarbonyl]tetrazole bis-trifluoroacetate The title compound is prepared in an analogous fashion. ESI mass spectrum z (rel. intensity) 473.3 (M+H, 100).

Example 135

1-(3'-Aminobenzisoxazol-5'-yl)-3-ethyl-5-[(2'-dimethylaminomethyl-3-fluoro-[1,1']-biphen-4-yl)aminocarbonyl]pyrazole bis-trifluoroacetate The title compound is prepared in an analogous fashion. ESI mass spectrum z (rel. intensity) 499.3 (M+H, 100).

Example 136

1-(3'-Aminobenzisoxazol-5'-yl)-3-ethyl-5-[4'-(2"-dimethylaminomethylimidazol-1"-yl)-2'-fluorophenyl)aminocarbonyl]pyrazole bis-trifluoroacetate The title compound is prepared in an analogous fashion. ESI mass spectrum z (rel. intensity) 489.3 (M+H, 100).

TABLE 1

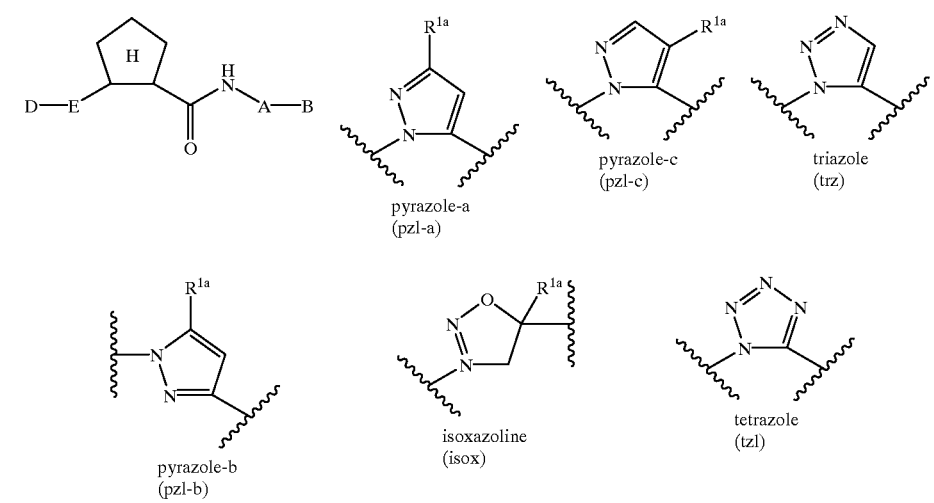

| Ex | D—E | Ring H | $R^{1a}$ | A—B | MS |
|---|---|---|---|---|---|
| 1 | 1'-Amino-isoquinol-7'-yl | pzl-a | Me | 2'-$NH_2SO_2$-[1,1']-biphen-4-yl | 499 |
| 2 | 1'-Amino-isoquinol-7'-yl | pzl-a | Me | 2'-$CH_3SO_2$-[1,1']-biphen-4-yl | 498 |
| 3 | 4'-amino-isoquinol-7'-yl | pzl-a | Me | 2'-$NH_2SO_2$-[1,1']-biphen-4-yl | 499 |
| 4 | isoquinol-7'-yl | pzl-a | Me | 2'-$NH_2SO_2$-[1,1']-biphen-4-yl | 484 |
| 5 | 1'-Amino-isoquinol-7'-yl | isox | Me | 2'-$NH_2SO_2$-[1,1']-biphen-4-yl | 502 |
| 6 | isoquinol-5'-yl | isox | Me | 2'-$NH_2SO_2$-[1,1']-biphen-4-yl | 487 |
| 7 | isoquinol-7'-yl | isox | Me | 2'-$NH_2SO_2$-[1,1']-biphen-4-yl | 487 |

TABLE 1-continued

| | | | | | |
|---|---|---|---|---|---|
| 8 | 2'-amino-benzimidazol-5'-yl | isox | Me | 2'-NH$_2$SO$_2$-[1,1']-biphen-4-yl | 491 |
| 9 | 3'-aminoindazol-5-yl | isox | Me | 2'-NH$_2$SO$_2$-[1,1']-biphen-4-yl | 491 |
| 10 | 3'-amino-benzisoxazol-5-yl | isox | Me | 2'-NH$_2$SO$_2$-[1,1']-biphen-4-yl | 492 |
| 11 | 3'-amino-benzisoxazol-5-yl | pzl-a | Me | 2'-NH$_2$SO$_2$-[1,1']-biphen-4-yl | 489 |
| 12 | 1'-Amino-isoquinol-7'-yl | trz | — | 2'-NH$_2$SO$_2$-[1,1']-biphen-4-yl | 486 |
| 13 | 4'-amino-isoquinol-7'-yl | trz | — | 2'-NH$_2$SO$_2$-[1,1']-biphen-4-yl | 486 |
| 14 | isoquinol-7'-yl | trz | — | 2'-NH$_2$SO$_2$-[1,1']-biphen-4-yl | 476 |
| 15 | quinol-2'-yl | pzl-a | Me | 2'-NH$_2$SO$_2$-[1,1']-biphen-4-yl | 484 |
| 16 | quinol-2'-yl | pzl-b | Me | 2'-NH$_2$SO$_2$-[1,1']-biphen-4-yl | 484 |
| 17 | 3'-amino-indazol-5-yl | pzl-a | Me | 2'-NH$_2$SO$_2$-[1,1']-biphen-4-yl | 488 |
| 18 | 3'-aminoindazol-5-yl | pzl-a | Me | 2'-NH$_2$SO$_2$-[1,1']-biphen-4-yl | 488 |
| 19 | 3'-amino-benzisoxazol-5-yl | pzl-a | Me | 5-(2'-NH$_2$SO$_2$-phenyl)pyrid-2-yl | 490 |
| 20 | 3'-amino-benzisoxazol-5-yl | pzl-a | Me | isoquin-7-yl | 385 |
| 21 | 1'-Amino-isoquinol-7'-yl | pzl-a | Et | 2'-NH$_2$SO$_2$-[1,1']-biphen-4-yl | 513 |
| 22 | 1'-Amino-isquinol-7'-yl | pzl-a | i-Pr | 2'-NH$_2$SO$_2$-[1,1']-biphen-4-yl | 527 |
| 23 | 2',4'-diamino-quinazol-7'-yl | pzl-a | Me | 2'-NH$_2$SO$_2$-[1,1']-biphen-4-yl | 515 |
| 24 | 4'-amino-quinazol-7'-yl | pzl-a | Me | 2'-NH$_2$SO$_2$-[1,1']-biphen-4-yl | 500 |
| 25 | 1'-Amino-isoquinol-7'-yl | pzl-a | Me | 4-(N-pyrrolidinyl-carbonyl)phenyl | 441 |
| 26 | 3'-amino-benzisoxazol-5'-yl | pzl-a | CF$_3$ | 3-F-2'-CH$_3$SO$_2$-[1,1']-biphen-4-yl | 501 |
| 27 | 1'-Amino-pthalazin-7'-yl | pzl-a | CH$_3$ | 2'-NH$_2$SO$_2$-[1,1']-biphen-4-yl | 500 |
| 28 | 3'-amino-benzisoxazol-5'-yl | isox | CH$_3$SO$_2$NH—CH$_2$ | 5-(2'-NH$_2$SO$_2$-phenyl)pyrid-2-yl | 586 |
| 29 | 3'-amino-benzisoxazol-5'-yl | pzl-a | CF$_3$ | 2-F-4-morpholinophenyl | 491 |
| 30 | 3'-amino-benzisoxazol-5'-yl | pzl-a | CF$_3$ | 2'-iPr-imidazol-1'-ylphenyl | 496 |
| 31 | 3'-amino-benzisoxazol-5'-yl | pzl-a | CF$_3$ | 2'-Et-imidazol-1'-ylphenyl | 482 |
| 32 | 3'-amino-benzisoxazol-5'-yl | pzl-a | CF$_3$ | 2'-(CH$_3$)$_2$NCH$_2$-imidazol-1'-ylphenyl | 511 |
| 33 | 3'-amino-benzisoxazol-5'-yl | pzl-a | CF$_3$ | 2'-CH$_3$OCH$_2$-imidazol-1'-ylphenyl | 498 |
| 34 | 3'-amino-benzisoxazol-5'-yl | pzl-a | CF$_3$ | 2-F-2'-(CH$_3$)$_2$NCH$_2$-imidazol-1'-ylphenyl | 529 |

TABLE 1-continued

| | | | | | |
|---|---|---|---|---|---|
| 35 | 3'-amino-benzisoxazol-5'-yl | pzl-a | CF$_3$ | 2-CH$_3$O-2'-CH$_3$-imidazol-1'-ylphenyl | 498 |
| 36 | 3'-amino-benzisoxazol-5'-yl | pzl-a | CF$_3$ | 2-F-2'-iPr-imidazol-1'-ylphenyl | 514 |
| 37 | 3'-amino-benzisoxazol-5'-yl | pzl-a | CF$_3$ | 2-F-2'-Et-imidazol-1'-ylphenyl | 500 |
| 38 | 3'-amino-benzisoxazol-5'-yl | pzl-a | Et | 2-F-2'-Et-imidazol-1'-ylphenyl | 460 |
| 39 | 3'-amino-benzisoxazol-5'-yl | pzl-a | Et | 2'-CH$_3$OCH$_2$-imidazol-1'-ylphenyl | 458 |
| 40 | 3'-amino-benzisoxazol-5'-yl | pzl-a | Et | 2'-(CH$_3$)$_2$NCH$_2$-imidazol-1'-ylphenyl | 471 |
| 41 | 3'-amino-benzisoxazol-5'-yl | pzl-a | Et | 2'-CH$_3$-benzimidazol-1'-ylphenyl | 478 |
| 42 | 3'-amino-benzisoxazol-5'-yl | pzl-a | Et | 2'-Et-imidazol-1'-ylphenyl | 442 |
| 43 | 3'-amino-benzisoxazol-5'-yl | pzl-a | Et | 2,5-diF-2'-Et-imidazol-1'-ylphenyl | 464 |
| 44 | 3'-amino-benzisoxazol-5'-yl | pzl-a | Et | 2-F-4-morpholinophenyl | 451 |
| 45 | 3'-amino-benzisoxazol-5'-yl | pzl-a | Et | 2'-iPr-imidazol-1'-ylphenyl | 456 |
| 46 | 3'-amino-benzisoxazol-5'-yl | pzl-a | Et | 2-F-2'-CH$_3$-imidazol-1'-ylphenyl | 446 |
| 47 | 3'-amino-benzisoxazol-5'-yl | pzl-a | Et | 3-NH$_2$-2'-NH$_2$SO$_2$-[1,1']-biphen-4-yl | 540 |
| 48 | 3'-amino-benzisoxazol-5'-yl | pzl-a | Et | 3-NO$_2$-2'-NH$_2$SO$_2$-[1,1']-biphen-4-yl | 548 |
| 49 | 3'-amino-benzisoxazol-5'-yl | pzl-a | Et | 2'-CH$_3$-imidazol-1'-ylphenyl | 428 |
| 50 | 3'-amino-benzisoxazol-5'-yl | pzl-a | Et | 2-(CH$_3$)$_2$N-4-(N-pyrrolidinocarbonyl)-phenyl | 488 |
| 51 | 3'-amino-benzisoxazol-5'-yl | pzl-a | Et | 2-pyrrolidino-4-(N-pyrrolidinocarbonyl)-phenyl | 514 |
| 52 | 3'-amino-benzisoxazol-5'-yl | pzl-a | Et | 2-F-4-(N-pyrrolidinocarbonyl)-phenyl | 463 |
| 53 | 3'-amino-benzisoxazol-5'-yl | pzl-a | Et | 3-F-2'-NH$_2$SO$_2$-[1,1']-biphen-4-yl | 542 |
| 54 | 3'-amino-benzisoxazol-5'-yl | pzl-a | Et | 5-(2'-CH$_3$SO$_2$-phenyl)pyrimid-2-yl | 525 |
| 55 | 3'-amino-benzisoxazol-5'-yl | pzl-a | Et | 3-F-2'-CH$_3$SO$_2$-[1,1']-biphen-4-yl | 542 |
| 56 | 3'-amino-benzisoxazol-5'-yl | pzl-a | Et | 5-(2'-NH$_2$SO$_2$-phenyl)pyrid-2-yl | 502 |
| 57 | 3'-amino-benzisoxazol-5'-yl | tzl | — | 3-F-2'-CH$_3$SO$_2$-[1,1']-biphen-4-yl | 494 |
| 58 | 3'-amino-benzisoxazol-5'-yl | tzl | — | 2'-CH$_3$-imidazol-1'-ylphenyl | 402 |
| 59 | 3'-amino-benzisoxazol-5'-yl | tzl | — | 2'-NH$_2$SO$_2$-[1,1']-biphen-4-yl | 475 |
| 60 | 3'-amino-benzisoxazol-5'-yl | tzl | — | 2-F-4-(N-pyrrolidinocarbonyl)-phenyl | 437 |

TABLE 1-continued

| | | | | | |
|---|---|---|---|---|---|
| 61 | 3'-amino-benzisoxazol-5'-yl | tzl | — | 2-pyrrolidino-4-(N-pyrrolidinocarbonyl)-phenyl | 488 |
| 62 | 1'-Amino-isoquinol-7'-yl | tzl | — | 3-F-2'-$NH_2SO_2$-[1,1']-biphen-4-yl | 505 |
| 63 | 1'-Amino-isoquinol-7'-yl | tzl | — | 3-F-2'-$CH_3SO_2$-[1,1']-biphen-4-yl | 504 |
| 64 | 1'-Amino-benzisoxazol-5'-yl | pzl-a | $CF_3$ | 5-(2'-$NH_2SO_2$-phenyl)pyrimid-2-yl | 545 |
| 65 | 1'-Amino-benzisoxazol-5'-yl | pzl-a | $CF_3$ | 2'-$CH_3$-imidazol-1'-ylphenyl | 468 |
| 66 | 1'-Amino-benzisoxazol-5'-yl | pzl-a | $CF_3$ | 2-F-2'-$CH_3$-imidazol-1'-ylphenyl | 486 |
| 67 | 1'-Amino-benzisoxazol-5'-yl | pzl-a | $CF_3$ | 2-F-1'-$CH_3$-imidazol-2'-ylphenyl | 486 |
| 68 | 1'-Amino-benzisoxazol-5'-yl | pzl-a | $CF_3$ | 2'-$NH_2$-imidazol-1'-ylphenyl | 469 |
| 69 | 1'-Amino-benzisoxazol-5'-yl | pzl-a | $CF_3$ | 2'-$(CH_3)_2NCH_2$-3-F-[1,1']-biphen-4-yl | 539 |
| 70 | 1'-Amino-benzisoxazol-5'-yl | pzl-a | $CO_2Et$ | 3-F-2'-$NH_2SO_2$-[1,1']-biphen-4-yl | 565 |
| 71 | 1'-Amino-benzisoxazol-5'-yl | pzl-a | $CO_2H$ | 3-F-2'-$NH_2SO_2$-[1,1']-biphen-4-yl | 537 |
| 72 | 1'-Amino-benzisoxazol-5'-yl | pzl-a | $CONH_2$ | 3-F-2'-$NH_2SO_2$-[1,1']-biphen-4-yl | 536 |
| 73 | 1'-Amino-benzisoxazol-5'-yl | pzl-a | $CO_2Et$ | 3-F-2'-$CH_3SO_2$-[1,1']-biphen-4-yl | 564 |
| 74 | 1'-Amino-benzisoxazol-5'-yl | pzl-a | $CO_2H$ | 3-F-2'-$CH_3SO_2$-[1,1']-biphen-4-yl | 534 |
| 75 | 1'-Amino-benzisoxazol-5'-yl | pzl-a | $CH_2OH$ | 3-F-2'-$CH_3SO_2$-[1,1']-biphen-4-yl | 522 |
| 76 | 1'-Amino-benzisoxazol-5'-yl | pzl-a | $(CH_3)_2N-CH_2$ | 3-F-2'-$CH_3SO_2$-[1,1']-biphen-4-yl | 549 |
| 77 | 1'-Amino-benzisoxazol-5'-yl | pzl-c | $CO_2Et$ | 3-F-2'-$CH_3SO_2$-[1,1']-biphen-4-yl | 564 |
| 78 | 1'-Amino-benzisoxazol-5'-yl | pzl-c | $CO_2H$ | 3-F-2'-$CH_3SO_2$-[1,1']-biphen-4-yl | 534 |
| 79 | 1',2',3',4'-tetrahydro-isoquinol-7'-yl | pzl-a | $CH_3$ | 2'-$NH_2SO_2$-[1,1']-biphen-4-yl | 488 |
| 80 | 1'-Amino-isoquinol-7'-yl | pzl-b | $CH_3$ | 2'-$CH_3NHSO_2$-[1,1']-biphen-4-yl | 513 |
| 81 | 4'-amino-isoquinol-7'-yl | pzl-a | $CH_3$ | 2'-$CH_3SO_2$-[1,1']-biphen-4-yl | 498 |
| 82 | 1'-Amino-isoquinol-7'-yl | pzl-a | $CF_3$ | 2'-$CH_3SO_2$-[1,1']-biphen-4-yl | 552 |
| 83 | 1'-Amino-isoquinol-7'-yl | pzl-a | $CF_3$ | 2-F-4-(N-pyrrolidinocarbonyl)-phenyl | 513 |
| 84 | 1'-Amino-isoquinol-7'-yl | pzl-a | $CF_3$ | 3-F-2'-$CH_3SO_2$-[1,1']-biphen-4-yl | 570 |
| 85 | 1'-Amino-isoquinol-7'-yl | pzl-a | $CF_3$ | 2'-$NH_2SO_2$-[1,1']-biphen-4-yl | 553 |
| 86 | 1'-Amino-isoquinol-7'-yl | pzl-a | $CF_3$ | 3-F-2'-$NH_2SO_2$-[1,1']-biphen-4-yl | 571 |

TABLE 1-continued

| | | | | | |
|---|---|---|---|---|---|
| 87 | 1'-Amino-isoquinol-7'-yl | pzl-a | CF$_3$ | 5-(2'-CH$_3$SO$_2$-phenyl)pyrid-2-yl | 553 |
| 88 | 1'-Amino-isoquinol-7'-yl | pzl-a | CH$_3$ | 3-F-2'-NH$_2$SO$_2$-[1,1']-biphen-4-yl | 517 |
| 89 | 1'-Amino-isoquinol-7'-yl | pzl-a | CH$_3$ | 3-F-2'-CH$_3$SO$_2$-[1,1']-biphen-4-yl | 516 |
| 90 | 1'-Amino-isoquinol-7'-yl | pzl-a | CF$_3$ | 2'-NH$_2$SO$_2$-3-Cl-[1,1']-biphen-4-yl | 587 |
| 91 | 1'-Amino-isoquinol-7'-yl | pzl-a | CF$_3$ | 2'-NH$_2$SO$_2$-3-CH$_3$-[1,1']-biphen-4-yl | 567 |
| 92 | 1'-Amino-isoquinol-7'-yl | pzl-a | CF$_3$ | 2'-CH$_3$NHSO$_2$-[1,1']-biphen-4-yl | 567 |
| 93 | 1'-Amino-isoquinol-7'-yl | pzl-a | Et | 2'-CH$_3$NHSO$_2$-[1,1']-biphen-4-yl | 527 |
| 94 | 1'-Amino-isoquinol-7'-yl | pzl-a | Et | 2'-CH$_3$SO$_2$-[1,1']-biphen-4-yl | 512 |
| 95 | 1'-Amino-isoquinol-7'-yl | pzl-a | n-Pr | 2'-NH$_2$SO$_2$-[1,1']-biphen-4-yl | 527 |
| 96 | 1'-Amino-isoquinol-7'-yl | pzl-a | n-Pr | 2'-CH$_3$NHSO$_2$-[1,1']-biphen-4-yl | 541 |
| 97 | 1'-Amino-isoquinol-7'-yl | pzl-a | n-Pr | 2'-CH$_3$SO$_2$-[1,1']-biphen-4-yl | 526 |
| 98 | 1'-Amino-isoquinol-7'-yl | pzl-a | Et | 3-F-2'-NH$_2$SO$_2$-[1,1']-biphen-4-yl | 531 |
| 99 | 1'-Amino-isoquinol-7'-yl | pzl-a | Et | 3-F-2'-CH$_3$SO$_2$-[1,1']-biphen-4-yl | 530 |
| 100 | 1'-Amino-isoquinol-7'-yl | pzl-a | Et | N-pyrrolidinocarbonyl | 455 |
| 101 | 1'-Amino-isoquinol-7'-yl | pzl-a | CF$_3$ | 4-(imidazol-1'-yl)-phenyl | 464 |
| 102 | 1'-Amino-isoquinol-7'-yl | pzl-a | CF$_3$ | 3-F-2'-CH$_3$-imidazol-1'-ylphenyl | 496 |
| 103 | 1'-Amino-isoquinol-7'-yl | pzl-a | CF$_3$ | 2'-CH$_3$-imidazol-1'-ylphenyl | 478 |
| 104 | 1'-Amino-isoquinol-7'-yl | pzl-a | CF$_3$ | 2-F-2'-CH$_3$-imidazol-1'-ylphenyl | 496 |
| 105 | 3'-amino-benzisoxazol-5'-yl | pzl-a | CH$_3$ | 2'-CH$_3$SO$_2$-[1,1']-biphen-4-yl | 488 |
| 106 | 3'-amino-benzisoxazol-5'-yl | pzl-a | CF$_3$ | 3-F-2'-NH$_2$SO$_2$-[1,1']-biphen-4-yl | 561 |
| 107 | 3'-amino-benzisoxazol-5'-yl | pzl-a | CF$_3$ | 2-F-4-(N-pyrrolidinocarbonyl)-phenyl | 503 |
| 108 | 3'-amino-benzisoxazol-5'-yl | pzl-a | CF$_3$ | 5-(2'-NH$_2$SO$_2$-phenyl)pyrid-2-yl | 544 |
| 109 | 3'-amino-benzisoxazol-5'-yl | pzl-a | CF$_3$ | 5-(2'-CH$_3$SO$_2$-phenyl)pyrimid-2-yl | 544 |
| 110 | 3'-amino-benzisoxazol-5'-yl | pzl-a | CH$_3$ | pyrid-3'-yl-phenyl | 411 |
| 111 | 3'-amino-benzisoxazol-5'-yl | pzl-a | CF$_3$ | 2-F-pyrid-2'-yl-phenyl | 483 |
| 112 | 3'-amino-indazol-5'-yl | pzl-a | CF$_3$ | 3-F-2'-NH$_2$SO$_2$-[1,1']-biphen-4-yl | 560 |

TABLE 1-continued

| | | | | | |
|---|---|---|---|---|---|
| 113 | 3'-amino-indazol-5'-yl | pzl-a | CF$_3$ | 3-F-2'-CH$_3$SO$_2$-[1,1']-biphen-4-yl | 559 |
| 114 | 3'-amino-indazol-5'-yl | pzl-a | CF$_3$ | 2-F-4-(N-pyrrolidinocarbonyl)-phenyl | 502 |
| 115 | 3'-amino-indazol-5'-yl | pzl-a | CH$_3$ | pyrid-3'-yl-phenyl | 410 |
| 116 | 3'-amino-indazol-5'-yl | pzl-a | CF$_3$ | 2-F-pyrid-2'-yl-phenyl | 482 |
| 117 | 3'-aminomethyl-naphthal-2'-yl | pzl-a | CF$_3$ | 3-F-2'-CH$_3$SO$_2$-[1,1']-biphen-4-yl | 583 |
| 118 | 3'-amino-benzisoxazol-5-yl | pzl-a | CF$_3$ | 3-F-2'-HOCH$_2$-[1,1']-biphen-4-yl | 510 (M − H) |
| 119 | 3'-amino-benzisoxazol-5-yl | pzl-a | CF$_3$ | 3-F-2'-(N-methylaminomethyl)-[1,1']-biphen-4-yl | 525 |
| 120 | 3'-amino-benzisoxazol-5-yl | pzl-a | CF$_3$ | 3-F-2'-bromomethyl-[1,1']-biphen-4-yl | 574 |
| 121 | 3'-amino-benzisoxazol-5-yl | pzl-a | CF$_3$ | 3-F-2'-(N-pyridiniummethyl)-[1,1']-biphen-4-yl | 573 |
| 122 | 3'-amino-benzisoxazol-5-yl | pzl-a | CF$_3$ | 3-F-2'-aminomethyl-[1,1']-biphen-4-yl | 511 |
| 123 | 3'-amino-benzisoxazol-yl | pzl-a | CF$_3$ | 3-F-2'-(N-pyrrolidinylmethyl)-[1,1']-biphen-4-yl | 565 |
| 124 | 3'-amino-benzisoxazol-5-yl | pzl-a | CF$_3$ | 3-F-2'-(N-imidazol-1-ylmethyl)-[1,1']-biphen-4-yl | 562 |
| 125 | 3'-amino-benzisoxazol-5-yl | pzl-a | CF$_3$ | 3-F-2'-(1"N-(4"N-t-butoxycarbonyl)-piperazinylmethyl)-[1,1']-biphen-4-yl | 680 |
| 126 | 3'-amino-benzisoxazol-5-yl | pzl-a | CF$_3$ | 3-F-2'-(N-(4"-N,N-dimethylamino)-pyridiniummethyl)-[1,1']-biphen-4-yl | 616 |
| 127 | 3'-amino-benzisoxazol-5-yl | pzl-a | CF$_3$ | 3-F-2'-(1"N-piperazinylmethyl)-[1,1']-biphen-4-yl | 580 |
| 128 | 3'-amino-benzisoxazol-5-yl | pzl-a | CF$_3$ | 3-F-2'-(1"N-methyl-1"N-morpholinium)-methyl)-[1,1']-biphen-4-yl | 695 |
| 129 | 3'-amino-benzisoxazol-5-yl | pzl-a | CF$_3$ | 3-F-2'-(N-morpholinomethyl)-[1,1']-biphen-4-yl | 581 |
| 130 | 3'-amino-benzisoxazol-5-yl | pzl-a | CF$_3$ | 3-F-2'-((N-methyl-N-methoxy)-aminomethyl)-[1,1']-biphen-4-yl | 555 |
| 131 | 3'-amino-benzisoxazol-5-yl | trz | — | 3-F-2'-CH$_3$SO$_2$-[1,1']-biphen-4-yl | 493 |
| 132 | 3'-amino-benzisoxazol-5-yl | trz | — | 3-F-2'-H$_2$NSO$_2$-[1,1']-biphen-4-yl | 494 |
| 133 | 3'-amino-benzisoxazol-5-yl | pzl-a | CF$_3$ | 3-F-2'-CH$_3$NHSO$_2$-[1,1']-biphen-4-yl | 575 |

TABLE 1-continued

| 134 | 3'-amino-benzisoxazol-5-yl | tzl | — | 2'-$(CH_3)_2NCH_2$-3-F-[1,1']-biphen-4-yl | 473 |
| 135 | 3'-amino-benzisoxazol-5-yl | pzl-a | $CH_3CH_2$ | 2'-$(CH_3)_2NCH_2$-3-F-[1,1']-biphen-4-yl | 499 |
| 136 | 3'-amino-benzisoxazol-5-yl | pzl-a | $CH_3CH_2$ | 2-F-(2'-$(CH_3)_2NCH_2$-imidazol-1'-yl)phenyl | 489 |

The following tables contain representative examples of the present invention. Each entry in each table is intended to be paired with each formulae at the start of the table. For example, example 1 in Table 2 is intended to be paired with each of formulae $a_1-y_9$.

TABLE 2

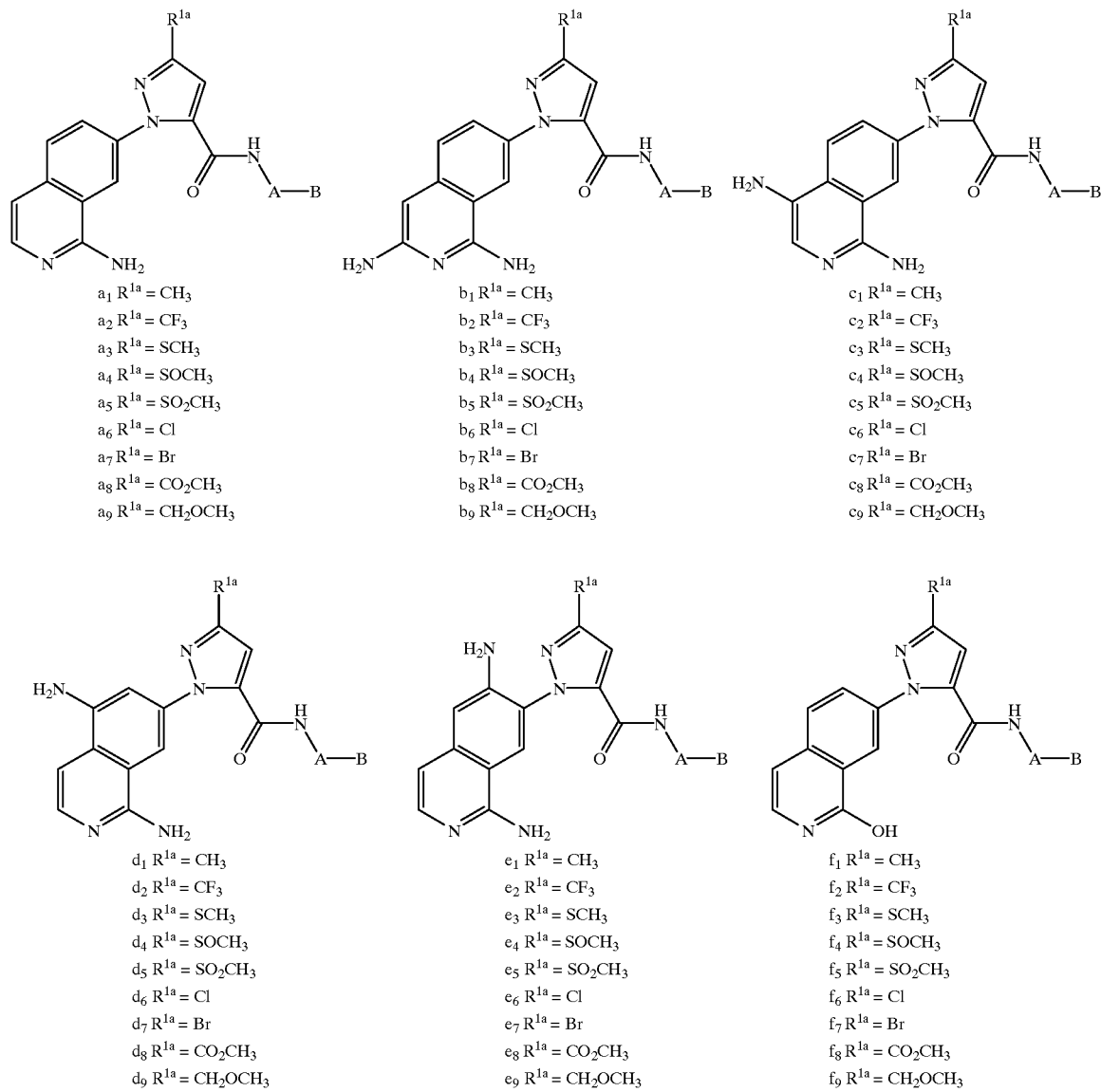

TABLE 2-continued

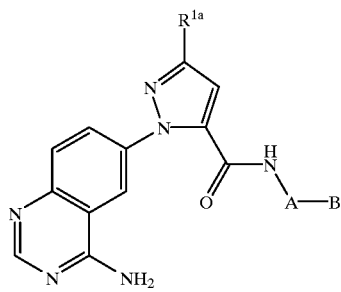

g₁ R¹ᵃ = CH₃
g₂ R¹ᵃ = CF₃
g₃ R¹ᵃ = SCH₃
g₄ R¹ᵃ = SOCH₃
g₅ R¹ᵃ = SO₂CH₃
g₆ R¹ᵃ = Cl
g₇ R¹ᵃ = Br
g₈ R¹ᵃ = CO₂CH₃
g₉ R¹ᵃ = CH₂OCH₃

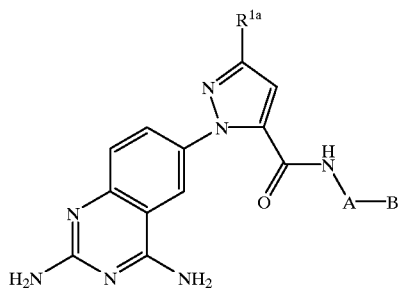

h₁ R¹ᵃ = CH₃
h₂ R¹ᵃ = CF₃
h₃ R¹ᵃ = SCH₃
h₄ R¹ᵃ = SOCH₃
h₅ R¹ᵃ = SO₂CH₃
h₆ R¹ᵃ = Cl
h₇ R¹ᵃ = Br
h₈ R¹ᵃ = CO₂CH₃
h₉ R¹ᵃ = CH₂OCH₃

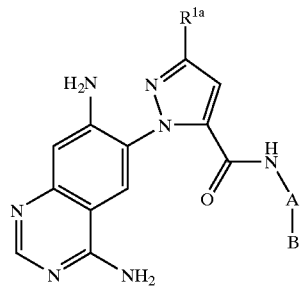

i₁ R¹ᵃ = CH₃
i₂ R¹ᵃ = CF₃
i₃ R¹ᵃ = SCH₃
i₄ R¹ᵃ = SOCH₃
i₅ R¹ᵃ = SO₂CH₃
i₆ R¹ᵃ = Cl
i₇ R¹ᵃ = Br
i₈ R¹ᵃ = CO₂CH₃
i₉ R¹ᵃ = CH₂OCH₃

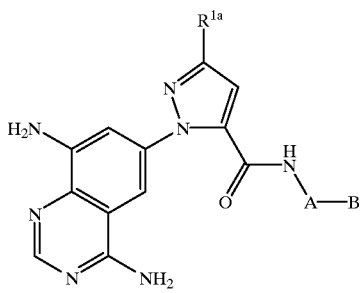

j₁ R¹ᵃ = CH₃
j₂ R¹ᵃ = CF₃
j₃ R¹ᵃ = SCH₃
j₄ R¹ᵃ = SOCH₃
j₅ R¹ᵃ = SO₂CH₃
j₆ R¹ᵃ = Cl
j₇ R¹ᵃ = Br
j₈ R¹ᵃ = CO₂CH₃
j₉ R¹ᵃ = CH₂OCH₃

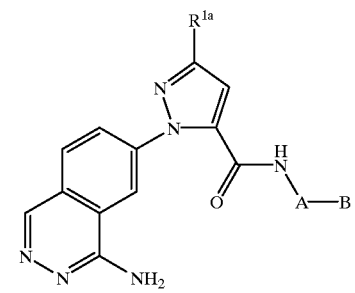

k₁ R¹ᵃ = CH₃
k₂ R¹ᵃ = CF₃
k₃ R¹ᵃ = SCH₃
k₄ R¹ᵃ = SOCH₃
k₅ R¹ᵃ = SO₂CH₃
k₆ R¹ᵃ = Cl
k₇ R¹ᵃ = Br
k₈ R¹ᵃ = CO₂CH₃
k₉ R¹ᵃ = CH₂OCH₃

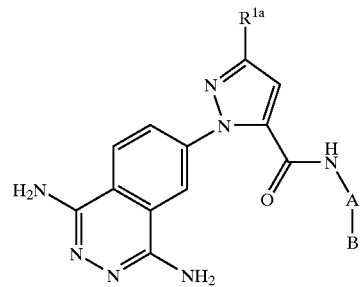

l₁ R¹ᵃ = CH₃
l₂ R¹ᵃ = CF₃
l₃ R¹ᵃ = SCH₃
l₄ R¹ᵃ = SOCH₃
l₅ R¹ᵃ = SO₂CH₃
l₆ R¹ᵃ = Cl
l₇ R¹ᵃ = Br
l₈ R¹ᵃ = CO₂CH₃
l₉ R¹ᵃ = CH₂OCH₃

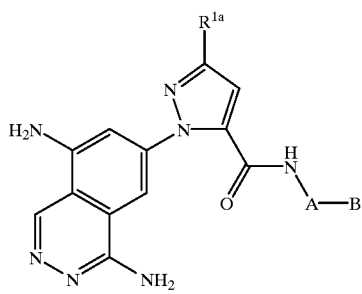

m₁ R¹ᵃ = CH₃
m₂ R¹ᵃ = CF₃
m₃ R¹ᵃ = SCH₃
m₄ R¹ᵃ = SOCH₃
m₅ R¹ᵃ = SO₂CH₃
m₆ R¹ᵃ = Cl
m₇ R¹ᵃ = Br
m₈ R¹ᵃ = CO₂CH₃
m₉ R¹ᵃ = CH₂OCH₃

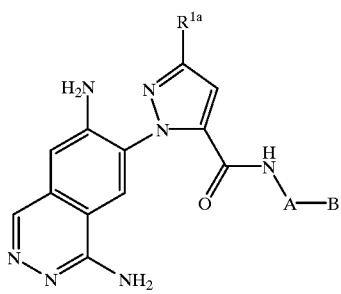

n₁ R¹ᵃ = CH₃
n₂ R¹ᵃ = CF₃
n₃ R¹ᵃ = SCH₃
n₄ R¹ᵃ = SOCH₃
n₅ R¹ᵃ = SO₂CH₃
n₆ R¹ᵃ = Cl
n₇ R¹ᵃ = Br
n₈ R¹ᵃ = CO₂CH₃
n₉ R¹ᵃ = CH₂OCH₃

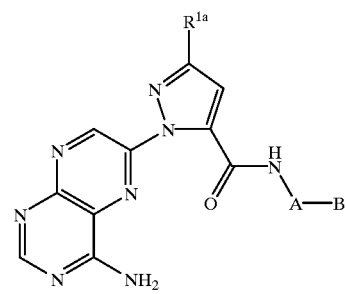

o₁ R¹ᵃ = CH₃
o₂ R¹ᵃ = CF₃
o₃ R¹ᵃ = SCH₃
o₄ R¹ᵃ = SOCH₃
o₅ R¹ᵃ = SO₂CH₃
o₆ R¹ᵃ = Cl
o₇ R¹ᵃ = Br
o₈ R¹ᵃ = CO₂CH₃
o₉ R¹ᵃ = CH₂OCH₃

TABLE 2-continued
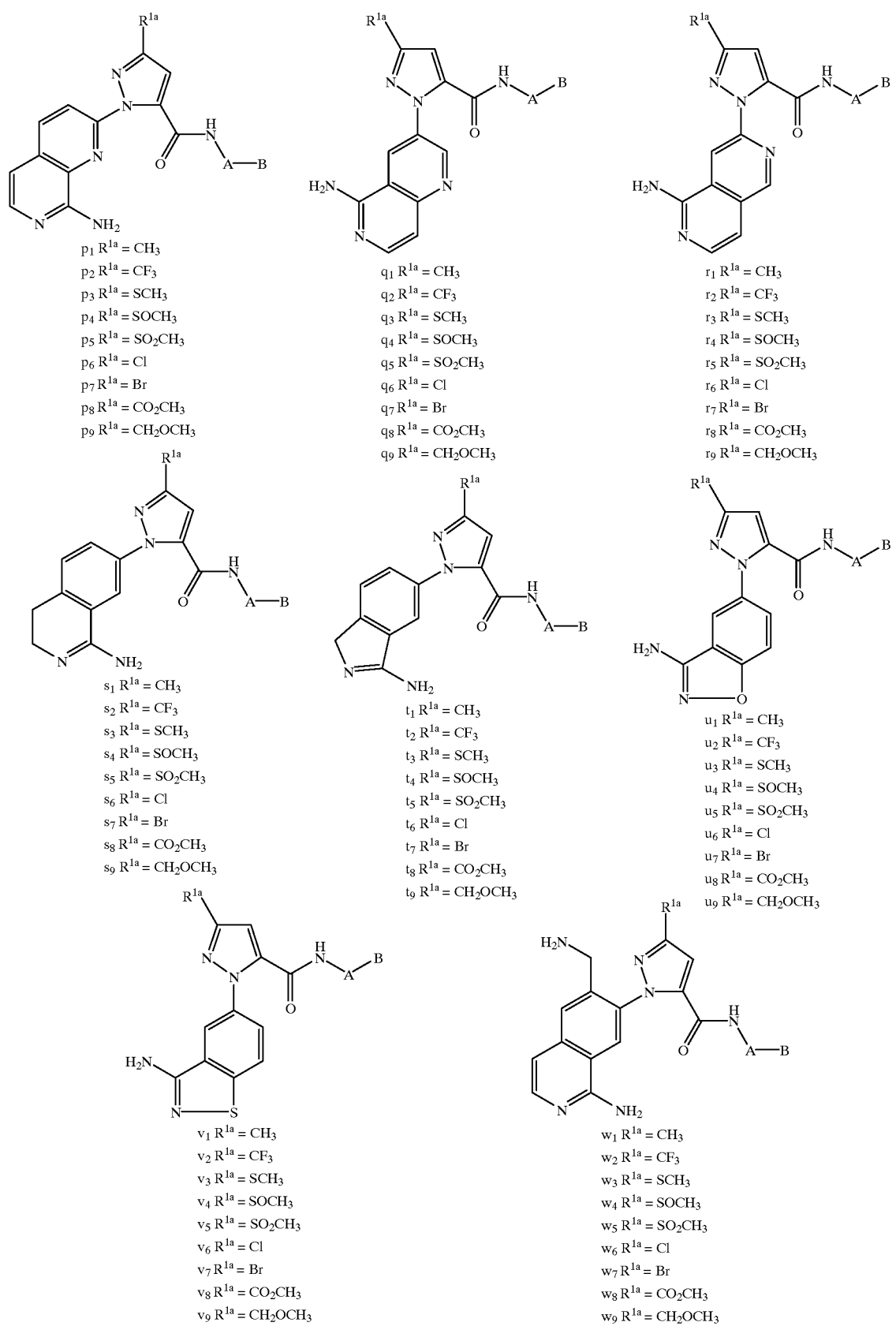

TABLE 2-continued

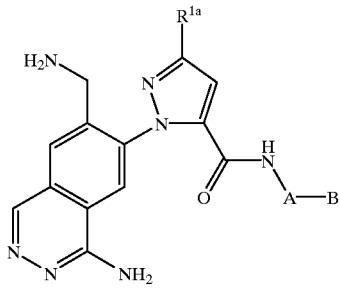

x$_1$ R$^{1a}$ = CH$_3$
x$_2$ R$^{1a}$ = CF$_3$
x$_3$ R$^{1a}$ = SCH$_3$
x$_4$ R$^{1a}$ = SOCH$_3$
x$_5$ R$^{1a}$ = SO$_2$CH$_3$
x$_6$ R$^{1a}$ = Cl
x$_7$ R$^{1a}$ = Br
x$_8$ R$^{1a}$ = CO$_2$CH$_3$
x$_9$ R$^{1a}$ = CH$_2$OCH$_3$

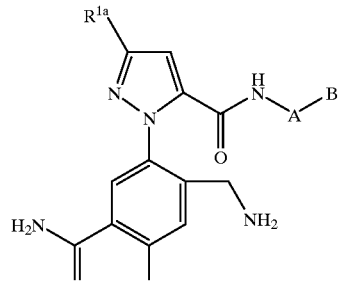

y$_1$ R$^{1a}$ = CH$_3$
y$_2$ R$^{1a}$ = CF$_3$
y$_3$ R$^{1a}$ = SCH$_3$
y$_4$ R$^{1a}$ = SOCH$_3$
y$_5$ R$^{1a}$ = SO$_2$CH$_3$
y$_6$ R$^{1a}$ = Cl
y$_7$ R$^{1a}$ = Br
y$_8$ R$^{1a}$ = CO$_2$CH$_3$
y$_9$ R$^{1a}$ = CH$_2$OCH$_3$

| Ex# | A | B |
| --- | --- | --- |
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | 2-pyridyl | 2-(aminosulfonyl)phenyl |
| 9 | 2-pyridyl | 2-(methylaminosulfonyl)phenyl |
| 10 | 2-pyridyl | 1-pyrrolidinocarbonyl |
| 11 | 2-pyridyl | 2-(methylsulfonyl)phenyl |
| 12 | 2-pyridyl | 4-morpholino |
| 13 | 2-pyridyl | 2-(1'-CF$_3$-tetrazol-2-yl)phenyl |
| 14 | 2-pyridyl | 4-morpholinocarbonyl |
| 15 | 3-pyridyl | 2-(aminosulfonyl)phenyl |
| 16 | 3-pyridyl | 2-(methylaminosulfonyl)phenyl |
| 17 | 3-pyridyl | 1-pyrrolidinocarbonyl |
| 18 | 3-pyridyl | 2-(methylsulfonyl)phenyl |
| 19 | 3-pyridyl | 4-morpholino |
| 20 | 3-pyridyl | 2-(1'-CF$_3$-tetrazol-2-yl)phenyl |
| 21 | 3-pyridyl | 4-morpholinocarbonyl |
| 22 | 2-pyrimidyl | 2-(aminosulfonyl)phenyl |
| 23 | 2-pyrimidyl | 2-(methylaminosulfonyl)phenyl |
| 24 | 2-pyrimidyl | 1-pyrrolidinocarbonyl |
| 25 | 2-pyrimidyl | 2-(methylsulfonyl)phenyl |
| 26 | 2-pyrimidyl | 4-morpholino |
| 27 | 2-pyrimidyl | 2-(1'-CF$_3$-tetrazol-2-yl)phenyl |
| 28 | 2-pyrimidyl | 4-morpholinocarbonyl |
| 29 | 5-pyrimidyl | 2-(aminosulfonyl)phenyl |
| 30 | 5-pyrimidyl | 2-(methylaminosulfonyl)phenyl |
| 31 | 5-pyrimidyl | 1-pyrrolidinocarbonyl |
| 32 | 5-pyrimidyl | 2-(methylsulfonyl)phenyl |
| 33 | 5-pyrimidyl | 4-morpholino |
| 34 | 5-pyrimidyl | 2-(1'-CF$_3$-tetrazol-2-yl)phenyl |
| 35 | 5-pyrimidyl | 4-morpholinocarbonyl |
| 36 | 2-Cl-phenyl | 2-(aminosulfonyl)phenyl |
| 37 | 2-Cl-phenyl | 2-(methylaminosulfonyl)phenyl |
| 38 | 2-Cl-phenyl | 1-pyrrolidinocarbonyl |
| 39 | 2-Cl-phenyl | 2-(methylsulfonyl)phenyl |
| 40 | 2-Cl-phenyl | 4-morpholino |
| 41 | 2-Cl-phenyl | 2-(1'-CF$_3$-tetrazol-2-yl)phenyl |
| 42 | 2-Cl-phenyl | 4-morpholinocarbonyl |
| 43 | 2-F-phenyl | 2-(aminosulfonyl)phenyl |
| 44 | 2-F-phenyl | 2-(methylaminosulfonyl)phenyl |
| 45 | 2-F-phenyl | 1-pyrrolidinocarbonyl |
| 46 | 2-F-phenyl | 2-(methylsulfonyl)phenyl |
| 47 | 2-F-phenyl | 4-morpholino |
| 48 | 2-F-phenyl | 2-(1'-CF$_3$-tetrazol-2-yl)phenyl |
| 49 | 2-F-phenyl | 4-morpholinocarbonyl |

TABLE 2-continued

| | | |
|---|---|---|
| 50 | 2,5-diF-phenyl | 2-(aminosulfonyl)phenyl |
| 51 | 2,5-diF-phenyl | 2-(methylaminosulfonyl)phenyl |
| 52 | 2,5-diF-phenyl | 1-pyrrolidinocarbonyl |
| 53 | 2,5-diF-phenyl | 2-(methylsulfonyl)phenyl |
| 54 | 2,5-diF-phenyl | 4-morpholino |
| 55 | 2,5-diF-phenyl | 2-(1'-CF$_3$-tetrazol-2-yl)phenyl |
| 56 | 2,5-diF-phenyl | 4-morpholinocarbonyl |
| 57 | phenyl | 2-(N-pyrrolidinyl-methyl)phenyl |
| 58 | phenyl | 2-(N-piperidinyl-methyl)phenyl |
| 59 | phenyl | 2-(N-morpholino-methyl)phenyl |
| 60 | phenyl | 2-(N,N'-methylmorpholinium-methyl)phenyl |
| 61 | phenyl | 2-(N-pyridinium-methyl)phenyl |
| 62 | phenyl | 2-(N-4-(N,N'-dimethylamino)-pyridinium-methyl)phenyl |
| 63 | phenyl | 2-(N-azatanyl-methyl)phenyl |
| 64 | phenyl | 2-(N-azetidinyl-methyl)phenyl |
| 65 | phenyl | 2-(N-piperazinyl-methyl)phenyl |
| 66 | phenyl | 2-(N,N'-BOC-piperazinyl-methyl)phenyl |
| 67 | phenyl | 2-(N-imidazolyl-methyl)phenyl |
| 68 | phenyl | 2-(N-methoxy-N-methylamino-methyl)phenyl |
| 69 | phenyl | 2-(N-pyridonyl-methyl)phenyl |
| 70 | phenyl | 2-(N-(N',N'-dimethylhydrazinyl-methyl)phenyl |
| 71 | phenyl | 2-(amidinyl)phenyl |
| 72 | phenyl | 2-(N-guanidinyl)phenyl |
| 73 | phenyl | 2-(imidazolyl)phenyl |
| 74 | phenyl | 2-(imidazolidinyl)phenyl |
| 75 | phenyl | 2-(2-imidazolidinyl-sulfonyl)phenyl |
| 76 | phenyl | 2-(2-pyrrolidinyl)phenyl |
| 77 | phenyl | 2-(2-piperidinyl)phenyl |
| 78 | phenyl | 2-(amidinyl-methyl)phenyl |
| 79 | phenyl | 2-(2-imidazolidinyl-methyl)phenyl |
| 80 | phenyl | 2-(N-(2-aminoimidazolyl)-methyl)phenyl |
| 81 | phenyl | 2-dimethylaminoimidazol-1-yl |
| 82 | phenyl | 2-(3-aminophenyl) |
| 83 | phenyl | 2-(3-pyrrolidinylcarbonyl) |
| 84 | phenyl | 2-glycinoyl |
| 85 | phenyl | 2-(imidazol-1-ylacetyl) |
| 86 | 2-pyridyl | 2-(N-pyrrolidinyl-methyl)phenyl |
| 87 | 2-pyridyl | 2-(N-piperidinyl-methyl)phenyl |
| 88 | 2-pyridyl | 2-(N-morpholino-methyl)phenyl |
| 89 | 2-pyridyl | 2-(N,N'-methylmorpholinium-methyl)phenyl |
| 90 | 2-pyridyl | 2-(N-pyridinium-methyl)phenyl |
| 91 | 2-pyridyl | 2-(N-4-(N,N'-dimethylamino)-pyridinium-methyl)phenyl |
| 92 | 2-pyridyl | 2-(N-azatanyl-methyl)phenyl |
| 93 | 2-pyridyl | 2-(N-azetidinyl-methyl)phenyl |
| 94 | 2-pyridyl | 2-(N-piperazinyl-methyl)phenyl |
| 95 | 2-pyridyl | 2-(N,N'-BOC-piperazinyl-methyl)phenyl |
| 96 | 2-pyridyl | 2-(N-imidazolyl-methyl)phenyl |
| 97 | 2-pyridyl | 2-(N-methoxy-N-methylaminomethyl)phenyl |
| 98 | 2-pyridyl | 2-(N-pyridonyl-methyl)phenyl |
| 99 | 2-pyridyl | 2-(N-(N',N'-dimethylhydrazinyl-methyl)phenyl |
| 100 | 2-pyridyl | 2-(amidinyl)phenyl |
| 101 | 2-pyridyl | 2-(N-guanidinyl)phenyl |
| 102 | 2-pyridyl | 2-(imidazolyl)phenyl |
| 103 | 2-pyridyl | 2-(imidazolidinyl)phenyl |
| 104 | 2-pyridyl | 2-(2-imidazolidinyl-sulfonyl)phenyl |
| 105 | 2-pyridyl | 2-(2-pyrrolidinyl)phenyl |
| 106 | 2-pyridyl | 2-(2-piperidinyl)phenyl |
| 107 | 2-pyridyl | 2-(amidinyl-methyl)phenyl |
| 108 | 2-pyridyl | 2-(2-imidazolidinyl-methyl)phenyl |
| 109 | 2-pyridyl | 2-(N-(2-aminoimidazolyl)-methyl)phenyl |
| 110 | 2-pyridyl | 2-dimethylaminoimidazol-1-yl |
| 111 | 2-pyridyl | 2-(3-aminophenyl) |
| 112 | 2-pyridyl | 2-(3-pyrrolidinylcarbonyl) |
| 113 | 2-pyridyl | 2-glycinoyl |
| 114 | 2-pyridyl | 2-(imidazol-1-ylacetyl) |
| 115 | 3-pyridyl | 2-(N-pyrrolidinyl-methyl)phenyl |
| 116 | 3-pyridyl | 2-(N-piperidinyl-methyl)phenyl |
| 117 | 3-pyridyl | 2-(N-morpholino-methyl)phenyl |
| 118 | 3-pyridyl | 2-(N,N'-methylmorpholinium-methyl)phenyl |
| 119 | 3-pyridyl | 2-(N-pyridinium-methyl)phenyl |
| 120 | 3-pyridyl | 2-(N-4-(N,N'-dimethylamino)-pyridinium-methyl)phenyl |
| 121 | 3-pyridyl | 2-(N-azatanyl-methyl)phenyl |
| 122 | 3-pyridyl | 2-(N-azetidinyl-methyl)phenyl |
| 123 | 3-pyridyl | 2-(N-piperazinyl-methyl)phenyl |

TABLE 2-continued

| | | |
|---|---|---|
| 124 | 3-pyridyl | 2-(N,N'-BOC-piperazinyl-methyl)phenyl |
| 125 | 3-pyridyl | 2-(N-imidazolyl-methyl)phenyl |
| 126 | 3-pyridyl | 2-(N-methoxy-N-methylamino-methyl)phenyl |
| 127 | 3-pyridyl | 2-(N-pyridonyl-methyl)phenyl |
| 128 | 3-pyridyl | 2-(N-(N',N'-dimethylhydrazinyl-methyl)phenyl |
| 129 | 3-pyridyl | 2-(amidinyl)phenyl |
| 130 | 3-pyridyl | 2-(N-guanidinyl)phenyl |
| 131 | 3-pyridyl | 2-(imidazolyl)phenyl |
| 132 | 3-pyridyl | 2-(imidazolidinyl)phenyl |
| 133 | 3-pyridyl | 2-(2-imidazolidinyl-sulfonyl)phenyl |
| 134 | 3-pyridyl | 2-(2-pyrrolidinyl)phenyl |
| 135 | 3-pyridyl | 2-(2-piperidinyl)phenyl |
| 136 | 3-pyridyl | 2-(amidinyl-methyl)phenyl |
| 137 | 3-pyridyl | 2-(2-imidazolidinyl-methyl)phenyl |
| 138 | 3-pyridyl | 2-(N-(2-aminoimidazolyl)-methyl)phenyl |
| 139 | 3-pyridyl | 2-dimethylaminoimidazol-1-yl |
| 140 | 3-pyridyl | 2-(3-aminophenyl) |
| 141 | 3-pyridyl | 2-(3-pyrrolidinylcarbonyl) |
| 142 | 3-pyridyl | 2-glycinoyl |
| 143 | 3-pyridyl | 2-(imidazol-1-ylacetyl) |
| 144 | 2-pyrimidyl | 2-(N-pyrrolidinyl-methyl)phenyl |
| 145 | 2-pyrimidyl | 2-(N-piperidinyl-methyl)phenyl |
| 146 | 2-pyrimidyl | 2-(N-morpholino-methyl)phenyl |
| 147 | 2-pyrimidyl | 2-(N,N'-methylmorpholinium-methyl)phenyl |
| 148 | 2-pyrimidyl | 2-(N-pyridinium-methyl)phenyl |
| 149 | 2-pyrimidyl | 2-(N-4-(N,N'-dimethylamino)-pyridinium-methyl)phenyl |
| 150 | 2-pyrimidyl | 2-(N-azatanyl-methyl)phenyl |
| 151 | 2-pyrimidyl | 2-(N-azetidinyl-methyl)phenyl |
| 152 | 2-pyrimidyl | 2-(N-piperazinyl-methyl)phenyl |
| 153 | 2-pyrimidyl | 2-(N,N'-BOC-piperazinyl-methyl)phenyl |
| 154 | 2-pyrimidyl | 2-(N-imidazolyl-methyl)phenyl |
| 155 | 2-pyrimidyl | 2-(N-methoxy-N-methylamino-methyl)phenyl |
| 156 | 2-pyrimidyl | 2-(N-pyridonyl-methyl)phenyl |
| 157 | 2-pyrimidyl | 2-(N-(N',N'-dimethylhydrazinyl-methyl)phenyl |
| 158 | 2-pyrimidyl | 2-(amidinyl)phenyl |
| 159 | 2-pyrimidyl | 2-(N-guanidinyl)phenyl |
| 160 | 2-pyrimidyl | 2-(imidazolyl)phenyl |
| 161 | 2-pyrimidyl | 2-(imidazolidinyl)phenyl |
| 162 | 2-pyrimidyl | 2-(2-imidazolidinyl-sulfonyl)phenyl |
| 163 | 2-pyrimidyl | 2-(2-pyrrolidinyl)phenyl |
| 164 | 2-pyrimidyl | 2-(2-piperidinyl)phenyl |
| 165 | 2-pyrimidyl | 2-(amidinyl-methyl)phenyl |
| 166 | 2-pyrimidyl | 2-(2-imidazolidinyl-methyl)phenyl |
| 167 | 2-pyrimidyl | 2-(N-(2-aminoimidazolyl)-methyl)phenyl |
| 168 | 2-pyrimidyl | 2-dimethylaminoimidazol-1-yl |
| 169 | 2-pyrimidyl | 2-(3-aminophenyl) |
| 170 | 2-pyrimidyl | 2-(3-pyrrolidinylcarbonyl) |
| 171 | 2-pyrimidyl | 2-glycinoyl |
| 172 | 2-pyrimidyl | 2-(imidazol-1-ylacetyl) |
| 173 | 2-Cl-phenyl | 2-(N-pyrrolidinyl-methyl)phenyl |
| 174 | 2-Cl-phenyl | 2-(N-piperidinyl-methyl)phenyl |
| 175 | 2-Cl-phenyl | 2-(N-morpholino-methyl)phenyl |
| 176 | 2-Cl-phenyl | 2-(N,N'-methylmorpholinium-methyl)phenyl |
| 177 | 2-Cl-phenyl | 2-(N-pyridinium-methyl)phenyl |
| 178 | 2-Cl-phenyl | 2-(N-4-(N,N'-dimethylamino)-pyridinium-methyl)phenyl |
| 179 | 2-Cl-phenyl | 2-(N-azatanyl-methyl)phenyl |
| 180 | 2-Cl-phenyl | 2-(N-azetidinyl-methyl)phenyl |
| 181 | 2-Cl-phenyl | 2-(N-piperazinyl-methyl)phenyl |
| 182 | 2-Cl-phenyl | 2-(N,N'-BOC-piperazinyl-methyl)phenyl |
| 183 | 2-Cl-phenyl | 2-(N-imidazolyl-methyl)phenyl |
| 184 | 2-Cl-phenyl | 2-(N-methoxy-N-methylamino-methyl)phenyl |
| 185 | 2-Cl-phenyl | 2-(N-pyridonyl-methyl)phenyl |
| 186 | 2-Cl-phenyl | 2-(N-(N',N'-dimethylhydrazinyl-methyl)phenyl |
| 187 | 2-Cl-phenyl | 2-(amidinyl)phenyl |
| 188 | 2-Cl-phenyl | 2-(N-guanidinyl)phenyl |
| 189 | 2-Cl-phenyl | 2-(imidazolyl)phenyl |
| 190 | 2-Cl-phenyl | 2-(imidazolidinyl)phenyl |
| 191 | 2-Cl-phenyl | 2-(2-imidazolidinyl-sulfonyl)phenyl |
| 192 | 2-Cl-phenyl | 2-(2-pyrrolidinyl)phenyl |
| 193 | 2-Cl-phenyl | 2-(2-piperidinyl)phenyl |
| 194 | 2-Cl-phenyl | 2-(amidinyl-methyl)phenyl |
| 195 | 2-Cl-phenyl | 2-(2-imidazolidinyl-methyl)phenyl |
| 196 | 2-Cl-phenyl | 2-(N-(2-aminoimidazolyl)-methyl)phenyl |
| 197 | 2-Cl-phenyl | 2-dimethylaminoimidazol-1-yl |

TABLE 2-continued

| | | |
|---|---|---|
| 198 | 2-Cl-phenyl | 2-(3-aminophenyl) |
| 199 | 2-Cl-phenyl | 2-(3-pyrrolidinylcarbonyl) |
| 200 | 2-Cl-phenyl | 2-glycinoyl |
| 201 | 2-Cl-phenyl | 2-(imidazol-1-ylacetyl) |
| 202 | 2-F-phenyl | 2-(N-pyrrolidinyl-methyl)phenyl |
| 203 | 2-F-phenyl | 2-(N-piperidinyl-methyl)phenyl |
| 204 | 2-F-phenyl | 2-(N-morpholino-methyl)phenyl |
| 205 | 2-F-phenyl | 2-(N,N'-methylmorpholinium-methyl)phenyl |
| 206 | 2-F-phenyl | 2-(N-pyridinium-methyl)phenyl |
| 207 | 2-F-phenyl | 2-(N-4-(N,N'-dimethylamino)-pyridinium-methyl)phenyl |
| 208 | 2-F-phenyl | 2-(N-azatanyl-methyl)phenyl |
| 209 | 2-F-phenyl | 2-(N-azetidinyl-methyl)phenyl |
| 210 | 2-F-phenyl | 2-(N-piperazinyl-methyl)phenyl |
| 211 | 2-F-phenyl | 2-(N,N'-BOC-piperazinyl-methyl)phenyl |
| 212 | 2-F-phenyl | 2-(N-imidazolyl-methyl)phenyl |
| 213 | 2-F-phenyl | 2-(N-methoxy-N-methylamino-methyl)phenyl |
| 214 | 2-F-phenyl | 2-(N-pyridonyl-methyl)phenyl |
| 215 | 2-F-phenyl | 2-(N-(N',N'-dimethylhydrazinyl-methyl)phenyl |
| 216 | 2-F-phenyl | 2-(amidinyl)phenyl |
| 217 | 2-F-phenyl | 2-(N-guanidinyl)phenyl |
| 218 | 2-F-phenyl | 2-(imidazolyl)phenyl |
| 219 | 2-F-phenyl | 2-(imidazolidinyl)phenyl |
| 220 | 2-F-phenyl | 2-(2-imidazolidinyl-sulfonyl)phenyl |
| 221 | 2-F-phenyl | 2-(2-pyrrolidinyl)phenyl |
| 222 | 2-F-phenyl | 2-(2-piperidinyl)phenyl |
| 223 | 2-F-phenyl | 2-(amidinyl-methyl)phenyl |
| 224 | 2-F-phenyl | 2-(2-imidazolidinyl-methyl)phenyl |
| 225 | 2-F-phenyl | 2-(N-(2-aminoimidazolyl)-methyl)phenyl |
| 226 | 2-F-phenyl | 2-dimethylaminoimidazol-1-yl |
| 227 | 2-F-phenyl | 2-(3-aminophenyl) |
| 228 | 2-F-phenyl | 2-(3-pyrrolidinylcarbonyl) |
| 229 | 2-F-phenyl | 2-glycinoyl |
| 230 | 2-F-phenyl | 2-(imidazol-1-ylacetyl) |
| 231 | 2,5-diF-phenyl | 2-(N-pyrrolidinyl-methyl)phenyl |
| 232 | 2,5-diF-phenyl | 2-(N-piperidinyl-methyl)phenyl |
| 233 | 2,5-diF-phenyl | 2-(N-morpholino-methyl)phenyl |
| 234 | 2,5-diF-phenyl | 2-(N,N'-methylmorpholinium-methyl)phenyl |
| 235 | 2,5-diF-phenyl | 2-(N-pyridinium-methyl)phenyl |
| 236 | 2,5-diF-phenyl | 2-(N-4-(N,N'-dimethylamino)-pyridinium-methyl)phenyl |
| 237 | 2,5-diF-phenyl | 2-(N-azatanyl-methyl)phenyl |
| 238 | 2,5-diF-phenyl | 2-(N-azetidinyl-methyl)phenyl |
| 239 | 2,5-diF-phenyl | 2-(N-piperazinyl-methyl)phenyl |
| 240 | 2,5-diF-phenyl | 2-(N,N'-BOC-piperazinyl-methyl)phenyl |
| 241 | 2,5-diF-phenyl | 2-(N-imidazolyl-methyl)phenyl |
| 242 | 2,5-diF-phenyl | 2-(N-methoxy-N-methylamino-methyl)phenyl |
| 243 | 2,5-diF-phenyl | 2-(N-pyridonyl-methyl)phenyl |
| 244 | 2,5-diF-phenyl | 2-(N-(N',N'-dimethylhydrazinyl-methyl)phenyl |
| 245 | 2,5-diF-phenyl | 2-(amidinyl)phenyl |
| 246 | 2,5-diF-phenyl | 2-(N-guanidinyl)phenyl |
| 247 | 2,5-diF-phenyl | 2-(imidazolyl)phenyl |
| 248 | 2,5-diF-phenyl | 2-(imidazolidinyl)phenyl |
| 249 | 2,5-diF-phenyl | 2-(2-imidazolidinyl-sulfonyl)phenyl |
| 250 | 2,5-diF-phenyl | 2-(2-pyrrolidinyl)phenyl |
| 251 | 2,5-diF-phenyl | 2-(2-piperidinyl)phenyl |
| 252 | 2,5-diF-phenyl | 2-(amidinyl-methyl)phenyl |
| 253 | 2,5-diF-phenyl | 2-(2-imidazolidinyl-methyl)phenyl |
| 254 | 2,5-diF-phenyl | 2-(N-(2-aminoimidazolyl)-methyl)phenyl |
| 255 | 2,5-diF-phenyl | 2-dimethylaminoimidazol-1-yl |
| 256 | 2,5-diF-phenyl | 2-(3-aminophenyl) |
| 257 | 2,5-diF-phenyl | 2-(3-pyrrolidinylcarbonyl) |
| 258 | 2,5-diF-phenyl | 2-glycinoyl |
| 259 | 2,5-diF-phenyl | 2-(imidazol-1-ylacetyl) |

TABLE 3
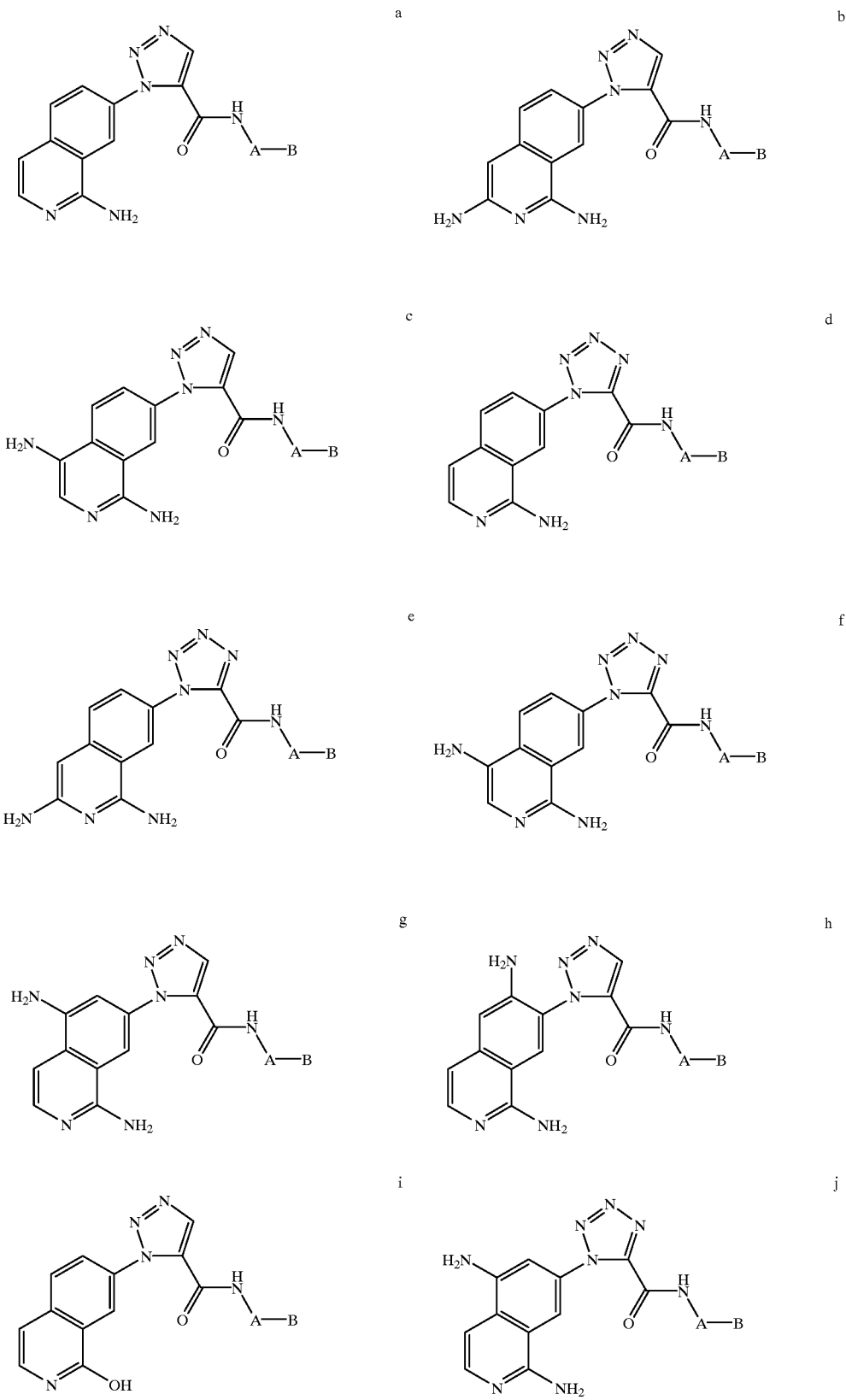

TABLE 3-continued
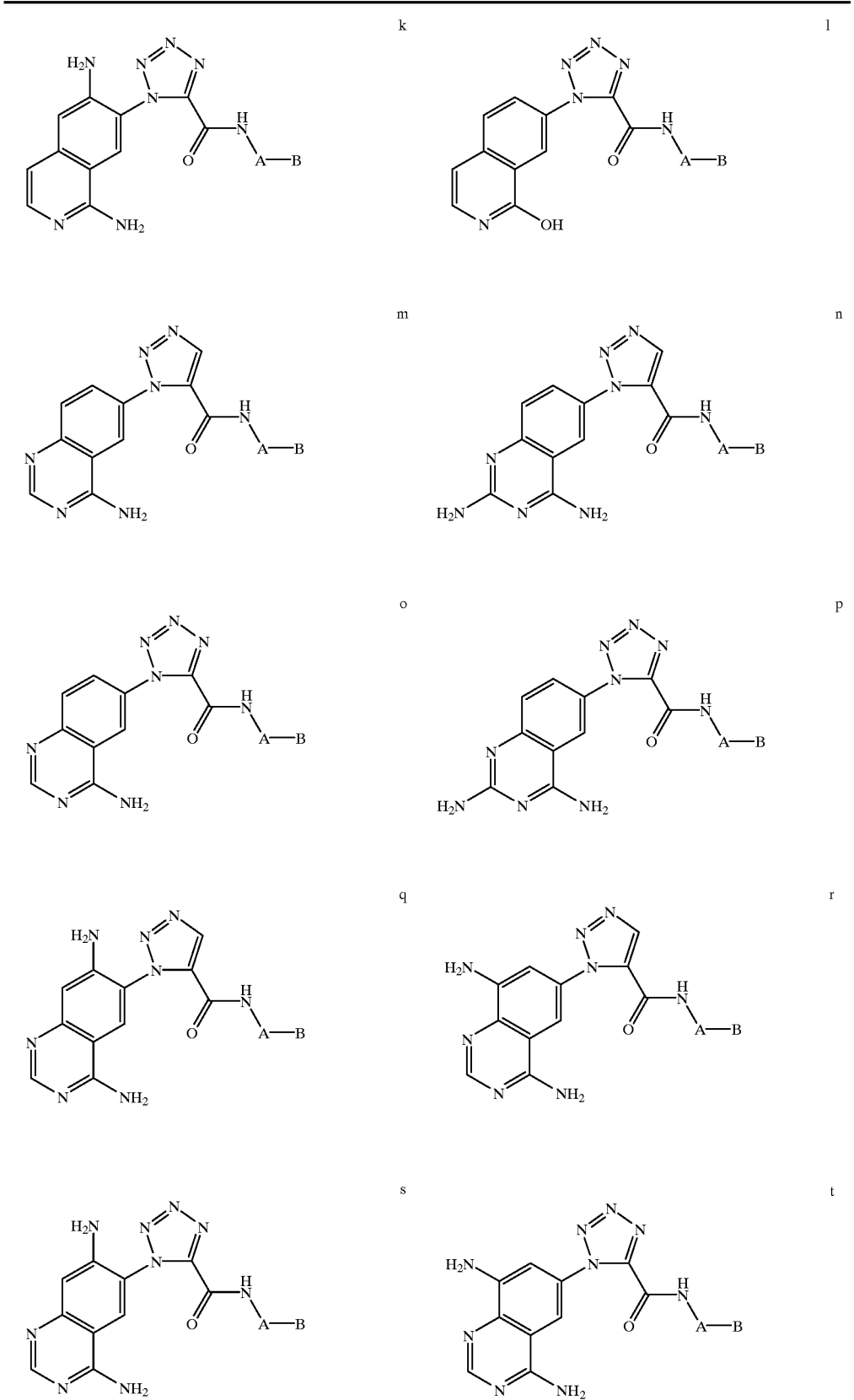

TABLE 3-continued
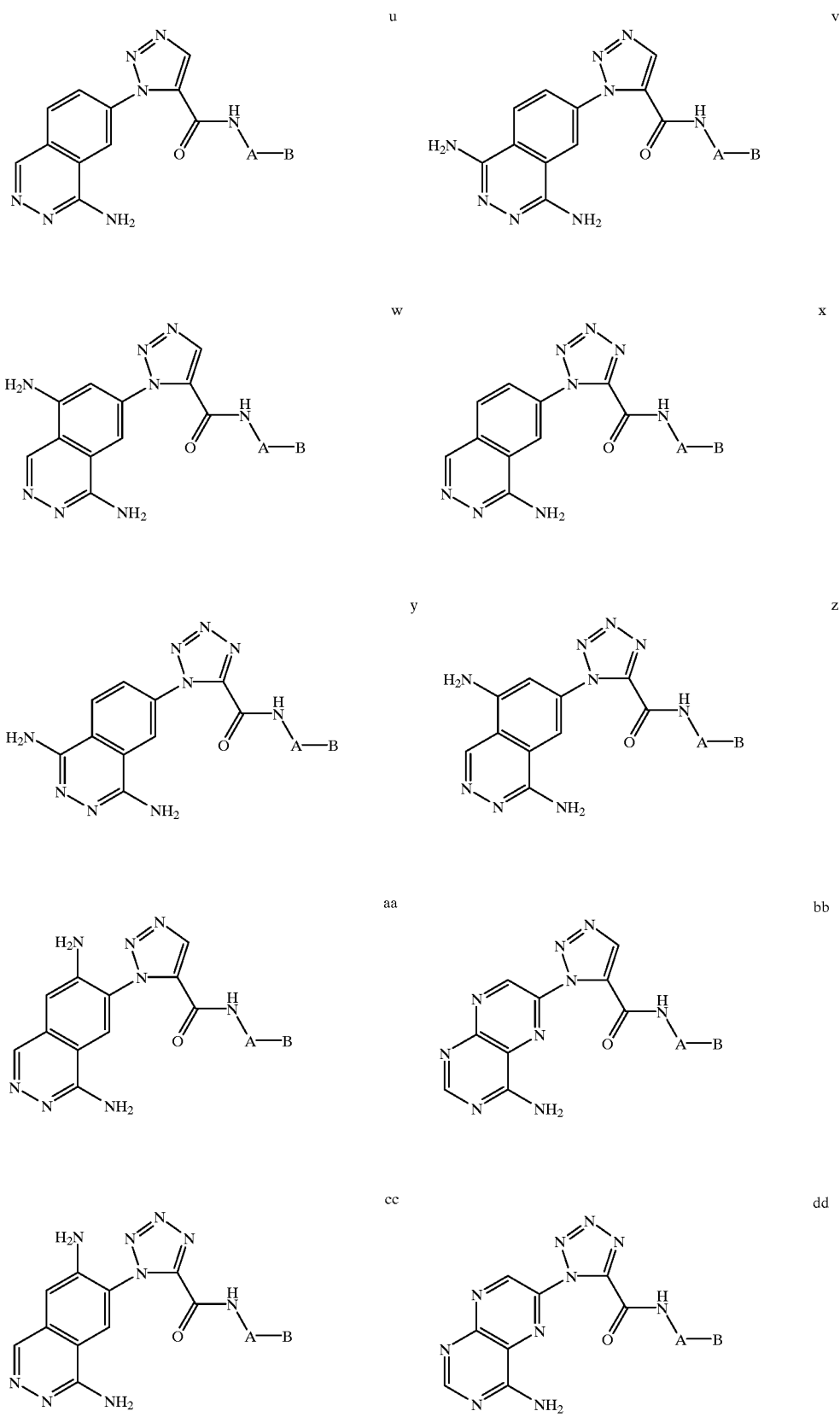

TABLE 3-continued
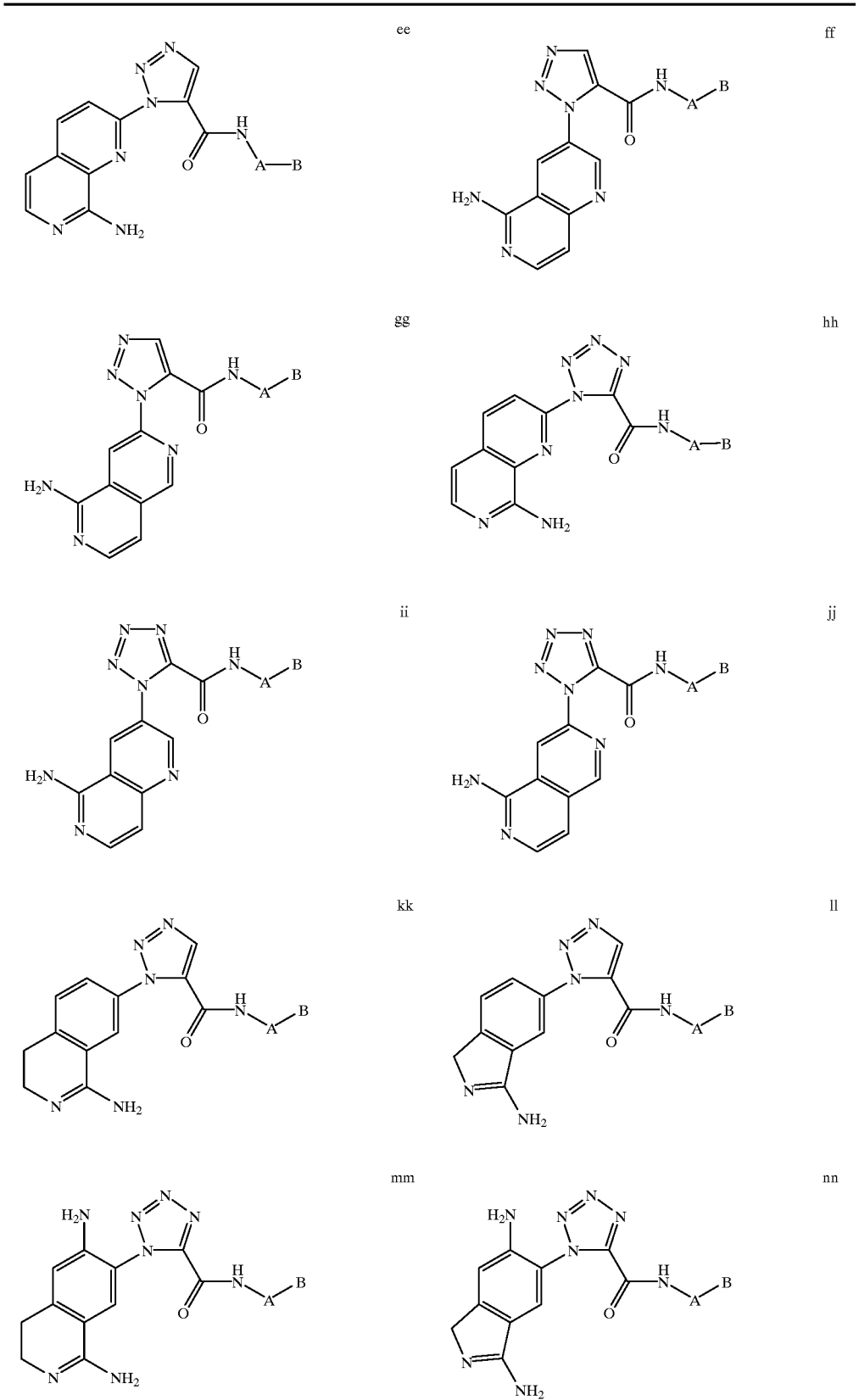

TABLE 3-continued

| | | | |
|---|---|---|---|
| oo | (structure) | pp | (structure) |
| qq | (structure) | rr | (structure) |

| Ex# | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-$CF_3$-tetrazol-2-yl)phenyl |
| 7 | phenyl | 4-morpholinocarbonyl |
| 8 | 2-pyridyl | 2-(aminosulfonyl)phenyl |
| 9 | 2-pyridyl | 2-(methylaminosulfonyl)phenyl |
| 10 | 2-pyridyl | 1-pyrrolidinocarbonyl |
| 11 | 2-pyridyl | 2-(methylsulfonyl)phenyl |
| 12 | 2-pyridyl | 4-morpholino |
| 13 | 2-pyridyl | 2-(1'-$CF_3$-tetrazol-2-yl)phenyl |
| 14 | 2-pyridyl | 4-morpholinocarbonyl |
| 15 | 3-pyridyl | 2-(aminosulfonyl)phenyl |
| 16 | 3-pyridyl | 2-(methylaminosulfonyl)phenyl |
| 17 | 3-pyridyl | 1-pyrrolidinocarbonyl |
| 18 | 3-pyridyl | 2-(methylsulfonyl)phenyl |
| 19 | 3-pyridyl | 4-morpholino |
| 20 | 3-pyridyl | 2-(1'-$CF_3$-tetrazol-2-yl)phenyl |
| 21 | 3-pyridyl | 4-morpholinocarbonyl |
| 22 | 2-pyrimidyl | 2-(aminosulfonyl)phenyl |
| 23 | 2-pyrimidyl | 2-(methylaminosulfonyl)phenyl |
| 24 | 2-pyrimidyl | 1-pyrrolidinocarbonyl |
| 25 | 2-pyrimidyl | 2-(methylsulfonyl)phenyl |
| 26 | 2-pyrimidyl | 4-morpholino |
| 27 | 2-pyrimidyl | 2-(1'-$CF_3$-tetrazol-2-yl)phenyl |
| 28 | 2-pyrimidyl | 4-morpholinocarbonyl |
| 29 | 5-pyrimidyl | 2-(aminosulfonyl)phenyl |
| 30 | 5-pyrimidyl | 2-(methylaminosulfonyl)phenyl |
| 31 | 5-pyrimidyl | 1-pyrrolidinocarbonyl |
| 32 | 5-pyrimidyl | 2-(methylsulfonyl)phenyl |
| 33 | 5-pyrimidyl | 4-morpholino |
| 34 | 5-pyrimidyl | 2-(1'-$CF_3$-tetrazol-2-yl)phenyl |
| 35 | 5-pyrimidyl | 4-morpholinocarbonyl |
| 36 | 2-Cl-phenyl | 2-(aminosulfonyl)phenyl |
| 37 | 2-Cl-phenyl | 2-(methylaminosulfonyl)phenyl |
| 38 | 2-Cl-phenyl | 1-pyrrolidinocarbonyl |
| 39 | 2-Cl-phenyl | 2-(methylsulfonyl)phenyl |
| 40 | 2-Cl-phenyl | 4-morpholino |
| 41 | 2-Cl-phenyl | 2-(1'-$CF_3$-tetrazol-2-yl)phenyl |
| 42 | 2-Cl-phenyl | 4-morpholinocarbonyl |
| 43 | 2-F-phenyl | 2-(aminosulfonyl)phenyl |
| 44 | 2-F-phenyl | 2-(methylaminosulfonyl)phenyl |
| 45 | 2-F-phenyl | 1-pyrrolidinocarbonyl |
| 46 | 2-F-phenyl | 2-(methylsulfonyl)phenyl |
| 47 | 2-F-phenyl | 4-morpholino |
| 48 | 2-F-phenyl | 2-(1'-$CF_3$-tetrazol-2-yl)phenyl |

TABLE 3-continued

| | | |
|---|---|---|
| 49 | 2-F-phenyl | 4-morpholinocarbonyl |
| 50 | 2,5-diF-phenyl | 2-(aminosulfonyl)phenyl |
| 51 | 2,5-diF-phenyl | 2-(methylaminosulfonyl)phenyl |
| 52 | 2,5-diF-phenyl | 1-pyrrolidinocarbonyl |
| 53 | 2,5-diF-phenyl | 2-(methylsulfonyl)phenyl |
| 54 | 2,5-diF-phenyl | 4-morpholino |
| 55 | 2,5-diF-phenyl | 2-(1'-CF$_3$-tetrazol-2-yl)phenyl |
| 56 | 2,5-diF-phenyl | 4-morpholinocarbonyl |
| 57 | phenyl | 2-(N-pyrrolidinyl-methyl)phenyl |
| 58 | phenyl | 2-(N-piperidinyl-methyl)phenyl |
| 59 | phenyl | 2-(N-morpholino-methyl)phenyl |
| 60 | phenyl | 2-(N,N'-methylmorpholinium-methyl)phenyl |
| 61 | phenyl | 2-(N-pyridinium-methyl)phenyl |
| 62 | phenyl | 2-(N-4-(N,N'-dimethylamino)-pyridinium-methyl)phenyl |
| 63 | phenyl | 2-(N-azatanyl-methyl)phenyl |
| 64 | phenyl | 2-(N-azetidinyl-methyl)phenyl |
| 65 | phenyl | 2-(N-piperazinyl-methyl)phenyl |
| 66 | phenyl | 2-(N,N'-BOC-piperazinyl-methyl)phenyl |
| 67 | phenyl | 2-(N-imidazolyl-methyl)phenyl |
| 68 | phenyl | 2-(N-methoxy-N-methylamino-methyl)phenyl |
| 69 | phenyl | 2-(N-pyridonyl-methyl)phenyl |
| 70 | phenyl | 2-(N-(N',N'-dimethylhydrazinyl-methyl)phenyl |
| 71 | phenyl | 2-(amidinyl)phenyl |
| 72 | phenyl | 2-(N-guanidinyl)phenyl |
| 73 | phenyl | 2-(imidazolyl)phenyl |
| 74 | phenyl | 2-(imidazolidinyl)phenyl |
| 75 | phenyl | 2-(2-imidazolidinyl-sulfonyl)phenyl |
| 76 | phenyl | 2-(2-pyrrolidinyl)phenyl |
| 77 | phenyl | 2-(2-piperidinyl)phenyl |
| 78 | phenyl | 2-(amidinyl-methyl)phenyl |
| 79 | phenyl | 2-(2-imidazolidinyl-methyl)phenyl |
| 80 | phenyl | 2-(N-(2-aminoimidazolyl)-methyl)phenyl |
| 81 | phenyl | 2-dimethylaminoimidazol-1-yl |
| 82 | phenyl | 2-(3-aminophenyl) |
| 83 | phenyl | 2-(3-pyrrolidinylcarbonyl) |
| 84 | phenyl | 2-glycinoyl |
| 85 | phenyl | 2-(imidazol-1-ylacetyl) |
| 86 | 2-pyridyl | 2-(N-pyrrolidinyl-methyl)phenyl |
| 87 | 2-pyridyl | 2-(N-piperidinyl-methyl)phenyl |
| 88 | 2-pyridyl | 2-(N-morpholino-methyl)phenyl |
| 89 | 2-pyridyl | 2-(N,N'-methylmorpholinium-methyl)phenyl |
| 90 | 2-pyridyl | 2-(N-pyridinium-methyl)phenyl |
| 91 | 2-pyridyl | 2-(N-4-(N,N'-dimethylamino)-pyridinium-methyl)phenyl |
| 92 | 2-pyridyl | 2-(N-azatanyl-methyl)phenyl |
| 93 | 2-pyridyl | 2-(N-azetidinyl-methyl)phenyl |
| 94 | 2-pyridyl | 2-(N-piperazinyl-methyl)phenyl |
| 95 | 2-pyridyl | 2-(N,N'-BOC-piperazinyl-methyl)phenyl |
| 96 | 2-pyridyl | 2-(N-imidazolyl-methyl)phenyl |
| 97 | 2-pyridyl | 2-(N-methoxy-N-methylamino-methyl)phenyl |
| 98 | 2-pyridyl | 2-(N-pyridonyl-methyl)phenyl |
| 99 | 2-pyridyl | 2-(N-(N',N'-dimethylhydrazinyl-methyl)phenyl |
| 100 | 2-pyridyl | 2-(amidinyl)phenyl |
| 101 | 2-pyridyl | 2-(N-guanidinyl)phenyl |
| 102 | 2-pyridyl | 2-(imidazolyl)phenyl |
| 103 | 2-pyridyl | 2-(imidazolidinyl)phenyl |
| 104 | 2-pyridyl | 2-(2-imidazolidinyl-sulfonyl)phenyl |
| 105 | 2-pyridyl | 2-(2-pyrrolidinyl)phenyl |
| 106 | 2-pyridyl | 2-(2-piperidinyl)phenyl |
| 107 | 2-pyridyl | 2-(amidinyl-methyl)phenyl |
| 108 | 2-pyridyl | 2-(2-imidazolidinyl-methyl)phenyl |
| 109 | 2-pyridyl | 2-(N-(2-aminoimidazolyl)-methyl)phenyl |
| 110 | 2-pyridyl | 2-dimethylaminoimidazol-1-yl |
| 111 | 2-pyridyl | 2-(3-aminophenyl) |
| 112 | 2-pyridyl | 2-(3-pyrrolidinylcarbonyl) |
| 113 | 2-pyridyl | 2-glycinoyl |
| 114 | 2-pyridyl | 2-(imidazol-1-ylacetyl) |
| 115 | 3-pyridyl | 2-(N-pyrrolidinyl-methyl)phenyl |
| 116 | 3-pyridyl | 2-(N-piperidinyl-methyl)phenyl |
| 117 | 3-pyridyl | 2-(N-morpholino-methyl)phenyl |
| 118 | 3-pyridyl | 2-(N,N'-methylmorpholinium-methyl)phenyl |
| 119 | 3-pyridyl | 2-(N-pyridinium-methyl)phenyl |
| 120 | 3-pyridyl | 2-(N-4-(N,N'-dimethylamino)-pyridinium-methyl)phenyl |
| 121 | 3-pyridyl | 2-(N-azatanyl-methyl)phenyl |
| 122 | 3-pyridyl | 2-(N-azetidinyl-methyl)phenyl |

TABLE 3-continued

| | | |
|---|---|---|
| 123 | 3-pyridyl | 2-(N-piperazinyl-methyl)phenyl |
| 124 | 3-pyridyl | 2-(N,N'-BOC-piperazinyl-methyl)phenyl |
| 125 | 3-pyridyl | 2-(N-imidazolyl-methyl)phenyl |
| 126 | 3-pyridyl | 2-(N-methoxy-N-methylamino-methyl)phenyl |
| 127 | 3-pyridyl | 2-(N-pyridonyl-methyl)phenyl |
| 128 | 3-pyridyl | 2-(N-(N',N'-dimethylhydrazinyl-methyl)phenyl |
| 129 | 3-pyridyl | 2-(amidinyl)phenyl |
| 130 | 3-pyridyl | 2-(N-guanidinyl)phenyl |
| 131 | 3-pyridyl | 2-(imidazolyl)phenyl |
| 132 | 3-pyridyl | 2-(imidazolidinyl)phenyl |
| 133 | 3-pyridyl | 2-(2-imidazolidinyl-sulfonyl)phenyl |
| 134 | 3-pyridyl | 2-(2-pyrrolidinyl)phenyl |
| 135 | 3-pyridyl | 2-(2-piperidinyl)phenyl |
| 136 | 3-pyridyl | 2-(amidinyl-methyl)phenyl |
| 137 | 3-pyridyl | 2-(2-imidazolidinyl-methyl)phenyl |
| 138 | 3-pyridyl | 2-(N-(2-aminoimidazolyl)-methyl)phenyl |
| 139 | 3-pyridyl | 2-dimethylaminoimidazol-1-yl |
| 140 | 3-pyridyl | 2-(3-aminophenyl) |
| 141 | 3-pyridyl | 2-(3-pyrrolidinylcarbonyl) |
| 142 | 3-pyridyl | 2-glycinoyl |
| 143 | 3-pyridyl | 2-(imidazol-1-ylacetyl) |
| 144 | 2-pyrimidyl | 2-(N-pyrrolidinyl-methyl)phenyl |
| 145 | 2-pyrimidyl | 2-(N-piperidinyl-methyl)phenyl |
| 146 | 2-pyrimidyl | 2-(N-morpholino-methyl)phenyl |
| 147 | 2-pyrimidyl | 2-(N,N'-methylmorpholinium-methyl)phenyl |
| 148 | 2-pyrimidyl | 2-(N-pyridinium-methyl)phenyl |
| 149 | 2-pyrimidyl | 2-(N-4-(N,N'-dimethylamino)-pyridinium-methyl)phenyl |
| 150 | 2-pyrimidyl | 2-(N-azatanyl-methyl)phenyl |
| 151 | 2-pyrimidyl | 2-(N-azetidinyl-methyl)phenyl |
| 152 | 2-pyrimidyl | 2-(N-piperazinyl-methyl)phenyl |
| 153 | 2-pyrimidyl | 2-(N,N'-BOC-piperazinyl-methyl)phenyl |
| 154 | 2-pyrimidyl | 2-(N-imidazolyl-methyl)phenyl |
| 155 | 2-pyrimidyl | 2-(N-methoxy-N-methylamino-methyl)phenyl |
| 156 | 2-pyrimidyl | 2-(N-pyridonyl-methyl)phenyl |
| 157 | 2-pyrimidyl | 2-(N-(N',N'-dimethylhydrazinyl-methyl)phenyl |
| 158 | 2-pyrimidyl | 2-(amidinyl)phenyl |
| 159 | 2-pyrimidyl | 2-(N-guanidinyl)phenyl |
| 160 | 2-pyrimidyl | 2-(imidazolyl)phenyl |
| 161 | 2-pyrimidyl | 2-(imidazolidinyl)phenyl |
| 162 | 2-pyrimidyl | 2-(2-imidazolidinyl-sulfonyl)phenyl |
| 163 | 2-pyrimidyl | 2-(2-pyrrolidinyl)phenyl |
| 164 | 2-pyrimidyl | 2-(2-piperidinyl)phenyl |
| 165 | 2-pyrimidyl | 2-(amidinyl-methyl)phenyl |
| 166 | 2-pyrimidyl | 2-(2-imidazolidinyl-methyl)phenyl |
| 167 | 2-pyrimidyl | 2-(N-(2-aminoimidazolyl)-methyl)phenyl |
| 168 | 2-pyrimidyl | 2-dimethylaminoimidazol-1-yl |
| 169 | 2-pyrimidyl | 2-(3-aminophenyl) |
| 170 | 2-pyrimidyl | 2-(3-pyrrolidinylcarbonyl) |
| 171 | 2-pyrimidyl | 2-glycinoyl |
| 172 | 2-pyrimidyl | 2-(imidazol-1-ylacetyl) |
| 173 | 2-Cl-phenyl | 2-(N-pyrrolidinyl-methyl)phenyl |
| 174 | 2-Cl-phenyl | 2-(N-piperidinyl-methyl)phenyl |
| 175 | 2-Cl-phenyl | 2-(N-morpholino-methyl)phenyl |
| 176 | 2-Cl-phenyl | 2-(N,N'-methylmorpholinium-methyl)phenyl |
| 177 | 2-Cl-phenyl | 2-(N-pyridinium-methyl)phenyl |
| 178 | 2-Cl-phenyl | 2-(N-4-(N,N'-dimethylamino)-pyridinium-methyl)phenyl |
| 179 | 2-Cl-phenyl | 2-(N-azatanyl-methyl)phenyl |
| 180 | 2-Cl-phenyl | 2-(N-azetidinyl-methyl)phenyl |
| 181 | 2-Cl-phenyl | 2-(N-piperazinyl-methyl)phenyl |
| 182 | 2-Cl-phenyl | 2-(N,N'-BOC-piperazinyl-methyl)phenyl |
| 183 | 2-Cl-phenyl | 2-(N-imidazolyl-methyl)phenyl |
| 184 | 2-Cl-phenyl | 2-(N-methoxy-N-methylamino-methyl)phenyl |
| 185 | 2-Cl-phenyl | 2-(N-pyridonyl-methyl)phenyl |
| 186 | 2-Cl-phenyl | 2-(N-(N',N'-dimethylhydrazinyl-methyl)phenyl |
| 187 | 2-Cl-phenyl | 2-(amidinyl)phenyl |
| 188 | 2-Cl-phenyl | 2-(N-guanidinyl)phenyl |
| 189 | 2-Cl-phenyl | 2-(imidazolyl)phenyl |
| 190 | 2-Cl-phenyl | 2-(imidazolidinyl)phenyl |
| 191 | 2-Cl-phenyl | 2-(2-imidazolidinyl-sulfonyl)phenyl |
| 192 | 2-Cl-phenyl | 2-(2-pyrrolidinyl)phenyl |
| 193 | 2-Cl-phenyl | 2-(2-piperidinyl)phenyl |
| 194 | 2-Cl-phenyl | 2-(amidinyl-methyl)phenyl |
| 195 | 2-Cl-phenyl | 2-(2-imidazolidinyl-methyl)phenyl |
| 196 | 2-Cl-phenyl | 2-(N-(2-aminoimidazolyl)-methyl)phenyl |

TABLE 3-continued

| | | |
|---|---|---|
| 197 | 2-Cl-phenyl | 2-dimethylaminoimidazol-1-yl |
| 198 | 2-Cl-phenyl | 2-(3-aminophenyl) |
| 199 | 2-Cl-phenyl | 2-(3-pyrrolidinylcarbonyl) |
| 200 | 2-Cl-phenyl | 2-glycinoyl |
| 201 | 2-Cl-phenyl | 2-(imidazol-1-ylacetyl) |
| 202 | 2-F-phenyl | 2-(N-pyrrolidinyl-methyl)phenyl |
| 203 | 2-F-phenyl | 2-(N-piperidinyl-methyl)phenyl |
| 204 | 2-F-phenyl | 2-(N-morpholino-methyl)phenyl |
| 205 | 2-F-phenyl | 2-(N,N'-methylmorpholinium-methyl)phenyl |
| 206 | 2-F-phenyl | 2-(N-pyridinium-methyl)phenyl |
| 207 | 2-F-phenyl | 2-(N-4-(N,N'-dimethylamino)-pyridinium-methyl)phenyl |
| 208 | 2-F-phenyl | 2-(N-azatanyl-methyl)phenyl |
| 209 | 2-F-phenyl | 2-(N-azetidinyl-methyl)phenyl |
| 210 | 2-F-phenyl | 2-(N-piperazinyl-methyl)phenyl |
| 211 | 2-F-phenyl | 2-(N,N'-BOC-piperazinyl-methyl)phenyl |
| 212 | 2-F-phenyl | 2-(N-imidazolyl-methyl)phenyl |
| 213 | 2-F-phenyl | 2-(N-methoxy-N-methylamino-methyl)phenyl |
| 214 | 2-F-phenyl | 2-(N-pyridonyl-methyl)phenyl |
| 215 | 2-F-phenyl | 2-(N-(N',N'-dimethylhydrazinyl-methyl)phenyl |
| 216 | 2-F-phenyl | 2-(amidinyl)phenyl |
| 217 | 2-F-phenyl | 2-(N-guanidinyl)phenyl |
| 218 | 2-F-phenyl | 2-(imidazolyl)phenyl |
| 219 | 2-F-phenyl | 2-(imidazolidinyl)phenyl |
| 220 | 2-F-phenyl | 2-(2-imidazolidinyl-sulfonyl)phenyl |
| 221 | 2-F-phenyl | 2-(2-pyrrolidinyl)phenyl |
| 222 | 2-F-phenyl | 2-(2-piperidinyl)phenyl |
| 223 | 2-F-phenyl | 2-(amidinyl-methyl)phenyl |
| 224 | 2-F-phenyl | 2-(2-imidazolidinyl-methyl)phenyl |
| 225 | 2-F-phenyl | 2-(N-(2-aminoimidazolyl)-methyl)phenyl |
| 226 | 2-F-phenyl | 2-dimethylaminoimidazol-1-yl |
| 227 | 2-F-phenyl | 2-(3-aminophenyl) |
| 228 | 2-F-phenyl | 2-(3-pyrrolidinylcarbonyl) |
| 229 | 2-F-phenyl | 2-glycinoyl |
| 230 | 2-F-phenyl | 2-(imidazol-1-ylacetyl) |
| 231 | 2,5-diF-phenyl | 2-(N-pyrrolidinyl-methyl)phenyl |
| 232 | 2,5-diF-phenyl | 2-(N-piperidinyl-methyl)phenyl |
| 233 | 2,5-diF-phenyl | 2-(N-morpholino-methyl)phenyl |
| 234 | 2,5-diF-phenyl | 2-(N,N'-methylmorpholinium-methyl)phenyl |
| 235 | 2,5-diF-phenyl | 2-(N-pyridinium-methyl)phenyl |
| 236 | 2,5-diF-phenyl | 2-(N-4-(N,N'-dimethylamino)-pyridinium-methyl)phenyl |
| 237 | 2,5-diF-phenyl | 2-(N-azatanyl-methyl)phenyl |
| 238 | 2,5-diF-phenyl | 2-(N-azetidinyl-methyl)phenyl |
| 239 | 2,5-diF-phenyl | 2-(N-piperazinyl-methyl)phenyl |
| 240 | 2,5-diF-phenyl | 2-(N,N'-BOC-piperazinyl-methyl)phenyl |
| 241 | 2,5-diF-phenyl | 2-(N-imidazolyl-methyl)phenyl |
| 242 | 2,5-diF-phenyl | 2-(N-methoxy-N-methylamino-methyl)phenyl |
| 243 | 2,5-diF-phenyl | 2-(N-pyridonyl-methyl)phenyl |
| 244 | 2,5-diF-phenyl | 2-(N-(N',N'-dimethylhydrazinyl-methyl)phenyl |
| 245 | 2,5-diF-phenyl | 2-(amidinyl)phenyl |
| 246 | 2,5-diF-phenyl | 2-(N-guanidinyl)phenyl |
| 247 | 2,5-diF-phenyl | 2-(imidazolyl)phenyl |
| 248 | 2,5-diF-phenyl | 2-(imidazolidinyl)phenyl |
| 249 | 2,5-diF-phenyl | 2-(2-imidazolidinyl-sulfonyl)phenyl |
| 250 | 2,5-diF-phenyl | 2-(2-pyrrolidinyl)phenyl |
| 251 | 2,5-diF-phenyl | 2-(2-piperidinyl)phenyl |
| 252 | 2,5-diF-phenyl | 2-(amidinyl-methyl)phenyl |
| 253 | 2,5-diF-phenyl | 2-(2-imidazolidinyl-methyl)phenyl |
| 254 | 2,5-diF-phenyl | 2-(N-(2-aminoimidazolyl)-methyl)phenyl |
| 255 | 2,5-diF-phenyl | 2-dimethylaminoimidazol-1-yl |
| 256 | 2,5-diF-phenyl | 2-(3-aminophenyl) |
| 257 | 2,5-diF-phenyl | 2-(3-pyrrolidinylcarbonyl) |
| 258 | 2,5-diF-phenyl | 2-glycinoyl |
| 259 | 2,5-diF-phenyl | 2-(imidazol-1-ylacetyl) |

TABLE 4
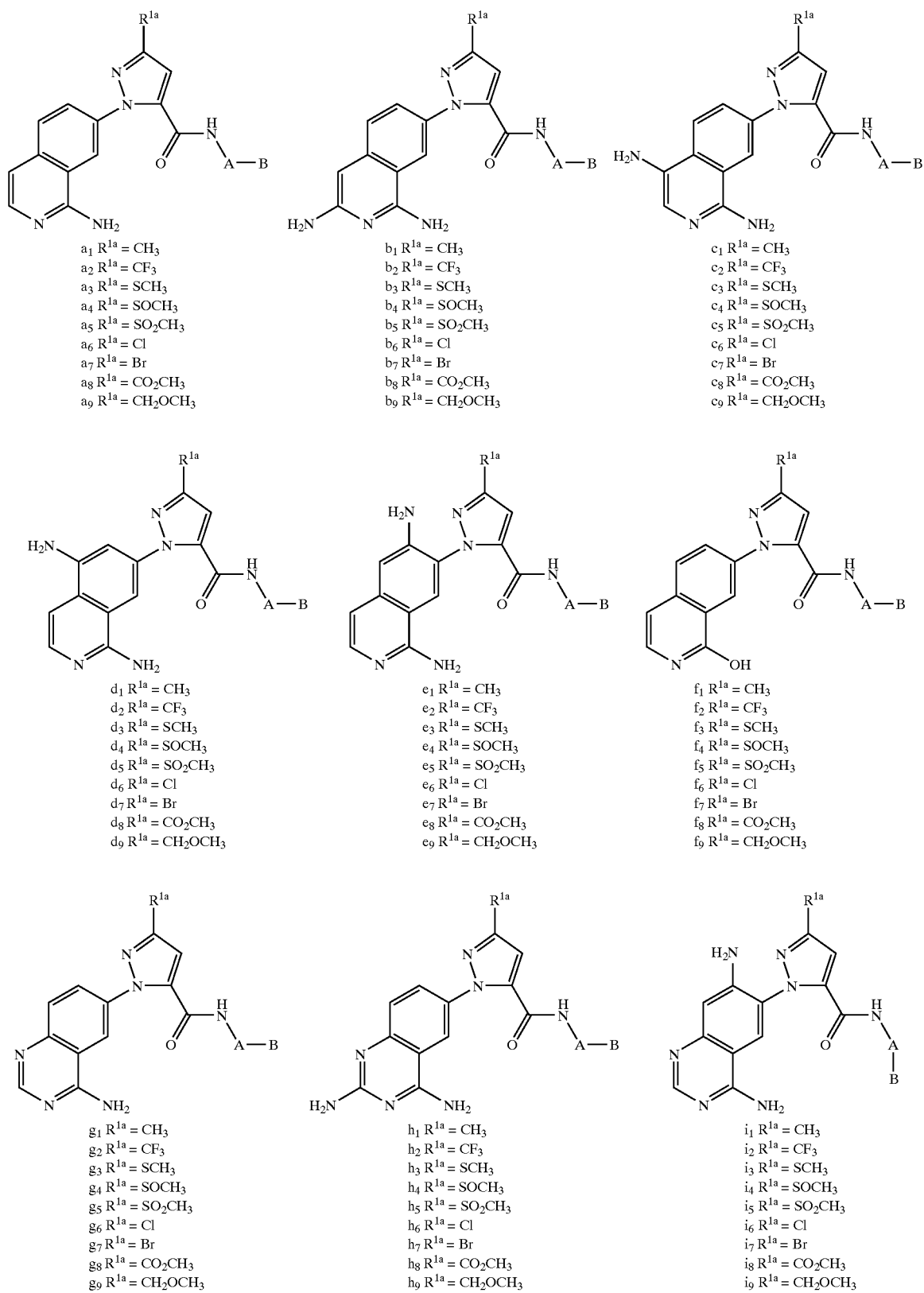

TABLE 4-continued

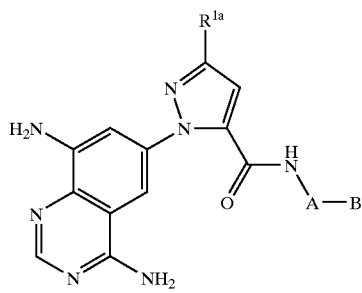

j₁ R¹ᵃ = CH₃
j₂ R¹ᵃ = CF₃
j₃ R¹ᵃ = SCH₃
j₄ R¹ᵃ = SOCH₃
j₅ R¹ᵃ = SO₂CH₃
j₆ R¹ᵃ = Cl
j₇ R¹ᵃ = Br
j₈ R¹ᵃ = CO₂CH₃
j₉ R¹ᵃ = CH₂OCH₃

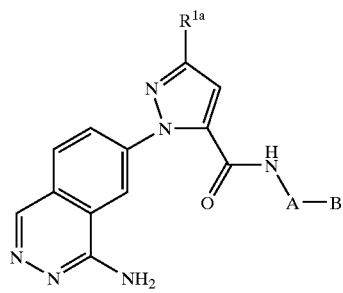

k₁ R¹ᵃ = CH₃
k₂ R¹ᵃ = CF₃
k₃ R¹ᵃ = SCH₃
k₄ R¹ᵃ = SOCH₃
k₅ R¹ᵃ = SO₂CH₃
k₆ R¹ᵃ = Cl
k₇ R¹ᵃ = Br
k₈ R¹ᵃ = CO₂CH₃
k₉ R¹ᵃ = CH₂OCH₃

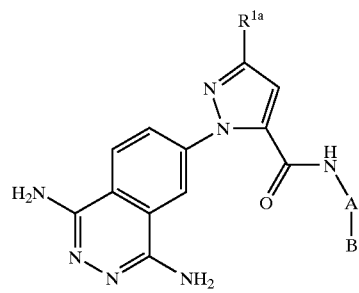

l₁ R¹ᵃ = CH₃
l₂ R¹ᵃ = CF₃
l₃ R¹ᵃ = SCH₃
l₄ R¹ᵃ = SOCH₃
l₅ R¹ᵃ = SO₂CH₃
l₆ R¹ᵃ = Cl
l₇ R¹ᵃ = Br
l₈ R¹ᵃ = CO₂CH₃
l₉ R¹ᵃ = CH₂OCH₃

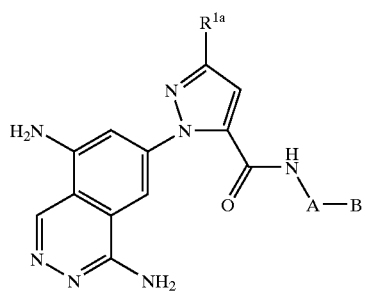

m₁ R¹ᵃ = CH₃
m₂ R¹ᵃ = CF₃
m₃ R¹ᵃ = SCH₃
m₄ R¹ᵃ = SOCH₃
m₅ R¹ᵃ = SO₂CH₃
m₆ R¹ᵃ = Cl
m₇ R¹ᵃ = Br
m₈ R¹ᵃ = CO₂CH₃
m₉ R¹ᵃ = CH₂OCH₃

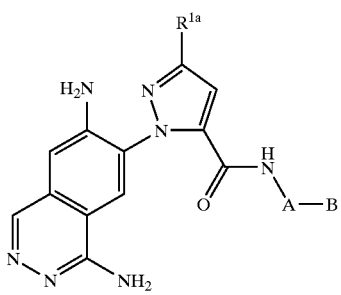

n₁ R¹ᵃ = CH₃
n₂ R¹ᵃ = CF₃
n₃ R¹ᵃ = SCH₃
n₄ R¹ᵃ = SOCH₃
n₅ R¹ᵃ = SO₂CH₃
n₆ R¹ᵃ = Cl
n₇ R¹ᵃ = Br
n₈ R¹ᵃ = CO₂CH₃
n₉ R¹ᵃ = CH₂OCH₃

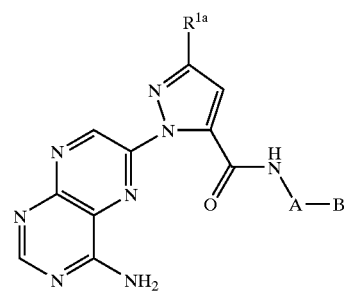

o₁ R¹ᵃ = CH₃
o₂ R¹ᵃ = CF₃
o₃ R¹ᵃ = SCH₃
o₄ R¹ᵃ = SOCH₃
o₅ R¹ᵃ = SO₂CH₃
o₆ R¹ᵃ = Cl
o₇ R¹ᵃ = Br
o₈ R¹ᵃ = CO₂CH₃
o₉ R¹ᵃ = CH₂OCH₃

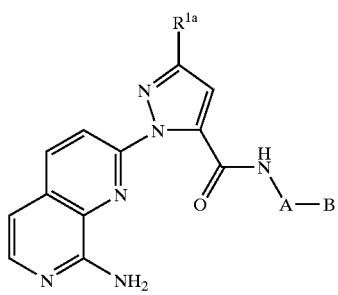

p₁ R¹ᵃ = CH₃
p₂ R¹ᵃ = CF₃
p₃ R¹ᵃ = SCH₃
p₄ R¹ᵃ = SOCH₃
p₅ R¹ᵃ = SO₂CH₃
p₆ R¹ᵃ = Cl
p₇ R¹ᵃ = Br
p₈ R¹ᵃ = CO₂CH₃
p₉ R¹ᵃ = CH₂OCH₃

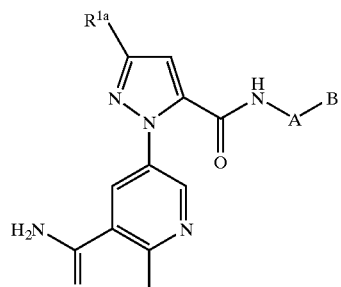

q₁ R¹ᵃ = CH₃
q₂ R¹ᵃ = CF₃
q₃ R¹ᵃ = SCH₃
q₄ R¹ᵃ = SOCH₃
q₅ R¹ᵃ = SO₂CH₃
q₆ R¹ᵃ = Cl
q₇ R¹ᵃ = Br
q₈ R¹ᵃ = CO₂CH₃
q₉ R¹ᵃ = CH₂OCH₃

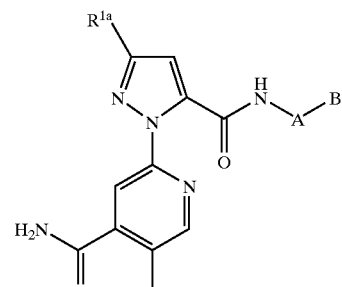

r₁ R¹ᵃ = CH₃
r₂ R¹ᵃ = CF₃
r₃ R¹ᵃ = SCH₃
r₄ R¹ᵃ = SOCH₃
r₅ R¹ᵃ = SO₂CH₃
r₆ R¹ᵃ = Cl
r₇ R¹ᵃ = Br
r₈ R¹ᵃ = CO₂CH₃
r₉ R¹ᵃ = CH₂OCH₃

TABLE 4-continued
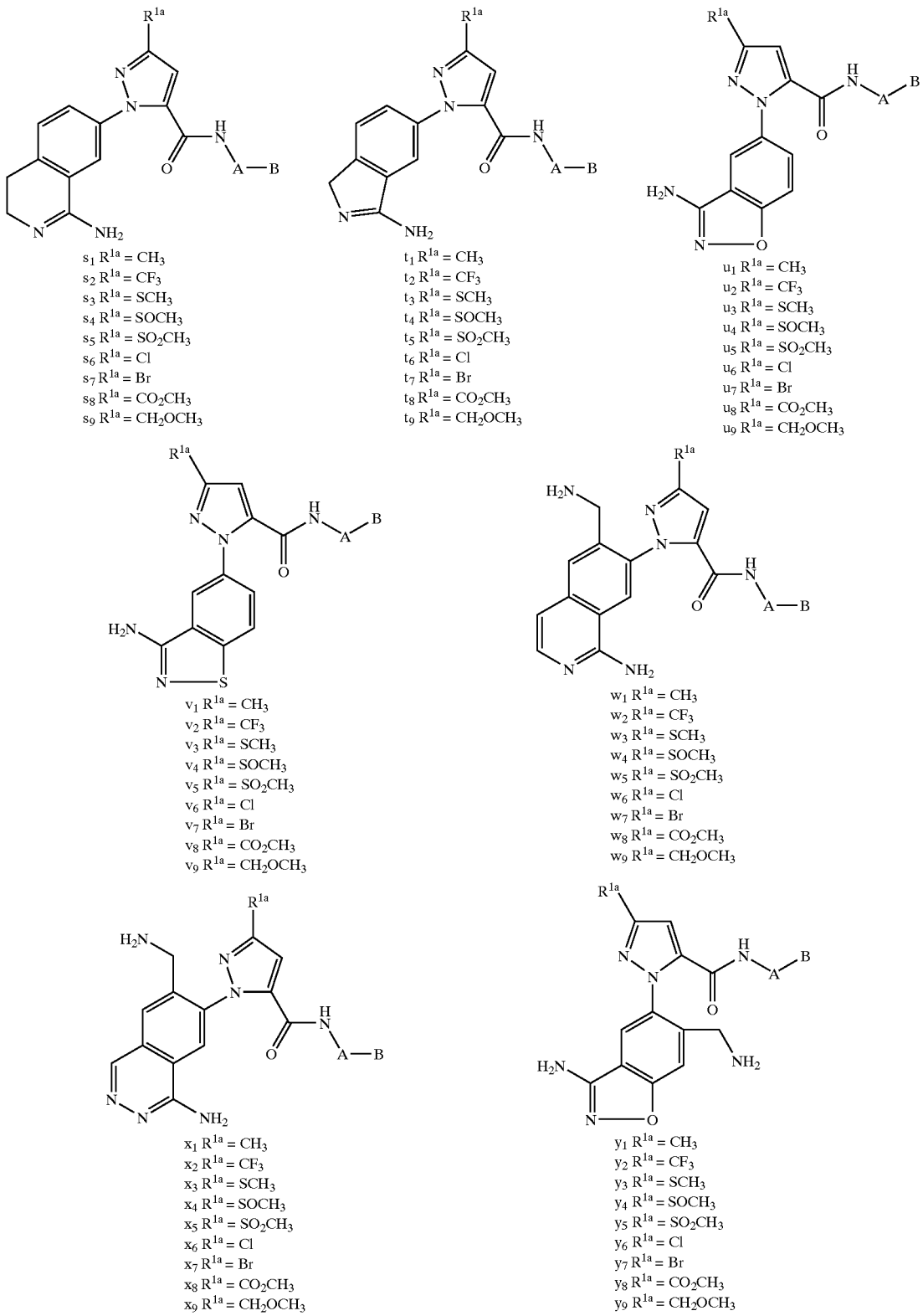
| Ex# | A | B |
|---|---|---|
| 1 | phenyl | 2-((Me)$_2$N-methyl)phenyl |
| 2 | phenyl | 2-((Me)NH-methyl)phenyl |

TABLE 4-continued

| | | |
|---|---|---|
| 3 | phenyl | 2-($H_2$N-methyl)phenyl |
| 4 | phenyl | 2-HOC$H_2$-phenyl |
| 5 | 2-F-phenyl | 2-((Me)$_2$N-methyl)phenyl |
| 6 | 2-F-phenyl | 2-((Me)NH-methyl)phenyl |
| 7 | 2-F-phenyl | 2-($H_2$N-methyl)phenyl |
| 8 | 2-F-phenyl | 2-HOC$H_2$-phenyl |
| 9 | phenyl | 2-methylimidazol-1-yl |
| 10 | phenyl | 2-ethylimidazol-1-yl |
| 11 | phenyl | 2-((Me)$_2$N-methyl)imidazol-1-yl |
| 12 | phenyl | 2-C$H_3$S$O_2$-imidazol-1-yl |
| 13 | phenyl | 2-C$H_3$OC$H_2$-imidazol-1-yl |
| 14 | 2-F-phenyl | 2-methylimidazol-1-yl |
| 15 | 2-F-phenyl | 2-ethylimidazol-1-yl |
| 16 | 2-F-phenyl | 2-((Me)$_2$N-methyl)imidazol-1-yl |
| 17 | 2-F-phenyl | 2-C$H_3$S$O_2$-imidazol-1-yl |
| 18 | 2-F-phenyl | 2-C$H_3$OC$H_2$-imidazol-1-yl |
| 19 | 2-Cl-phenyl | 2-methylimidazol-1-yl |
| 20 | 2-Cl-phenyl | 2-ethylimidazol-1-yl |
| 21 | 2-Cl-phenyl | 2-((Me)$_2$N-methyl)imidazol-1-yl |
| 22 | 2-Cl-phenyl | 2-C$H_3$S$O_2$-imidazol-1-yl |
| 23 | 2-Cl-phenyl | 2-C$H_3$OC$H_2$-imidazol-1-yl |
| 24 | 2-(Me)$_2$N-phenyl | 2-methylimidazol-1-yl |
| 25 | 2-(Me)$_2$N-phenyl | 2-ethylimidazol-1-yl |
| 26 | 2-(Me)$_2$N-phenyl | 2-((Me)$_2$N-methyl)imidazol-1-yl |
| 27 | 2-(Me)$_2$N-phenyl | 2-C$H_3$S$O_2$-imidazol-1-yl |
| 28 | 2-(Me)$_2$N-phenyl | 2-C$H_3$OC$H_2$-imidazol-1-yl |
| 29 | phenyl | N-methylimidazol-2-yl |
| 30 | phenyl | 4-methylimidazol-5-yl |
| 31 | phenyl | 5-C$F_3$-pyrazol-1-yl |
| 32 | 2-F-phenyl | N-methylimidazol-2-yl |
| 33 | 2-F-phenyl | 4-methylimidazol-5-yl |
| 34 | 2-F-phenyl | 5-C$F_3$-pyrazol-1-yl |
| 35 | phenyl | guanidino |
| 36 | phenyl | 2-thiazolin-2-ylamine |
| 37 | phenyl | N-methyl-2-imidazolin-2-yl |
| 38 | phenyl | N-methyl-1,4,5,6-tetrahydropyrimid-2-yl |
| 39 | phenyl | N-methylimidazol-2-ylthiol |
| 40 | phenyl | t-butoxycarbonylamine |
| 41 | phenyl | (N-pyrrolidino)formylimino |
| 42 | phenyl | (N-pyrrolidino)formyl-N-methanesulfamoyl)imino |
| 43 | 2-F-phenyl | guanidino |
| 44 | 2-F-phenyl | 2-thiazolin-2-ylamine |
| 45 | 2-F-phenyl | N-methyl-2-imidazolin-2-yl |
| 46 | 2-F-phenyl | N-methyl-1,4,5,6-tetrahydropyrimid-2-yl |
| 47 | 2-F-phenyl | N-methylimidazol-2-ylthio |
| 48 | 2-F-phenyl | t-butoxycarbonylamine |
| 49 | 2-F-phenyl | (N-pyrrolidino)formylimino |
| 50 | 2-F-phenyl | (N-pyrrolidino)formyl-N-methanesulfamoyl)imino |
| 51 | 2-C$H_3$O-phenyl | (N-pyrrolidino)formylimino |
| 52 | 2-C$H_3$O-phenyl | (N-pyrrolidino)formyl-N-(methanesulfamoyl)imino |

TABLE 5

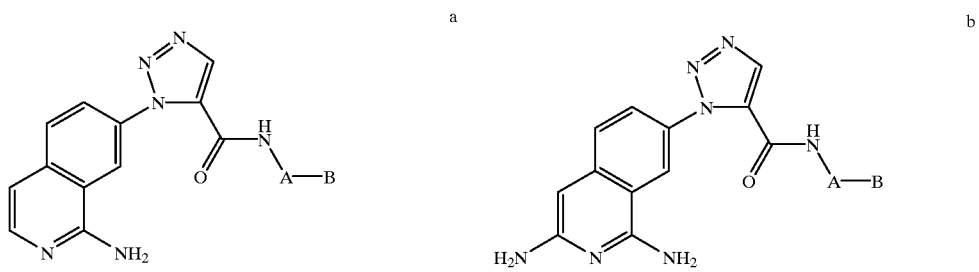

TABLE 5-continued
c
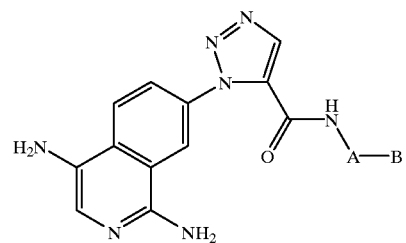
d
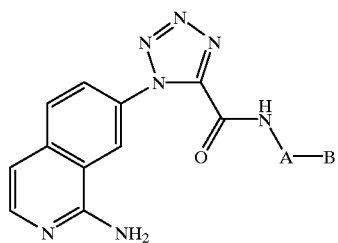
e
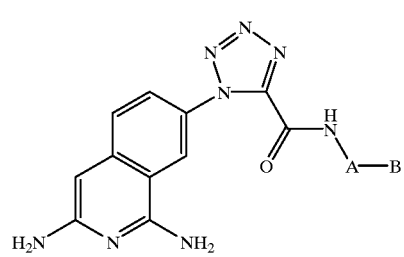
f
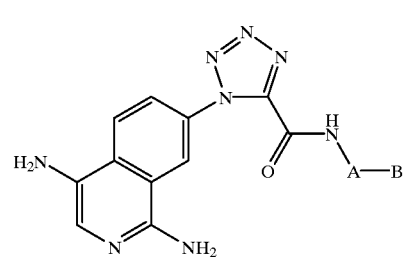
g
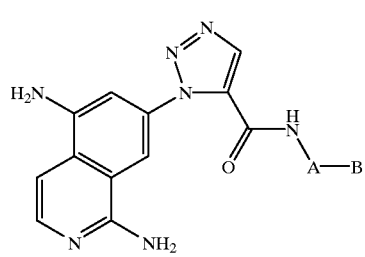
h
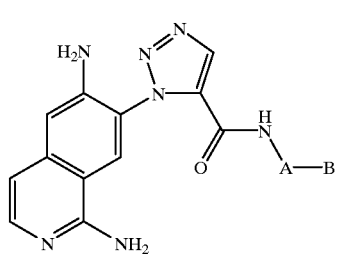
i
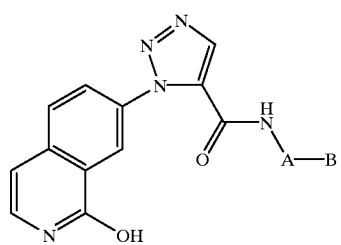
j
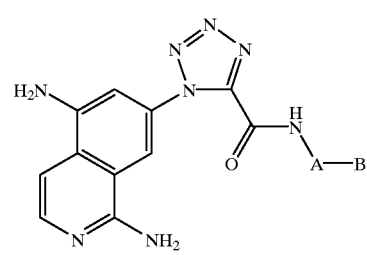
k
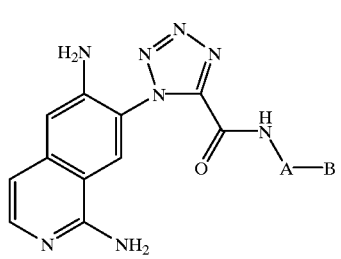
l
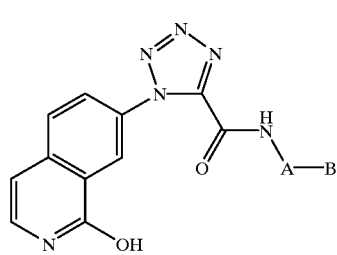

TABLE 5-continued
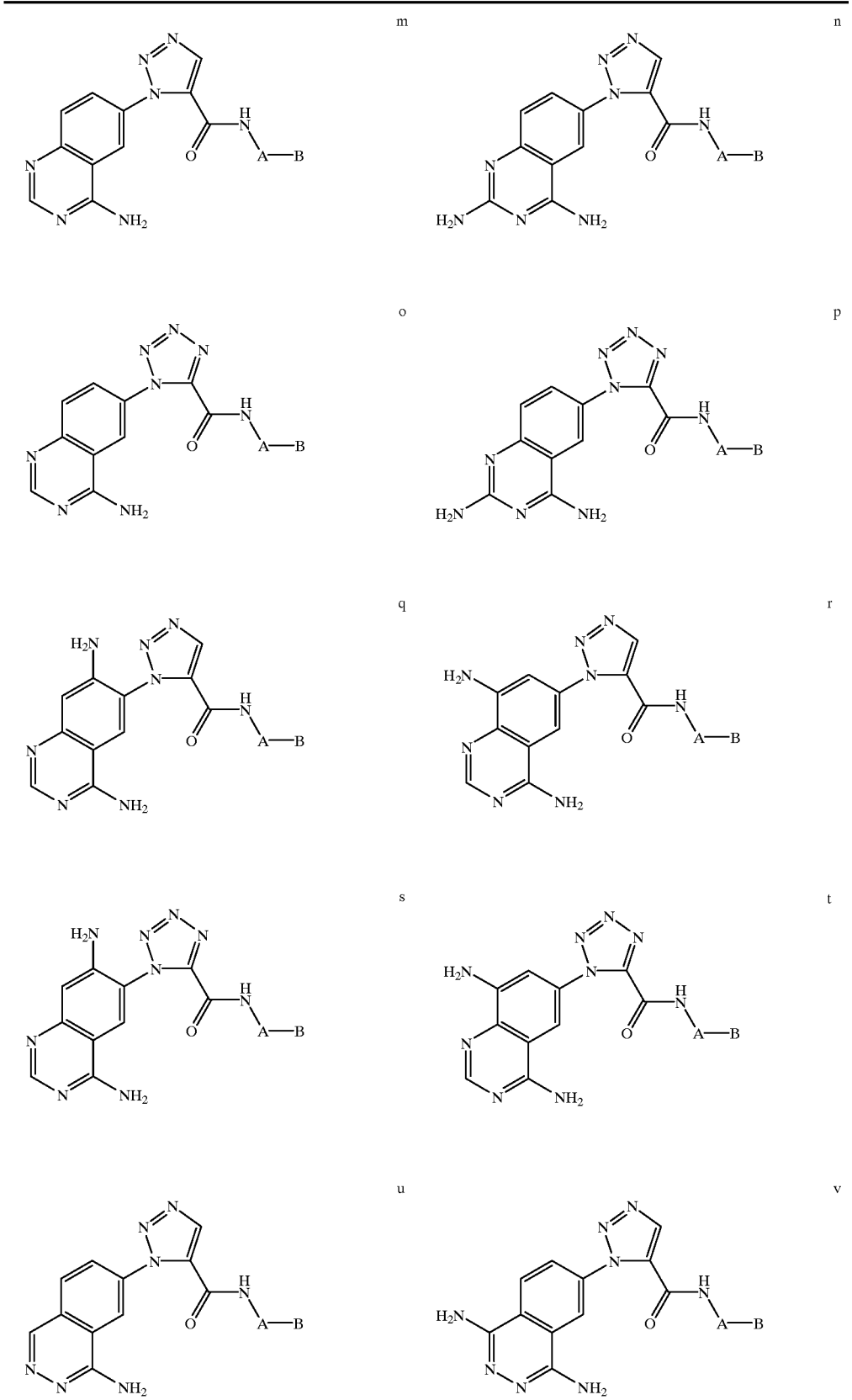

TABLE 5-continued
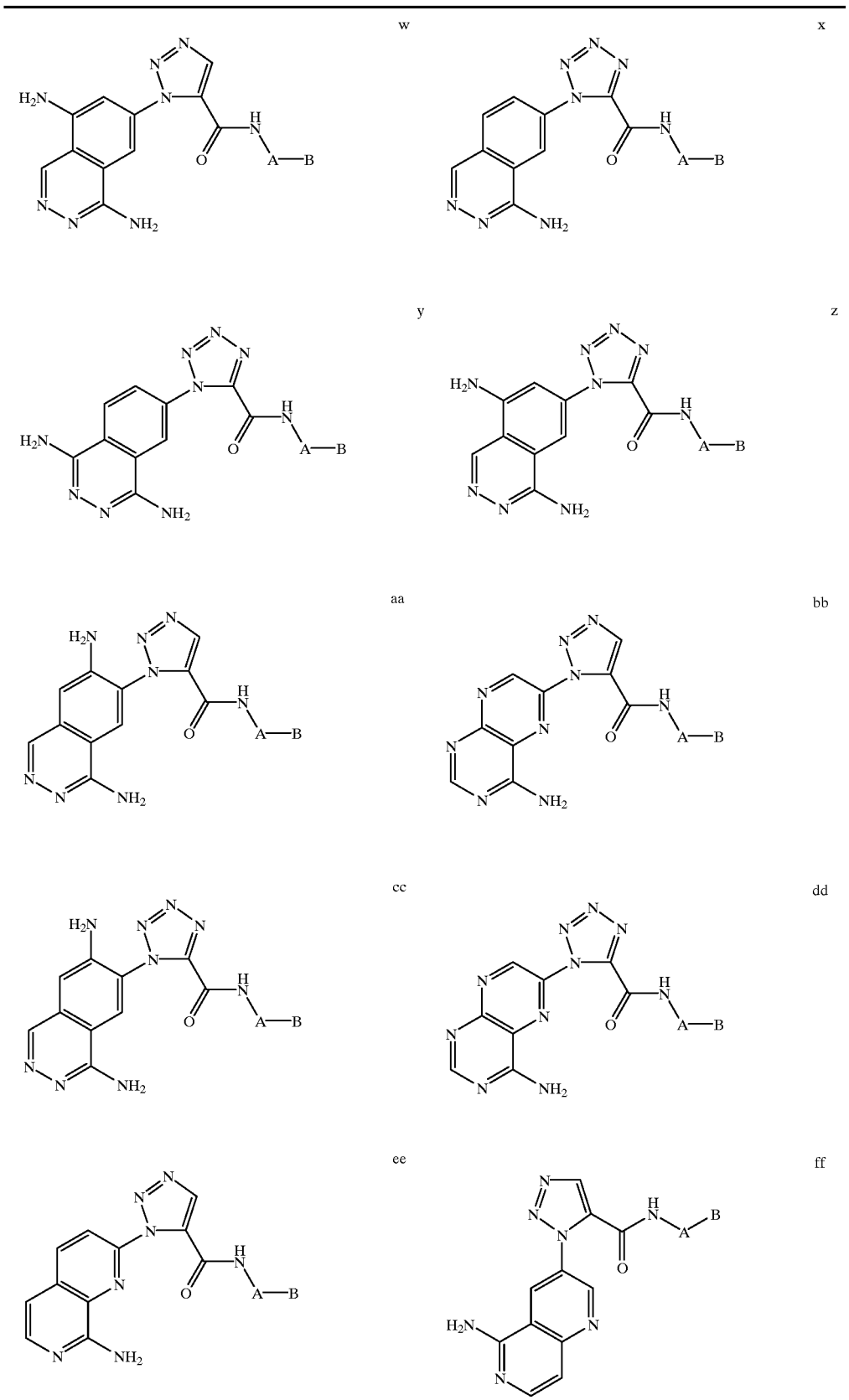

TABLE 5-continued
| | |
|---|---|
| gg 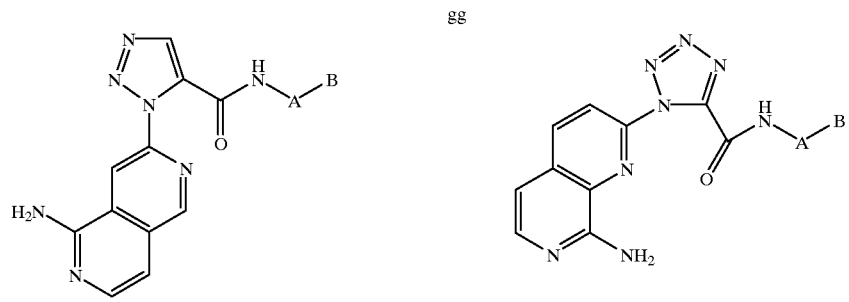 | hh |
| ii 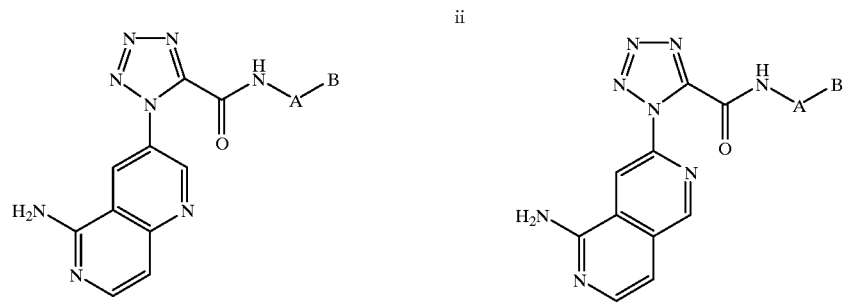 | jj |
| kk 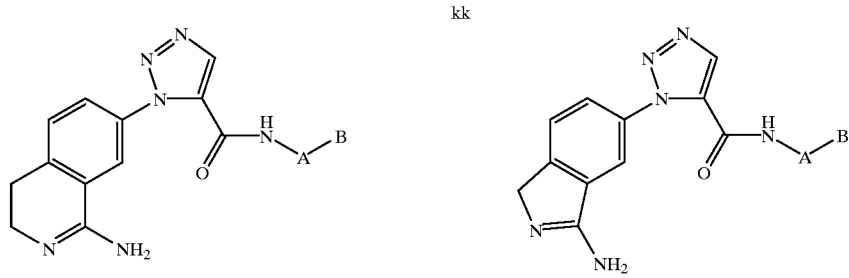 | ll |
| mm 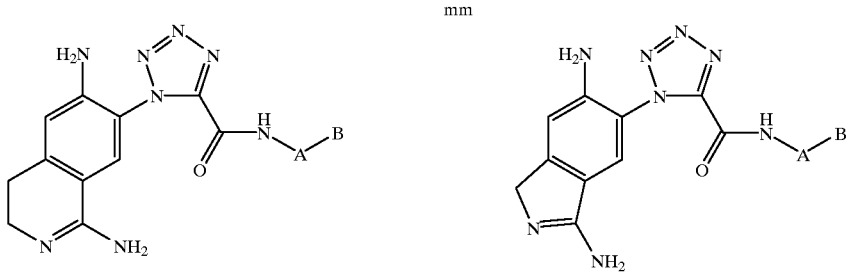 | nn |
| oo 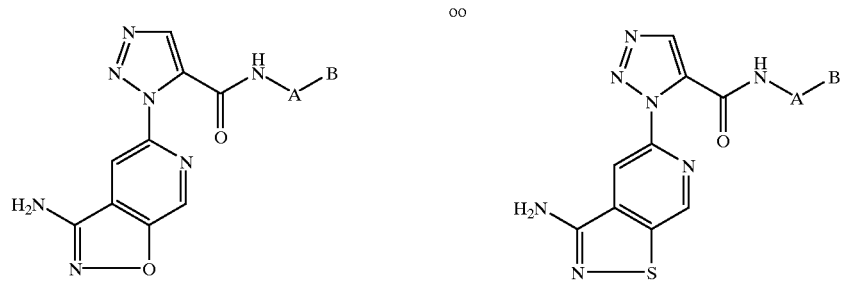 | pp |

TABLE 5-continued

| | qq | rr |
|---|---|---|

| Ex# | A | B |
|---|---|---|
| 1 | phenyl | 2-((Me)₂N-methyl)phenyl |
| 2 | phenyl | 2-((Me)NH-methyl)phenyl |
| 3 | phenyl | 2-(H₂N-methyl)phenyl |
| 4 | phenyl | 2-HOCH₂-phenyl |
| 5 | 2-F-phenyl | 2-((Me)₂N-methyl)phenyl |
| 6 | 2-F-phenyl | 2-((Me)NH-methyl)phenyl |
| 7 | 2-F-phenyl | 2-(H₂N-methyl)phenyl |
| 8 | 2-F-phenyl | 2-HOCH₂-phenyl |
| 9 | phenyl | 2-methylimidazol-1-yl |
| 10 | phenyl | 2-ethylimidazol-1-yl |
| 11 | phenyl | 2-((Me)₂N-methyl)imidazol-1-yl |
| 12 | phenyl | 2-CH₃SO₂-imidazol-1-yl |
| 13 | phenyl | 2-CH₃OCH₂-imidazol-1-yl |
| 14 | 2-F-phenyl | 2-methylimidazol-1-yl |
| 15 | 2-F-phenyl | 2-ethylimidazol-1-yl |
| 16 | 2-F-phenyl | 2-((Me)₂N-methyl)imidazol-1-yl |
| 17 | 2-F-phenyl | 2-CH₃SO₂-imidazol-1-yl |
| 18 | 2-F-phenyl | 2-CH₃OCH₂-imidazol-1-yl |
| 19 | 2-Cl-phenyl | 2-methylimidazol-1-yl |
| 20 | 2-Cl-phenyl | 2-ethylimidazol-1-yl |
| 21 | 2-Cl-phenyl | 2-((Me)₂N-methyl)imidazol-1-yl |
| 22 | 2-Cl-phenyl | 2-CH₃SO₂-imidazol-1-yl |
| 23 | 2-Cl-phenyl | 2-CH₃OCH₂-imidazol-1-yl |
| 24 | 2-(Me)₂N-phenyl | 2-methylimidazol-1-yl |
| 25 | 2-(Me)₂N-phenyl | 2-ethylimidazol-1-yl |
| 26 | 2-(Me)₂N-phenyl | 2-((Me)₂N-methyl)imidazol-1-yl |
| 27 | 2-(Me)₂N-phenyl | 2-CH₃SO₂-imidazol-1-yl |
| 28 | 2-(Me)₂N-phenyl | 2-CH₃OCH₂-imidazol-1-yl |
| 29 | phenyl | N-methylimidazol-2-yl |
| 30 | phenyl | 4-methylimidazol-2-yl |
| 31 | phenyl | 5-CF₃-pyrazol-1-yl |
| 32 | 2-F-phenyl | N-methylimidazol-2-yl |
| 33 | 2-F-phenyl | 4-methylimidazol-2-yl |
| 34 | 2-F-phenyl | 5-CF₃-pyrazol-1-yl |
| 35 | phenyl | guanidino |
| 36 | phenyl | 2-thiazolin-2-ylamine |
| 37 | phenyl | N-methyl-2-imidazolin-2-yl |
| 38 | phenyl | N-methyl-1,4,5,6-tetrahydropyrimid-2-yl |
| 39 | phenyl | N-methylimidazol-2-ylthiol |
| 40 | phenyl | t-butoxycarbonylamine |
| 41 | phenyl | (N-pyrrolidino)formylimino |
| 42 | phenyl | (N-pyrrolidino)formyl-N-methanesulfamoyl)imino |
| 43 | 2-F-phenyl | guanidino |
| 44 | 2-F-phenyl | 2-thiazolin-2-ylamine |
| 45 | 2-F-phenyl | N-methyl-2-imidazolin-2-yl |
| 46 | 2-F-phenyl | N-methyl-1,4,5,6-tetrahydropyrimid-2-yl |
| 47 | 2-F-phenyl | N-methylimidazol-2-ylthio |
| 48 | 2-F-phenyl | t-butoxycarbonylamine |
| 49 | 2-F-phenyl | (N-pyrrolidino)formylimino |
| 50 | 2-F-phenyl | (N-pyrrolidino)formyl-N-methanesulfamoyl)imino |
| 51 | 2-CH₃O-phenyl | (N-pyrrolidino)formylimino |
| 52 | 2-CH₃O-phenyl | (N-pyrrolidino)formyl-N-(methanesulfamoyl)imino |

TABLE 6
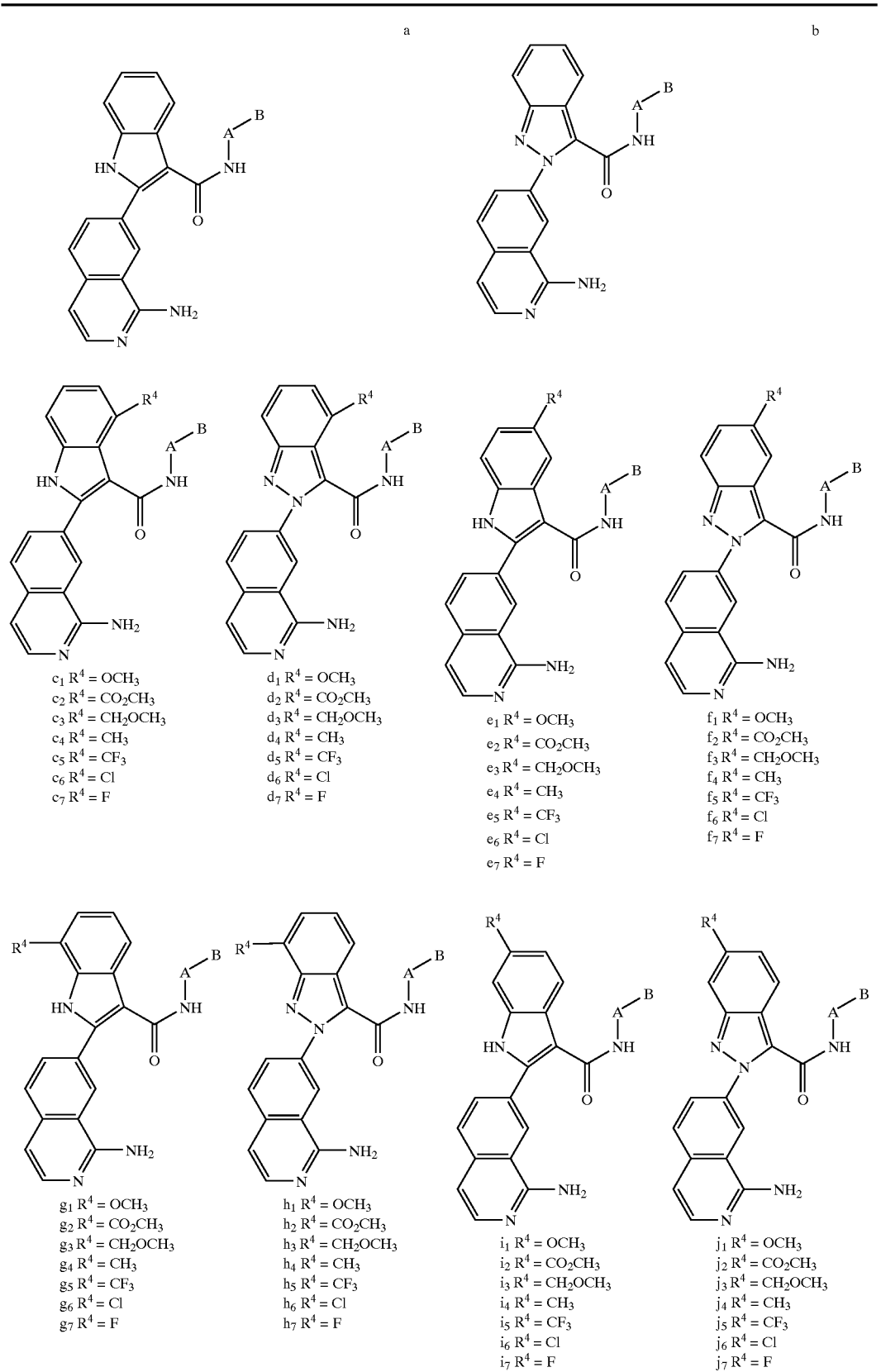

TABLE 6-continued k

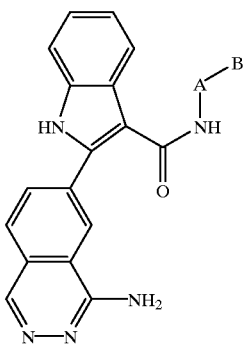

l

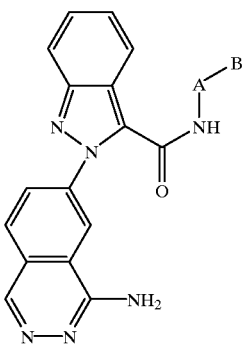

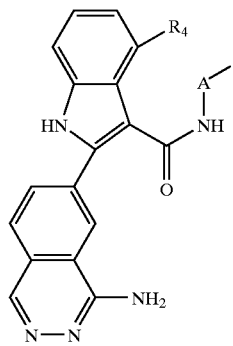

m₁ R⁴ = OCH₃
m₂ R⁴ = CO₂CH₃
m₃ R⁴ = CH₂OCH₃
m₄ R⁴ = CH₃
m₅ R⁴ = CF₃
m₆ R⁴ = Cl
m₇ R⁴ = F

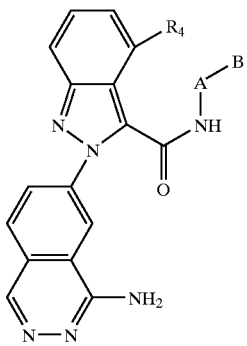

n₁ R⁴ = OCH₃
n₂ R⁴ = CO₂CH₃
n₃ R⁴ = CH₂OCH₃
n₄ R⁴ = CH₃
n₅ R⁴ = CF₃
n₆ R⁴ = Cl
n₇ R⁴ = F

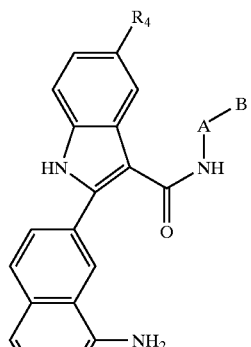

o₁ R⁴ = OCH₃
o₂ R⁴ = CO₂CH₃
o₃ R⁴ = CH₂OCH₃
o₄ R⁴ = CH₃
o₅ R⁴ = CF₃
o₆ R⁴ = Cl
o₇ R⁴ = F

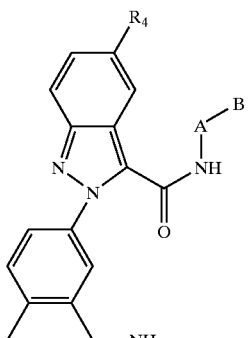

p₁ R⁴ = OCH₃
p₂ R⁴ = CO₂CH₃
p₃ R⁴ = CH₂OCH₃
p₄ R⁴ = CH₃
p₅ R⁴ = CF₃
p₆ R⁴ = Cl
p₇ R⁴ = F

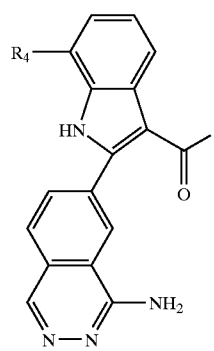

q₁ R⁴ = OCH₃
q₂ R⁴ = CO₂CH₃
q₃ R⁴ = CH₂OCH₃
q₄ R⁴ = CH₃
q₅ R⁴ = CF₃
q₆ R⁴ = Cl
q₇ R⁴ = F

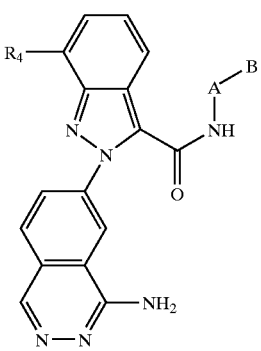

r₁ R⁴ = OCH₃
r₂ R⁴ = CO₂CH₃
r₃ R⁴ = CH₂OCH₃
r₄ R⁴ = CH₃
r₅ R⁴ = CF₃
r₆ R⁴ = Cl
r₇ R⁴ = F

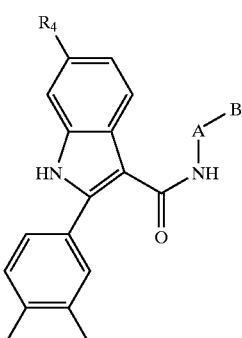

s₁ R⁴ = OCH₃
s₂ R⁴ = CO₂CH₃
s₃ R⁴ = CH₂OCH₃
s₄ R⁴ = CH₃
s₅ R⁴ = CF₃
s₆ R⁴ = Cl
s₇ R⁴ = F

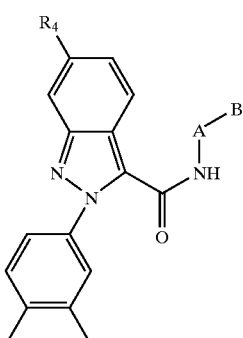

t₁ R⁴ = OCH₃
t₂ R⁴ = CO₂CH₃
t₃ R⁴ = CH₂OCH₃
t₄ R⁴ = CH₃
t₅ R⁴ = CF₃
t₆ R⁴ = Cl
t₇ R⁴ = F

TABLE 6-continued
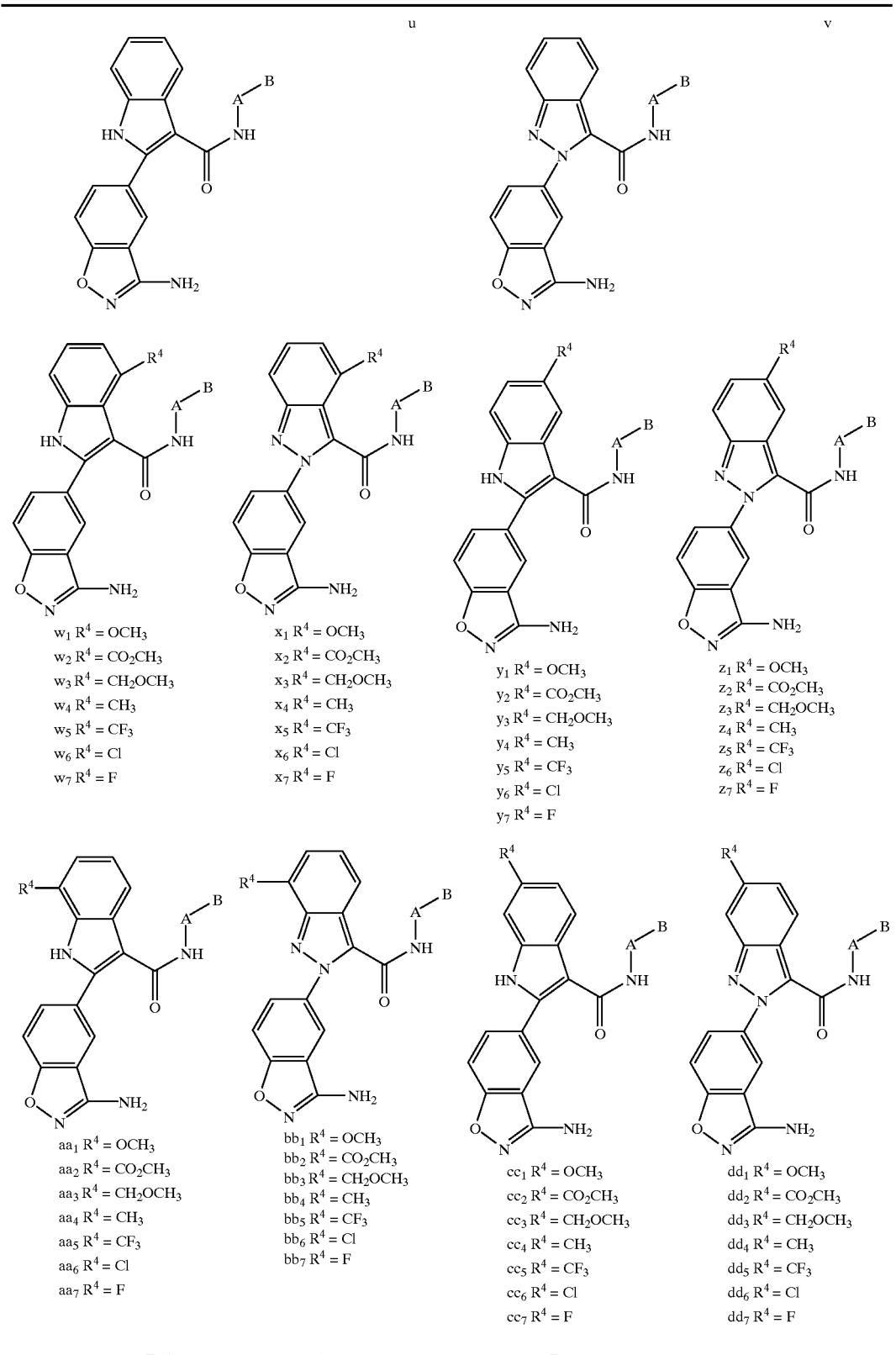
| Ex# | A | B |
|-----|---|---|
| 1 | phenyl | 2-(aminosulfonyl)phenyl |
| 2 | phenyl | 2-(methylaminosulfonyl)phenyl |

TABLE 6-continued

| | | |
|---|---|---|
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | 2-pyridyl | 2-(aminosulfonyl)phenyl |
| 9 | 2-pyridyl | 2-(methylaminosulfonyl)phenyl |
| 10 | 2-pyridyl | 1-pyrrolidinocarbonyl |
| 11 | 2-pyridyl | 2-(methylsulfonyl)phenyl |
| 12 | 2-pyridyl | 4-morpholino |
| 13 | 2-pyridyl | 2-(1'-CF$_3$-tetrazol-2-yl)phenyl |
| 14 | 2-pyridyl | 4-morpholinocarbonyl |
| 15 | 3-pyridyl | 2-(aminosulfonyl)phenyl |
| 16 | 3-pyridyl | 2-(methylaminosulfonyl)phenyl |
| 17 | 3-pyridyl | 1-pyrrolidinocarbonyl |
| 18 | 3-pyridyl | 2-(methylsulfonyl)phenyl |
| 19 | 3-pyridyl | 4-morpholino |
| 20 | 3-pyridyl | 2-(1'-CF$_3$-tetrazol-2-yl)phenyl |
| 21 | 3-pyridyl | 4-morpholinocarbonyl |
| 22 | 2-pyrimidyl | 2-(aminosulfonyl)phenyl |
| 23 | 2-pyrimidyl | 2-(methylaminosulfonyl)phenyl |
| 24 | 2-pyrimidyl | 1-pyrrolidinocarbonyl |
| 25 | 2-pyrimidyl | 2-(methylsulfonyl)phenyl |
| 26 | 2-pyrimidyl | 4-morpholino |
| 27 | 2-pyrimidyl | 2-(1'-CF$_3$-tetrazol-2-yl)phenyl |
| 28 | 2-pyrimidyl | 4-morpholinocarbonyl |
| 29 | 5-pyrimidyl | 2-(aminosulfonyl)phenyl |
| 30 | 5-pyrimidyl | 2-(methylaminosulfonyl)phenyl |
| 31 | 5-pyrimidyl | 1-pyrrolidinocarbonyl |
| 32 | 5-pyrimidyl | 2-(methylsulfonyl)phenyl |
| 33 | 5-pyrimidyl | 4-morpholino |
| 34 | 5-pyrimidyl | 2-(1'-CF$_3$-tetrazol-2-yl)phenyl |
| 35 | 5-pyrimidyl | 4-morpholinocarbonyl |
| 36 | 2-Cl-phenyl | 2-(aminosulfonyl)phenyl |
| 37 | 2-Cl-phenyl | 2-(methylaminosulfonyl)phenyl |
| 38 | 2-Cl-phenyl | 1-pyrrolidinocarbonyl |
| 39 | 2-Cl-phenyl | 2-(methylsulfonyl)phenyl |
| 40 | 2-Cl-phenyl | 4-morpholino |
| 41 | 2-Cl-phenyl | 2-(1'-CF$_3$-tetrazol-2-yl)phenyl |
| 42 | 2-Cl-phenyl | 4-morpholinocarbonyl |
| 43 | 2-F-phenyl | 2-(aminosulfonyl)phenyl |
| 44 | 2-F-phenyl | 2-(methylaminosulfonyl)phenyl |
| 45 | 2-F-phenyl | 1-pyrrolidinocarbonyl |
| 46 | 2-F-phenyl | 2-(methylsulfonyl)phenyl |
| 47 | 2-F-phenyl | 4-morpholino |
| 48 | 2-F-phenyl | 2-(1'-CF$_3$-tetrazol-2-yl)phenyl |
| 49 | 2-F-phenyl | 4-morpholinocarbonyl |
| 50 | 2,5-diF-phenyl | 2-(aminosulfonyl)phenyl |
| 51 | 2,5-diF-phenyl | 2-(methylaminosulfonyl)phenyl |
| 52 | 2,5-diF-phenyl | 1-pyrrolidinocarbonyl |
| 53 | 2,5-diF-phenyl | 2-(methylsulfonyl)phenyl |
| 54 | 2,5-diF-phenyl | 4-morpholino |
| 55 | 2,5-diF-phenyl | 2-(1'-CF$_3$-tetrazol-2-yl)phenyl |
| 56 | 2,5-diF-phenyl | 4-morpholinocarbonyl |

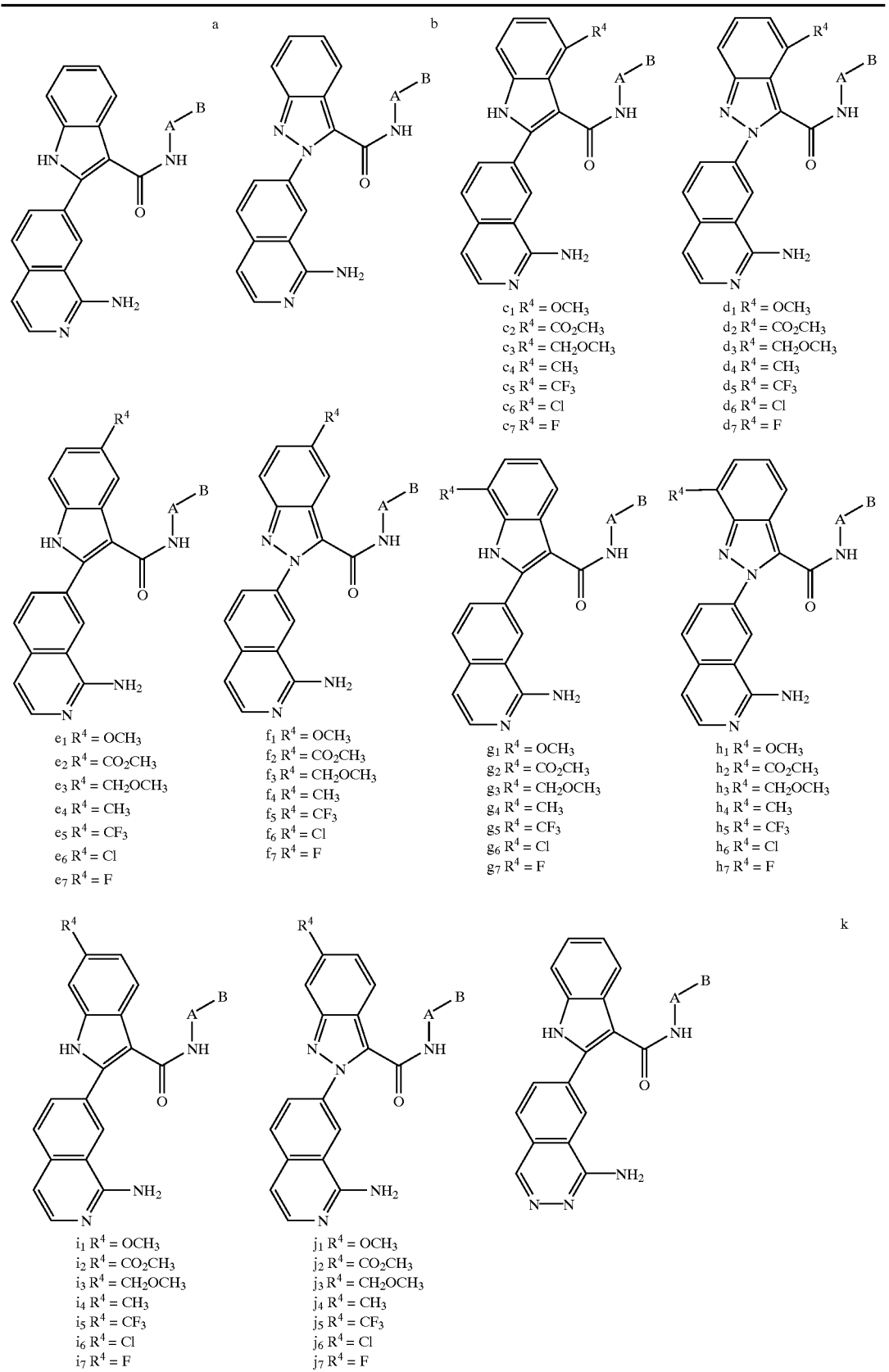

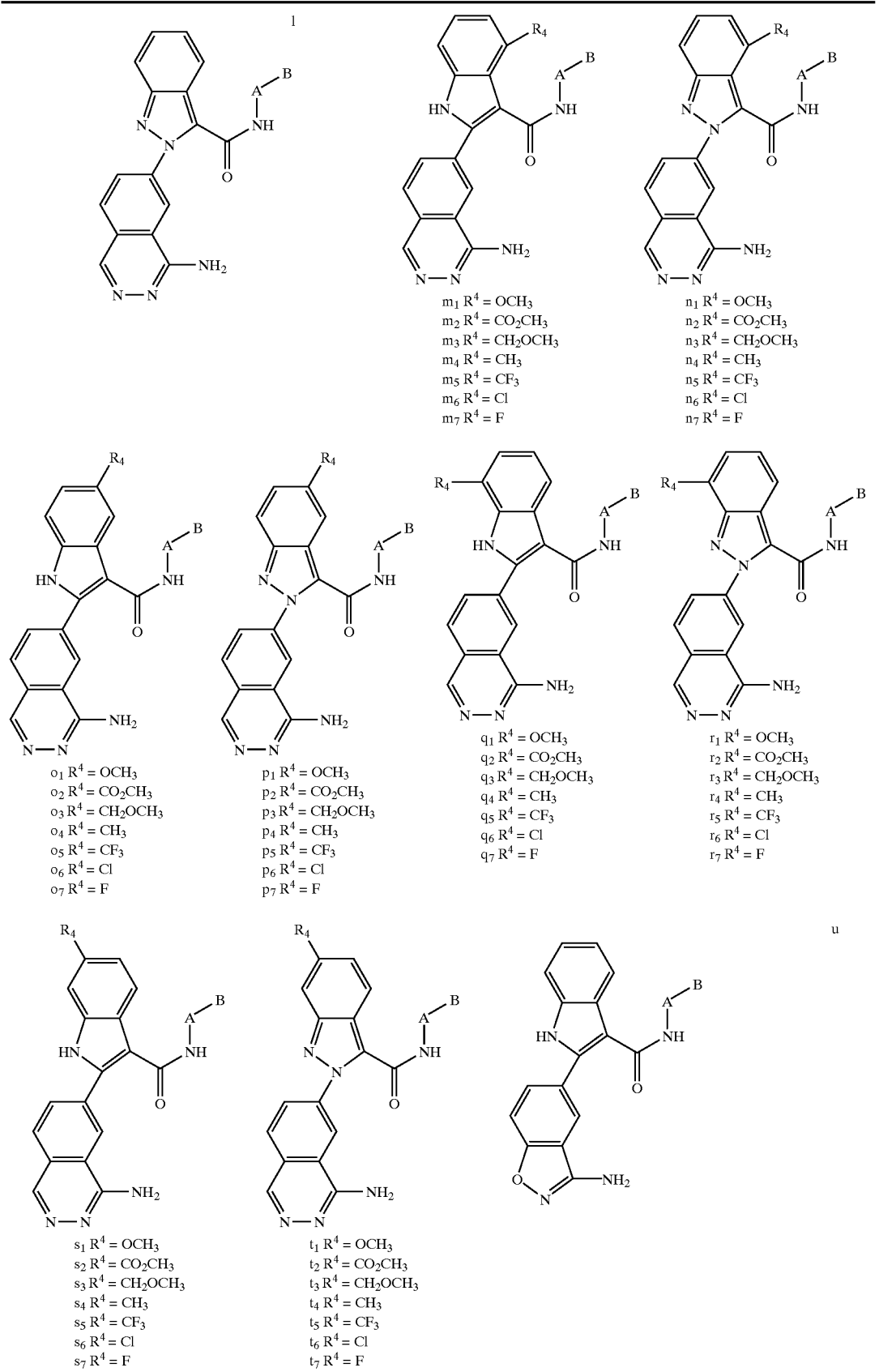

TABLE 7-continued
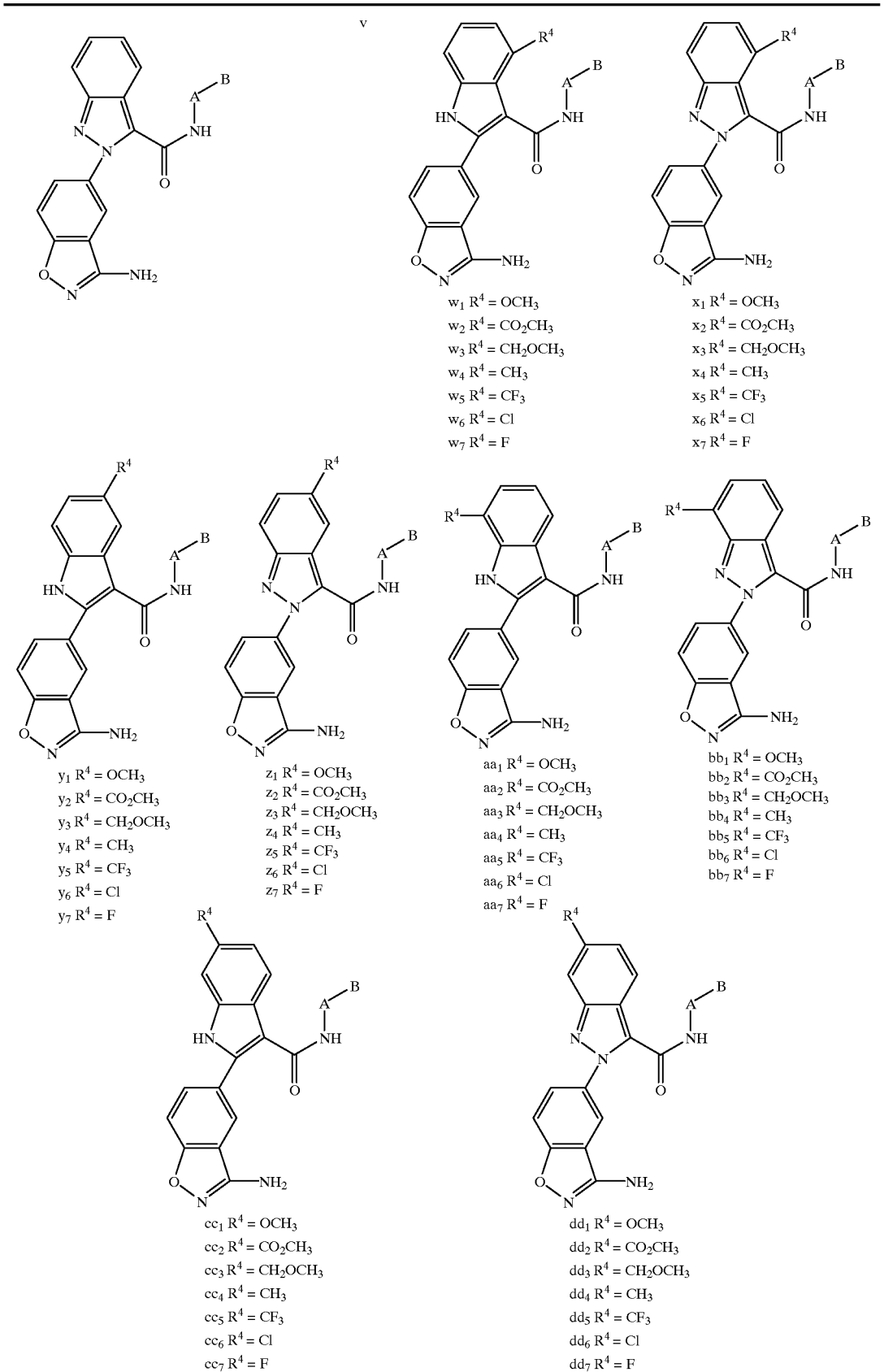

TABLE 7-continued

| Ex# | A | B |
|---|---|---|
| 1 | phenyl | 2-((Me)$_2$N-methyl)phenyl |
| 2 | phenyl | 2-((Me)NH-methyl)phenyl |
| 3 | phenyl | 2-(H$_2$N-methyl)phenyl |
| 4 | phenyl | 2-HOCH$_2$-phenyl |
| 5 | 2-F-phenyl | 2-((Me)$_2$N-methyl)phenyl |
| 6 | 2-F-phenyl | 2-((Me)NH-methyl)phenyl |
| 7 | 2-F-phenyl | 2-(H$_2$N-methyl)phenyl |
| 8 | 2-F-phenyl | 2-HOCH$_2$-phenyl |
| 9 | phenyl | 2-methylimidazol-1-yl |
| 10 | phenyl | 2-ethylimidazol-1-yl |
| 11 | phenyl | 2-((Me)$_2$N-methyl)imidazol-1-yl |
| 12 | phenyl | 2-CH$_3$SO$_2$-imidazol-1-yl |
| 13 | phenyl | 2-CH$_3$OCH$_2$-imidazol-1-yl |
| 14 | 2-F-phenyl | 2-methylimidazol-1-y1 |
| 15 | 2-F-phenyl | 2-ethylimidazol-1-yl |
| 16 | 2-F-phenyl | 2-((Me)$_2$N-methyl)imidazol-1-yl |
| 17 | 2-F-phenyl | 2-CH$_3$SO$_2$-imidazol-1-yl |
| 18 | 2-F-phenyl | 2-CH$_3$OCH$_2$-imidazol-1-yl |
| 19 | 2-Cl-phenyl | 2-methylimidazol-1-yl |
| 20 | 2-Cl-phenyl | 2-ethylimidazol-1-yl |
| 21 | 2-Cl-phenyl | 2-((Me)$_2$N-methyl)imidazol-1-yl |
| 22 | 2-Cl-phenyl | 2-CH$_3$SO$_2$-imidazol-1-yl |
| 23 | 2-Cl-phenyl | 2-CH$_3$OCH$_2$-imidazol-1-yl |
| 24 | 2-(Me)$_2$N-phenyl | 2-methylimidazol-1-yl |
| 25 | 2-(Me)$_2$N-phenyl | 2-ethylimidazol-1-yl |
| 26 | 2-(Me)$_2$N-phenyl | 2-((Me)$_2$N-methyl)imidazol-1-yl |
| 27 | 2-(Me)$_2$N-phenyl | 2-CH$_3$SO$_2$-imidazol-1-yl |
| 28 | 2-(Me)$_2$N-phenyl | 2-CH$_3$OCH$_2$-imidazol-1-yl |
| 29 | phenyl | N-methylimidazol-2-yl |
| 30 | phenyl | 4-methylimidazol-5-yl |
| 31 | phenyl | 5-CF$_3$-pyrazol-1-yl |
| 32 | 2-F-phenyl | N-methylimidazol-2-yl |
| 33 | 2-F-phenyl | 4-methylimidazol-5-yl |
| 34 | 2-F-phenyl | 5-CF$_3$-pyrazol-1-yl |
| 35 | phenyl | guanidino |
| 36 | phenyl | 2-thiazolin-2-ylamine |
| 37 | phenyl | N-methyl-2-imidazolin-2-yl |
| 38 | phenyl | N-methyl-1,4,5,6-tetrahydropyrimid-2-yl |
| 39 | phenyl | N-methylimidazol-2-ylthiol |
| 40 | phenyl | t-butoxycarbonylamine |
| 41 | phenyl | (N-pyrrolidino)formylimino |
| 42 | phenyl | (N-pyrrolidino)formyl-N-methanesulfamoyl)imino |
| 43 | 2-F-phenyl | guanidino |
| 44 | 2-F-phenyl | 2-thiazolin-2-ylamine |
| 45 | 2-F-phenyl | N-methyl-2-imidazolin-2-yl |
| 46 | 2-F-phenyl | N-methyl-1,4,5,6-tetrahydropyrimid-2-yl |
| 47 | 2-F-phenyl | N-methylimidazol-2-ylthio |
| 48 | 2-F-phenyl | t-butoxycarbonylamine |
| 49 | 2-F-phenyl | (N-pyrrolidino)formylimino |
| 50 | 2-F-phenyl | (N-pyrrolidino)formyl-N-methanesulfamoyl)imino |
| 51 | 2-CH$_3$O-phenyl | (N-pyrrolidino)formylimino |
| 52 | 2-CH$_3$O-phenyl | (N-pyrrolidino)formyl-N-(methanesulfamoyl)imino |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5%

PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1 + S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of $\leq 15\,\mu M$, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 15 $\mu m$, thereby confirming the utility of the compounds of the present invention as effective Xa inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula I:

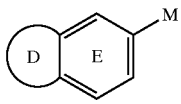

I or a stereoisomer or pharmaceutically acceptable salt thereof, wherein;

ring D is selected from —$CH_2N=CH$—, —$CH_2CH_2N=CH$—, and a 5–6 membered aromatic ring consisting of carbon atoms and 0–2 heteroatoms selected from the group N, O, and S;

ring D is substituted with 0–2 R, provided that when ring D is unsubstituted, at least one ring heteroatom is present therein;

ring E contains 0–2 N atom and is substituted by 0–1 R

R is selected from Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

M is selected from the group:

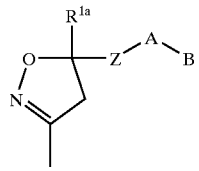
a

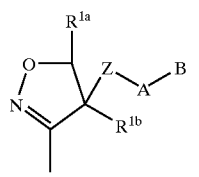
b

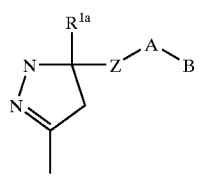
c

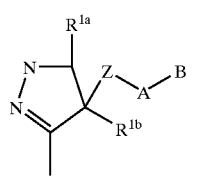
d

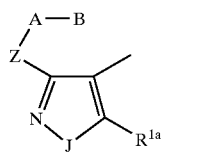
e

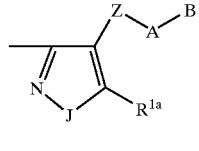
f

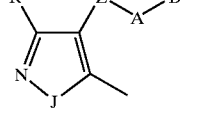
g

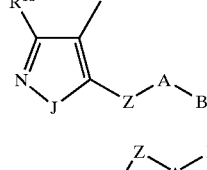
h

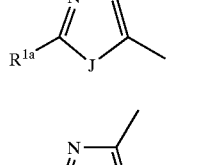
i

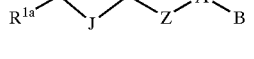
j

-continued
k 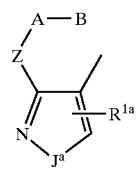
l 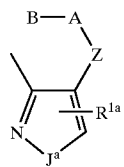
m 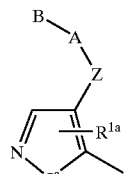
n 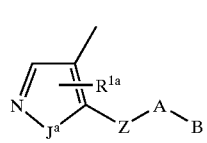
o 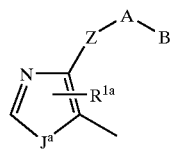
p 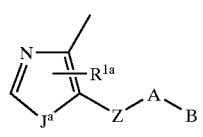
q 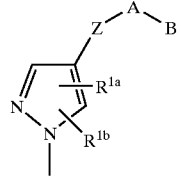
r 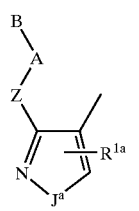
s 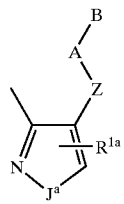
-continued
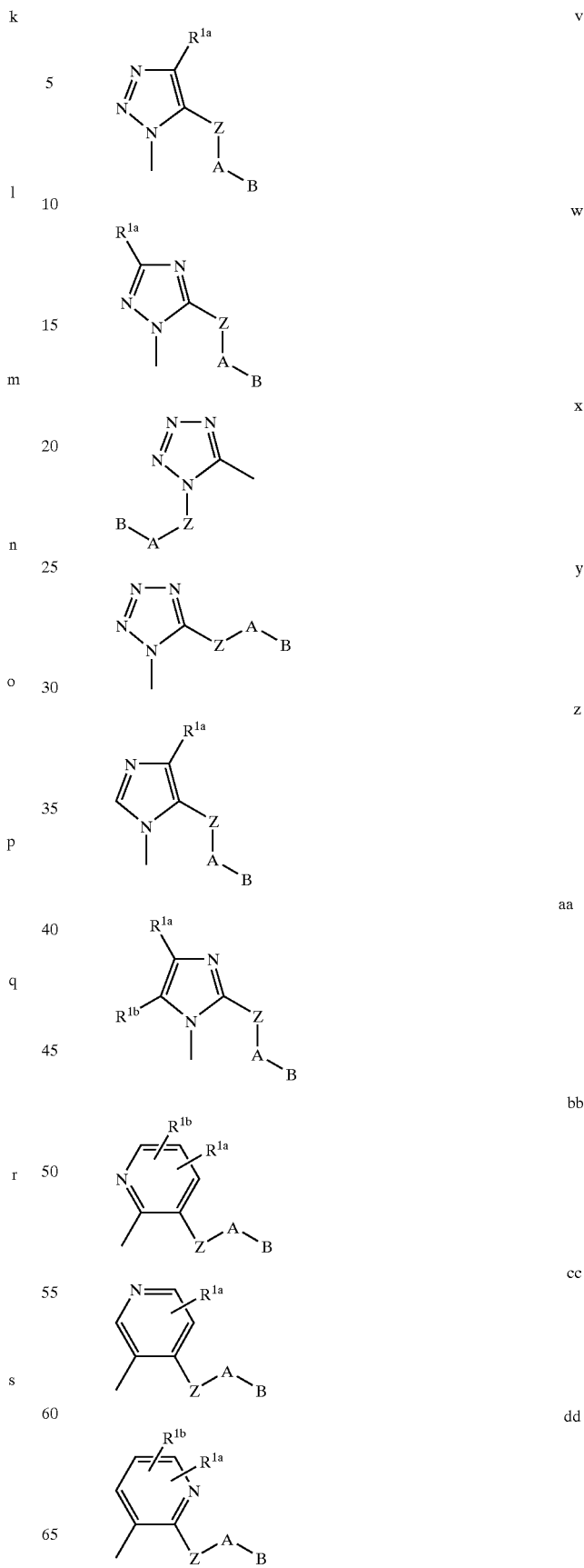

227
-continued
ee 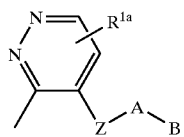
ff 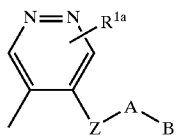
gg 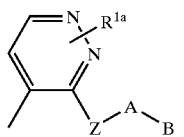
hh 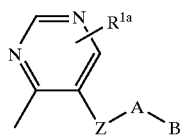
ii 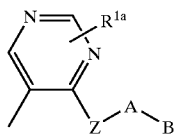
jj 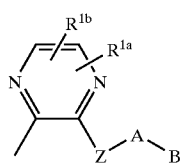
kk 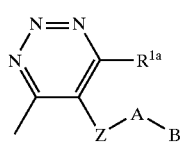
ll 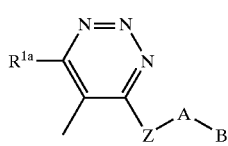
mm 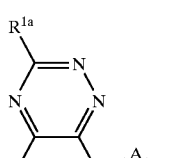
nn 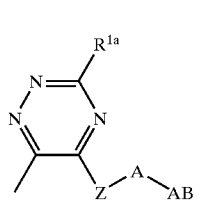
228
-continued
oo 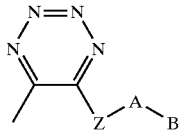
pp 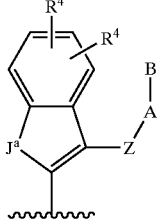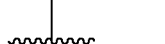
qq 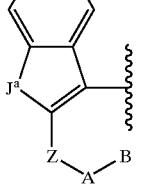
rr 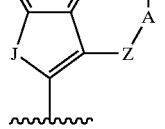
ss 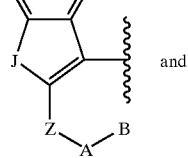 and
tt 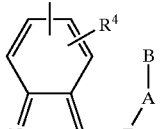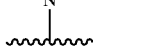
J is O or S;
$J^a$ is NH or $NR^{1a}$;
Z is selected from $C_{1-4}$ alkylene, $(CH_2)_rO(CH_2)_r$, $(CH_2)_r$ $NR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_r$ $NR^3C(O)(CH_2)_r$, $(CH_2)_rOC(O)O(CH_2)_r$, $(CH_2)_rOC(O)$ $NR^3(CH_2)_r$, $(CH_2)_rNR^3C(O)O(CH_2)_r$, $(CH_2)_rNR^3C$ $(O)NR^3(CH_2)_r$, $(CH_2)_rS(O)_p(CH_2)_r$, $(CH_2)_rSO_2NR^3$ $(CH_2)_r$, $(CH_2)_rNR^3SO_2(CH_2)_r$, and $(CH_2)_r$ NR³SO₂NR³(CH₂)ᵣ, provided that Z does not form a N—N, N—O, N—S, NCH₂N, NCH₂O, or NCH₂S bond with ring M or group A;

R¹ᵃ and R¹ᵇ are independently H or selected from —(CH₂)ᵣ—R¹', —CH═CH—R¹', NCH₂R¹", OCH₂R¹", SCH₂R¹", NH(CH₂)₂(CH₂)ᵣR¹', O(CH₂)₂(CH₂)ᵣR¹', and S(CH₂)₂(CH₂)ᵣR¹';

alternatively, R¹ᵃ and R¹ᵇ, when attached to adjacent carbon atoms, together with the atoms to which they are attached form a 5–8 membered saturated, partially saturated or unsaturated ring substituted with 0–2 R⁴ and which consist of carbon atoms and 0–2 heteroatoms selected from the group consisting of N, O, and S;

alternatively, when Z is C(O)NH and R¹ᵃ is attached to a ring carbon adjacent to Z, then R¹ᵃ is a C(O) which replaces the amide hydrogen of Z to form a cyclic imide;

R¹' is selected from H, C₁₋₃ alkyl, F, Cl, Br, I, —CN, —CHO, (CF₂)ᵣCF₃, (CH₂)ᵣOR², NR²R²ᵃ, C(O)R²ᶜ, OC(O)R², (CF₂)ᵣCO₂R²ᶜ, S(O)ₚR²ᵇ, NR²(CH₂)ᵣOR², C(═NR²ᶜ)NR²R²ᵃ, NR²C(O)R²ᵇ, NR²C(O)NHR²ᵇ, NR²C(O)₂R²ᵃ, OC(O)NR²ᵃR²ᵇ, C(O)NR²R²ᵃ, C(O)NR²(CH₂)ᵣOR², SO₂NR²R²ᵃ, NR²SO₂R²ᵇ, C₃₋₆ carbocyclic substituted with 0–2 R⁴, and 5–10 membered heterocycle consisting of carbon atoms and 1–4 heteroatoms selected from the group consisting of N, O, and S substituted with 0–2 R⁴;

R¹" is selected from H, CH(CH₂OR²)₂, C(O)R²ᶜ, C(O)NR²R²ᵃ, S(O)R²ᵇ, S(O)₂R²ᵇ, and SO₂NR²R²ᵃ;

R², at each occurrence, is selected from H, CF₃, C₁₋₆ alkyl, benzyl, C₃₋₆ carbocycle substituted with 0–2 R⁴ᵇ, and 5–6 membered heterocycle consisting of carbon atoms and 1–4 heteroatoms selected from the group consisting of N, O, and S substituted with 0–2 R⁴ᵇ;

R²ᵃ, at each occurrence, is selected from H, CF₃, C₁₋₆ alkyl, benzyl, C₃₋₆ carbocycle substituted with 0–2 R⁴ᵇ, and 5–6 membered heterocycle consisting of carbon atoms and 1–4 heteroatoms selected from the group consisting of N, O, and S substituted with 0–2 R⁴ᵇ;

R²ᵇ, at each occurrence, is selected from CF₃, C₁₋₆ alkyl, benzyl, phenethyl, C₃₋₆ carbocycle substituted with 0–2 R⁴ᵇ, and 5–6 membered heterocycle consisting of carbon atoms and 1–4 heteroatoms selected from the group consisting of N, O, and S substituted with 0–2 R⁴ᵇ;

R²ᶜ, at each occurrence, is selected from CF₃, OH, C₁₋₄ alkoxy, C₁₋₆ alkyl, benzyl, C₃₋₆ carbocycle substituted with 0–2 R⁴ᵇ, and 5–6 membered heterocycle consisting of carbon atoms and 1–4 heteroatoms selected from the group consisting of N, O, and S substituted with 0–2 R⁴ᵇ;

alternatively, R² and R²ᵃ, together with the atom to which they are attached, combine to form a 5 or 6 membered saturated, partially saturated or unsaturated ring substituted with 0–2 R⁴ᵇ, wherein 0–1 additional ring heteroatoms selected from the group consisting of N, O, and S;

R³, at each occurrence, is selected from H, C₁₋₄ alkyl, and phenyl;

R³ᵃ, at each occurrence, is selected from H, C₁₋₄ alkyl, and phenyl;

R³ᶜ, at each occurrence, is selected from C₁₋₄ alkyl, and phenyl;

A is selected from:
C₅₋₆ carbocycle substituted with 0–2 R⁴, and
5–6 membered heterocycle consisting of carbon atoms and 1–4 heteroatoms selected from the group consisting of N, O, and S substituted with 0–2 R⁴;

B is selected from: H, Y, and X—Y;

X is selected from C₁₋₄ alkylene, —CR²(CR²R²ᵇ)(CH₂)ᵣ—, —C(O)—, —C(═NR¹")—, —CR²(NR¹"R²)—, —CR²(OR²)—, —CR²(SR²)—, —C(O)CR²R²ᵃ—, —CR²R²ᵃC(O), —S(O)ₚ—, —S(O)ₚCR²R²ᵃ—, —CR²R²ᵃS(O)ₚ—, —S(O)₂NR²—, —NR²S(O)₂—, —NR²S(O)₂CR²R²ᵃ—, —CR²R²ᵃS(O)₂NR²—, —NR²S(O)₂NR²—, —C(O)NR²—, —NR²C(O)—, —C(O)NR²CR²R²ᵃ—, —NR²C(O)CR²R²ᵃ—, —CR²R²ᵃC(O)NR²—, —CR²R²ᵃNR²C(O)—, —NR²C(O)O—, —OC(O)NR²—, —NR²C(O)NR²—, —NR²—, —NR²CR²R²ᵃ—, —CR²R²ᵃNR²—, O, —CR²R²ᵃO—, and —OCR²R²ᵃ—;

Y is selected from:
(CH₂)ᵣNR²R²ᵃ, provided that X–Y do not form a N—N, O—N, or S—N bond,
C₃₋₁₀ carbocycle substituted with 0–2 R⁴ᵃ, and
5–10 membered heterocycle consisting of carbon atoms and 1–4 heteroatoms selected from the group consisting of N, O, and S substituted with 0–2 R⁴ᵃ;

R⁴, at each occurrence, is selected from H, ═O, (CH₂)ᵣOR², F, Cl, Br, I, C₁₋₄ alkyl, —CN, NO₂, (CH₂)ᵣNR²R²ᵃ, (CH₂)ᵣC(O)R²ᶜ, NR²C(O)R²ᵇ, C(O)NR²R²ᵃ, NR²C(O)NR²R²ᵃ, C(═NR²)NR²R²ᵃ, C(═NS(O)₂R⁵)NR²R²ᵃ, NHC(═NR²)NR²R²ᵃ, C(O)NHC(═NR²)NR²R²ᵃ, SO₂NR²R²ᵃ, NR²SO₂NR²R²ᵃ, NR²SO₂—C₁₋₄ alkyl, NR²SO₂R⁵, S(O)ₚR⁵, (CF₂)ᵣCF₃, NCH₂R¹", OCH₂R¹", SCH₂R¹", N(CH₂)₂(CH₂)ᵣR¹', O(CH₂)₂(CH₂)ᵣR¹', and S(CH₂)₂(CH₂)ᵣR¹';

alternatively, one R⁴ is a 5–6 membered aromatic heterocycle consisting of carbon atoms and 1–4 heteroatoms selected from the group consisting of N, O, and S;

provided that if B is H, then R⁴ is other than tetrazole, C(O)-alkoxy, and C(O)NR²R²ᵃ;

R⁴ᵃ, at each occurrence, is selected from H, ═O, (CH₂)ᵣOR², (CH₂)ᵣ—F, (CH₂)ᵣ—Br, (CH₂)ᵣ—Cl, I, C₁₋₄ alkyl, —CN, NO₂, (CH₂)ᵣNR²R²ᵃ, (CH₂)ᵣNR²R²ᵇ, (CH₂)ᵣC(O)R²ᶜ, NR²C(O)R²ᵇ, C(O)NR²R²ᵃ, C(O)NH(CH₂)₂NR²R²ᵃ, NR²C(O)NR²R²ᵃ, C(═NR²)NR²R²ᵃ, NHC(═NR²)NR²R²ᵃ, SO₂NR²R²ᵃ, NR²SO₂NR²R²ᵃ, NR²SO₂—C₁₋₄ alkyl, C(O)NHSO₂—C₁₋₄ alkyl, NR²SO₂R⁵, S(O)ₚR⁵, and (CF₂)ᵣCF₃;

alternatively, one R⁴ᵃ is a 5–6 membered aromatic heterocycle consisting of carbon atoms and 1–4 heteroatoms selected from the group consisting of N, O, and S and substituted with 0–1 R⁵;

R⁴ᵇ, at each occurrence, is selected from H, ═O, (CH₂)ᵣOR³, F, Cl, Br, I, C₁₋₄ alkyl, —CN, NO₂, (CH₂)ᵣNR³R³ᵃ, (CH₂)ᵣC(O)R³, (CH₂)ᵣC(O)OR³ᶜ, NR³C(O)R³ᵃ, C(O)NR³R³ᵃ, NR³C(O)NR³R³ᵃ, C(═NR³)NR³R³ᵃ, NH³C(═NR³)NR³R³ᵃ, SO₂NR³R³ᵃ, NR³SO₂NR³R³ᵃ, NR³SO₂—C₁₋₄ alkyl, NR³SO₂CF₃, NR³SO₂-phenyl, S(O)ₚCF₃, S(O)ₚ—C₁₋₄ alkyl, S(O)ₚ-phenyl, and (CF₂)ᵣCF₃;

R⁵, at each occurrence, is selected from CF₃, C₁₋₆ alkyl, phenyl substituted with 0–2 R⁶, and benzyl substituted with 0–2 R⁶;

R⁶, at each occurrence, is selected from H, OH, (CH₂)ᵣOR², F, Cl, Br, I, C₁₋₄ alkyl, CN, NO₂, (CH₂)ᵣNR²R²ᵃ, (CH₂)ᵣC(O)R²ᵇ, NR²C(O)R²ᵇ, NR²C(O)NR²R²ᵃ, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

p is selected from 0, 1, and 2;
r is selected from 0, 1, 2, and 3;
s is selected from 0, 1, and,
t is selected from 0 and 1.

2. A compound according to claim 1, wherein:
D-E is selected from the group:
1-aminoisoquinolin-7-yl; 1,3-diaminoisoquinolin-7-yl; 1,4-diaminoisoquinolin-7-yl; 1,5-diaminoisoquinolin-7-yl; 1,6-diaminoisoquinolin-7-yl; 1-amino-3-hydroxy-isoquinolin-7-yl; 1-amino-4-hydroxy-isoquinolin-7-yl; 1-amino-5-hydroxy-isoquinolin-7-yl; 1-amino-6-hydroxy-isoquinolin-7-yl; 1-amino-3-methoxy-isoquinolin-7-yl; 1-amino-4-methoxy-isoquinolin-7-yl; 1-amino-5-methoxy-isoquinolin-7-yl; 1-amino-6-methoxy-isoquinolin-7-yl; 1-hydroxy-isoquinolin-7-yl; 4-aminoquinazol-6-yl; 2,4-diaminoquinazol-6-yl; 4,7-diaminoquinazol-6-yl 4,8-diaminoquinazol-6-yl; 1-aminophthalaz-7-yl; 1,4-diaminophthalaz-7-yl; 1,5-diaminophthalaz-7-yl; 1,6-diaminophthalaz-7-yl; 4-aminopterid-6-yl; 2,4-aminopterid-6-yl; 4,6-diaminopterid-6-yl; 8-amino-1,7-naphthyrid-2-yl; 6,8-diamino-1,7-naphthyrid-2-yl; 5,8-diamino-1,7-naphthyrid-2-yl; 4,8-diamino-1,7-naphthyrid-2-yl; 3,8-diamino-1,7-naphthyrid-2-yl; 5-amino-2,6-naphthyrid-3-yl; 5,7-diamino-2,6-naphthyrid-3-yl; 5,8-diamino-2,6-naphthyrid-3-yl; 1,5-diamino-2,6-naphthyrid-3-yl; 5-amino-1,6-naphthyrid-3-yl; 5,7-diamino-1,6-naphthyrid-3-y; 5,8-diamino-1,6-naphthyrid-3-yl; 2,5-diamino-1,6-naphthyrid-3-yl; 3-aminoindazol-5-yl; 3-hydroxyindazol-5-yl; 3-aminobenzisoxazol-5-yl; 3-hydroxybenzisoxazol-5-yl; 3-aminobenzisothiazol-5-yl; 3-hydroxybenzisothiazol-5-yl; 1-amino-3,4-dihydroisoquinolin-7-yl; and, 1-aminoisoindol-6-yl;

M is selected from the group:

a
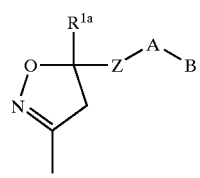

b
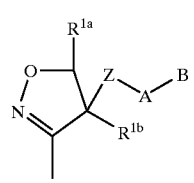

f
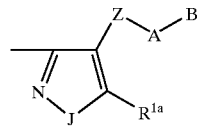

j
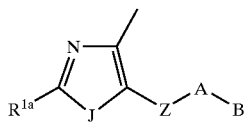

l
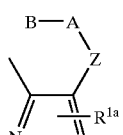

m
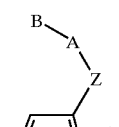

n
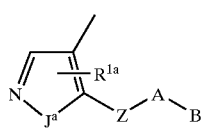

o
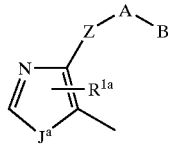

s
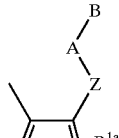

v
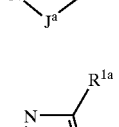

w
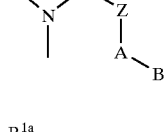

y
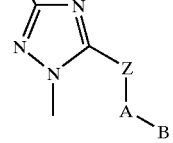

-continued

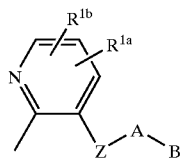
bb

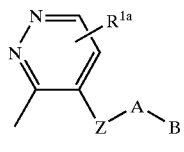
ee

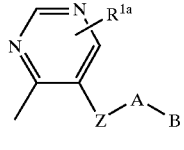
hh

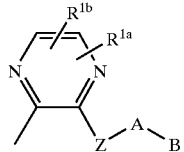
jj

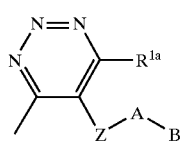
kk

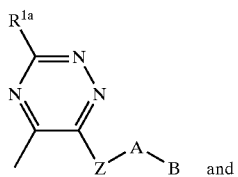 and
mm

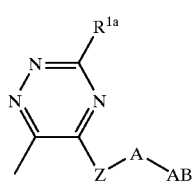
nn

Z is selected from $(CH_2)_rC(O)(CH_2)_r$, $(CH_2)_rC(O)O(CH_2)_r$, $(CH_2)_rC(O)NR^3(CH_2)_r$, $(CH_2)_rS(O)_p(CH_2)_r$, and $(CH_2)_rSO_2NR^3(CH_2)_r$; and, Y is selected from one of the following rings which are substituted with 0–2 $R^{4a}$;
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole;

alternatively, Y is selected from the following bicyclic heteroaryl ring systems:

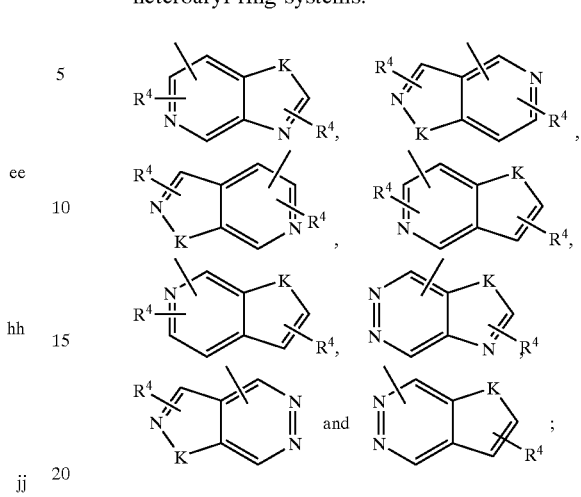

K is selected from O, S, NH, and N.

3. A compound according to claim 2, wherein:

D-E is selected from the group:
1-aminoisoquinolin-7-yl; 1,3-diaminoisoquinolin-7-yl; 1,4-diaminoisoquinolin-7-yl; 1,5-diaminoisoquinolin-7-yl; 1,6-diaminoisoquinolin-7-yl; 1-hydroxy-isoquinolin-7-yl; 4-aminoquinazol-6-yl; 2,4-diaminoquinazol-6-yl; 4,7-diaminoquinazol-6-yl; 4,8-diaminoquinazol-6-yl; 1-aminophthalaz-7-yl; 1,4-diaminophthalaz-7-yl; 1,5-diaminophthalaz-7-yl; 1,6-diaminophthalaz-7-yl; 4-aminopterid-6-yl; 8-amino-1,7-naphthyrid-2-yl; 5-amino-1,6-naphthyrid-3-y; 5-amino-2,6-naphthyrid-3-yl; 3-aminobenzisoxazol-5-yl; 3-aminobenzisothiazol-5-yl; 1-amino-3,4-dihydroisoquinolin-7-yl; and, 1-aminoisoindol-6-yl;

M is selected from the group:

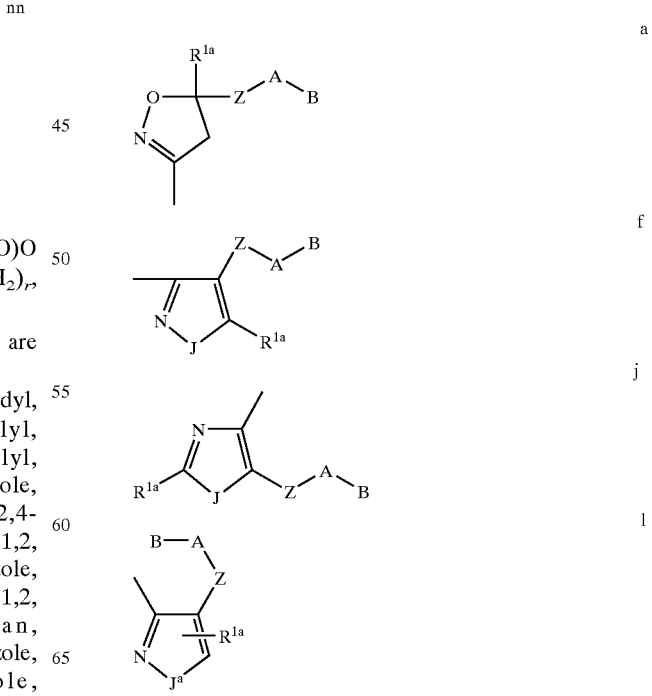

235
-continued

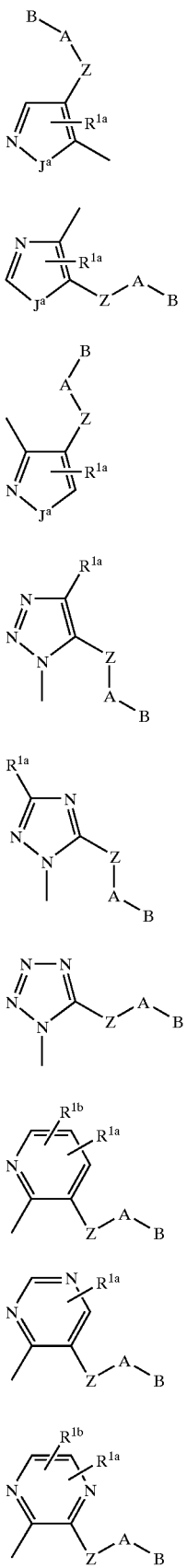

m n s v w bb hh jj

Z is selected from $(CH_2)_rC(O)(CH_2)_r$ and $(CH_2)_rC(O)NR^3(CH_2)_r$; and,

Y is selected from one of the following rings which are substituted with 0–2 $R^{4a}$;
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole.

4. A compound according to claim 3, wherein:

D-E is selected from the group:
1-aminoisoquinolin-7-yl; 1,3-diaminoisoquinolin-7-yl; 1,4-diaminoisoquinolin-7-yl; 1,5-diaminoisoquinolin-7-yl; 1,6-diaminoisoquinolin-7-yl; 1-aminophthalaz-7-yl; 1,4-diaminophthalaz-7-yl; 1,5-diaminophthalaz-7-yl; 1,6-diaminophthalaz-7-yl; 4-aminopterid-6-yl; 8-amino-1,7-naphthyrid-2-yl; 5-amino-1,6-naphthyrid-3-y; 5-amino-2,6-naphthyrid-3-yl; 3-aminobenzisoxazol-5-yl; 1-amino-3,4-dihydroisoquinolin-7-yl; and, 1-aminoisoindol-6-yl;

M is selected from the group:

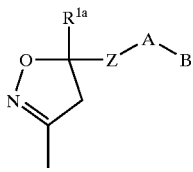

a

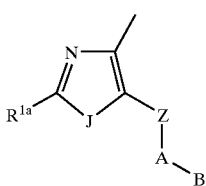

j

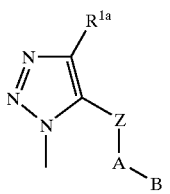

v

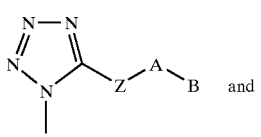

y and

-continued

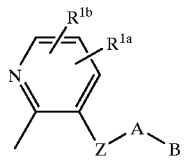

bb

A is selected from:
C$_{5-6}$ carbocycle substituted with 0–2 R$^4$, and
5–6 membered heterocycle consisting of carbon atoms and 1–4 heteroatoms selected from the group consisting of N, O, and S substituted with 0–2 R$^4$;

Y is selected from one of the following rings which are substituted with 0–2 R$^{4a}$;
phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole;

R$^2$, at each occurrence, is selected from H, CF$_3$, C$_{1-6}$ alkyl, benzyl, C$_{5-6}$ carbocycle substituted with 0–2 R$^{4b}$, and 5–6 membered heterocycle containing of carbon atoms and 1–4 heteroatoms selected from the group consisting of N, O and S substituted with 0–2 R$^{4b}$;

R$^{2a}$, at each occurrence, is selected from H, CF$_3$, C$_{1-6}$ alkyl, benzyl, phenethyl, C5-6 carbocyclic residue substituted with 0–2 R$^{4b}$, and 5–6 membered heterocycle consisting of carbon atoms and 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzyl, C$_{5-6}$ carbocyclic substituted with 0–2 R$^{4b}$, and 5–6 membered heterocycle consisting of carbon atoms and 1–4 heteroatoms selected from the group consisting of N, O, and S substituted with 0–2 R$^{4b}$;

R$^{2c}$, at each occurrence, is selected from CF$_3$, OH, C$_{1-4}$ alkoxy, C$_{1-6}$ alkyl, benzyl, C$_{5-6}$ carbocyclic substituted with 0–2 R$^{4b}$, and 5–6 membered heterocycle consisting of carbon atoms and 1–4 heteroatoms selected from the group consisting of N, O, and S substituted with 0–2 R$^{4b}$;

alternatively, R$^2$ and R$^{2a}$, together with the atom to which they are attached, combine to form a ring selected from imidazolyl, morpholino, piperazinyl, pyridyl, and pyrrolidinyl, substituted with 0–2 R$^{4b}$;

R$^4$, at each occurrence, is selected from H, =O, OR$^2$, CH$_2$OR$^2$, F, Cl, C$_{1-4}$ alkyl, NR$^2$R$^{2a}$, CH$_2$NR$^2$R$^{2a}$, C(O)R$^{2c}$, CH$_2$C(O)R$^{2c}$, C(O)NR$^2$R$^{2a}$, C(=NR$^2$)NR$^2$R$^{2a}$, C(=NS(O)$_2$R$^5$)NR$^2$R$^{2a}$, SO$_2$NR$^2$R$^{2a}$, NR$^2$SO$_2$—C$_{1-4}$ alkyl, S(O)$_2$R$^5$, and CF$_3$
provided that if B is H, then R$^4$ is other than tetrazole, C(O)-alkoxy, and C(O)NR$^2$R$^{2a}$;

R$^{4a}$, at each occurrence, is selected from H, =O, (CH$_2$)$_r$OR$^2$, F, Cl, C$_{1-4}$ alkyl, NR$^2$R$^{2a}$, CH$_2$NR$^2$R$^{2a}$, NR$^2$R$^{2b}$, CH$_2$NR$^2$R$^{2b}$, (CH$_2$)$_r$C(O)R$^{2c}$, NR$^2$C(O)R$^{2b}$, C(O) NR$^2$R$^{2a}$, C(O)NH(CH$_2$)$_2$NR$^2$R$^{2a}$, NR$^2$C(O)NR$^2$R$^{2a}$, SO$_2$NR$^2$R$^{2a}$, S(O)$_2$R$^5$, and CF$_3$; and, R$^{4b}$, at each occurrence, is selected from H, =O, (CH$_2$)$_r$OR$^3$, F, Cl, C$_{1-4}$ alkyl, NR$^3$R$^{3a}$, CH$_2$NR$^3$R$^{3a}$, C(O)R$^3$, CH$_2$C(O)R$^3$, C(O)OR$^{3c}$, C(O)NR$^3$R$^{3a}$, C(=NR$^3$) NR$^3$R$^{3a}$, SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_2$CF$_3$, S(O)$_2$—C$_{1-4}$ alkyl, S(O)$_2$-phenyl, and CF$_3$.

5. A compound according to claim 4, wherein: the compounds are selected from:
D-E is selected from the group:
1-aminoisoquinolin-7-yl; 1,3-diaminoisoquinolin-7-yl; 1,4-diaminoisoquinolin-7-yl; 1,5-diaminoisoquinolin-7-yl; 1,6-diaminoisoquinolin-7-yl; 8-amino-1,7-naphthyrid-2-yl; 5-amino-1,6-naphthyrid-3-y; 5-amino-2,6-naphthyrid-3-yl; 3-aminobenzisoxazol-5-yl; 1-amino-3,4-dihydroisoquinolin-7-yl; and, 1-aminoisoindol-6-yl.

6. A compound according to claim 1, wherein the compound is selected from:
3-(1'-Amino-isoquinol-7'-yl)-5-[(2'-aminosulfonyl-[1,1']-biphen-4-yl)carbonylamino]-5-methylisoxazoline;
3-(Isoquinol-5'-yl)-5-[(2'-aminosulfonyl-[1,1']-biphen-4-yl)carbonylamino]-5-methylisoxazoline;
3-(Isoquinol-7'-yl)-5-[(2'-aminosulfonyl-[1,1']-biphen-4-yl)carbonylamino]-5-methylisoxazoline;
3-(2'-Aminobenzimidazol-5'-yl)-5-[(2'-aminosulfonyl-[1,1']-biphen-4-yl)aminocarbonyl]-5-methylisoxazoline;
3-(3'-Aminoindazol-5'-yl)-5-[(2'-aminosulfonyl-[1,1']-biphen-4-yl)aminocarbonyl]-5-methylisoxazoline;
3-(3'-Aminobenzisoxazol-5'-yl)-5-[(2'-aminosulfonyl-[1,1']-biphen-4-yl)aminocarbonyl]-5-methylisoxazoline
3-(1-Amino-isoquinol-7-yl)-4-[(2'-aminosulfonyl-[1,1']-biphen-4-yl)aminocarbonyl]-1,2,3-triazole;
3-(4-amino-isoquinol-7-yl)-4-[(2'-aminosulfonyl-[1,1']-biphen-4-yl)aminocarbonyl]-1,2,3-triazole;
3-(isoquinol-7-yl)-4-[(2'-aminosulfonyl-[1,1']-biphen-4-yl)aminocarbonyl]-1,2,3-triazole;
3-(3'-Aminobenzisoxazol-5'-yl)-5-[[5-[(2'-aminosulfonyl)phenyl]pyrid-2-yl]aminocarbonyl]-5-(methylsulfonylaminomethyl)isoxazoline;
1-(3'-Aminobenzisoxazol-5'-yl)-5-[[(2'-methylsulfonyl)-3-fluoro-[1,1']-biphen-4-yl]aminocarbonyl]tetrazole;
1-(3'-Aminobenzisoxazol-5'-yl)-5-[[4-(2'-methylimidazol-1'-yl)phenyl]aminocarbonyl]tetrazole;
1-(3'-Aminobenzisoxazol-5'-yl)-5-[(2'-aminosulfonyl-[1,1']-biphen-4-yl)aminocarbonyl]tetrazole;
1-(3'-Aminobenzisoxazol-5'-yl)-5-[(2-fluoro-4-(N-pyrrolidinocarbonyl)phenyl)aminocarbonyl]tetrazole;
1-(3'-Aminobenzisoxazol-5'-yl)-5-[(2-(N-pyrrolidino)-4-(N-pyrrolidinocarbonyl)phenyl)aminocarbonyl]tetrazole;
1-(1'-Amino-isoquinol-7'-yl)-5-[[(2'-aminosulfonyl)-3-fluoro-[1,1']-biphen-4-yl]aminocarbonyl]tetrazole;
1-(1'-Amino-isoquinol-7'-yl)-5-[[(2'-methylsulfonyl)-3-fluoro-[1,1']-biphen-4-yl]aminocarbonyl]tetrazole;
1-(3'-Aminobenzisoxazol-5'-yl)-5-[(2'-methylsulfonyl-3-fluoro-[1,1']-biphen-4-yl)aminocarbonyl]triazole;
1-(3'-Aminobenzisoxazol-5'-yl)-5-[(2'-aminosulfonyl-3-fluoro-[1,1']-biphen-4-yl)aminocarbonyl]triazole;
or pharmaceutically acceptable salt thereof.

7. A pharmaceutical composition, comprising: a pharmaceutically acceptable carrier and a therapeutically effective amount of a compound according to claim 1 or a pharmaceutically acceptable salt thereof.

8. A pharmaceutical composition, comprising: a pharmaceutically acceptable carrier and a therapeutically effective amount of a compound according to claim 2 or a pharmaceutically acceptable salt thereof.

9. A pharmaceutical composition, comprising: a pharmaceutically acceptable carrier and a therapeutically effective amount of a compound according to claim 3 or a pharmaceutically acceptable salt thereof.

10. A pharmaceutical composition, comprising: a pharmaceutically acceptable carrier and a therapeutically effective amount of a compound according to claim 4 or a pharmaceutically acceptable salt thereof.

11. A pharmaceutical composition, comprising: a pharmaceutically acceptable carrier and a therapeutically effective amount of a compound according to claim 5 or a pharmaceutically acceptable salt thereof.

12. A pharmaceutical composition, comprising: a pharmaceutically acceptable carrier and a therapeutically effective amount of a compound according to claim 6 or a pharmaceutically acceptable salt thereof.

13. A method for treating or preventing a thromboembolic disorder, comprising: administering to a patient in need thereof a therapeutically effective amount of a compound according to claim 1 or a pharmaceutically acceptable salt thereof.

14. A method for treating or preventing a thromboembolic disorder, comprising: administering to a patient in need thereof a therapeutically effective amount of a compound according to claim 2 or a pharmaceutically acceptable salt thereof.

15. A method for treating or preventing a thromboembolic disorder, comprising: administering to a patient in need thereof a therapeutically effective amount of a compound according to claim 3 or a pharmaceutically acceptable salt thereof.

16. A method for treating or preventing a thromboembolic disorder, comprising: administering to a patient in need thereof a therapeutically effective amount of a compound according to claim 4 or a pharmaceutically acceptable salt thereof.

17. A method for treating or preventing a thromboembolic disorder, comprising: administering to a patient in need thereof a therapeutically effective amount of a compound according to claim 5 or a pharmaceutically acceptable salt thereof.

18. A method for treating or preventing a thromboembolic disorder, comprising: administering to a patient in need thereof a therapeutically effective amount of a compound according to claim 6 or a pharmaceutically acceptable salt thereof.

* * * * *